United States Patent
Allawi et al.

(10) Patent No.: US 12,049,671 B2
(45) Date of Patent: *Jul. 30, 2024

(54) DETECTION OF COLON NEOPLASIA BY ANALYSIS OF METHYLATED DNA

(71) Applicants: EXACT SCIENCES CORPORATION, Madison, WI (US); Mayo Foundation for Medical Education and Research, Rochester, MN (US)

(72) Inventors: Hatim T. Allawi, Middleton, WI (US); Michael W. Kaiser, Stoughton, WI (US); Graham P. Lidgard, Middleton, WI (US); William R. Taylor, Lake City, MN (US); Tamara J. Sander, Mazomanie, WI (US); Abram M. Vaccaro, Rio, WI (US)

(73) Assignees: Exact Sciences Corporation, Madison, WI (US); Mayo Foundation for Medical Education and Research, Rochester, MN (US)

( * ) Notice: Subject to any disclaimer, the term of this patent is extended or adjusted under 35 U.S.C. 154(b) by 110 days.

This patent is subject to a terminal disclaimer.

(21) Appl. No.: 17/409,132

(22) Filed: Aug. 23, 2021

(65) Prior Publication Data

US 2022/0056526 A1 Feb. 24, 2022

Related U.S. Application Data

(63) Continuation of application No. 15/881,409, filed on Jan. 26, 2018, now Pat. No. 11,118,228.

(60) Provisional application No. 62/622,107, filed on Jan. 25, 2018, provisional application No. 62/451,327, filed on Jan. 27, 2017.

(51) Int. Cl.
| | | |
|---|---|---|
| *C12Q 1/6883* | (2018.01) | |
| *C12Q 1/6809* | (2018.01) | |
| *C12Q 1/6827* | (2018.01) | |
| *C12Q 1/6853* | (2018.01) | |
| *C12Q 1/6886* | (2018.01) | |
| *G01N 33/533* | (2006.01) | |
| *G01N 33/574* | (2006.01) | |
| *G16Z 99/00* | (2019.01) | |

(52) U.S. Cl.
CPC ......... *C12Q 1/6883* (2013.01); *C12Q 1/6809* (2013.01); *C12Q 1/6827* (2013.01); *C12Q 1/6853* (2013.01); *C12Q 1/6886* (2013.01); *G01N 33/533* (2013.01); *G01N 33/57419* (2013.01); *G16Z 99/00* (2019.02); *C12Q 2600/106* (2013.01); *C12Q 2600/112* (2013.01); *C12Q 2600/118* (2013.01); *C12Q 2600/154* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,486,530 A | 12/1984 | David et al. |
| 4,683,195 A | 7/1987 | Mullis et al. |
| 4,683,202 A | 7/1987 | Mullis |
| 4,735,214 A | 4/1988 | Berman |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,475,610 A | 12/1995 | Atwood et al. |
| 5,494,810 A | 2/1996 | Barany et al. |
| 5,508,169 A | 4/1996 | Deugau et al. |
| 5,538,871 A | 7/1996 | Nuovo et al. |
| 5,602,756 A | 2/1997 | Atwood et al. |
| 5,612,473 A | 3/1997 | Wu et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,786,146 A | 7/1998 | Herman et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |

(Continued)

FOREIGN PATENT DOCUMENTS

| | | |
|---|---|---|
| CN | 104781421 | 7/2015 |
| JP | 2008-502890 | 1/2008 |

(Continued)

OTHER PUBLICATIONS

Anderson et al., Methylated DNA Markers for Detection of Sporadic Colorectal Neoplasia: Comparison Between Age Groups Younger Than and Older Than 50. Abstract Su2013. Gastroenterology Apr. 1, 2016;150(4):S-611.

(Continued)

*Primary Examiner* — Angela M. Bertagna
*Assistant Examiner* — Carolyn L Greene
(74) *Attorney, Agent, or Firm* — Casimir Jones, S.C.; Mary Ann D. Brow

(57) ABSTRACT

Provided herein is technology for neoplasia screening, and particularly, but not exclusively, to methods, compositions, and related uses for detecting the presence of cancer, in particular, colorectal cancer.

13 Claims, 59 Drawing Sheets

Specification includes a Sequence Listing.

(56) References Cited

U.S. PATENT DOCUMENTS

| | | |
|---|---|---|
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,251,594 B1 | 6/2001 | Gonzalgo et al. |
| 6,329,178 B1 | 12/2001 | Patel et al. |
| 6,335,167 B1 | 1/2002 | Pinkel et al. |
| 6,395,524 B2 | 5/2002 | Loeb et al. |
| 6,602,695 B2 | 8/2003 | Patel et al. |
| 6,605,451 B1 | 8/2003 | Marmaro et al. |
| 6,872,816 B1 | 3/2005 | Hall et al. |
| 7,037,650 B2 | 5/2006 | Gonzalgo et al. |
| 7,087,414 B2 | 8/2006 | Gerdes et al. |
| 7,122,364 B1 | 10/2006 | Lyamichev et al. |
| 7,256,020 B2 | 8/2007 | Lyamichev et al. |
| 7,662,594 B2 | 2/2010 | Kong et al. |
| 7,790,393 B2 | 9/2010 | Lyamichev et al. |
| 8,304,214 B2 | 11/2012 | Gerdes et al. |
| 8,361,720 B2 | 1/2013 | Oldham-Haltom et al. |
| RE44,596 E | 11/2013 | Stroun et al. |
| 8,715,937 B2 | 5/2014 | Zou et al. |
| 8,808,990 B2 | 8/2014 | Lidgard et al. |
| 8,916,344 B2 | 12/2014 | Zou et al. |
| 8,962,250 B2 | 2/2015 | Stanley |
| 9,000,146 B2 | 4/2015 | Bruinsma et al. |
| 9,096,893 B2 | 8/2015 | Allawi et al. |
| 9,127,318 B2 | 9/2015 | Oldham-Haltom et al. |
| 9,163,278 B2 | 10/2015 | Bruinsma et al. |
| 9,169,511 B2 | 10/2015 | Lidgard et al. |
| 9,212,392 B2 | 12/2015 | Allawi et al. |
| 9,315,853 B2 | 4/2016 | Domanico et al. |
| 9,422,592 B2 | 8/2016 | Morris et al. |
| 9,428,746 B2 | 8/2016 | Holmberg et al. |
| 9,546,403 B1 | 1/2017 | Warren et al. |
| 9,637,792 B2 | 5/2017 | Ahlquist et al. |
| 9,657,511 B2 | 5/2017 | Lidgard et al. |
| 9,726,670 B2 | 8/2017 | Ataman-Onal et al. |
| 10,011,878 B2 | 7/2018 | Ahlquist et al. |
| 10,030,272 B2 | 7/2018 | Ahlquist et al. |
| 10,292,687 B2 | 5/2019 | Maguire et al. |
| 10,327,742 B2 | 6/2019 | Fitzgerald et al. |
| 10,370,726 B2 | 8/2019 | Ahlquist et al. |
| 10,385,406 B2 | 8/2019 | Allawi et al. |
| 10,435,755 B2 | 10/2019 | Ahlquist et al. |
| 10,465,248 B2 | 11/2019 | Allawi et al. |
| 10,519,510 B2 | 12/2019 | Ahlquist et al. |
| 10,648,025 B2 | 5/2020 | Allawi et al. |
| 10,648,035 B2 | 5/2020 | Agarwal et al. |
| 10,704,081 B2 | 7/2020 | Lidgard et al. |
| 10,822,638 B2 | 11/2020 | Allawi et al. |
| 11,118,228 B2 | 9/2021 | Allawi et al. |
| 11,479,823 B2 | 10/2022 | Allawi et al. |
| 2003/0224040 A1 | 12/2003 | Baylin et al. |
| 2003/0224437 A1 | 12/2003 | Gerdes et al. |
| 2004/0072182 A1 | 4/2004 | Lyamichev et al. |
| 2004/0175733 A1 | 9/2004 | Andersen et al. |
| 2004/0234960 A1 | 11/2004 | Olek et al. |
| 2005/0048527 A1 | 3/2005 | Allawi et al. |
| 2005/0214926 A1 | 9/2005 | Zielenski et al. |
| 2005/0239101 A1 | 10/2005 | Sukumar et al. |
| 2006/0134663 A1 | 6/2006 | Harkin et al. |
| 2006/0147955 A1 | 7/2006 | Allawi et al. |
| 2006/0171952 A1 | 8/2006 | Mather et al. |
| 2007/0048748 A1 | 3/2007 | Williams et al. |
| 2007/0161062 A1 | 7/2007 | Tacke et al. |
| 2007/0190540 A1 | 8/2007 | Stanley |
| 2007/0202525 A1 | 8/2007 | Quake et al. |
| 2008/0003571 A1 | 1/2008 | Mckernan et al. |
| 2009/0203011 A1 | 8/2009 | Liebenberg et al. |
| 2009/0253142 A1 | 10/2009 | Allawi et al. |
| 2010/0075334 A1 | 3/2010 | Kim et al. |
| 2011/0009277 A1 | 1/2011 | Devos et al. |
| 2011/0123990 A1 | 5/2011 | Baker et al. |
| 2011/0160446 A1 | 6/2011 | Ritt et al. |
| 2011/0287424 A1 | 11/2011 | Chen |
| 2011/0318738 A1 | 12/2011 | Jones et al. |
| 2012/0122088 A1 | 5/2012 | Zou et al. |
| 2012/0122105 A1 | 5/2012 | Oldham-Haltom et al. |
| 2012/0122106 A1 | 5/2012 | Zou et al. |
| 2012/0288868 A1 | 11/2012 | Bruinsma et al. |
| 2013/0231256 A1 | 9/2013 | Oldham-Haltom et al. |
| 2014/0087382 A1 | 3/2014 | Allawi et al. |
| 2015/0292029 A1 | 10/2015 | Agarwal et al. |
| 2016/0010081 A1 | 1/2016 | Allawi et al. |
| 2016/0090634 A1 | 3/2016 | Kisiel et al. |
| 2016/0168643 A1 | 6/2016 | Ahlquist et al. |
| 2016/0194721 A1 | 7/2016 | Allawi et al. |
| 2016/0312299 A1 | 10/2016 | Tyler et al. |
| 2016/0333424 A1 | 11/2016 | Morris et al. |
| 2017/0121704 A1 | 5/2017 | Allawi et al. |
| 2017/0121757 A1 | 5/2017 | Lidgard et al. |
| 2017/0321286 A1 | 11/2017 | Allawi et al. |
| 2017/0335401 A1 | 11/2017 | Allawi et al. |
| 2018/0143198 A1 | 5/2018 | Wen et al. |
| 2018/0245157 A1 | 8/2018 | Allawi et al. |
| 2019/0085406 A1 | 3/2019 | Mortimer et al. |
| 2019/0177769 A1 | 6/2019 | Allawi et al. |
| 2019/0218601 A1 | 7/2019 | Allawi et al. |
| 2019/0330702 A1 | 10/2019 | Allawi et al. |
| 2020/0291458 A1 | 9/2020 | Lidgard et al. |
| 2022/0071605 A1 | 3/2022 | Eisele et al. |
| 2022/0349009 A1 | 11/2022 | Taylor et al. |

FOREIGN PATENT DOCUMENTS

| | | |
|---|---|---|
| JP | 2010-533853 | 10/2010 |
| WO | WO 1992/02258 | 2/1992 |
| WO | WO 1993/10820 | 6/1993 |
| WO | WO 1994/22892 | 10/1994 |
| WO | WO 1994/24144 | 10/1994 |
| WO | WO 1995/000669 | 1/1995 |
| WO | WO 1995/015373 | 6/1995 |
| WO | WO 1997/046705 | 12/1997 |
| WO | WO 1999/028498 | 6/1998 |
| WO | WO 2001/94634 | 12/2001 |
| WO | WO 2002/070755 | 9/2002 |
| WO | WO 2005/023091 | 3/2005 |
| WO | WO 2005/038041 | 4/2005 |
| WO | WO 2005/038051 | 4/2005 |
| WO | WO 2005/098050 | 10/2005 |
| WO | WO 2005/124356 | 12/2005 |
| WO | WO 2006/084132 | 8/2006 |
| WO | WO 2006/113770 | 10/2006 |
| WO | WO 2007/121489 | 10/2007 |
| WO | WO 2008/084219 | 7/2008 |
| WO | WO 2008/100913 | 8/2008 |
| WO | WO 2008/103763 | 8/2008 |
| WO | WO 2009/035447 | 3/2009 |
| WO | WO 2009/102788 | 8/2009 |
| WO | WO 2010/074924 | 7/2010 |
| WO | WO 2010/086389 | 8/2010 |
| WO | WO 2010/089538 | 8/2010 |
| WO | WO 2011/119934 | 9/2011 |
| WO | WO 2012/067831 | 5/2012 |
| WO | WO 2012/106525 | 8/2012 |
| WO | WO 2012/155072 | 11/2012 |
| WO | WO 2013/058868 | 4/2013 |
| WO | WO 2013/070950 | 5/2013 |
| WO | WO 2013/116375 | 8/2013 |

(56) References Cited

FOREIGN PATENT DOCUMENTS

| WO | WO 2013/142545 | 9/2013 |
|---|---|---|
| WO | WO 2014/039556 | 3/2014 |
| WO | WO 2014/062218 | 4/2014 |
| WO | WO 2014/159650 | 10/2014 |
| WO | WO 2014/159652 | 10/2014 |
| WO | WO 2014/160117 | 10/2014 |
| WO | WO 2015/066695 | 5/2015 |
| WO | WO 2015/095689 | 6/2015 |
| WO | WO 2015/153283 | 10/2015 |
| WO | WO 2015/153284 | 10/2015 |
| WO | WO 2016/094813 | 6/2016 |
| WO | WO 2016/094839 | 6/2016 |
| WO | WO 2017/040627 | 3/2017 |
| WO | WO 2017/075061 | 5/2017 |
| WO | WO 2017/129716 | 8/2017 |
| WO | WO 2017/180886 | 10/2017 |
| WO | WO 2017/192221 | 11/2017 |
| WO | WO 2017/223216 | 12/2017 |
| WO | WO 2018/017740 | 1/2018 |
| WO | WO 2018/045322 | 3/2018 |
| WO | WO 2018/160576 | 9/2018 |
| WO | WO 2019/108626 | 6/2019 |
| WO | WO 2020/112869 | 7/2020 |
| WO | WO 2020/154665 | 7/2020 |
| WO | WO 2020/206256 | 10/2020 |
| WO | WO 2021/041726 | 3/2021 |
| WO | WO 2021/055508 | 3/2021 |
| WO | WO 2021/076969 | 4/2021 |
| WO | WO 2021/087275 | 5/2021 |
| WO | WO 2021/212031 | 10/2021 |
| WO | WO 2021/226071 | 11/2021 |
| WO | WO 2021/226074 | 11/2021 |
| WO | WO 2021/226074 | 2/2022 |
| WO | WO 2022/040306 | 2/2022 |
| WO | WO 2022/165247 | 8/2022 |
| WO | WO 2022/187695 | 9/2022 |
| WO | WO 2023/081796 | 5/2023 |

OTHER PUBLICATIONS

Ballester et al., Novel Methylated DNA Markers for the Detection of Colorectal Neoplasia in Lynch Syndrome. Abstract 307. Gastroenterology 2016;150(4):S-70.
Chen et al., DNA Methylation Identifies Loci Distinguishing Hereditary Nonpolyposis Colorectal Cancer Without Germ-Line MLH1/MSH2 Mutation from Sporadic Colorectal Cancer. Clin Transl Gastroenterol. Dec. 15, 2016;7(12):e208.
Gevaert et al., Pancancer analysis of DNA methylation-driven genes using MethylMix. Genome Biol. Jan. 29, 2015;16(1):17.
Kisiel et al., New DNA Methylation Markers for Pancreatic Cancer: Discovery, Tissue Validation, and Pilot Testing in Pancreatic Juice. Clin Cancer Res. Oct. 1, 2015;21(19):4473-81.
Kisiel et al., Novel Stool DNA Markers for Inflammatory Bowel Disease Associated Colorectal Cancer High Grade Dysplasia: High Specificity Across Three Independent International Populations. Abstract 185. Gastroenterology 2016;150(4):S-48.
Knute et al., MicroRNAs as Novel Targets for NSAID Chemoprevention of Color Carcinogenesis. Gastroenterology. May 2011; 140(5):S-41.
Lange et al., Genome-scale discovery of DNA-methylation biomarkers for blood-based detection of colorectal cancer. PLoS One. 2012;7(11):e50266.
Medina-Aguilar et al., Methylation Landscape of Human Breast Cancer Cells in Response to Dietary Compound Resveratrol. PLoS One. Jun. 29, 2016;11(6):e0157866.
Mitchell et al., A panel of genes methylated with high frequency in colorectal cancer. BMC Cancer. Jan. 31, 2014;14:54.
Mitchell et al., Evaluation of Methylation Biomarkers for Detection of Circulating Tumor DNA and Application to Colorectal Cancer. Genes (Basel). Dec. 15, 2016;7(12):125.
Taylor et al., Discovery of Novel DNA Methylation Markers for the Detection of Colorectal Neoplasia: Selection by Methylome-Wide Analysis. Abstract 109. Gastroenterology May 1, 2014;146(5)S-30.
Weisenberger et al., Comprehensive DNA Methylation Analysis on the Illumina® Infinium® Assay Platform. Jan. 1, 2010. https://emea.illumina.com/content/dam/illumina-marketing/documents/products/appnotes/appnote_dna_methylation_analysis_infinium.pdf. Retrieved Dec. 4, 2020. 4 pages.
Wu et al., Detection of Colorectal Cancer Using a Simplified SEPT9 Gene Methylation Assay Is a Reliable Method for Opportunistic Screening. J Mol Diagn. Jul. 2016;18(4):535-45.
European Supplemental Search Report for EP18744801.4, dated Dec. 14, 2020, 23 pages.
Bentley et al., Accurate Whole Human Genome Sequencing using Reversible Terminator Chemistry. Nature. Nov. 6, 2008; 456(7218): 53-59.
Berezikov et al., Approaches to microRNA discovery. Nat Genet. Jun. 2006;38 Suppl:S2-7.
Chapman et al., Autoantibodies in lung cancer: possibilities for early detection and subsequent cure. Thorax. Mar. 2008;63(3):228-33.
Dassonville et al., Expression of epidermal growth factor receptor and survival in upper aerodigestive tract cancer. J Clin Oncol. Oct. 1993;11(10):1873-8.
Egeblad et al., New functions for the matrix metalloproteinases in cancer progression. Nat Rev Cancer. Mar. 2002;2(3):161-74.
Elbashir et al, RNA interference is mediated by 21- and 22-nucleotide RNAs. Genes Dev. Jan. 15, 2001;15(2):188-200.
Extended European Search Report for EP 19890483.1, dated Sep. 29, 2022, 10 pages.
Fedurco et al., BTA, a novel reagent for DNA attachment on glass and efficient generation of solid-phase amplified DNA colonies. Nucleic Acids Res. Feb. 9, 2006;34(3):e22.
Gatlin et al., Automated identification of amino acid sequence variations in proteins by HPLC/microspray tandem mass spectrometry. Anal Chem. Feb. 15, 2000;72(4):757-63.
Gemperle et al., Regulation of the formyl peptide receptor 1 (FPR1) gene in primary human macrophages. PLoS One. 2012;7(11):e50195. 6 pages.
GenBank Accession No. NM005621. National Library of Medicine. Retrieved from the internet Sep. 29, 2022. 4 pages.
GenPept Accession No. NP05612. 11—Sep. 2022. 3 pages.
Grandis et al., TGF-alpha and EGFR in Head and Neck Cancer. Journal of Cellular Biochemistry, 1993; Supplement 17f:188-191.
Harris et al., Single-molecule DNA sequencing of a viral genome. Science. Apr. 4, 2008;320(5872):106-9.
Heid et al., Real time quantitative PCR . Genome Res. Oct. 1996;6(10):986-94.
Hua et al., Quantitative methylation analysis of multiple genes using methylation-sensitive restriction enzyme-based quantitative PCR for the detection of hepatocellular carcinoma. Exp Mol Pathol. Aug. 2011;91(1):455-60.
Huang et al., Transactivation of the epidermal growth factor receptor by formylpeptide receptor exacerbates the malignant behavior of human glioblastoma cells. Cancer Res. Jun. 15, 2007;67(12):5906-13.
International Preliminary Report on Patentability for PCT/US2020/048270, dated Mar. 10, 2022. 11 pages.
International Search Report and Written Opinion for PCT/US2020/048270, dated Dec. 7, 2020. 12 pages.
Jongeneel et al., An atlas of human gene expression from massively parallel signature sequencing (MPSS) Genome Res. Jul. 2005;15(7):1007-14.
Kling. Ultrafast DNA sequencing. Nat Biotechnol. Dec. 2003;21(12):1425-7.
Mandal et al., Lipopolysaccharide induces formyl peptide receptor 1 gene expression in macrophages and neutrophils via transcriptional and posttranscriptional mechanisms. J Immunol. Nov. 1, 2005;175(9):6085-91.
Mandal et al., Signaling in lipopolysaccharide-induced stabilization of formyl peptide receptor 1 mRNA in mouse peritoneal macrophages. J Immunol. Feb. 15, 2007;178(4):2542-8.

(56) References Cited

OTHER PUBLICATIONS

Marabella et al., Serum ribonuclease in patients with lung carcinoma. J Surg Oncol. 1976;8(6):501-5.
Margulies et al., Genome sequencing in microfabricated high-density picolitre reactors. Nature. Sep. 15, 2005;437(7057):376-80.
Melnikov et al., MSRE-PCR for analysis of gene-specific DNA methylation. Nucleic Acids Res. Jun. 8, 2005;33(10):e93.
Monte et al., Cloning, chromosome mapping and functional characterization of a human homologue of murine gtse-1 (B99) gene. Gene. Aug. 22, 2000;254(1-2):229-36.
Monte et al., hGTSE-1 expression stimulates cytoplasmic localization of p53. J Biol Chem. Mar. 19, 2004;279(12):11744-52.
Morris et al., Whole blood FPR1 mRNA expression predicts both non-small cell and small cell lung cancer. Int J Cancer. Jun. 1, 2018;142(11):2355-2362.
NCBI Ref. Seq. NM_001193306.1. Apr. 9, 2019. Retrieved from NIH Sep. 29, 2022. 5 pages.
Neuwelt et al., Possible sites of origin of human plasma ribonucleases as evidenced by isolation and partial characterization of ribonucleases from several human tissues. Cancer Res. Jan. 1978;38(1):88-93.
O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.
Osman et al., Expression of matrix metalloproteinases and tissue inhibitors of metalloproteinases define the migratory characteristics of human monocyte-derived dendritic cells. Immunology. Jan. 2002;105(1):73-82.
Reddi et al., Elevated serum ribonuclease in patients with pancreatic cancer. Proc Natl Acad Sci U S A. Jul. 1976;73(7):2308-10.
Reinartz et al., Massively parallel signature sequencing (MPSS) as a tool for in-depth quantitative gene expression profiling in all organisms. Brief Funct Genomic Proteomic. Feb. 2002;1(1):95-104.
Ronaghi et al., A sequencing method based on real-time pyrophosphate. Science. Jul. 17, 1998;281(5375):363, 365.
Ronaghi et al., Real-time DNA sequencing using detection of pyrophosphate release. Anal Biochem. Nov. 1, 1996;242(1):84-9.
Rothberg et al., An integrated semiconductor device enabling non-optical genome sequencing. Nature. Jul. 20, 2011;475(7356):348-52.
Santani et al., Characterization, quantification, and potential clinical value of the epidermal growth factor receptor in head and neck squamous cell carcinomas. Head & Neck, 1991; 13(2): 132-139.
Schuuring et al., Characterization of the EMS1 gene and its product, human Cortactin. Cell Adhes Commun. 1998;6(2-3):185-209.
Schuuring et al., Identification and cloning of two overexpressed genes, U21B31/PRAD1 and EMS1, within the amplified chromosome 11q13 region in human carcinomas. Oncogene. Feb. 1992;7(2):355-61.
Shao et al., Formyl peptide receptor ligands promote wound closure in lung epithelial cells. Am J Respir Cell Mol Biol. Mar. 2011;44(3):264-9.
Shendure et al., Accurate multiplex polony sequencing of an evolved bacterial genome. Science. Sep. 9, 2005;309(5741):1728-32.
Shendure et al., Next-generation DNA sequencing. Nat Biotechnol. Oct. 2008;26(10):1135-45.
Turcatti et al., A new class of cleavable fluorescent nucleotides: synthesis and optimization as reversible terminators for DNA sequencing by synthesis. Nucleic Acids Res. Mar. 2008;36(4):e25. 13 pages.
Türeci et al., Humoral immune responses of lung cancer patients against tumor antigen NY-ESO-1. Cancer Lett. May 8, 2006;236(1):64-71.
Turner et al., Role of matrix metalloproteinase 9 in pituitary tumor behavior. J Clin Endocrinol Metab. Aug. 2000;85(8):2931-5.
Umu et al., A comprehensive profile of circulating RNAs in human serum. RNA Biol. Feb. 1, 2018;15(2):242-250.
Vancompernolle et al., Expression and function of formyl peptide receptors on human fibroblast cells. J Immunol. Aug. 15, 2003;171(4):2050-6.
Wang et al., Crosstalk to stromal fibroblasts induces resistance of lung cancer to epidermal growth factor receptor tyrosine kinase inhibitors. Clin Cancer Res. Nov. 1, 2009;15(21):6630-8.
Wang et al., DNA methylation study of fetus genome through a genome-wide analysis. BMC Med Genomics. Apr. 15, 2014;7:18.
Williams et al., Amplification of complex gene libraries by emulsion PCR. Nat Methods. Jul. 2006;3(7):545-50.
Yu et al., Significance of combined detection of LunX mRNA and tumor markers in diagnosis of lung carcinoma. Chin J Cancer Res. Feb. 2014;26(1):89-94.
Zhou et al., Massively parallel signature sequencing. Methods Mol Biol. 2006;331:285-311.
Nilsson et al., Altered DNA Methylation and Differential Expression of Genes Influencing Metabolism and Inflammation in Adipose Tissue From Subjects With Type 2 Diabetes. Diabetes. Sep. 2014;63:2962-76.
Ahlquist et al., Colorectal cancer screening by detection of altered human DNA in stool: Feasibility of a multitarget assay panel. Gastroenterology, 2000;119:1219-27.
Ahlquist et al., Next-Generation Stool DNA Test Accurately Detects Colorectal Cancer and Large Adenomas. Gastroenterology, 2012;142:248-56.
Ahlquist et al., Novel Use of Hypermethylated DNA Markers in Stool for Detection of Colorectal Cancer: A Feasibility Study. Gastroenterology 2002;122:Suppl A40.
Ahlquist et al., Stool DNA and Occult Blood Testing for Screen Detection of Colorectal Neoplasia. Ann Intern Med, 2008;149(7):441-50.
Allawi et al., Abstract 712: Detection of lung cancer by assay of novel methylated DNA markers in plasma. Proceedings: AACR Annual Meeting Apr. 1-5, 2017, Washington, DC. 3 pages.
Andersson et al., Properties of targeted preamplification in DNA and cDNA quantification. Expert Rev Mol Diagn. 2015;15(8):1085-100.
Antequera et al., High levels of de novo methylation and altered chromatin structure at CpG islands in cell lines. Cell. Aug. 10, 1990;62(3):503-14.
Arneson et al., GenomePlex Whole-Genome Amplification. Cold Spring Harb. Protoc. 2008; doi:10.1101/pdb.prot4920, 7 pages.
Aronchick CA, et al., A novel tableted purgative for colonoscopic preparation: Efficacy and safety comparisons with Colyte and Fleet Phospho-Soda. Gastrointestinal endoscopy, 2000;52:346-52.
Ballabio, et al., Screening for steroid sulfatase (STS) gene deletions by multiplex DNA amplification, Human Genetics, 1990, 84(6): 571-573.
Barany, Genetic disease detection and DNA amplification using cloned thermostable ligase, Proc. Natl. Acad. Sci USA, 1991, 88:189-93.
Bardan E, et al., Colonoscopic resection of large colonic polyps—a prospective study. Israel journal of medical sciences, 1997;33(12):777-80.
Barnay, Genetic disease detection and DNA amplification using cloned thermostable ligase, Proc. Natl. Acad. Sci USA, 1991, 88:189-93.
Belinsky SA, et al., Promoter Hypermethylation of Multiple Genes in Sputum Precedes Lung Cancer Incidence in a High-Risk Cohort. Cancer Res, 2006;66(6):3338-44.
Berger BM, et al., Stool DNA screening for colorectal neoplasia: biological and technical basis for high detection rates. Pathology 2012;44(2):80-8.
Bibikova, GoldenGate? Assay for Methyltion of BeadArrayTM Technology. Jan. 1, 2009; retrieved from http://agtc.wayne.edu/pdfs/goldengate_methylation_brochure.pdf, retrieved Aug. 29, 2016, 7 pages.
Boynton KA, et al., DNA Integrity as a Potential Marker for Stool-based Detection of Colorectal Cancer. Clin Chem 2003;49(7):1058-65.
Budd et al., Circulating tumor cells versus imaging—predicting overall survival in metastatic breast cancer. Clin Cancer Res. Nov. 1, 2006;12(21):6403-9.
Bustin, Absolute quantification of mRNA using real-time reverse transcription polymerase chain reaction assays, J. Molecular Endocrinology, 2000, 25:169-193.

(56) References Cited

OTHER PUBLICATIONS

Carvalho et al., Genome-wide DNA methylation profiling of non-small cell lung carcinomas. Epigenetics Chromatin. Jun. 22, 2012;5(1):9.
Certified U.S. Appl. No. 60/900,713, filed Feb. 12, 2007, in the name of Baylin et al., 188 pages.
Ceska et al., Structure-specific DNA cleavage by 5' nucleases. Trends Biochem Sci. Sep. 1998;23(9):331-6.
Chamberlain et al., Deletion screening of the Duchenne muscular dystrophy locus via multiplex DNA amplification, Nucleic Acids Research, 1988, 16(23):11141-11156.
Chen et al., Detection in Fecal DNA of Colon Cancer—Specific Methylation of the Nonexpressed Vimentin Gene. J Natl Cancer Inst, 2005;97:1124-32.
Chen et al., HOPX is methylated and exerts tumour-suppressive function through Ras-induced senescence in human lung cancer. J Pathol. Feb. 2015;235(3):397-407.
Cohen et al., Relationship of circulating tumor cells to tumor response, progression-free survival, and overall survival in patients with metastatic colorectal cancer. J Clin Oncol. Jul. 1, 2008;26(19):3213-21.
Cristofanilli et al., Circulating tumor cells, disease progression, and survival in metastatic breast cancer. N Engl J Med. Aug. 19, 2004;351(8):781-91.
Dammann et al., The CpG island of the novel tumor suppressor gene RASSF1A is intensely methylated in primary small cell lung carcinomas. Oncogene. Jun. 14, 2001;20(27):3563-7.
Devos et al., Circulating methylated SEPT9 DNA in plasma is a biomarker for colorectal cancer. Clin Chem. Jul. 2009;55(7):1337-46.
Don et al., 'Touchdown' PCR to circumvent spurious priming during gene amplification, Nucleic Acids Research, 1991, 19(14):4008.
Eads et al., CpG island hypermethylation in human colorectal tumors is not associated with DNA methyltransferase overexpression. Cancer Res. May 15, 1999;59(10):2302-6.
Ebert, MP, et al., Aristaless-like Homeobox-4 Gene Methylation Is a Potential Marker for Colorectal Adenocarcinomas. Gastroenterology, 2006;131:1418-30.
European Supplemental Search Report for EP17792973.4, dated Jan. 3, 2020, 15 pages.
Fackler et al., Quantitative multiplex methylation-specific PCR assay for the detection of promoter hypermethylation in multiple genes in breast cancer. Cancer Res. Jul. 1, 2004;64(13):4442-52.
Fasman, "Practical Handbook of Biochemistry and Molecular Biology", pp. 385-394, 1989, CRC Press, Boca Raton, FL.
Feil et al., Methylation analysis on individual chromosomes: improved protocol for bisulphite genomic sequencing. Nucleic Acids Res. Feb. 25, 1994;22(4):695-6.
Frommer et al., A genomic sequencing protocol that yields a positive display of 5-methylcytosine residues in individual DNA strands. Proc Natl Acad Sci U S A. Mar. 1, 1992;89(5):1827-31.
Gonzalgo et al., Identification and characterization of differentially methylated regions of genomic DNA by methylation-sensitive arbitrarily primed PCR. Cancer Res. Feb. 15, 1997;57(4):594-9.
Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.
Grady WM, et al., Detection of Aberrantly Methylated hMLH1 Promoter DNA in the Serum of Patients with Microsatellite Unstable Colon Cancer. Cancer Res 2001;61:900-2.
Grafstrom et al., The characteristics of DNA methylation in an in vitro DNA synthesizing system from mouse fibroblasts. Nucleic Acids Res. Apr. 25, 1985;13(8):2827-42.
Grafstrom RH, et al., The characteristics of DNA methylation in an in vitro DNA synthesizing system from mouse fibroblasts. Nucleic Acids Res. 1985;13(8): 2827-2842.
Grigg et al., Sequencing 5-methylcytosine residues in genomic DNA. Bioessays. Jun. 1994;16(6):431-6.
Grigg, Sequencing 5-methylcytosine residues by the bisulphite method. DNA Seq. 1996;6(4):189-98.
Grunau et al., Bisulfite genomic sequencing: systematic investigation of critical experimental parameters. Nucleic Acids Res. Jul. 1, 2001;29(13):E65-5.
Gu et al., Genome-scale DNA methylation mapping of clinical samples at single-nucleotide resolution. Nat Methods. Feb. 2010;7(2):133-6.
Guilfoyle et al., Ligation-mediated PCR amplification of specific fragments from a class-II restriction endonuclease total digest, Nucleic Acids Research, 1997, 25:1854-1858.
Hall et al., Sensitive detection of DNA polymorphisms by the serial invasive signal amplification reaction, PNAS, 2000, 97:8272.
Hardcastle, JD, et al., Randomised controlled trial of faecal-occult-blood screening for colorectal cancer. Lancet. 1996, 348:1472-7.
Hayden et al., Multiplex-Ready PCR: A new method for multiplexed SSR and SNP genotyping, BMC Genomics, 2008, 9:80.
Hayes et al., Circulating tumor cells at each follow-up time point during therapy of metastatic breast cancer patients predict progression-free and overall survival. Clin Cancer Res. Jul. 15, 2006;12(14 Pt 1):4218-24.
Hecker et al., High and low annealing temperatures increase both specificity and yield in touchdown and stepdown PCR, Biotechniques, 1996, 20(3):478-485.
Heitman, SJ, et al., Colorectal Cancer Screening for Average-Risk North Americans: An Economic Evaluation. PLoS Med, 2010;7(11):e1000370.
Heller et al., Lung cancer: from single-gene methylation to methylome profiling. Cancer Metastasis Rev. Mar. 2010;29(1):95-107.
Henegariu et al., Multiplex PCR: critical parameters and step-by-step protocol. Biotechniques. Sep. 1997;23(3):504-11.
Heresbach, D., et al., Review in depth and meta-analysis of controlled trials on colorectal cancer screening by faecal occult blood test. Eur J Gastroenterol Hepatol. 2006, 18(4):427-33.
Herman et al., Methylation-specific PCR: a novel PCR assay for methylation status of CpG islands. Proc Natl Acad Sci USA 1996; 93: 9821-9826.
Higuchi et al., A general method of in vitro preparation and specific mutagenesis of DNA fragments: study of protein and DNA interactions, Nucleic Acids Research, 1988, 16(15):7351-7367.
Higuchi et al., Simultaneous amplification and detection of specific DNA sequences, Biotechnology, 1992, 10:413-417.
Higuchi et al.,Kinetic PCR analysis: real-time monitoring of DNA amplification reactions, Biotechnology, 1993, 11:1026-1030.
Hoque et al., Genome-Wide Promoter Analysis Uncovers Portions of the Cancer Methylome. J Clin Oncol. 2005;23:6569-75.
Imperiale et al., Fecal DNA versus Fecal Occult Blood for Colorectal-Cancer Screening in an Average-Risk Population. N Engl J Med, 2004;351:2704-14.
International Search Report and Written Opinion for PCT/US2016/058875, dated Apr. 21, 2017, 17 pages.
International Search Report and Written Opinion for PCT/US2017/024468, dated Sep. 1, 2017, 17 pages.
International Search Report and Written Opinion for PCT/US2018/015535, dated Jun. 25, 2018, 20 pages.
International Search Report and Written Opinion for PCT/US2019/063401, dated Feb. 20, 2020, 12 pages.
Itzkowitz, SH, et al., Improved Fecal DNA Test for Colorectal Cancer Screening. Clin Gastroenterol Hepatol 2007;5(1):111-7.
Jiang et al., Lengthening and shortening of plasma DNA in hepatocellular carcinoma patients. Proc Natl Acad Sci U S A. Mar. 17, 2015;112(11):E1317-25.
Kaiser et al., A comparison of eubacterial and archaeal structure-specific 5'-exonucleases. J Biol Chem. Jul. 23, 1999;274(30):21387-94.
Kalinina et al., Nanoliter scale PCR with TaqMan detection, Nucleic Acids Research, 1997, 25:1999-2004.
Kann et al., Improved Marker Combination for Detection of De Novo Genetic Variation and Aberrant DNA in Colorectal Neoplasia. Clin Chem 2006;52:2299-302.
Karl et al., Improved Diagnosis of Colorectal Cancer Using a Combination of Fecal Occult Blood and Novel Fecal Protein Markers. Clin Gastroenterol Hepatol, 2008;6(10):1122-8.

(56) References Cited

OTHER PUBLICATIONS

Kneip et al., SHOX2 DNA methylation is a biomarker for the diagnosis of lung cancer in plasma. J Thorac Oncol. Oct. 2011;6(10):1632-8.

Kober et al., Methyl-CpG binding col. based identification of nine genes hypermethylated in colorectal cancer. Mol Carcinog. Nov. 2011;50(11):846-56.

Korbie et al., Multiplex bisulfite PCR resequencing of clinical FFPE DNA. Clin Epigenetics. Mar. 17, 2015;7:28.

Kronborg et al., Randomized Study of Biennial Screening with a Faecal Occult Blood Test: Results After Nine Screening Rounds. Scand J Gastroenterol, 2004; 39:846-51.

Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.

Leontiou et al., Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058.

Leung et al., Detection of Epigenetic Changes in Fecal DNA as a Molecular Screening Test for Colorectal Cancer: A Feasibility Study. Clin Chem, 2004;50(11):2179-82.

Levin et al., Screening and Surveillance for the Early Detection of Colorectal Cancer and Adenomatous Polyps, 2008: A Joint Guideline From the American Cancer Society, the US Multi-Society Task Force on Colorectal Cancer, and the American College of Radiology. Gastroenterology, 2008;134(5):1570-95.

Liu et al., Flap endonuclease 1: a central component of DNA metabolism. Annu Rev Biochem. 2004;73:589-615.

Lokk et al., Methylation markers of early-stage non-small cell lung cancer. PLoS One. 2012;7(6):e39813.

Louwagie et al., Feasibility of a DNA methylation assay for noninvasive CRC screening. Clin Cancer Res. Oct. 2007;13(19 Suppl):B16.

Lyamichev et al.,Polymorphism identification and quantitative detection of genomic DNA by invasive cleavage of oligonucleotide probes, Nat. Biotech., 1999, 17:292-296.

Mandel et al., Reducing Mortality from Colorectal Cancer by Screening for Fecal Occult Blood. N Engl J Med. 1993, 328:1365-71.

Martin et al., Genomic sequencing indicates a correlation between DNA hypomethylation in the 5' region of the pS2 gene and its expression in human breast cancer cell lines. Gene. May 19, 1995;157(1-2):261-4.

Maxwell® RSC ccfDNA Plasma Kit, Technical Manual, Instructions for Use of Product AS1480, Promega Corporation, Feb. 2016.

Meissner et al., Patterns of Colorectal Cancer Screening Uptake among Men and Women in the United States. Cancer Epidemiol Biomarkers Prev., 2006; 15:389-94.

Meissner et al., Reduced representation bisulfite sequencing for comparative high-resolution DNA methylation analysis. Nucleic Acids Res. Oct. 13, 2005;33(18):5868-77.

Moreno et al., Circulating tumor cells predict survival in patients with metastatic prostate cancer. Urology. Apr. 2005;65(4):713-8.

Muller et al., Methylation changes in faecal DNA: a marker for colorectal cancer screening? Lancet, 2004;363:1283-5.

Munson et al., Recovery of bisulfite-converted genomic sequences in the methylation-sensitive QPCR. Nucleic Acids Res. 2007;35(9):2893-903.

Notice of Opposition and Statement filed in EP Pat 3434791, filed Mar. 5, 2021, 16 pages.

Noutsias et al., Preamplification techniques for real-time RT-PCR analyses of endomyocardial biopsies. BMC Molecular Biology Jan. 14, 2008;9:3.

Nyce et al. Variable effects of DNA-synthesis inhibitors upon DNA methylation in mammalian cells. Nucleic Acids Res. 1986;14:4353-4367.

Nyce et al., Variable effects of DNA-synthesis inhibitors upon DNA methylation in mammalian cells. Nucleic Acids Res. May 27, 1986;14(10):4353-67.

Olek et al., A modified and improved method for bisulphite based cytosine methylation analysis. Nucleic Acids Res. Dec. 15, 1996;24(24):5064-6.

Olek et al., The pre-implantation ontogeny of the H19 methylation imprint. Nat Genet. Nov. 1997;17(3):275-6.

Olivier, The Invader assay for SNP genotyping, Mutat Res. Jun. 3, 2005;573(1-2):103-10.

Olkhov-Mitsel et al., Novel multiplex MethyLight protocol for detection of DNA methylation in patient tissues and bodily fluids. Sci Rep. Mar. 21, 2014;4:4432.

Ooki et al., Potential utility of HOP homeobox gene promoter methylation as a marker of tumor aggressiveness in gastric cancer. Oncogene. Jun. 3, 2010;29(22):3263-75.

Orpana, Fluorescence resonance energy transfer (FRET) using ssDNA binding fluorescent dye, Biomol Eng. Apr. 2004;21(2):45-50.

Osborn et al. Stool screening for colorectal cancer: Molecular approaches. Gastroenterology, 2005;128(1):192-206.

Pantel et al., Detection, clinical relevance and specific biological properties of disseminating tumour cells. Nat Rev Cancer. May 2008;8(5):329-40.

Parekh et al., As tests evolve and costs of cancer care rise: reappraising stool-based screening for colorectal neoplasia. Aliment Pharmacol Ther 2008;27:697-712.

Petko et al., Aberrantly Methylated CDKN2A, MGMT, and MLH1 in Colon Polyps and in Fecal DNA from Patients with Colorectal Polyps. Clin Cancer Res, 2005;11:1203-9.

Ponomaryova et al., Potentialities of aberrantly methylated circulating DNA for diagnostics and post-treatment follow-up of lung cancer patients. Lung Cancer. Sep. 2013;81(3):397-403.

Ramsahoye et al., Non-CpG methylation is prevalent in embryonic stem cells and may be mediated by DNA methyltransferase 3a. Proc Natl Acad Sci U S A. May 9, 2000;97(10):5237-42.

Ramsahoye et al., Non-CpG methylation is prevalent in embryonic stem cells and may be mediated by DNA methyltransferase 3a. Proc. Natl. Acad. Sci. USA, 2000;97(10): 5237-5242.

Rein et al., Identifying 5-methylcytosine and related modifications in DNA genomes. Nucleic Acids Res. May 15, 1998;26(10):2255-64.

Rex et al., American College of Gastroenterology Guidelines for Colorectal Cancer Screening 2008. Am J Gastroenterol, 2009;104:739-50.

Roux, Using mismatched primer-template pairs in touchdown PCR, Biotechniques, 1994, 16(5):812-814.

Ruano et al., Biphasic amplification of very dilute DNA samples via 'booster' PCR. Nucleic Acids Res. Jul. 11, 1989;17(13):5407.

Sadri et al., Rapid analysis of DNA methylation using new restriction enzyme sites created by bisulfite modification. Nucleic Acids Res. Dec. 15, 1996;24(24):5058-9.

Salomon et al., Methylation of mouse DNA in vivo: di- and tripyrimidine sequences containing 5-methylcytosine. Biochim Biophys Acta. Apr. 15, 1970;204(2):340-51.

Salomon R. et al., Methylation of Mouse DNA In Vivo: DI- and Tripyrimidine Sequences Containing 5-Methylcytosine. Biochim. Biophys. Acta. 1970;204: 340-351.

Schmidt et al., SHOX2 DNA methylation is a biomarker for the diagnosis of lung cancer based on bronchial aspirates. Send to BMC Cancer. Nov. 3, 2010;10:600.

Schouten et al., Relative quantification of 40 nucleic acid sequences by multiplex ligation-dependent probe amplification, Nucleic Acids Research, 2002, 30(12): e57.

Schuebel et al., Comparing the DNA hypermethylome with gene mutations in human colorectal cancer. PLoS Genet. Sep. 2007;3(9):1709-23.

Selvin, Fluorescence resonance energy transfer, 1995, Methods Enzymol. 1995;246:300-34.

Sharaf et al., Comparative Effectiveness and Cost-Effectiveness of Screening Colonoscopy vs. Sigmoidoscopy and Alternative Strategies. Am J Gastroenterol. 2013;108:120-32.

(56) References Cited

OTHER PUBLICATIONS

Siegel et al., Cancer Statistics, 2013. CA Cancer J Clin. 2013;63:11-30.
Singer-Sam et al., A quantitative HpaII-PCR assay to measure methylation of DNA from a small number of cells. Nucleic Acids Res. Feb. 11, 1990;18(3):687.
Singer-Sam et al., A sensitive, quantitative assay for measurement of allele-specific transcripts differing by a single nucleotide. PCR Methods Appl. Feb. 1992;1(3):160-3.
Singh, H, et al., Risk of Developing Colorectal Cancer Following a Negative Colonoscopy Examination Evidence for a 10-Year Interval Between Colonoscopies. JAMA. 2006, 295:2366-73.
Straub et al., Base5, a versatile, highly integrated high-throughput methylation profiling for methylation specific PCR based marker identification applied to colorectal cancer. Clin Cancer Res. Oct. 2007; 13(19 Suppl):A61.
Stryer, Fluorescence energy transfer as a spectroscopic ruler, Annu Rev Biochem. 1978;47:819-46.
Swift-Scanlan et al., Two-color quantitative multiplex methylation-specific PCR. Biotechniques. Feb. 2006;40(2):210-9.
Szabo et al., Allele-specific expression and total expression levels of imprinted genes during early mouse development: implications for imprinting mechanisms. Genes Dev. Dec. 15, 1995;9(24):3097-108.
Toyota et al., Identification of differentially methylated sequences in colorectal cancer by methylated CpG island amplification. Cancer Res. May 15, 1999;59(10):2307-12.
Triglia et al., A procedure for in vitro amplification of DNA segments that lie outside the boundaries of known sequences, Nucleic Acids Res., 1988, 16:8186.
Vogelstein et al. Digital PCR. Proc Natl Acad Sci USA. 1999;96; 9236-41.
Vogelstein et al., Cancer Genome Landscapes. Science, 2013;339:1546-58.
Vogelstein et al., Digital PCR, PNAS, 1999, 96: 9236-41.
Winawer et al., Screening for Colorectal Cancer With Fecal Occult Blood Testing and Sigmoidoscopy. J Natl Cancer Inst. 1993, 85(16):1311-8.
Woodcock et al. The majority of methylated deoxycytidines in human DNA are not in the CpG dinucleotide. Biochem. Biophys. Res. Commun. 1987; 145: 888-894.
Woodcock et al., The majority of methylated deoxycytidines in human DNA are not in the CpG dinucleotide. Biochem Biophys Res Commun. Jun. 15, 1987;145(2):888-94.
Wrangle et al., Functional identification of cancer-specific methylation of CDO1, HOXA9, and TAC1 for the diagnosis of lung cancer. Clin Cancer Res. Apr. 1, 2014;20(7):1856-64.
Xiong et al., COBRA: a sensitive and quantitative DNA methylation assay. Nucleic Acids Res. Jun. 15, 1997;25(12):2532-4.
Yamada et al., Fluorometric identification of 5-methylcytosine modification in DNA: combination of photosensitized oxidation and invasive cleavage. Bioconjug Chem. Jan. 2008;19(1):20-3.
Yoo et al., Epigenetic therapy of cancer: past, present and future. Nat Rev Drug Discov. Jan. 2006;5(1):37-50.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zou et al., A Sensitive Method to Quantify Human Long DNA in Stool: Relevance to Colorectal Cancer Screening. Cancer Epidemiol Biomarkers Prev, 2006;15(6):1115-9.
Zou et al., Detection of Aberrant p16 Methylation in the Serum of Colorectal Cancer Patients. Clin Cancer Res 2002;8(1):188-91.
Zou et al., Quantification of methylated markers with a multiplex methylation-specific technology. Clin Chem 2012; 58: 375-383.
Zou et al., Quantification of methylated markers with a multiplex methylation-specific technology. Clin Chem. Feb. 2012;58(2):375-83.
Zou et al., Sensitive quantification of methylated markers with a novel methylation specific technology. Abstract D-144, Clin Chem 2010;56(6)Suppl:A199.
Dowdy et al., Statistics for Research, John Wiley & Sons, New York, 1983. TOC only. 6 pages.
Extended European Search Report for 21195952.3, dated Apr. 12, 2022. 8 pages.
Finger et al., The wonders of flap endonucleases: structure, function, mechanism and regulation. Subcell Biochem. 2012;62:301-26.
Gardiner-Garden et al., CpG Islands in Vertebrate Genomes. J. Mol. Biol. 1987:196: 261-281.
Iyer et al., Accurate nonendoscopic detection of Barrett's esophagus by methylated DNA Markers: A multisite case control study. Am J Gastroenterol 2020;115:1201-1209.
Iyer et al., Accurate non-endoscopic detection of Barrett's esophagus in a multicenter prospective validation cohort: the sos 2 trial. AGA Abstracts. 2018:878. S-175-S-176.
Iyer et al., Independent validation of an accurate methylated DNA marker panel for the non-endoscopic detection of Barrett's esophagus: a multisite case control study. AGA Abstracts. 2020; 1084: S-211.
Kawai et al., Comparison of DNA methylation patterns among mouse cell lines by restriction landmark genomic scanning. Mol Cell Biol. Nov. 1994;14(11):7421-7.
Moon et al., Identification of novel hypermethylated genes and demethylating effect of vincristine in colorectal cancer. J Exp Clin Cancer Res. 2014;33:4. 10 pages.
Shen et al., Multiple but dissectible functions of FEN-1 nucleases in nucleic acid processing, genome stability and diseases. Bioessays. Jul. 2005;27(7):717-29.
Levin et al., Genetic Biomarker Prevalence Is Similar in Fecal Immunochemical Test Positive and Negative Colorectal Cancer Tissue. Dig Dis Sci. Mar. 2017;62(3):678-688.
Feng et al., Genome-wide analysis of DNA methylation and their associations with long noncoding RNA/mRNA expression in non-small-cell lung cancer. Epigenomics. Jan. 2017;9(2):137-153.
He et al., Development of a multiplex MethyLight assay for the detection of multigene methylation in human colorectal cancer. Cancer Genetics and Cytogenetics. 2010, 202, 1-10
Hosono et al., Multiplex PCR-based real-time invader assay (mPCR-RETINA): a novel SNP-based method for detecting allelic asymmetries within copy number variation regions. Hum Mutat. Jan. 2008;29(1): 182-9.
Kwiatkowski et al., Clinical, genetic, and pharmacogenetic applications of the Invader assay. Mol Diagn. Dec. 1999;4(4): 353-64.
Tadokoro et al., Classification of hepatitis B virus genotypes by the PCR-Invader method with genotype-specific probes. J Virol Methods. Dec. 2006;138(1-2):30-9.
Toth et al., Detection of Methylated SEPT9 in Plasma Is a Reliable Screening Method for Both Left- and Right-Sided Colon Cancers. PLOS One. 2012;7(9):e46000.
Zheng et al., Detection of single nucleotide polymorphism genotyping by real-time polymerase chain reaction coupled with high specific invader assay in single tube. Chin J Anal Chem, 2015, 43(7), 1001-1008.
International Search Report and Written Opinion for PCT/US2021/027770. Mailed Aug. 5, 2021. 10 pages.

FIG. 1

ANKRD13B
>hg19_dna range=chr17:279940470-279940578 strand=+

Untreated Target (UT) Target Sequence (SEQ ID NO: 1)

GGAGCTACGACGAGCAGCTGCGGCTGGGCGATGAACTGTCGGCCAGGAGCAGGAGGAGAGGCGGCGGCGCCAGGAGGAGGAG
GAGCTGGAGCGGCATCCTGAG

Bisulfite-treated Target (BT) Target Sequence (SEQ ID NO: 2)

GGAGTTACGACGAGTAGTTGCGGTTGGGC<u>ATGGAATTGTCG</u>GCGTAGGAGTAGGAGGAGAGGCGGCGGCGCGTTAGGAGGAGGAG
GAGTTGGAGCGTATTTTGAG

| ANKRD13B forward primer | AGTTACGACGAGTAGTTGCG | (SEQ ID NO: 3) |
| ANKRD13B reverse primer | TCCTCCTACTCCTACGCC | (SEQ ID NO: 4) |
| ANKRD13B probe (arm 5) | CCACGGACGCGACAATTCCAT/3C6/ | (SEQ ID NO: 5) |

FIG. 1 (cont'd)

B3GALT6
>hg19_dna range=chr1:1163595-1163733 strand=+

Untreated Target (UT) Target Sequence (SEQ ID NO: 6)

GGCCACACAGGCCCACTCTGGCCCTCTGAGCCCCCGGCGGACCCAGGGCATTCAAGGAGCGGCTCTGGGCTGCCAGCGCAGGCCTCCGC
GCAAACACAGCAGGCTGGAAGTGGCGCTCATCACCGGCACGTCTTCCCAG

Bisulfite-treated Target (BT) Target Sequence (SEQ ID NO: 7)

GGTTATATAGGTTTATTTGGTTTTTTGAGTTTTCG GCGGATTTAGGG TATTTAAGGAGCGGTTTTTGGGTTGTTAGCGTAGGTTTTCGC
GTAAATATAGTAGGTTGGAAGTGGCGTTTATTATTCGTACGTTTTTTAG

B3GALT6 forward primer      GGTTTATTTGGTTTTTTGAGTTTTCGG        (SEQ ID NO: 8)
B3GALT6 reverse primer      TCCAACCTACTATATTTACGCGAA           (SEQ ID NO: 9)
B3GALT6 probe (arm 5)       CCACGGACGGCGATTAGGG/3C6/           (SEQ ID NO: 10)

FIG. 1 (cont'd)

CHST2_7890
>hg19_dna range=chr3:142838847-142839000 strand=-

Untreated Target (UT) Target Sequence (SEQ ID NO: 11)

CGCTTTCGGCCTCCGTGCGGCGAATTTTCCCACCTCTCTGGCAGCGGTGGATGGGGCACAGCGCGACCCCGCAGCGGGCGGGCGGCTG
CTTCCATCACCGGGACGGAGGATGCCCGGGGCAACAGCAGGCAACCCCGCCTCCGCAGCCTCCG

Bisulfite-treated Target (BT) Target Sequence (SEQ ID NO: 12)

GCGGTGGATGGGGTATAGCGCGATTTCGTAGCGGCGGCGGTTGTTTTATTATCGGGAGGATGTTCGGGCGGATAGCGTAGGTAAT
TTTCGTCG

| | | |
|---|---|---|
| CHST2_7890 forward primer | GTATAGCGCGATTTCGTAGCG | (SEQ ID NO: 13) |
| CHST2_7890 reverse primer | AATTACCTACGCTATCCGCCC | (SEQ ID NO: 14) |
| CHST2_7890 probe (arm 5) | CCACGGACGCGAACATCCTCC/3C6/ | (SEQ ID NO: 15) |
| CHST2_7890 probe (arm 1) | CGCCGAGGCGAACATCCTCC/3C6/ | (SEQ ID NO: 175) |

FIG. 1 (cont'd)

CHST2_7889
>hg19_dna range= chr 3: 142838300-142838388

Untreated Target (UT) Target Sequence (SEQ ID NO: 136)

TCACCAACTCTTTTCTGAGAGCAAAAACATGGGGCCGAGTCCGGCAGCTGCACGGCAGAATCCAACTCTCTGGCAGCTCTCGGCACCGACG
AGCTCCAGATCCCGCGTTCGCATCCCGGCGCTTTGCGCGCCAGAGCTAAGCCTTCGGACCCGTGGA

Bisulfite-treated Target (BT) Target Sequence (SEQ ID NO: 137)

TATGGGGTCGAGTTCGGTAGTTGTACGTAGAATTTAATTTTTTGGTAGTTTTCGGTATCGACGAGTTTTAGATTTCGCGTTCGTATTTC
GGCGTTTTGC

| | | |
|---|---|---|
| CHST2_7889 forward primer | CGAGTTCGGTAGTTGTACGTAGA | (SEQ ID NO: 138) |
| CHST2_7889 reverse primer | CGAAATACGAACGCGAAATCTAAAACT | (SEQ ID NO: 139) |
| CHST2_7889 probe (arm 5) | CCACGGACGTCGTCGATACCG/3C6/ | (SEQ ID NO: 140) |
| CHST2_7889 probe (arm 1) | CGCCGAGGTCGTCGATACCG/3C6/ | (SEQ ID NO: 176) |

FIG. 1 (cont'd)

CNNM1(806)
>hg19_dna range=chr10:101089034-101089143 strand=-

Untreated Target (UT) Target Sequence (SEQ ID NO: 16)

CTGCACCCAGCGCAGCTGCACGTGATACTGCAGGAAGCCGAGCTGGAGGAGGAGCCGAGCTGGGAACCCAGCCGCAGG
CAGGTCACCACGTGTACGCCC

Bisulfite-treated Target (BT) Target Sequence (SEQ ID NO: 17)

TTGTATTTAGCGTAGTTGTACGTGATATTGTAGGA<u>AGTCGAGCGAGA</u>GTTGGAGGAGGAGAGTCGGAGTTGGGAATTTAGTCGTAGG
TAGGTTATTACGTGTACGTTT

| | | |
|---|---|---|
| CNNM1(806) forward primer | CGTAGTTGTACGTGATATTGTAGGAA | (SEQ ID NO: 18) |
| CNNM1(806) reverse primer | GACTAAATTCCCAACTCCGACT | (SEQ ID NO: 19) |
| CNNM1(806) probe (arm 5) | <u>CCACGGACGAGTCGAGCGAGA</u>/3C6/ | (SEQ ID NO: 20) |

FIG. 1 (cont'd)

DOCK2
>hg19_dna range=chr5:169064370- 169064454 strand=-

Untreated Target (UT) Target Sequence (SEQ ID NO: 21)

GCCGGCCCGCAGCATCCTCCTGCTCGGGGCTCTCCCGCCACCTGTCCCGCTCCCTGCCGCCCTGGGGCCCGCACCTACCCAC

Bisulfite-treated Target (BT) Target Sequence (SEQ ID NO: 22)

GTCGGTTTCGTAGTATTTTTTTGTTCGCGGGTTTTTTCGTTATTTGTTTCGTTTTTTCGTTTTTGGGGTTCGTATTTATTTAT

| | | |
|---|---|---|
| DOCK2 forward primer | CGGTTTCGTAGTATTTTTTGTTCG | (SEQ ID NO: 23) |
| DOCK2 reverse primer | GAACCCCAAAACGCGAC | (SEQ ID NO: 24) |
| DOCK2 probe (arm 1) | CGCCGAGGGCGGTTTTTTCG/3C6/ | (SEQ ID NO: 25) |

FIG. 1 (cont'd)

DTX1
>hg19_dna range=chr12:113494567-113494700 strand=-

Untreated Target (UT) Target Sequence (SEQ ID NO: 26)

CGCCTCCTGGGCTCCCCCCGGAGTGGGAGGAGCCGCGGTCCCGGCCCTCCGGCCCCTCGGCCGCCGCCGAG
CTTCCGCCGCCGTGGACAGACTGCCCGGACGGAGGACGCAGG

Bisulfite-treated Target (BT) Target Sequence (SEQ ID NO: 27)

CGTTTTTTGGGTTTTTTTCGGAGTGGGAGGAGTCGCGGTTTCGTTTT<u>CGCCGTTCGTTTT</u>TTTTTTAGGTTTTTCGGTCGTCGCCGTCGAG
TTTTTCGCCGCCGTGGATAGATTGTTCGGTCGTCGACGACGGACGTAGG

DTX1 forward primer Ver3   AGGGAGTCGCGGTTTCG              (SEQ ID NO: 28)
DTX1 reverse primer Ver3   GCGACGACCGAAAAACCT             (SEQ ID NO: 29)
DTX1 probe (arm 1) Ver3    CGCCGAGGGTTTTCGCGTTC/3C6/      (SEQ ID NO: 30)

FIG. 1 (cont'd)

FERMT3
>hg19_dna range=chr11:63974820-63974959 strand=+

Untreated Target (UT) Target Sequence (SEQ ID NO: 31)

TAGCAGCAGCCGCAGCCATGGCGGGGATGAAGACAGCCTCCGGGGACTACATCGACTCGTCATGGGAGCTGCGGGTGTTTGTGGGAGAG
GAGGACCCAGAGGCCGAGTCGGTCACCCTGCGGGTCACTGGGAGTCGCAC

Bisulfite-treated Target (BT) Target Sequence (SEQ ID NO: 32)

TAGTAGTAGTCGTAGTTATGGCGGGGATGAAGATAGTTTTCGGGGATTATATCGATTCGTTATGGGAGTTGCGGGTGTTTGTGGGAGAG
GAGGATTTAGAGGTCGAGTCGGTTATTTTGCGGGTTATTGGGAGTCGTAT

| | | |
|---|---|---|
| FERMT3 forward primer | GTTTTCGGGGATTATATCGATTCG | (SEQ ID NO: 33) |
| FERMT3 reverse primer | CCCAATAACCCGCAAAATAACC | (SEQ ID NO: 34) |
| FERMT3 probe (arm 1) | CGCCGAGGCGACTCGACCTC/3C6/ | (SEQ ID NO: 35) |

FIG. 1 (cont'd)

FLI1
>hg19_dna range=chr11:128564081-128564188 strand=+

Untreated Target (UT) Target Sequence (SEQ ID NO: 36)

AGGGGCTGcGAGGTCAGGCTGTAACCGGGTCAATGTGTGGAATATTGGGGGGCTCGGCTGCAGACTTGGCCAAATGGACGGGACTATTA
AGGTAAGcGGGCGGGGCAAC

Bisulfite-treated Target (BT) Target Sequence (SEQ ID NO: 37)

AGGGGGTTGcGAGGTTAGGTTGTAA[ATCGGGTTAATG]TGTGGAATATTGGGGGGTTCGGTTGTAGATTTGGTTAAATGGACGGGATTATTA
AGGTAAGcGGGCGGGGGTAAC

| | | |
|---|---|---|
| FLI1 forward primer | GGTTGCGAGGTTAGGTTGTAA | (SEQ ID NO: 38) |
| FLI1 reverse primer | TCCATTTAACCAAATCTACAACCGA | (SEQ ID NO: 39) |
| FLI1 probe (arm 1) | CGCCGAGGATCGGGTTAATG/3C6/ | (SEQ ID NO: 40) |

FIG. 1 (cont'd)

GRIN2D
>hg19_dna range=chr19:48918160-48918300 strand=-

Untreated Target (UT) Target Sequence (SEQ ID NO: 41)

CGCCCCCTCACCTCCCCGATCATGCCGTTCCAGACGCGCCATCGATCTTCTTTCCGTGCTTGCCATTGGTGTGACCAGGTAGAGGTCGTAGCT
GAAGCCGATGGTATGCGCCAGCCGCTTCAGAATGTCGATGCAGAAACCCTTG

Bisulfite-treated Target (BT) Target Sequence (SEQ ID NO: 42)

CGTTTTTTTATTTTTTCGATTATGTCGTTTTAGACGCGTTATCGATTTTTTTTTCGTGTTTGTTATTGGTGTGATTAGGTAGAGGTCGTAGTT
GAAGTCGATGGTATGCGTTAGTCGTTTTAGAATGTCGATGTAGAAATTTTTG

| | | |
|---|---|---|
| GRIN2D forward primer | TCGATTATGTCGTTTTAGACGTTATCG | (SEQ ID NO: 43) |
| GRIN2D reverse primer | TCTACATCGACATTCTAAAACGACTAAC | (SEQ ID NO: 44) |
| GRIN2D probe (arm 5) | CCACGGACGCGCATACCATCG/3C6/ | (SEQ ID NO: 45) |

FIG. 1 (cont'd)

JAM3
>hg19_dna range=chr11:133938908-133939011 strand=-

Untreated Target (UT) Target Sequence (SEQ ID NO: 46)

GAGCCGGAGTCGCGGTGGCCGCCTCAGCGGCCATGTCGAGGGTTGCTGAGGGGCCAGCGGCGGCCGGCTTGTAGTCCCCGGCG
CATGCGCCCAGCCTG

Bisulfite-treated Target (BT) Target Sequence (SEQ ID NO: 47)

GAGTCGGAGTCGCGGTGGTCGTTTTAGCGTTATGTCGTTTTAGCGTTATGTCGAGGGTTGTTGAGGGGTTAGCGGTAGCGCGGCGCGGTTTGTAGTTTTCGCGCG
TATGCGTTTAGTTTG

| | | |
|---|---|---|
| JAM3 forward primer | TGGTCGTTTTAGCGTTATGTCG | (SEQ ID NO: 48) |
| JAM3 reverse primer | CGAAAACTACAAACCCGCGC | (SEQ ID NO: 49) |
| JAM3 probe (arm 5) | CCACGGACGCCGCGCTACCGC/3C6/ | (SEQ ID NO: 50) |

FIG. 1 (cont'd)

LRRC4
>hg19_dna range=chr7:127671974-127672282 5'pad=0 3'pad=0 strand=-

Untreated (UT) Target Sequence (SEQ ID NO: 51)

GGCGCGGGCGGCTGGAAGGCGCCGGGCGTTAACCCCGCGAGGCAGGCGACGGAGGGGAGCGGCTAATACATAAGAGCACTGCATCACGC
TAATCTTC

Bisulfite-treated Target (BT) Target Sequence (SEQ ID NO: 52)

GGCGCGGGCGGCGTTGGAAGGCGTCGGCGTTAATTTCGCGAGGTAGGCCGACGGAGGGGAGCGGCGTTAATATATAAGAGTATTGTATTACGT
TAATTTTT

| | | |
|---|---|---|
| LRRC4 forward primer | GCGTTAATTTCGCGAGGTA | (SEQ ID NO: 53) |
| LRRC4 reverse primer | ACAATACTCTTATATATTAACGCCGCTC | (SEQ ID NO: 54) |
| LRRC4 probe (arm 1) | CGCCGAGGCGACGGAGG/3C6/ | (SEQ ID NO: 55) |

FIG. 1 (cont'd)

OPLAH
>hg19_dna range=chr8:145106777-145106865 strand=-

Untreated Target (UT) Target Sequence (SEQ ID NO: 56)
CTGTCAGTGCTGACCGAGCGCCGGCCTTCCGGCCATACGGGGCTCCACGGTGCGCGGTTCCCCAGCCCTCGCGGCCCTCCCCGCCCCCG Bisulfite-treated Target (BT) Target Sequence (SEQ ID NO: 57)
TTGTTAGTGTTGATCGAGCGTCGCGTTTTCGGTTATACGGGTTTTACGGTGCGCGGGTTTTTTTAGTTTTCGCGGTTTTTTCGTTTTCG

| | | |
|---|---|---|
| OPLAH forward primer | CGTCGCGTTTTTCGGTTATACG | (SEQ ID NO: 58) |
| OPLAH reverse primer | CGCGAAAACTAAAAAAACCGCG | (SEQ ID NO: 59) |
| OPLAH probe (arm 5) | CCACGGACGGCACCGTAAAAC/3C6/ | (SEQ ID NO: 60) |

FIG. 1 (cont'd)

PDGFD
>hg19_dna range=chr11:104034783-104034920 strand=-

Untreated Target (UT) Target Sequence (SEQ ID NO: 61)

CGGAGGGGGCGAACAAACAAGCGTCAACCTGTGTTGTTTGTCCCGTCACCATTTATCAGCTCAGCACCACAAGGAAGTGCGGCACCCACAC
GCGCTCGGAAAGTTCAGCATGCAGGAAGTTTGGGGAGAGCTCGGCGATT

Bisulfite-treated Target (BT) Target Sequence (SEQ ID NO: 62)

AGGGGGCGAATAAATAAACGTTAATTTGTTGTTTGTTTCGTTATTATTTATTAGTTTAGTATTA<u>TAAGGAAGTGCG</u>GTATTTATACGCG
TTCGGAAAGTTTAGTATGTAGG

PDGFD forward primer   GCGAATAAATAAACGTTAATTTGTTGTTTGTTTCG   (SEQ ID NO: 63)
PDGFD reverse primer   ACTTTCCGAACGCGTATAAATACC              (SEQ ID NO: 64)
PDGFD probe (arm 5)    CCACGGACGCGCACTTCCTTA/3C6/            (SEQ ID NO: 65)

FIG. 1 (cont'd)

PKIA
>hg19_dna range=chr8:79428611-79428695 strand=+

Untreated Target (UT) Target Sequence (SEQ ID NO: 66)

CCGGCGCGAGCTGACCGAGCACTCGGCGGGCGGGACTGCGGCCGTGCGGCCGTGCGGGACCTGCGCTGACTAGGTC

Bisulfite-treated Target (BT) Target Sequence (SEQ ID NO: 67)

TCGGCGCGAGTTGATCGAGTATTCGGCGGGCGGGATTGCGGTTCG[TGGCGGGCGTGCG]CGGGGATTTGCGTTGATTAGGTT

| | | |
|---|---|---|
| PKIA forward primer | GCGAGTTGATCGAGTATTCGG | (SEQ ID NO: 68) |
| PKIA reverse primer | CTAATCAACGCAAATCCCCGC | (SEQ ID NO: 69) |
| PKIA probe (arm 5) | CCACGGACGCCACGCCGCCA/3C6/ | (SEQ ID NO: 70) |

FIG. 1 (cont'd)

PPP2R5C
>hg19_dna range=chr14:102247749-102247852 strand=+

Untreated Target (UT) Target Sequence (SEQ ID NO: 71)

TGCGCGTGGGGCCAGGCTTCGACCTCACTCCCTGTTGTCGCTGCAGACCCGCTGGGCCTCCCGCCGGGCCCTCCTGCCGCCCCCAGCCTC
CCCGCCCCCTGCCCTT

Bisulfite-treated Target (BT) Target Sequence (SEQ ID NO: 72)

TGCGCGTGGGGTTAGGTTCGATTTTATTTTTTGTCGTTGTAG<u>ATTCGCGTTGGGT</u>TTTCGTCGGGTTTTTTGTCGTTTTTAGTTTT
TTCGTTTTTGTTTT

| | | |
|---|---|---|
| PPP2R5C forward primer | TTCGATTTTATTTTTGTTGTCGTTGTAGA | (SEQ ID NO: 73) |
| PPP2R5C reverse primer | ACGACAAAAAAACCCGACG | (SEQ ID NO: 74) |
| PPP2R5C probe (arm 1) | CGCCGAGGATTCGCGTGGGT /3C6/ | (SEQ ID NO: 75) |

FIG. 1 (cont'd)

QKI
>hg19_dna range=chr6:163834737-163834821 strand=+

Untreated Target (UT) Target Sequence (SEQ ID NO: 76)

GCCGAGGGCGCCGGCGTTCGGCGTAGAGTCCCGCAGAGGCGGACGCCGGCGCCGCCTCGAAAAGCCTCAAACTCTTATCCTCGGCTCT

Bisulfite-treated Target (BT) Target Sequence (SEQ ID NO: 77)

GTCGAGGGCGTTCGGCGTAGAGTTTCGTAGAGGCGGACGTCGCGGTACGCGTTTCGAAAAGTTTTAAATTTTTATTTTCGGTTTT

| | | |
|---|---|---|
| QKI forward primer | GTTCGGCGTAGAGTTTCGTAGA | (SEQ ID NO: 78) |
| QKI reverse primer | GAAAATAAAAATTTAAAACTTTTCGAAACGCG | (SEQ ID NO: 79) |
| QKI probe (arm 1) | CGCCGAGGGTACCGGACGT/3C6/ | (SEQ ID NO: 80) |

FIG. 1 (cont'd)

SEP9R092
>hg19_dna range=chr17:75370092-75370204 5'pad=0 3'pad=0 strand=-

Untreated Target (UT) Target Sequence (SEQ ID NO: 81)

TCGGTGCTCCCGGCCCACGGGCTGCACAACTTGGCGGCCCCGAAACTGGCGTGGGGAGGGAGGGCTGTCCACCCGAGCAGGACGCGG
CTGTCCACTCAGTCGGAGGTGAGG

Bisulfite-treated Target (BT) Target Sequence (SEQ ID NO: 82)

TCGGTGTTTTCGGTTTACGGGTTGTATAATTTGGCG GTTTCGAAATTGGCG TGGGGAGGGAGGGTTGTTTATTCGAGTAGGACGCGG
TTGTTTATTTAGTCGGAGGTGAGG

| | | |
|---|---|---|
| SEP9_R092 forward primer | CGGGTTGTATAATTTGGCGG | (SEQ ID NO: 83) |
| SEP9_R092 reverse primer | AACCGCGTCCTACTCGA | (SEQ ID NO: 84) |
| SEP9_R092 probe (arm 1) | CGCCGAGGGTTTCGAAATTG/3C6/ | (SEQ ID NO: 85) |

FIG. 1 (cont'd)

SFMBT2_897
>hg19_dna range=chr10:7452865-7452976 strand=+

Untreated Target (UT) Target Sequence (SEQ ID NO: 86)

GTCGCCGCCCGGGAGGGCACCGGCTCGCTTGCCCGCCTCGCTCCCCGCCTCCCTCGCGCG
CCCGCTCCGGTCCTCCGGCTCCC

Bisulfite-treated Target (BT) Target Sequence (SEQ ID NO: 87)

GTCGTCGTTCGGGAGGGT[ATCGGTTTCGTT]CGTTTGTTCGTTCGTTCGTTTTGTTCGTTCGTTTTTCGTTCGTCGT

| SFMBT2_897v5 forward primer | GTCGTCGTTCGAGAGGGTA | (SEQ ID NO: 88) |
| SFMBT2_897v4 reverse primer | GAACAAAAACGAACGAACGAACA | (SEQ ID NO: 89) |
| SFMBT2_897v5 probe (arm 5) | CCACGGACGATCGGTTTCGTT/3C6/ | (SEQ ID NO: 90) |
| SFMBT2_897v5 probe (arm 1) | CGCCGAGGATCGGTTTCGTT/3C6/ | (SEQ ID NO: 141) |

FIG. 1 (cont'd)

SFMBT2_895
>hg19_dna range=chr10: 7452337-7452406

Untreated Target (UT) Target Sequence (SEQ ID NO: 142)

CGGGGCAGCCTGTCCCCTCCGCCGCCCACCTTCCTCGTTTCTGCACTCATTTTAGCGACGCCGCTGTACCTACCCCGCGC
TCCCGCGTCTCCTCCGCGTGGGGTCTCCCCTTTCTTTGGTTTGGGTTTGGGTGGGAGAAAAGATGGTG

Bisulfite-treated Target (BT) Target Sequence (SEQ ID NO: 143)

GTATTTATTTTAGCGACGTAGTCGTCGTTGTTATTTA[TTTCGCGTTTTTCGCGTTTTTTTCGCGTTGGGGTTTTTTTT

| | | |
|---|---|---|
| SFMBT2_895v2 forward primer | GCGACGTAGTCGTCGTTGT | (SEQ ID NO: 144) |
| SFMBT2_895v2 reverse primer | CCAAACGCGAAAAAACGCG | (SEQ ID NO: 145) |
| SFMBT2_895v2 probe (arm 1) | CGCCGAGGGAAAACGCGAAA/3C6/ | (SEQ ID NO: 146) |

FIG. 1 (cont'd)

SLC12A8
>hg19_dna range=chr3:124860704-124860791 strand=+

Untreated Target (UT) Target Sequence (SEQ ID NO: 91)

CGGAGCTAGGAGGGTGGGGCTCGGAGGGCGCAGGAAGAGCGGCTCTGCGAGGAAAGGAGAGGCCGCTTCTGGGAAGGGACCC

Bisulfite-treated Target (BT) Target Sequence (SEQ ID NO: 92)

CGGAGTTAGGAGGGTGGGGTTC[GGAGGGCGTAGG]AAGAGCGGTTTTGCGAGGAAAGGAGAGGTCGTTTTTGGGAAGGGATTT

| | | |
|---|---|---|
| SLC12A8 forward primer | TTAGGAGGGTGGGGTTCG | (SEQ ID NO: 93) |
| SLC12A8 reverse primer | CTTTCCTCGCAAAACCGC | (SEQ ID NO: 94) |
| SLC12A8 probe (arm 5) | CCACGGACGGGAGGGCGTAGG/3C6/ | (SEQ ID NO: 95) |

FIG. 1 (cont'd)

TBX15Reg2
>hg19_dna range=chr1:119532813-119532920 strand=-

Untreated Target (UT) Target Sequence (SEQ ID NO: 96)

GGAAGGAAATTGCGGGTTCCCGTCCTGCCTGTCTCCAGCTTCTCTGCTGAAGCCCGGTAGCAGTGAATGCGCGCTGACTTTCAGCGACG
ACTCCTGGAAGCAACGCCA

Bisulfite-treated Target (BT) Target Sequence (SEQ ID NO: 97)

GGAAGGAAATTGCGGGTTTTCGTTTTGTTTTTAGTTTTTTTGTTGAAGTTCGGTAGTAGTGAATGCGCGTTGATTTTTAGCGACG
ATTTTTGGAAGTAACGTTA

| | | |
|---|---|---|
| TBX15_Reg2 forward primer | AGGAAATTGCGGGTTTTCG | (SEQ ID NO: 98) |
| TBX15_Reg2 reverse primer | CCAAAAATCGTCGCTAAAAATCAAC | (SEQ ID NO: 99) |
| TBX15_Reg2 probe (arm 5) | CCACGGACGCGCGCATTCACT/3C6/ | (SEQ ID NO: 100) |

FIG. 1 (cont'd)

TSPYL5
>hg19_dna range=chr8:98290016-98290134 strand=+

Untreated Target (UT) Target Sequence (SEQ ID NO: 101)

GCCTTTGCCCCGGTTTTTGGCGCGGGAGGACTTTCGACCCCGACTTCGGCCGCTCATGGTGGCGGGAGGCAGCTTCAAAGACACGCT
GTGACCCTGCGGGCTCCTGACGGCCAGCTCTC

Bisulfite-treated Target (BT) Target Sequence (SEQ ID NO: 102)

GTTTTTGTTTCGGTTTTTGGC|GCGGGAGGATTT|TCGATTTCGATTTCGGTCGTCGTTTATGGTGGCGGGAGGTAGTTTTAAAGATACGTT
GTGATTTTGCGGTTTTTGACGTTAGTTTTT

TSPYL5 forward primer    TTTGTTTCGGTTTTTGGCG      (SEQ ID NO: 103)
TSPYL5 reverse primer    ACCATAAACGACCGAAATCGA    (SEQ ID NO: 104)
TSPYL5 probe (arm 5)     CCACGGACGGCGGGAGGATTT    (SEQ ID NO: 105)

FIG. 1 (cont'd)

VAV3_877
>hg19_dna range=chr1:108507608-108507679 strand=-

Untreated Target (UT) Target Sequence (SEQ ID NO: 106)

GGGACCGGAGCCGAGCCTAGCGGCGCCCGGGACCCGTCAGCCGCGGCTCCCTCGATCCCGGCGCG

Bisulfite-treated Target (BT) Target Sequence (SEQ ID NO: 107)

GGGATCGGAGTTCGAGTTTAGCGG CGGCGTTCGCGA TTTCGTTAGTCGCGGTTTTGTTTTTCGATTTCGCGCG

| | | |
|---|---|---|
| VAV3_877 forward primer | TCGGAGTCGAGTTTAGCGC | (SEQ ID NO: 108) |
| VAV3_877 reverse primer | CGAAATCGAAAAACAAAAACCGC | (SEQ ID NO: 109) |
| VAV3_877 probe (arm 1) | CGCCGAGGCGGCGTTCGCGA/3C6/ | (SEQ ID NO: 110) |
| VAV3_877 probe (arm 5) | CCACGGACGCGGCGTTCGCGA/3C6/ | (SEQ ID NO: 147) |

FIG. 1 (cont'd)

VAV3_11878
> hg19_dna range=chr1: 108507406-108507499

Untreated Target (UT) Target Sequence (SEQ ID NO: 148)

CCGGAGGTTGTTAAGCAGCAGGACAGAGCAGGACTCCATCGCGGAGGGTCTGCGCAAGGTCGAACACCTGAGCCGAGTCCCAGGTCACCC
GGTGGTTGGTGGGCAGCCAGACCACCTTGCAATGAGCCACTGCCTGCCGCCACTGCTTCCACGGCTCCATGCCCGACGGCTC

Bisulfite-treated Target (BT) Target Sequence (SEQ ID NO: 149)

TCGGAGGTTGTTAAGTAGTAGGATTTTATCGCGGAGGGTTTGCGTAAGGTCGAATATTTGAGTCGAGTTTTAGGTTATTC
GGTGGTTGGTGGGTAGTAT TTTGTAATGGATGAGTTATTGCGGTATTGTTTTTACGGTTTTATGTTCGACGGTTT

VAV3_11878 forward primer    GAGTCGAGTTTTAGGTTATTCGGT            (SEQ ID NO: 150)
VAV3_11878 reverse primer    CGTCGAACATAAAACCGTAAAAACAA          (SEQ ID NO: 151)
VAV3_11878 probe (arm 5)     CCACGGACGATACGCGCAATA/3C6/          (SEQ ID NO: 152)

FIG. 1 (cont'd)

VIM
>hg19_dna range=chr10:17271438- 17271565 '5pad=0 3'pad=0 strand=+

Untreated Target (UT) Target Sequence (SEQ ID NO: 111)

TGTCCTCGTCCTCCTACCGCAGGATGTTCGGCGGCCCGGGCACCCGGCCGAGCTCCAGCCGGAGCTACGTGACTGTCCACC
CGCACCTACAGCCTGGGCAGCGCGCTGCGC

Bisulfite-treated Target (BT) Target Sequence (SEQ ID NO: 112)

TGTTTTCGTTTTTTATCGTAGGATGTTCGG CGGTTTCGGGTAT CGCGAGTCCGAGTTTTAGTCGGAGTTACGTGATTACGTTTATT
CGTATTTATAGTTTGGGTAGCGCGTTGCGT

| | | |
|---|---|---|
| VIM_REG2 forward primer | TTTTATCGTAGGATGTTCGGC | (SEQ ID NO: 113) |
| VIM_REG2 reverse primer | TCCGACTAAAACTCGACCGA | (SEQ ID NO: 114) |
| VIM_REG2 probe (arm 5) | CCACGGACGCGGTTCGGGTAT/3C6/ | (SEQ ID NO: 115) |

FIG. 1 (cont'd)

ZDHHC1
>hg19_dna range=chr16:67428559-67428628 strand=-

Untreated Target (UT) Target Sequence (SEQ ID NO: 116)
GGGGCCGGGGCCGACAGCCCACGCTGGCGCGGCCAGGCGCGTGCGCCCGCCGTTTCGTGAGCCCGAGCAG Bisulfite-treated Target (BT) Target Sequence (SEQ ID NO: 117)
GGGGTCGGGGTCGATAGTTTACGTTGGCGCGGTAGGCG|CGTGCGTTCGTC|GTTTCGTGAGTTCGAGTAG

| | | |
|---|---|---|
| ZDHHC1 forward primer | GTCGGGGTCGATAGTTTACG | (SEQ ID NO: 118) |
| ZDHHC1 reverse primer | ACTCGAACTCACGAAAACG | (SEQ ID NO: 119) |
| ZDHHC1 probe (arm 5) | CCACGGACGGACGAACGCACG /3C6/ | (SEQ ID NO: 120) |

FIG. 1 (cont'd)

ZNF304
>hg19_dna range=chr19:57862592-57862691 strand=+

Untreated Target (UT) Target Sequence (SEQ ID NO: 121)

GCTGCTCTGGGCTGCAGGGGCGAGACTTCTGGCGTCGCCGTCGTGACGTATTTTCCTATGCCCGGTCCGTGCATTCTGGTTGTGAAGG
CTGAGTTCTAG

Bisulfite-treated Target (BT) Target Sequence (SEQ ID NO: 122)

GTTGTTTTTGGGTTGTGAGGGGCGAGATTTTTGGCGTCGTCGTCGTGACGTATTTTTTTATGTTCGGTTCGTGTATTTGGTTGTGAAGG
TTGAGTTTTAG

| | | |
|---|---|---|
| ZNF304 forward primer | GAGATTTTTGGCGTCGTCG | (SEQ ID NO: 123) |
| ZNF304 reverse primer | CAACCAAAATACACGAACCGAAC | (SEQ ID NO: 124) |
| ZNF304 probe (arm 5) | CCACGGACGGTCGTGACGTAT/3C6/ | (SEQ ID NO: 125) |

FIG. 1 (cont'd)

ZNF568
>hg19_dna range=chr19:37407263-37407375 strand=-

Untreated Target (UT) Target Sequence (SEQ ID NO: 126)

CGTCACCTGCCGGAAACACCCGAATGTTCATCCCGCGCGCAGTTTCTGAGATGCTGGGTGAAGGCGACCCGCAGATAGGTCTGTGACAG
ACGCCTAAAGGCGCGAACCATCCC

Bisulfite-treated Target (BT) Target Sequence (SEQ ID NO: 127)

CGTTATTTGTCGGAAATATTCGAATGTTTATTTCGCGCGTAGTTTTTGAGATGTTGGGTGAAGGCGATTCGTAGATAGGTTTGTGATAG
ACGTTTAAAGGCGTCGAATTATTT

| | | |
|---|---|---|
| ZNF568 forward primer | CGGAAATATTCGAATGTTTATTTCGCG | (SEQ ID NO: 128) |
| ZNF568 reverse primer | TCACAAACCTATCTACGAATCGC | (SEQ ID NO: 129) |
| ZNF568 probe (arm 1) | CGCCGAGGGCGTAGTTTTTG/3C6/ | (SEQ ID NO: 130) |

FIG. 1 (cont'd)

ZNF671
>hg19_dna range=chr19:58238790-58238906 strand=+

Untreated Target (UT) Target Sequence (SEQ ID NO: 131)

CCGTGGGCGCGGACAGCTGCCGGGAGCGGCAGGCCGTCTCGATCGGGACGCAGGCACTTCCGTCCCTGCAGAGCATCAGACGCGTCTCG
GGACACTGGGGACAACATCTCCTCCGCG

Bisulfite-treated Target (BT) Target Sequence (SEQ ID NO: 132)

TCGTGGGCGCGGATAGTTGTCGGGAGCGGTAG|GCGTTTCGATCG|GGGACGTAGGTATTTTCGTTTTTGTAGAGTATTAGACGCGTTTCG
GGATATTGGGGATAAATATTTTTTCGCG

| | | |
|---|---|---|
| ZNF671 forward primer | GTTGTCGGGAGCGGTAGG | (SEQ ID NO: 133) |
| ZNF671 reverse primer | CCAATATCCCGAAACGCGTCT | (SEQ ID NO: 134) |
| ZNF671 probe (arm 5) | CCACGGACGGCGTTTCGATCG/3C6/ | (SEQ ID NO: 135) |

FIG. 1 (cont'd)

FER1L4
>hg19_dna range=chr20:34189490-34189607 strand = -

Untreated Target (UT) Target Sequence (SEQ ID NO: 153)

CCCGAATGGAACGAGCAGCTGAGCTTCGTGGAGCTCTTCCCGCCGCAGCTCCGCCTGCAGCTGCGGGACGACGCGCCCCT
GGTCGACGCGCACTCGCTACGCACGTGC

Bisulfite-treated Target (BT) Target Sequence (SEQ ID NO: 154)

TTCGAATGGAACGAGTAGTTGAGTTTCGTGGAGTTTTTTCGTCGTTGACGCGTAGTTTTCGTTTGTAGTTGCGGGACGCGTTTTT
GGTCGACGCGTATTCGTTACGTACGTGT

| | | |
|---|---|---|
| FER1L4 forward primer | CGTTGACGCGTAGTTTTCG | (SEQ ID NO: 155) |
| FER1L4 reverse primer | GTCGACCAAAAACGCGTC | (SEQ ID NO: 156) |
| FER1L4 Probe (arm 1) | CGCCGAGGCGTCCCGCAACT/3C6/ | (SEQ ID NO: 157) |

FIG. 1 (cont'd)

Zebra Fish_RASSF1

Untreated Target (UT) Target Sequence (SEQ ID NO: 158)

TCTGGACAGGTGGAGCAGAGGGAAGGTGGTGCCATGGTGTGGGCGAGCGCGCGCCTGGAGGACCCCGATTGGCTGACGTGTAAACCAG
GACGAGGACATGACTTT

Bisulfite-treated Target (BT) Target Sequence (SEQ ID NO: 159)

GAATTCTTTGGATAGGTGGAGTAGAGGGAAGGTGGTGCGTATGGTGGGGCGAGCGCGTGCGTTTGGAGGATTTCGATTGGTTGACGTGTA
AATTAGGACGAGGATATGATTTTTAGTTTTGGAATTC

| | | |
|---|---|---|
| ZF_RASSF1_forward primer | TGCGTATGGTGGGCGAG | (SEQ ID NO: 160) |
| ZF_RASSF1_reverse primer | CCTAATTTACACGTCAACCAATCGAA | (SEQ ID NO: 161) |
| ZF_RASSF1_probe (arm 1) | CGCCGAGGGCGCGTGCGTTT/3C6/ | (SEQ ID NO: 162) |

FIG. 1 (cont'd)

β-ACTIN
> hg19_dna range=chr 7:5568511-5568609 strand=-

Untreated Target (UT) Target Sequence (SEQ ID NO: 163)

CTCTGACCTGAGTCTCCTTTGGAACTCTGCAGGTTCTATTTGCTTTTTCTGGTGTTTGTCTCTCTGACTAG
GTGTCTAAGACAGTGTTGTGGGTGTAGGTACTAACACTGGCTCGTGTGACAAGGCCATGAGGCTGGTAAAGCGGCCTTGGAGTGTGT
ATTAAGTAGGTGCACAGTAGGTCTGAACAGACTCCCCATCCCAAGA

ACTB_forward primer     CCATGAGGCTGGTGTAAAG     (SEQ ID NO: 164)
ACTB_reverse primer     CTACTGTGCACCTACTTAATACAC     (SEQ ID NO: 165)
ACTB probe (arm 1)     CGCCGAGGGCGGCCTTGGAG /3C6/     (SEQ ID NO: 166)

Bisulfite-treated Target (BT) Target Sequence (SEQ ID NO: 167)

TGGTGTGTTTGTTTTTTGATTAGGTGTTTAAGATAGTGTTGTGGGTGTAGGTATTAATATTGGTTTGTGTGATAAGGTTATGAGGTTGGT
GTAAAGCGGGTTTTGG

BTACT_forward primer 65     GTGTTTGTTTTTTGATTAGGTGTTTAAGA     (SEQ ID NO: 168)
BTACT_reverse primer 65     CTTTACCACCAACCTCATAACCTTATC     (SEQ ID NO: 169)
BTACT probe (arm 3)     GACGCGGAGATAGTGTTGTGG /3C6/     (SEQ ID NO: 170)

FIG. 2

| SEQ ID NO. | Description | Sequence (all are shown 5' to 3') |
|---|---|---|
| SEQ ID NO:1 | ANKRD13B Target DNA | GGAGCTACGACGAGCAGCTGCGGCTGGCACTGTCGGCGATGGAACTGTCGGCCGATGGAGCAGGAGGAGAGGCGGCGGCGCGGCGCGCCA |
| SEQ ID NO:2 | ANKRD13B Bisulfite-treated Target DNA | GGAGGAGGAGAGCTGGAGCGCATCCTGAG GGAGTTACGACGAGTAGTTGCGGTTGGCGATGGAATTGTCGGCGTAGGAGTAGGAGGAGAGAGGCGGCGGCGCGGCGTTA |
| SEQ ID NO:3 | ANKRD13B forward primer | GGAGGAGGAGAGTTGGAGCGTATTTGAG |
| SEQ ID NO:4 | ANKRD13B reverse primer | AGTTACGACGAGTAGTTGCG |
| SEQ ID NO:5 | ANKRD13B probe (arm 5) | TCCTCCTACTCCTACGCC |
| SEQ ID NO:6 | B3GALT6 Target DNA | CCACGGACGCGACAATTCCAT/3C6/ |
| | | GGCCACACAGGCCCACTCTGCCCTCTGAGCCCCGGCGACCCAGGGACTCAAGGAGGCGGCTCTGGGCTGCCAGCGCAG GCCTCCGCGCAAACACAGCAGGCTGGAAGTGGCGCTCATCACCGGCACGTCTTCCCAG |
| SEQ ID NO:7 | B3GALT6 Bisulfite-treated Target DNA | GGTTATATAGGGTTTATTTGGTTTTTGAGTTTTCGGCGGATTTAGGGTATTTAAGGAGGCGGTTTTGGGTTTTAGCGTAGGT TTTCGCGTAAATATAGTAGGTTGGAAGTGGCGTTTATTATCGGTACGTTTTTAG |
| SEQ ID NO:8 | B3GALT6 forward primer | GGTTTATTTTGGTTTTTGAGTTTTCGG |
| SEQ ID NO:9 | B3GALT6 reverse primer | TCCAACCTACTATATTTACGCGAA |
| SEQ ID NO:10 | B3GALT6 probe (arm 5) | CCACGGACG GCGGATTTAGGG/3C6/ |
| SEQ ID NO:11 | CHST2_7890 Target DNA | CGCTTTCGGCCTCGTGCGGCGAATTTCCACCTCTCTGGCAGGCGGTGGATGGGCACAGCGCGACCCCGCAGCGGCGGC GGCGGCTGCTTCCATCACCGGGAGGATGCCCGGCGGACAGCCCAGGCAACCCCGCGCTCCGCAGCCTCCG |
| SEQ ID NO:12 | CHST2_7890 Bisulfite-treated Target DNA | GCGTGGAATGGGGTATAGCGCGATTTCGTAGCGGCGGTTGTTTTTATTATCGGGAGGATGTTCGGGCGGATAGCG TAGGTAATTTTCGTCG |
| SEQ ID NO:13 | CHST2_7890 forward primer | GTATAGCGCGATTTCGTAGCG |
| SEQ ID NO:14 | CHST2_7890 reverse primer | AATTACCTACGCTATCCGCCC |
| SEQ ID NO:15 | CHST2_7890 probe (arm 5) | CCACGGACGCGAACATCCTCC/3C6/ |
| SEQ ID NO:175 | CHST2_7890 probe (arm 1) | CGCCGAGGCGAACATCCTCC/3C6/ |
| SEQ ID NO:136 | CHST2_7889 Target DNA | TCACCAACTCTTTCTGAGAGCAAAAACATGGGGCCGAGTCCGAGTCGCACGCAGAATCAACTCTGGCAGCTCTCGGC ACCGACGAGCTCCAGATCCCGCGTTCGCATCCCGGCCGTTTGCGCGCAGAGCTAAGCCTTCGGACCCGTGGA |
| SEQ ID NO:137 | CHST2_7889 Bisulfite-treated Target DNA | TATGGGGTTCGAGTTCGGTAGTTGTACGTAGAATTTAATTTTCGGTATCGACGAGTTTTAGAATTTCGCGTTCG TATTTCGGCGTTTGC |
| SEQ ID NO:138 | CHST2_7889 forward primer | CGAGTTCGGTAGTTGTACGTAGA |
| SEQ ID NO:139 | CHST2_7889 reverse primer | CGAAATACGAACGCGAAATCTAAAACT |
| SEQ ID NO:140 | CHST2_7889 probe (arm 5) | CCACGGACGTCGTCGATACCG/3C6/ |
| SEQ ID NO:176 | CHST2_7889 probe (arm 1) | CGCCGAGGTCGTCGATACCG/3C6/ |

FIG. 2 (cont'd)

| SEQ ID NO. | Description | Sequence (all are shown 5' to 3') |
|---|---|---|
| SEQ ID NO:16 | CNNM1(806) Target DNA | CTGCACCCAGCGCAGTCGCAGTGATACTGCAGGAAGCCGAGCGAGAGCTGGAGGAGGAGGAGCTGGGAACCC AGCCGCAGGCAGGTCACCACGTGTACGCCC |
| SEQ ID NO:17 | CNNM1(806) Bisulfite-treated Target DNA | TTGTATTTAGCGTAGTTGTACGTGATATTGTAGGAAGTCGAGCGAGAGTCGAGGGAGGAGGAGGAGTCGGAGTTGGGAATTTA GTCGTAGGTAGGTTATTACGTGTACGTTT |
| SEQ ID NO:18 | CNNM1(806) forward primer | CGTAGTTGTACGTGATATTGTAGGAA |
| SEQ ID NO:19 | CNNM1(806) reverse primer | GACTAAATTCCCAACTCCGACT |
| SEQ ID NO:20 | CNNM1(806) probe (arm 5) | CCACGGACAGTCGAGCGAGA/3C6/ |
| SEQ ID NO:21 | DOCK2 Target DNA | GCGGGCCCGCAGCATCCTCGTCGCGCCCACTGTCCCGCTCTCCCGCCACCTACCCTGCCGCGCCCTGGGCGCCGCACCTACCC AC |
| SEQ ID NO:22 | DOCK2 Bisulfite-treated Target DNA | GTCGGTTTCGTAGTATTTTTTGTTCGCGGTTTTTTCGTTATTATTGTTTTTTCGTTTTTCGTTATTTATTTAT |
| SEQ ID NO:23 | DOCK2 forward primer | CGGTTTCGTAGTATTTTTTGTTCG |
| SEQ ID NO:24 | DOCK2 reverse primer | GAACCCCAAAACGCGAC |
| SEQ ID NO:25 | DOCK2 probe (arm 1) | CGCCGAGGGCGGTTTTTCG/3C6/ |
| SEQ ID NO:26 | DTX1 Target DNA | CGCCTCCTGGGCTCCCCCGAGTGGGAGGAGCCGGAGCCGCCGTTCCCTCCGCCGCCGTTCCCTCCCAGGCCCCCTCGGCCGCCG CGCCGAGCTTTCCGCGCGTGGACAGACTGCCCGGCCGACGACGCGACGACGCAGG |
| SEQ ID NO:27 | DTX1 Bisulfite-treated Target DNA | CGTTTTTGGGGTTTTTTCGGAGTGGGAGGAGTCGCGGTTTCGTTTTCGCGTTCGTTTTTTAGGTTTTTCGGTCGTCGCG TCGAGTTTTCGCGCGTGGATAGATTGTTCGGTCGACGACGACGTAGG |
| SEQ ID NO:28 | DTX1 forward primer | AGGGAGTCGCGGTTTCG |
| SEQ ID NO:29 | DTX1 reverse primer | GCGACGACCGAAAAACCT |
| SEQ ID NO:30 | DTX1 probe (arm 1) | CGCCGAGGGTTTTCGCGTTC/3C6/ |
| SEQ ID NO:31 | FERMT3 Target DNA | TAGCAGCAGCCGCAGCCATGGCGGGGATGAAGACAGCCTCCGGGACTACGACTCGTCATGGGAGCTGCGGGGTGTTTG TGGGAGAGGAGGACCCAGAGGCCGAGTCGGTCACCCTGCCGGGTCACTGGGAGTCGCAC |
| SEQ ID NO:32 | FERMT3 Bisulfite-treated Target DNA | TAGTAGTAGTCGTAGTTATCGTAGTTATGGCGGGGATGAAGATAGTTTTCGGGGATTATATCGATTCGTTATGGGAGTTGCGGGGTGTTTGT GGGAGAGGAGGATTTAGAGGTTCGAGTCGGTTATTTTGCCGGGGTTATTGGGAGTCGTAT |
| SEQ ID NO:33 | FERMT3 forward primer | GTTTTCGGGGATTATATCGATTCG |
| SEQ ID NO:34 | FERMT3 reverse primer | CCCAATAACCCGCAAAATAACC |
| SEQ ID NO:35 | FERMT3 probe (arm 1) | CGCCGAGGCGACTCGACCTC/3C6/ |

FIG. 2 (cont'd)

| SEQ ID NO. | Description | Sequence (all are shown 5' to 3') |
|---|---|---|
| SEQ ID NO:36 | FLI1 Target DNA | AGGGGCTGcGGAAGTCAGGCTGTAACCGGGTCAATGTGTGGAATATTGGGGGCTCGGCTGCAGACTTGGCCAAATGGACG GGACTATTAAGGTAAGcGGCGGGGCAAC |
| SEQ ID NO:37 | FLI1 Bisulfite-treated Target DNA | AGGGGTTGcGAGGTTAGGTTGTAATCGGGTTAATGTGTGGAATATTGGGGGGTTCGGTTGTAGATTTGGTTAAATGGACGG GATTATTAAGGTAAGcGGCGGGGTAAC |
| SEQ ID NO:38 | FLI1 forward primer | GGTTGCGAGGTTAGGTTGTAA |
| SEQ ID NO:39 | FLI1 reverse primer | TCCATTTAACCAAATCTACAACCGA |
| SEQ ID NO:40 | FLI1 probe (arm 1) | CGCCGAGGATCGGGTTAATG/3C6/ |
| SEQ ID NO:41 | GRIN2D Target DNA | CGCCCCCACCTCCCCGATCATGCGTTCCAGACGCCATGCTCTTCCGTGCTGCCATTGGTGACCAGGTAGAGGTC GTAGCTGAAGCCGATGGTATGCCGCAGCCGCCTTCAGAATGTCGATGCAGAAACCCTTG |
| SEQ ID NO:42 | GRIN2D Bisulfite-treated Target DNA | CGTTTTTTATTTTCGATTATGCGTTAGTCGTTTTTAGACGTTATCGATTTTTTCGTTTTGTTATTGGTGATTAGGTAGAGGTCGT AGTTGAAGTCGATGGTATGCCGTTAGTCGTTAGAAATGTCGATGCAGAAATTTTG |
| SEQ ID NO:43 | GRIN2D forward primer | TCGATTATGTCGTTTTAGACGTTATCG |
| SEQ ID NO:44 | GRIN2D reverse primer | TCTACATCGACATTCTAAAACGACTAAC |
| SEQ ID NO:45 | GRIN2D probe (arm 5) | CCACGACGCGCATACCATCG/3C6/ |
| SEQ ID NO:46 | JAM3 Target DNA | GAGCCGGAGTCGCGGTGGCGCCTCAGCGCGCCATGTCGAGGGGTTGCTGAGGGTGCAGCGCGGGCGCGCGTTGTAGT CCCCGCGCGAGTCGCATGCGCCCAGCCTG |
| SEQ ID NO:47 | JAM3 Bisulfite-treated Target DNA | GAGTCGGAGTCGCGGTGGCGCGGTGGTCGTTTTAGCGTTATGTCGAGGGGTTGTTGAGGGGTTAGCGGTAGCGCGGCGCGCGTTGTAGTT TTCGCGCGTATGCGTTTAGTTTG |
| SEQ ID NO:48 | JAM3 forward primer | TGGTCGTTTTAGCGTTATGTCG |
| SEQ ID NO:49 | JAM3 reverse primer | CGAAAACTACAAACCGCGC |
| SEQ ID NO:50 | JAM3 probe (arm 5) | CCACGACGCCGCTACCGC/3C6/ |
| SEQ ID NO:51 | LRRC4 Target DNA | GGCGCGGCGCTGGAAGGCGCCGCGGCCGTTAACCCGCGGAGGCAGGCGACGGAGGGGGAGCGGCTAATACATAAGAGCAC TGCATCACGCTAATCTTC |
| SEQ ID NO:52 | LRRC4 Bisulfite-treated Target DNA | GGCGCGGCGTTGGAAGGCGTCGGCGTTAATTTCGCGAGGTAGGCGACGGAGGGGAGCGGCGTTAATATATAAGAGTATT GTATTACGTTAATTTT |
| SEQ ID NO:53 | LRRC4 forward primer | GCGTTAATTTCGCGAGGTA |
| SEQ ID NO:54 | LRRC4 reverse primer | ACAATACTCTTATATATTAACGCCGCTC |
| SEQ ID NO:55 | LRRC4 probe (arm 1) | CGCCGAGGAGGCGACGGAGG/3C6/ |
| SEQ ID NO:56 | OPLAH Target DNA | CTGTCAGTGCTGACCGAGCGCCGCCCTTCCGGCCATACGGGCTCCACGGTGCCGCGGTTCCCCAGCCTCGCGGCCCTCCCC GCCCCCG |
| SEQ ID NO:57 | OPLAH Bisulfite-treated Target DNA | TTGTTAGTGTTGATCGAGCGTCGCGTTTTCGGTTATACGGGTTTACGGTGCCGCGGTTTTTAGTTTTCGCGGTTTTTTCGT TTTCG |
| SEQ ID NO:58 | OPLAH forward primer | CGTCGCGTTTTTCGGTTATACG |
| SEQ ID NO:59 | OPLAH reverse primer | CGCGAAAACTAAAAAACCGCG |
| SEQ ID NO:60 | OPLAH probe (arm 5) | CCACGACGGCACCGTAAAAC/3C6/ |

FIG. 2 (cont'd)

| SEQ ID NO. | Description | Sequence (all are shown 5' to 3') |
|---|---|---|
| SEQ ID NO:61 | PDGFD Target DNA | CGGAGGGGGCGAACAACAAACAAACGTCAACCTGTTGTTTGTCCCGTCACCATTTATCAGCTCAGCACCACAAGGAAGTGCGGCA |
| SEQ ID NO:62 | PDGFD Bisulfite-treated Target DNA | CCCACACGCGCTCGAAAGTTCAGCATGCAGGAAGTTTGGGGAGAGCTCGGCGATT |
| SEQ ID NO:63 | PDGFD forward primer | AGGGGGCGAATAAATAAATAAACGTTAATTTGTTGTTTGTTTCGTTATTATTTAGTATTATAAGGAAGTGCGGTATTTAT |
| SEQ ID NO:64 | PDGFD reverse primer | ACGCGTTCGGAAAGTTTAGTATGTAGG |
| SEQ ID NO:65 | PDGFD probe (arm 5) | GCGAATAAATAAACGTTAATTTGTTGTTTGTTTCG |
| SEQ ID NO:66 | PKIA Target DNA | ACTTTCCGAACGCGTATAAATACC |
| | | CCACGACGCGCACTTCCTTA/3C6/ |
| | | CCGGCGCGAGCTGACCGAGCACTCGGCGGGGCGCGGGGACTGCGGCCCGTGGCGCGTGCGGGGACCTGCGCTGACT |
| SEQ ID NO:67 | PKIA Bisulfite-treated Target DNA | AGGTC |
| SEQ ID NO:68 | PKIA forward primer | TCGGCGCGAGTTGATCGAGTATTCGGCGGCGGGGCGCGGCGGCGGGGATTGCGGTTCGTTGGCGCGTGCGGCGGGGATTTGCGTTGATT |
| SEQ ID NO:69 | PKIA reverse primer | AGGTT |
| SEQ ID NO:70 | PKIA probe (arm 5) | GCGAGTTGATCGAGTATTCGG |
| | | CTAATCAACGCAAATCCCCGC |
| | | CCACGGACGCGCACGCCGCCA/3C6/ |
| SEQ ID NO:71 | PPP2R5C Target DNA | TGCGCGTGGGGCGCCAGGGTCGACCTCACTCCTGTTGTCGCTGCAGACCCGCGTGGGCTCCGCGTGGGCTCCCGCCCCCTCGCGCCCCC |
| | | CAGCCTCCCCGCCCCTGCCCTT |
| | | TGCGCGTGGGGTTAGGTTCGATTTTATTTTGTTGTTGTGTAGATTCGCGTGGGTTTTCGTCGGGTTTTTTTGTGTTTTTA |
| SEQ ID NO:72 | PPP2R5C Bisulfite-treated Target DNA | GTTTTTTCGTTTTGTTTT |
| SEQ ID NO:73 | PPP2R5C forward primer | TTCGATTTTATTTTGTTGTTGTGTAGA |
| SEQ ID NO:74 | PPP2R5C reverse primer | ACGACAAAAAAACCCGACG |
| SEQ ID NO:75 | PPP2R5C probe (arm 1) | CGCCGAGGATTCGCGTGGGT /3C6/ |
| | | GCCGAGGGCGCCCGGCGAGAGTCCCGCAGAGGCGGACGCCGGCACGCGCCTCGAAAAGCCTCAAACTCTTATCCTCGG |
| SEQ ID NO:76 | QKI Target DNA | CTCT |
| | | GTCGAGGGCGTTCGGCGTAGAGTTTCGTGGCGTAGAGGCGGACGTCGCGGTACGCGTTCGAAAAGTTTAAATTTTATTTTCGGT |
| SEQ ID NO:77 | QKI Bisulfite-treated Target DNA | TTT |
| SEQ ID NO:78 | QKI forward primer | GTTCGGCGTAGAGTTTCGTAGA |
| SEQ ID NO:79 | QKI reverse primer | GAAAATAAAAATTTAAAACTTTTCGAAACGCG |
| SEQ ID NO:80 | QKI probe (arm 1) | CGCCGAGGGTACCGCGACGT/3C6/ |
| | | TCGGTGCTCCCGGCCCACGGGCTGCACAACTTGGCGCCCCGAAACTTGGCGTGGGGAGGGGAGGCTGTCCACCCGAGC |
| SEQ ID NO:81 | SEP9R092 Target DNA | AGGACGCGGCTGTCCACTCAGTCGGAGGTGAGG |
| | | TCGGTGTTTTCGGTTTTACGGCGGTTGTATAATTTGGCGGTTTCGAAATTGGCGTGGGGAGGGGAGGGTTGTTATTCGAGTAG |
| SEQ ID NO:82 | SEP9R092 Bisulfite-treated Target DNA | GACGCGGTTGTTTATTTAGTCGGAGGTGAGG |
| SEQ ID NO:83 | SEP9R092 forward primer | CGGGTTGTATAATTTGGCGG |
| SEQ ID NO:84 | SEP9R092 reverse primer | AACCGCGTCCTACTCGA |
| SEQ ID NO:85 | SEP9R092 probe (arm 1) | CGCCGAGGGTTTCGAAATTG/3C6/ |

FIG. 2 (cont'd)

| SEQ ID NO. | Description | Sequence (all are shown 5' to 3') |
|---|---|---|
| SEQ ID NO:86 | SFMBT2_897 Target DNA | GTCGCCGCCGGGAGGGCACCGGCCTGCTCGCTCGCCGCCCTTGCCCGCCGCTCGCTCCCCGCCGCCGCCTCCCT |
| SEQ ID NO:87 | SFMBT2_897 Bisulfite-treated Target DNA | CGCCGCCCCGCCTCCGGTCCTCCGGCTCCC |
| SEQ ID NO:88 | SFMBT2_897 forward primer | GTCGTCGTTCGGGAGGGTATCGGTTTCGTTCGTTCGTTCGTTTTCGTTTTCGTTCGTCGT |
| SEQ ID NO:89 | SFMBT2_897 reverse primer | GTCGTCGTTCGAGAGGGTA |
| SEQ ID NO:90 | SFMBT2_897 probe (arm 5) | GAACAAAAACGAACGAACGAACA |
| SEQ ID NO:141 | SFMBT2_897 probe (arm 1) | CCACGGACGATCGGTTTCGTT/3C6/ |
| SEQ ID NO:142 | SFMBT2_895 Target DNA | CGCCGAGGATCGGTTTCGTT/3C6/ |
| | | CGGGCGCAGCCTGCTCCCTCCCGCCGCCCACCTTCTCGTTCTGCACTCATTTAGCGACGCAGCCGCCGCTGCTACCTACCC |
| SEQ ID NO:143 | SFMBT2_895 Bisulfite-treated Target DNA | CGCCTCCCGCGTCTCCTCCGCGCTGGGGTCTCCCCTTTCTTTTGGTTGGGTGGGAGAAAAAGATGGTG |
| SEQ ID NO:144 | SFMBT2_895 forward primer | GTATTATTTTAGCGACGTAGTCGTCGTTGTTATTTATTTCGCGTTTTCGCGGTTTTTTT |
| SEQ ID NO:145 | SFMBT2_895 reverse primer | GCGACGTAGTCGTCGTGT |
| SEQ ID NO:146 | SFMBT2_895 probe (arm 5) | CCAACGCGAAAAAAACGCG |
| | SFMBT2_895 probe (arm 1) | CGCCGAGGGAAAACGCGAAA/3C6/ |
| SEQ ID NO:91 | SLC12A8 Untreated Target DNA | CGGAGCTAGGAGGAGGGTGGGGCTCGGAGGGCGCAGGGAAGAGAGCGGCTCTGCGAGGAAGAGGGAAAGGAGAGAGGCCGCTTCTGC |
| SEQ ID NO:92 | SLC12A8 Bisulfite-treated Target DNA | CGGAGTTAGGAGGGTGGGGTTCGGAGGGCGTAGGAAGAGCGGTTTTGCGAGGAAGAGGGAAAGGAGAGGAGGGTCGTTTTTGGC |
| SEQ ID NO:93 | SLC12A8 forward primer | AAGGGATTT |
| SEQ ID NO:94 | SLC12A8 reverse primer | TTAGGAGGGTGGGGTTCG |
| SEQ ID NO:95 | SLC12A8 probe (arm 5) | CTTTCCTCCGCAAAACCGC |
| | | CCACGGACGGAGGGCGTAGG/3C6/ |
| SEQ ID NO:96 | TBX15Reg2 Target DNA | GGAAGGAAATTGCGGGTTTCCGTCGCCTTCTCTGTCTGCCAGCTTCTCTGCTGCTGAAGCCCGGTAGCAGTGAATGCGCGCTGACTTTC |
| | | AGCGACGACTTCTGGAAGCAACGCCA |
| SEQ ID NO:97 | TBX15Reg2 Bisulfite-treated Target DNA | GGAAGGAAATTGCGGGTTTTCGTTGTTTTTGTTTTAGTTTTTTTTGTTGAAGTTCGGTAGTAGTGAATGCGCGTTGATTTTTAG |
| SEQ ID NO:98 | TBX15Reg2 forward primer | CGACGATTTTTGGAAGTAACGTTA |
| SEQ ID NO:99 | TBX15Reg2 reverse primer | AGGGAAATTGCGGGTTTTCG |
| SEQ ID NO:100 | TBX15Reg2 probe (arm 5) | CCAAAAATCGTCGCTAAAAATCAAC |
| | | CCACGGACGCGCATTCACT/3C6/ |
| SEQ ID NO:101 | TSPYL5 Target DNA | GCCTTTGCCCCGGTTTTTGGCGCGGGGAGGACTTTCGACCCGACTTCGGCCGCCCTCATGGTGGCGGGAGGCAGCTTCAAAG |
| | | ACACGCTGTGACCCTGCCGCTCCTGACGCCAGCTCTC |
| SEQ ID NO:102 | TSPYL5 Bisulfite-treated Target DNA | GTTTTTGTTTCGGTTTTCGGCGCGGGGAGGATTTCGATTTCGGTCGTTTATGGTGGCGGGAGGTAGTTTTAAAGA |
| SEQ ID NO:103 | TSPYL5 forward primer | TACGTTGTGATTTTCGTTTTTGACGTTAGTTTTT |
| SEQ ID NO:104 | TSPYL5 reverse primer | TTTGTTTCGGTTTTTGGCG |
| | | ACCATAAACGACCGAAATCGA |

FIG. 2 (cont'd)

| SEQ ID NO. | Description | Sequence (all are shown 5' to 3') |
|---|---|---|
| SEQ ID NO:105 | TSPYL5 probe (arm 5) | CCACGGACGGCGGAGGAGGATTT |
| SEQ ID NO:106 | VAV3_877 Target DNA | GGGAccGGAGCcGAGCCTAGCGCGGCGCCCGACCCGTCAGCCGCGGCTCCTGCTCCCTCGATCCCGCGCG |
| SEQ ID NO:107 | VAV3_877 Bisulfite-treated Target DNA | GGGGATCGGAGTCGAGTTTAGCGCGGCGCCCGATTCGCGGTTCGATTCGTTAGTCGCGGTTTTGTTTTCGATTTCGCGCG |
| SEQ ID NO:108 | VAV3_877 forward primer | TCGGAGTCGAGTTTAGCGC |
| SEQ ID NO:109 | VAV3_877 reverse primer | CGAAATCGAAAAAACAAAAACCGC |
| SEQ ID NO:110 | VAV3_877 probe (arm 1) | CGCCGAGGCGGGCGTTCGCGA/3C6/ |
| SEQ ID NO:147 | VAV3_877 probe (arm 5) | CCACGGACGCGGCGTTCGCGA/3C6/ |
| SEQ ID NO:148 | VAV3_11878 Target DNA | CCGGAGGTTGTTAAGCAGCTGGCAGAGAGCAGGACTCCATGCGGAGGGTCTGCGCAAGGTCGAACACCTGAGCCGAGTCCCAGGTCACCCGGTGGTTGGTGGGCAGCACCTTGCAATGGATGAGCACTGCGCGCACTGCTTCCACGGCTCCATGCCCGACGGCTC |
| SEQ ID NO:149 | VAV3_11878 Bisulfite-treated Target DNA | TCGGAGGTTGTTAAGTAGTTGGTAGAGTAGGATTTTATCGCGGAGGGTTTGCGTAAGGTCGAATATTTGAGTCGAGTTTTAGGTTATTCGGTGGTTGGTGGGTAGTAGTATTTTGTAATGGATGAGTTATTGCGCGTATTGTTTTATGTTCGACGGTTT |
| SEQ ID NO:150 | VAV3_11878 forward primer | GAGTCGAGTTTTAGGTTATTCGGC |
| SEQ ID NO:151 | VAV3_11878 reverse primer | CGTCGAACATAAAACCGTAAAAACAA |
| SEQ ID NO:152 | VAV3_11878 probe (arm 5) | CCACGGACGATACGCGCAATA/3C6/ |
| SEQ ID NO:111 | VIM Target DNA | TGTCCTCGTCCTCTACCGCAGGATGTTCGGCGACGAGCCTGGGCAGCGCGTGCGC |
| SEQ ID NO:112 | VIM Bisulfite-treated Target DNA | TGTTTTCGTTTTTTATCGTAGGATGTTCGGCGGTTCGGGTATCGCGAGTCGGTCGAGTTTTAGTCGGAGGTTACGTCGATTACG |
| SEQ ID NO:113 | VIM forward primer | TTTATTCGTATTTATAGTTTGGGTAGCGCGTTGCGT |
| SEQ ID NO:114 | VIM reverse primer | TTTTATCGTAGGATGTTCGGC |
| SEQ ID NO:115 | VIM probe (arm 5) | TCCGACTAAAACTCGACCGA |
| SEQ ID NO:116 | ZDHHC1 Target DNA | CCACGGACGGCGGGTTCGGGTAT/3C6/ |
| SEQ ID NO:117 | ZDHHC1 Bisulfite-treated Target DNA | GGGGCGGCGGGCCGACACCCTGGCGCGGCAGGCGCGTGCGCCCGCGTTTCGTGAGCCCGAGCAG |
| SEQ ID NO:118 | ZDHHC1 forward primer | GGGGTCGGGGTCGATAGTTTACGTTGGGCGGCGGTAGGGCGCGTGCGTTCGTCGTTCGTGAGTTCGAGTAG |
| SEQ ID NO:119 | ZDHHC1 reverse primer | GTCGGGGTCGATAGTTTACG |
| SEQ ID NO:120 | ZDHHC1 probe (arm 5) | ACTCGAACTCACGAAAACG |
| SEQ ID NO:121 | ZNF304 Target DNA | CCACGGACGGACGAACGCACG/3C6/ |
| SEQ ID NO:122 | ZNF304 Bisulfite-treated Target DNA | GCTGCTCTGGGCTGCAGGGGCGAGACTTCGCCGTCGTCGACGTATTTTCCTATGCCCGGTCGTGCATTCTGGTTGTGAAGGCTGAGTTCTAG |
| SEQ ID NO:123 | ZNF304 forward primer | GTTGTTTTGGGTTGTAGGGGCGAGATTTTTGGCGTCGTCGTGACGTATTTTTTTATGTTCGGTTCGTGTATTTTGGTTGT GAAGGTGAGTTTTAG |
| SEQ ID NO:124 | ZNF304 reverse primer | GAGATTTTTGGCGTCGTCG |
|  |  | CAACCAAAATACACGAACCGAAC |

FIG. 2 (cont'd)

| SEQ ID NO. | Description | Sequence (all are shown 5' to 3') |
|---|---|---|
| SEQ ID NO:125 | ZNF304 probe (arm 5) | CCACGGACGTCGTGACGTAT/3C6/ |
| SEQ ID NO:126 | ZNF568 Target DNA | CGTCACCTGCCGGAAACACCCGAATGTTCATCCCGCGCGAATGTTCTGAGATGCTGGGTGAAGGCGACCCGCAGATAGGTCT GTGACAGACGCCTAAAGCGCCGAACCATCCC |
| SEQ ID NO:127 | ZNF568 Bisulfite-treated Target DNA | CGTTATTTGTCGGAAATATTCGAATGTTTATTTCGCGCGAATGTTTTTGAGATGTTGGGTGAAGGCGATTCGTAGATAGGTTTG TGATAGACGTTTAAAGCGTCGAATTATTT |
| SEQ ID NO:128 | ZNF568 forward primer | CGGAAATATTCGAATGTTTATTTCGCG |
| SEQ ID NO:129 | ZNF568 reverse primer | TCACAAACCTATCTACGAATCGC |
| SEQ ID NO:130 | ZNF568 probe (arm 1) | CGCCGAGGGCGTAGTTTTG/3C6/ |
| SEQ ID NO:131 | ZNF671 Target DNA | CCGTGGGCGCGGACAGCTGCCGGGAGGCGGCAGGCGCTCGATCGGGACGCAGGCACTTCCGTCCTGCAGAGCATCAGA CGCGTCTCGGGACACTGGGACAACATCTCTCCGCG |
| SEQ ID NO:132 | ZNF671 Bisulfite-treated Target DNA | TCGTGGGCGCGGATAGTTGTCGGGAGGCGGTAGGCGTTTCGATCGGGACGTAGGTATTTCGTTTTTGTAGAGTATTAGAC GCGTTTCGGGATATTGGGATAATATTTTTCGCG |
| SEQ ID NO:133 | ZNF671 forward primer | GTTGTCGGGAGCGGTAGG |
| SEQ ID NO:134 | ZNF671 reverse primer | CCAATATCCCGAAACGCGTCT |
| SEQ ID NO:135 | ZNF671 probe (arm 5) | CCACGGACGCGTTTCGATCG/3C6/ |
| SEQ ID NO:153 | FER1L4 Target DNA | CCCGAATGGAACGAGCAGCTGAGCTTCGTGGAGCTCTCCCGCCGCTGACGCGCAGCCTCCGCAGCGCGGGACGAC GCGCCCCTGGTCGTCGACGCGGCACTCGCTACGCACGTGC |
| SEQ ID NO:154 | FER1L4 Bisulfite-treated Target DNA | TTCGAATGGAACGAGTAGTTGAGTTTCGTGGAGTTTTTCGTCGTTGACGCGTAGTTTCGTTTGTAGTTGCGGGACGACGC GTTTTTGGTCGTCGACGCGGTATTCGTTACGTACGTGT |
| SEQ ID NO:155 | FER1L4 forward primer | CGTTGACGCGTAGTTTCG |
| SEQ ID NO:156 | FER1L4 reverse primer | GTCGACCAAAAACGCGTC |
| SEQ ID NO:157 | FER1L4 probe (arm 1) | CGCCGAGGCGTCCCGCAACT/3C6/ |
| SEQ ID NO:158 | Zebra Fish RASSF1 Target DNA | TCTGGACAGGTGGAGCAGAGGAAGGTGTGCGCATGTGGGCGAGCGCGTGCGCCTGGAGGACCCCGATTGGCTGACGT GTAAACCAGGACGGAGGACATGACTTT |
| SEQ ID NO:159 | Zebra Fish RASSF1 Bisulfite-treated Target DNA | GAATTCTTTGGATAGGTGGAGTAGAGGAAGGTTGTGCGTATGGTGGGCGAGCGCGTGCGTTTGGAGGATTTCGATTGGT TGACGTGTAAATTAGGACGAGAGGATATGATTTTTAGTTTTGAATTC |
| SEQ ID NO:160 | Zebra Fish RASSF1 forward primer | TGCGTATGGTGGGCGAG |
| SEQ ID NO:161 | Zebra Fish RASSF1 reverse primer | CCTAATTTACACGTCAACCAATCGAA |
| SEQ ID NO:162 | Zebra Fish RASSF1 probe (arm 1) | CGCCGAGGGCGCGTGCGTTT/3C6/ |
| SEQ ID NO:163 | β-Actin Target DNA (ACTB) | CTCTGACCTGAGTCTCCTTGGAACTCTGCAGGTTCTCTATTGCTTTTCCAGATGAGCTCTTTTTCTGGTGTTTGTCTCTGA CTAGGTGTCTAAGACAGTGTTGTGGGTTAGGTACTAACACTGGCTCGTGTGACAAGGCCATGACACTGTGTAAAGCGGC CTTGGAGTGTGTATTAAGTAGGTGCACAGTAGGTCTGAACAGACTCCCATCCAAGA |
| SEQ ID NO:164 | β-Actin (ACTB) forward primer | CCATGAGGCTGGTGTAAAG |
| SEQ ID NO:165 | ACTB reverse primer | CTACTGTGCACCTACTTAATACAC |
| SEQ ID NO:166 | ACTB probe (arm 1) | CGCCGAGGGCGGCCTTGGAG/3C6/ |

FIG. 2 (cont'd)

| SEQ ID NO. | Description | Sequence (all are shown 5' to 3') |
|---|---|---|
| SEQ ID NO:167 | β-Actin Bisulfite-treated (BTACT) Target DNA | TGGTGTTTGTTTTTGATTAGGTGTTTAAGATAGTGTTGTGGGTGTAGGTATTAATATTGGTTTGTGTGATAAGGTTATGAGGTTGGTGTAAAGCGGTTTTGG |
| SEQ ID NO:168 | β-Actin Bisulfite-treated (BTACT) Forward primer | GTGTTTGTTTTTGATTAGGTGTTTAAGA |
| SEQ ID NO:169 | BTACT reverse primer | CTTTACACCAACCTCATAACCTTATC |
| SEQ ID NO:170 | BTACT probe (arm 3) | GACGCGGAGATAGTGTTGTGG /3C6/ |
| SEQ ID NO:171 | Arm 1 FRET cassette HEX | /HEX/TCT/BHQ-1/AGCCGGGTTTTCCGGCTGAGACCTCGGCG/3C6/ |
| SEQ ID NO:172 | Arm 5 FRET cassette FAM | /FAM/TCT/BHQ-1/AGCCGGTTTTCCGGCTGAGACGTCCGTGG/3C6/ |
| SEQ ID NO:173 | Arm 3 FRET cassette QUASAR-670 | /Q670/TCT/BHQ-2/AGCCGGTTTTCCGGCTGAGACTCCGGTC/3C6/ |
| SEQ ID NO:174 | Arm 1 FRET cassette QUASAR-670 | /Q670/TCT/BHQ-2/AGCCGGTTTTCCGGCTGAGACCTCGGCG/3C6/ |

FIG. 3

| Sample ID | CEA | WTZF RASSF1 | ACTB | VAV3 | ZNF671 | CHST2 | FLI1 | JAM3 | SFMBT2 | PDGFD | DTX1 | TSPY15 | ZNF568 | GRIN2D | QKI |
|---|---|---|---|---|---|---|---|---|---|---|---|---|---|---|---|
| Units | pg/mL | | | | | | | | Strands/assay | | | | | | |
| 4 | 2480 | 551 | 506 | 2 | 61 | 96 | 445 | 68 | 0 | 0 | 113 | 241 | 0 | 52 | 112 |
| 5 | 579 | 493 | 485 | 0 | 0 | 0 | 111 | 6 | 0 | 0 | 32 | 42 | 9 | 17 | 0 |
| 29 | 380 | 565 | 355 | 0 | 0 | 0 | 75 | 0 | 0 | 0 | 4 | 70 | 0 | 0 | 0 |
| 52 | 267 | 630 | 328 | 0 | 0 | 0 | 226 | 0 | 0 | 0 | 16 | 0 | 0 | 0 | 10 |
| 58 | 1288 | 672 | 393 | 0 | 0 | 0 | 120 | 0 | 0 | 0 | 11 | 72 | 0 | 0 | 0 |
| 60 | 399 | 761 | 790 | 0 | 0 | 0 | 461 | 0 | 0 | 0 | 40 | 183 | 0 | 112 | 0 |
| 70 | 1057 | 748 | 1293 | 0 | 14 | 0 | 691 | 0 | 11 | 0 | 136 | 504 | 0 | 10 | 0 |
| 72 | 1185 | 604 | 620 | 0 | 0 | 0 | 544 | 227 | 0 | 0 | 19 | 16 | 1 | 43 | 0 |
| 75 | 8390 | 584 | 377 | 295 | 586 | 279 | 402 | 435 | 76 | 0 | 456 | 855 | 228 | 299 | 285 |
| 90 | 1680 | 646 | 420 | 0 | 0 | 0 | 433 | 0 | 0 | 13 | 53 | 353 | 0 | 23 | 0 |
| 94 | 1131 | 652 | 620 | 0 | 0 | 0 | 208 | 0 | 0 | 0 | 3 | 0 | 4 | 25 | 0 |
| 102 | 640 | 600 | 248 | 0 | 0 | 0 | 182 | 0 | 0 | 0 | 1 | 940 | 16 | 0 | 10 |
| 120 | 536 | 696 | 743 | 0 | 0 | 0 | 142 | 0 | 0 | 0 | 0 | 49 | 8 | 16 | 0 |
| 122 | 3740 | 571 | 133 | 0 | 0 | 0 | 179 | 0 | 0 | 0 | 35 | 27 | 0 | 0 | 0 |
| 128 | 532 | 633 | 385 | 0 | 0 | 0 | 584 | 0 | 0 | 9 | 0 | 1341 | 1 | 18 | 0 |
| 133 | 1229 | 627 | 541 | 0 | 0 | 0 | 417 | 1 | 0 | 0 | 1 | 139 | 11 | 20 | 0 |
| 139 | 1399 | 599 | 320 | 0 | 0 | 0 | 153 | 0 | 0 | 8 | 10 | 382 | 0 | 51 | 76 |
| 142 | 347 | 642 | 423 | 0 | 0 | 0 | 226 | 0 | 0 | 0 | 0 | 9 | 0 | 41 | 4 |
| 158 | 1234 | 700 | 378 | 0 | 0 | 0 | 191 | 284 | 436 | 24 | 137 | 1794 | 0 | 74 | 0 |
| 177 | 442 | 609 | 290 | 0 | 0 | 0 | 205 | 0 | 0 | 0 | 5 | 266 | 130 | 0 | 0 |
| 179 | 430 | 562 | 406 | 0 | 0 | 0 | 114 | 0 | 0 | 0 | 2 | 7 | 0 | 0 | 0 |
| 3 | 1074 | 528 | 325 | 0 | 602 | 171 | 431 | 284 | 0 | 121 | 110 | 529 | 72 | 173 | 272 |
| 13 | 6656 | 526 | 787 | 0 | 0 | 0 | 354 | 0 | 0 | 359 | 0 | 690 | 0 | 185 | 0 |
| 16 | 263 | 547 | 514 | 0 | 186 | 0 | 316 | 136 | 0 | 0 | 4 | 73 | 48 | 0 | 0 |
| 17 | 478 | 714 | 895 | 0 | 0 | 0 | 1048 | 0 | 125 | 104 | 43 | 18 | 0 | 4 | 67 |
| 24 | 12001 | 663 | 1269 | 0 | 1410 | 0 | 708 | 165 | 0 | 0 | 46 | 1071 | 236 | 278 | 0 |
| 44 | 1100 | 599 | 510 | 0 | 0 | 0 | 348 | 1 | 0 | 128 | 13 | 414 | 0 | 33 | 0 |
| 48 | 661 | 714 | 833 | 0 | 0 | 0 | 477 | 0 | 0 | 0 | 24 | 143 | 0 | 0 | 0 |
| 71 | 6726 | 881 | 2571 | 0 | 0 | 76 | 1599 | 117 | 0 | 1 | 619 | 1245 | 1 | 55 | 31 |
| 74 | 1212 | 881 | 1257 | 0 | 0 | 0 | 1069 | 1 | 0 | 54 | 341 | 1187 | 9 | 299 | 0 |
| 87 | 685 | 548 | 401 | 0 | 0 | 0 | 149 | 0 | 0 | 0 | 5 | 119 | 0 | 0 | 0 |
| 96 | 2026 | 558 | 386 | 0 | 178 | 0 | 401 | 94 | 23 | 0 | 65 | 44 | 48 | 40 | 0 |
| 104 | 1829 | 619 | 715 | 0 | 4 | 0 | 903 | 0 | 0 | 36 | 36 | 3126 | 382 | 0 | 80 |
| 106 | 1401 | 614 | 446 | 6 | 154 | 0 | 159 | 19 | 0 | 5 | 3 | 351 | 0 | 0 | 0 |

FIG. 3 (con'd)

| Sample ID | Pathology | stage | 1st | 2nd | 3rd | Volume | Site | Site Group | Final Assay Result |
|---|---|---|---|---|---|---|---|---|---|
| Units | | | Tumor | | | cm³ | | | |
| 4 | Cancer | I | 3.6 | 2.7 | 1.9 | 18.468 | Cecum | Proximal | Pos |
| 5 | Cancer | I | 3 | | | | Hepatic flexure | Proximal | Neg |
| 29 | Cancer | I | 2.1 | 2 | 0.3 | 1.26 | Hepatic flexure | Proximal | Neg |
| 52 | Cancer | I | 0.4 | 0.3 | | | Rectosigmoid (NOS) | Distal | Neg |
| 58 | Cancer | I | 1.4 | 1.2 | 0.4 | 0.672 | Rectosigmoid (NOS) | Distal | Neg |
| 60 | Cancer | I | 2.5 | 2 | 1 | 5 | Rectosigmoid (NOS) | Distal | Neg |
| 70 | Cancer | I | 6 | 4.5 | 2.2 | 59.4 | Ascending | Proximal | Pos |
| 72 | Cancer | I | 4.3 | 3 | 1.1 | 14.19 | Sigmoid | Distal | Pos |
| 75 | Cancer | I | 4 | | | | Rectum | Distal | Pos |
| 90 | Cancer | I | 1 | 1 | 0.3 | 0.3 | Ascending | Proximal | Neg |
| 94 | Cancer | I | 1.7 | 1.5 | 0.5 | 1.275 | Cecum | Proximal | Neg |
| 102 | Cancer | I | 1.8 | 0.6 | 0.3 | 0.324 | Cecum | Proximal | Neg |
| 120 | Cancer | I | 3 | 2.5 | 0.6 | 4.5 | Ascending | Proximal | Neg |
| 122 | Cancer | I | 2 | | | | Sigmoid | Distal | Pos |
| 128 | Cancer | I | 3.5 | | | | Rectum | Distal | Neg |
| 133 | Cancer | I | 1 | 0.3 | | | Rectosigmoid (NOS) | Distal | Neg |
| 139 | Cancer | I | 2 | | | | Hepatic flexure | Proximal | Neg |
| 142 | Cancer | I | 2.2 | 1.5 | 0.6 | 1.98 | Splenic flexure | Distal | Neg |
| 158 | Cancer | I | 0.5 | | | | Rectum | Distal | Pos |
| 177 | Cancer | I | 5 | | | | Rectum | Distal | Pos |
| 179 | Cancer | I | 0.9 | 0.5 | 0.3 | 0.135 | Rectum | Distal | Neg |
| 3 | Cancer | II | 12.2 | 5.9 | 1.6 | 115.168 | Cecum | Proximal | Pos |
| 13 | Cancer | II | 3.2 | 3.1 | 0.9 | 8.928 | Ascending | Proximal | Pos |
| 16 | Cancer | II | 3.4 | 3.3 | 0.7 | 7.854 | Descending | Distal | Pos |
| 17 | Cancer | II | | | | | Rectum | Distal | Neg |
| 24 | Cancer | II | | | | | Rectum | Distal | Pos |
| 44 | Cancer | II | 3.4 | 2.2 | 0.4 | 2.992 | Ascending | Proximal | Pos |
| 48 | Cancer | II | 1.1 | 0.8 | 0.6 | 0.528 | Hepatic flexure | Proximal | Neg |
| 71 | Cancer | II | 4 | | | | Rectum | Distal | Pos |
| 74 | Cancer | II | 2.6 | 1.3 | 0.5 | 1.69 | Ascending | Proximal | Pos |
| 87 | Cancer | II | 3 | | | | Rectum | Distal | Neg |
| 96 | Cancer | II | 5 | 4.7 | 0.7 | 16.45 | Cecum | Proximal | Pos |
| 104 | Cancer | II | 3.1 | 2.3 | 1 | 7.13 | Cecum | Proximal | Pos |
| 106 | Cancer | II | 2.7 | 1.7 | 1.6 | 7.344 | Sigmoid | Distal | Pos |

FIG. 3 (con'd)

| Sample ID | CEA | WTZF RASSF1 | ACTB | VAV3 | ZNF671 | CHST2 | FLI1 | JAM3 | SFMBT2 | PDGFD | DTX1 | TSPYL5 | ZNF568 | GRIN2D | QKI |
|---|---|---|---|---|---|---|---|---|---|---|---|---|---|---|---|
| Units | pg/mL | | | | | | | | Strands/assay | | | | | | |
| 110 | 802 | 753 | 722 | 760 | 2322 | 1465 | 660 | 816 | 231 | 576 | 75 | 1568 | 1244 | 1 | 824 |
| 126 | 2014 | 603 | 420 | 0 | 2126 | 0 | 235 | 0 | 0 | 78 | 20 | 1386 | 0 | 310 | 197 |
| 127 | 509 | 643 | 769 | 0 | 829 | 0 | 455 | 16 | 297 | 32 | 143 | 1523 | 291 | 418 | 0 |
| 129 | 1290 | 688 | 638 | 31 | 1433 | 61 | 1236 | 478 | 134 | 2 | 470 | 852 | 0 | 116 | 381 |
| 138 | 532 | 1193 | 20394 | 0 | 10 | 1 | 10633 | 3 | 0 | 426 | 852 | 6218 | 467 | 845 | 106 |
| 140 | 1610 | 652 | 616 | 0 | 0 | 0 | 144 | 4 | 0 | 0 | 64 | 55 | 0 | 0 | 0 |
| 167 | 34648 | 802 | 648 | 0 | 0 | 0 | 368 | 0 | 0 | 0 | 25 | 264 | 3 | 41 | 63 |
| 170 | 841 | 575 | 373 | 0 | 0 | 17 | 139 | 5 | 0 | 0 | 8 | 15 | 0 | 36 | 0 |
| 174 | 722 | 844 | 867 | 0 | 0 | 0 | 281 | 0 | 0 | 0 | 2 | 235 | 0 | 44 | 0 |
| 178 | 2226 | 627 | 198 | 21 | 0 | 0 | 133 | 94 | 52 | 0 | 0 | 267 | 79 | 0 | 0 |
| 183 | 895 | 733 | 863 | 0 | 0 | 0 | 338 | 0 | 0 | 0 | 17 | 211 | 0 | 38 | 0 |
| 184 | 591 | 733 | 608 | 0 | 0 | 0 | 357 | 0 | 0 | 20 | 14 | 41 | 0 | 0 | 1 |
| 1 | 2685 | 598 | 578 | 0 | 293 | 0 | 408 | 59 | 0 | 0 | 151 | 760 | 0 | 355 | 66 |
| 2 | 3713 | 593 | 187 | 0 | 0 | 0 | 175 | 0 | 62 | 0 | 25 | 6 | 9 | 17 | 0 |
| 7 | 6161 | 432 | 282 | 0 | 0 | 0 | 172 | 0 | 0 | 0 | 10 | 10 | 0 | 0 | 0 |
| 18 | 382 | 972 | 6238 | 0 | 0 | 0 | 7634 | 8 | 0 | 445 | 123 | 6414 | 1159 | 748 | 621 |
| 22 | 382 | 597 | 465 | 0 | 0 | 0 | 268 | 0 | 0 | 0 | 31 | 85 | 0 | 0 | 0 |
| 36 | 3324 | 724 | 693 | 0 | 111 | 0 | 161 | 0 | 25 | 0 | 25 | 114 | 0 | 30 | 0 |
| 39 | 7924 | 637 | 844 | 20106 | 50447 | 24702 | 15576 | 17511 | 17490 | 5957 | 9990 | 21424 | 36309 | 7400 | 17668 |
| 40 | 44785 | 585 | 380 | 0 | 4146 | 1837 | 1096 | 406 | 486 | 0 | 14 | 1251 | 1130 | 568 | 1098 |
| 47 | 733 | 749 | 509 | 534 | 3039 | 1241 | 1058 | 1558 | 1200 | 1062 | 166 | 1286 | 1275 | 1076 | 1160 |
| 93 | 792 | 626 | 777 | 0 | 0 | 0 | 421 | 0 | 71 | 0 | 14 | 516 | 8 | 0 | 58 |
| 101 | 1116 | 643 | 1022 | 0 | 121 | 433 | 451 | 0 | 403 | 86 | 11 | 453 | 0 | 11 | 453 |
| 107 | 700 | 580 | 403 | 294 | 1718 | 944 | 1073 | 835 | 3 | 219 | 480 | 1517 | 705 | 332 | 588 |
| 111 | 595 | 554 | 355 | 656 | 509 | 302 | 446 | 850 | 0 | 488 | 132 | 1320 | 1131 | 203 | 0 |
| 114 | 2967 | 677 | 496 | 0 | 0 | 0 | 190 | 0 | 0 | 0 | 1 | 184 | 0 | 0 | 0 |
| 115 | 614 | 625 | 570 | 0 | 0 | 0 | 145 | 0 | 55 | 0 | 1 | 16 | 0 | 1 | 58 |
| 131 | 11772 | 676 | 718 | 4 | 104 | 0 | 681 | 11 | 0 | 141 | 86 | 593 | 135 | 0 | 0 |
| 132 | 27172 | 604 | 536 | 1535 | 10311 | 1346 | 592 | 3464 | 2107 | 2112 | 326 | 4381 | 3616 | 1458 | 2008 |
| 135 | 5745 | 586 | 526 | 0 | 466 | 0 | 292 | 0 | 0 | 0 | 21 | 192 | 0 | 121 | 0 |
| 145 | 795 | 712 | 704 | 0 | 0 | 0 | 411 | 0 | 0 | 0 | 86 | 407 | 97 | 52 | 0 |
| 148 | 916 | 756 | 1108 | 0 | 0 | 0 | 312 | 2 | 0 | 19 | 89 | 853 | 0 | 37 | 0 |
| 159 | 864 | 727 | 833 | 0 | 8 | 0 | 465 | 9 | 0 | 0 | 17 | 182 | 0 | 42 | 0 |

FIG. 3 (con'd)

| Sample ID | Pathology | stage | 1st | 2nd | 3rd | Volume | Site | Site Group | Final Assay Result |
|---|---|---|---|---|---|---|---|---|---|
| Units | | | Tumor | | | cm³ | | | |
| 110 | Cancer | II | 9.1 | 5.6 | 1.8 | 91.728 | Ascending | Proximal | Pos |
| 126 | Cancer | II | 5.1 | 4.6 | 0.7 | 16.422 | Rectosigmoid (NOS) | Distal | Pos |
| 127 | Cancer | II | 5.4 | 2.7 | 0.7 | 10.206 | Sigmoid | Distal | Pos |
| 129 | Cancer | II | | | | | Rectum | Distal | Pos |
| 138 | Cancer | II | 4 | 4 | 1 | 16 | Ascending | Proximal | Pos |
| 140 | Cancer | II | 3.2 | 2 | 0.8 | 5.12 | Ascending | Proximal | Neg |
| 167 | Cancer | II | 14.5 | 9.9 | 8.2 | 1177.11 | Sigmoid | Distal | Pos |
| 170 | Cancer | II | 5.7 | 3.2 | 0.8 | 14.592 | Sigmoid | Distal | Pos |
| 174 | Cancer | II | 4 | 3.5 | 2.5 | 35 | Splenic flexure | Distal | Neg |
| 178 | Cancer | II | 3.2 | | | | Sigmoid | Distal | Pos |
| 183 | Cancer | II | 2 | 1.5 | 1 | 3 | Sigmoid | Distal | Neg |
| 184 | Cancer | II | 3.7 | 3.1 | 1.4 | 16.058 | Cecum | Proximal | Neg |
| 1 | Cancer | III | 4 | 3.5 | 2 | 28 | Sigmoid | Distal | Pos |
| 2 | Cancer | III | | | | | Rectum | Distal | Pos |
| 7 | Cancer | III | 4.3 | 3.9 | 1.1 | 18.447 | Cecum | Proximal | Pos |
| 18 | Cancer | III | 2.5 | | | | Rectum | Distal | Pos |
| 22 | Cancer | III | 1.9 | 1.5 | 0.9 | 2.565 | Transverse | Proximal | Neg |
| 36 | Cancer | III | 8.7 | 8.4 | 1.1 | 80.388 | Sigmoid | Distal | Pos |
| 39 | Cancer | III | | | | | Rectum | Distal | Pos |
| 40 | Cancer | III | 7.4 | 4.3 | 1.5 | 47.73 | Ascending | Proximal | Pos |
| 47 | Cancer | III | 5 | | | | Rectum | Distal | Pos |
| 93 | Cancer | III | 3.9 | 3.1 | 1.2 | 14.508 | Descending | Distal | Neg |
| 101 | Cancer | III | 5 | | | | Rectum | Distal | Pos |
| 107 | Cancer | III | 8 | 5.5 | 1.5 | 66 | Sigmoid | Distal | Pos |
| 111 | Cancer | III | 1.9 | 1.6 | 0.5 | 1.52 | Cecum | Proximal | Pos |
| 114 | Cancer | III | 2.1 | 1.2 | 0.6 | 1.512 | Hepatic flexure | Proximal | Pos |
| 115 | Cancer | III | 2.8 | 1.9 | 1 | 5.32 | Rectum | Distal | Neg |
| 131 | Cancer | III | 4.7 | 4.5 | 2.5 | 52.875 | Ascending | Proximal | Pos |
| 132 | Cancer | III | 3 | | | | Rectosigmoid (NOS) | Distal | Pos |
| 135 | Cancer | III | 6.5 | | | | Rectum | Distal | Pos |
| 145 | Cancer | III | | | | | Rectum | Distal | Pos |
| 148 | Cancer | III | 3.7 | 2.6 | 0.8 | 7.696 | Cecum | Proximal | Neg |
| 159 | Cancer | III | 2.8 | 2 | 1.1 | 6.16 | Transverse | Proximal | Neg |

FIG. 3 (con'd)

| Sample ID | CEA | WTZF RASSF1 | ACTB | VAV3 | ZNF671 | CHST2 | FLI1 | JAM3 | SFMBT2 | PDGFD | DTX1 | TSPYL5 | ZNF568 | GRIN2D | QKI |
|---|---|---|---|---|---|---|---|---|---|---|---|---|---|---|---|
| Units | pg/mL | | | | | | | | Strands/assay | | | | | | |
| 160 | 45578 | 665 | 604 | 0 | 0 | 0 | 247 | 0 | 0 | 0 | 34 | 3 | 0 | 0 | 0 |
| 161 | 1129 | 674 | 977 | 0 | 0 | 0 | 658 | 0 | 0 | 71 | 19 | 40 | 0 | 0 | 0 |
| 169 | 678 | 554 | 397 | 0 | 0 | 0 | 177 | 17 | 0 | 0 | 43 | 332 | 30 | 44 | 0 |
| 6 | 520 | 543 | 260 | 63 | 0 | 0 | 149 | 256 | 85 | 0 | 7 | 116 | 4 | 95 | 0 |
| 10 | 990 | 621 | 471 | 0 | 1062 | 384 | 267 | 659 | 61 | 410 | 4 | 1921 | 0 | 1594 | 0 |
| 25 | 187119 | 1023 | 9323 | 372711 | 1399080 | 415141 | 642527 | 972165 | 378417 | 287712 | 438961 | 1041077 | 65111 | 422599 | 427376 |
| 31 | 242 | 525 | 294 | 0 | 0 | 0 | 135 | 0 | 0 | 0 | 3 | 0 | 0 | 0 | 0 |
| 43 | 389987 | 947 | 7045 | 283935 | 399648 | 262779 | 408144 | 406662 | 88298 | 117424 | 43023 | 367926 | 326776 | 166188 | 261423 |
| 46 | 49195 | 728 | 1269 | 0 | 76898 | 147 | 2184 | 21206 | 0 | 0 | 60 | 92946 | 42341 | 30247 | 39004 |
| 57 | 7602 | 647 | 220 | 57 | 0 | 195 | 249 | 137 | 0 | 0 | 1 | 328 | 0 | 49 | 0 |
| 79 | 122890 | 715 | 2589 | 59092 | 103391 | 42554 | 44264 | 81022 | 18734 | 27744 | 32623 | 38965 | 77837 | 25481 | 37306 |
| 88 | 964 | 551 | 815 | 33125 | 55625 | 24320 | 21148 | 30920 | 18712 | 17742 | 24676 | 34740 | 32343 | 9437 | 15689 |
| 103 | 98511 | 834 | 5775 | 0 | 508943 | 0 | 6473 | 75 | 0 | 0 | 15 | 95574 | 15 | 91455 | 64 |
| 113 | 16681 | 740 | 1176 | 12239 | 45985 | 486 | 23953 | 21454 | 0 | 13720 | 17833 | 96867 | 7919 | 19472 | 0 |
| 118 | 614 | 709 | 549 | 858 | 4810 | 2177 | 1915 | 782 | 896 | 371 | 482 | 2786 | 900 | 599 | 1497 |
| 134 | 625 | 705 | 648 | 0 | 0 | 0 | 468 | 0 | 18 | 3 | 47 | 150 | 44 | 0 | 0 |
| 136 | 446 | 787 | 780 | 9434 | 9019 | 6838 | 4424 | 9148 | 3458 | 4766 | 3720 | 6213 | 7256 | 2864 | 2435 |
| 144 | 39517 | 1149 | 44322 | 2857951 | 4565595 | 1384663 | 723120 | 2213968 | 1348928 | 1057305 | 1004340 | 4445441 | 2705344 | 1251937 | 2512375 |
| 151 | 1199 | 600 | 217 | 7119 | 8115 | 2302 | 2843 | 3816 | 3050 | 2802 | 2638 | 4928 | 4823 | 1752 | 1815 |
| 155 | 38497 | 661 | 362 | 6867 | 24658 | 10595 | 9579 | 11916 | 9544 | 5465 | 8482 | 33813 | 9075 | 4393 | 5412 |
| 166 | 105465 | 639 | 693 | 28 | 4449 | 2799 | 2324 | 3057 | 2276 | 0 | 333 | 4295 | 1512 | 1235 | 1073 |
| 173 | 11251 | 959 | 10398 | 191298 | 827835 | 675 | 99731 | 11322 | 0 | 149558 | 257827 | 660828 | 71070 | 16082 | 204874 |
| 8 | 628 | 485 | 190 | 0 | 0 | 0 | 89 | 0 | 0 | 0 | 2 | 78 | 0 | 11 | 0 |
| 9 | 431 | 619 | 535 | 0 | 0 | 0 | 418 | 0 | 0 | 3 | 47 | 375 | 1 | 67 | 63 |
| 11 | 2529 | 554 | 239 | 0 | 0 | 0 | 292 | 0 | 0 | 0 | 62 | 140 | 0 | 1 | 0 |
| 12 | 1511 | 535 | 239 | 0 | 0 | 0 | 55 | 0 | 0 | 0 | 17 | 1515 | 0 | 0 | 0 |
| 14 | 504 | 526 | 204 | 0 | 0 | 0 | 74 | 0 | 0 | 0 | 11 | 34 | 0 | 1 | 0 |
| 15 | 1911 | 580 | 601 | 0 | 0 | 0 | 488 | 1 | 0 | 0 | 42 | 173 | 0 | 0 | 0 |
| 19 | 557 | 636 | 785 | 0 | 0 | 0 | 363 | 0 | 0 | 0 | 22 | 63 | 0 | 0 | 0 |
| 20 | 258 | 597 | 802 | 0 | 0 | 0 | 386 | 0 | 0 | 0 | 0 | 23 | 16 | 0 | 0 |
| 21 | 1998 | 534 | 409 | 0 | 0 | 0 | 182 | 0 | 0 | 0 | 37 | 50 | 0 | 0 | 0 |
| 23 | 904 | 521 | 285 | 0 | 0 | 0 | 322 | 0 | 0 | 19 | 55 | 136 | 0 | 54 | 0 |
| 26 | 385 | 534 | 403 | 0 | 0 | 0 | 128 | 0 | 0 | 0 | 6 | 86 | 0 | 98 | 0 |

FIG. 3 (con'd)

| Sample ID | Pathology | stage | Tumor 1st | 2nd | 3rd | Volume cm³ | Site | Site Group | Final Assay Result |
|---|---|---|---|---|---|---|---|---|---|
| Units | | | | | | | | | |
| 160 | Cancer | III | 2 | | | | Rectum | Distal | Pos |
| 161 | Cancer | III | 2 | 2 | 0.4 | 1.6 | Rectum | Distal | Neg |
| 169 | Cancer | III | | | | | Rectum | Distal | Neg |
| 6 | Cancer | IV | 4 | | | | Rectum | Distal | Pos |
| 10 | Cancer | IV | 5.6 | 5.1 | 4.6 | 131.376 | Cecum | Proximal | Pos |
| 25 | Cancer | IV | | | | | Sigmoid | Distal | Pos |
| 31 | Cancer | IV | 4 | | | | Rectum | Distal | Neg |
| 43 | Cancer | IV | | | | | Hepatic flexure | Proximal | Pos |
| 46 | Cancer | IV | 9 | | | | Rectum | Distal | Pos |
| 57 | Cancer | IV | 3.5 | | | | Rectum | Distal | Pos |
| 79 | Cancer | IV | 6.5 | 3.5 | 1.5 | 34.125 | Cecum | Proximal | Pos |
| 88 | Cancer | IV | 3 | | | | Ascending | Proximal | Pos |
| 103 | Cancer | IV | | | | | Rectum | Distal | Pos |
| 113 | Cancer | IV | | | | | Rectum | Distal | Pos |
| 118 | Cancer | IV | | | | | Transverse | Proximal | Pos |
| 134 | Cancer | IV | 5.5 | 5 | 3 | 82.5 | Ascending | Proximal | Pos |
| 136 | Cancer | IV | 4 | | | | Rectum | Distal | Pos |
| 144 | Cancer | IV | 7 | 3.5 | 3 | 73.5 | Ascending | Proximal | Pos |
| 151 | Cancer | IV | 3 | | | | Rectosigmoid (NOS) | Distal | Pos |
| 155 | Cancer | IV | 8 | | | | Rectum | Distal | Pos |
| 166 | Cancer | IV | 4.8 | 4.6 | 1.7 | 37.536 | Rectosigmoid (NOS) | Distal | Pos |
| 173 | Cancer | IV | 10 | | | | Sigmoid | Distal | Pos |
| 8 | Normal | N/A | N/A | N/A | N/A | N/A | N/A | N/A | Neg |
| 9 | Normal | N/A | N/A | N/A | N/A | N/A | N/A | N/A | Neg |
| 11 | Normal | N/A | N/A | N/A | N/A | N/A | N/A | N/A | Neg |
| 12 | Normal | N/A | N/A | N/A | N/A | N/A | N/A | N/A | Neg |
| 14 | Normal | N/A | N/A | N/A | N/A | N/A | N/A | N/A | Neg |
| 15 | Normal | N/A | N/A | N/A | N/A | N/A | N/A | N/A | Neg |
| 19 | Normal | N/A | N/A | N/A | N/A | N/A | N/A | N/A | Neg |
| 20 | Normal | N/A | N/A | N/A | N/A | N/A | N/A | N/A | Neg |
| 21 | Normal | N/A | N/A | N/A | N/A | N/A | N/A | N/A | Neg |
| 23 | Normal | N/A | N/A | N/A | N/A | N/A | N/A | N/A | Neg |
| 26 | Normal | N/A | N/A | N/A | N/A | N/A | N/A | N/A | Neg |

FIG. 3 (con'd)

| Sample ID | CEA | WTZF RASSF1 | ACTB | VAV3 | ZNF671 | CHST2 | FLI1 | JAM3 | SFMBT2 | PDGFD | DTX1 | TSPYL5 | ZNF568 | GRIN2D | QKI |
|---|---|---|---|---|---|---|---|---|---|---|---|---|---|---|---|
| Units | pg/mL | Strands/assay | | | | | | | | | | | | | |
| 27 | 860 | 530 | 246 | 0 | 0 | 0 | 128 | 0 | 0 | 0 | 21 | 12 | 0 | 25 | 0 |
| 28 | 1221 | 532 | 180 | 0 | 0 | 0 | 69 | 0 | 0 | 110 | 28 | 0 | 0 | 0 | 0 |
| 30 | 1761 | 767 | 806 | 0 | 0 | 0 | 299 | 0 | 0 | 0 | 31 | 97 | 28 | 0 | 0 |
| 32 | 712 | 550 | 371 | 0 | 0 | 0 | 173 | 0 | 0 | 0 | 18 | 178 | 0 | 70 | 0 |
| 33 | 5414 | 648 | 453 | 0 | 0 | 0 | 248 | 0 | 0 | 0 | 56 | 571 | 0 | 0 | 0 |
| 34 | 421 | 601 | 538 | 0 | 0 | 0 | 120 | 76 | 0 | 0 | 10 | 539 | 91 | 17 | 0 |
| 35 | 1992 | 573 | 266 | 0 | 0 | 0 | 27 | 0 | 0 | 0 | 1 | 64 | 57 | 0 | 0 |
| 37 | 951 | 963 | 6454 | 0 | 0 | 0 | 4844 | 10 | 0 | 151 | 523 | 16959 | 1310 | 399 | 221 |
| 38 | 751 | 582 | 434 | 0 | 230 | 0 | 108 | 0 | 0 | 0 | 10 | 32 | 7 | 0 | 0 |
| 41 | 1990 | 654 | 230 | 0 | 0 | 0 | 172 | 0 | 0 | 0 | 0 | 0 | 0 | 76 | 0 |
| 42 | 979 | 724 | 503 | 0 | 0 | 0 | 162 | 0 | 0 | 97 | 5 | 0 | 0 | 0 | 21 |
| 45 | 628 | 530 | 182 | 0 | 0 | 0 | 70 | 0 | 0 | 0 | 4 | 7 | 88 | 0 | 0 |
| 49 | 1310 | 615 | 428 | 0 | 0 | 0 | 224 | 0 | 0 | 54 | 56 | 131 | 13 | 17 | 0 |
| 50 | 671 | 808 | 836 | 0 | 0 | 0 | 608 | 44 | 0 | 0 | 118 | 96 | 0 | 0 | 0 |
| 51 | 459 | 745 | 514 | 0 | 0 | 0 | 99 | 0 | 0 | 0 | 22 | 39 | 0 | 0 | 0 |
| 53 | 842 | 610 | 363 | 0 | 0 | 0 | 157 | 45 | 0 | 0 | 10 | 0 | 0 | 0 | 0 |
| 54 | 545 | 679 | 508 | 0 | 0 | 0 | 161 | 0 | 0 | 0 | 75 | 57 | 0 | 17 | 0 |
| 55 | 790 | 597 | 458 | 0 | 0 | 0 | 152 | 0 | 0 | 0 | 7 | 214 | 0 | 15 | 0 |
| 56 | 1236 | 584 | 512 | 0 | 0 | 0 | 163 | 0 | 0 | 0 | 33 | 20 | 0 | 0 | 0 |
| 59 | 365 | 639 | 330 | 0 | 0 | 0 | 174 | 0 | 0 | 9 | 2 | 40 | 0 | 84 | 0 |
| 61 | 668 | 866 | 901 | 0 | 576 | 0 | 426 | 0 | 0 | 277 | 87 | 328 | 0 | 45 | 0 |
| 62 | 885 | 764 | 1147 | 0 | 0 | 0 | 380 | 9 | 0 | 3 | 9 | 179 | 0 | 0 | 0 |
| 63 | 3551 | 602 | 321 | 0 | 0 | 0 | 78 | 0 | 0 | 0 | 21 | 24 | 0 | 0 | 0 |
| 64 | 490 | 686 | 432 | 0 | 0 | 0 | 184 | 0 | 0 | 0 | 41 | 369 | 32 | 1 | 0 |
| 65 | 877 | 567 | 412 | 0 | 0 | 0 | 111 | 0 | 0 | 0 | 20 | 406 | 17 | 0 | 319 |
| 66 | 1250 | 734 | 447 | 0 | 0 | 0 | 131 | 0 | 0 | 9 | 14 | 25 | 0 | 0 | 0 |
| 67 | 719 | 738 | 1204 | 0 | 0 | 0 | 536 | 0 | 0 | 0 | 4 | 4 | 0 | 166 | 0 |
| 68 | 1715 | 625 | 699 | 0 | 0 | 0 | 262 | 0 | 0 | 0 | 26 | 173 | 0 | 0 | 0 |
| 69 | 1258 | 664 | 650 | 0 | 0 | 0 | 186 | 0 | 0 | 0 | 10 | 48 | 4 | 0 | 39 |
| 73 | 974 | 554 | 238 | 0 | 0 | 0 | 92 | 0 | 0 | 0 | 11 | 32 | 0 | 43 | 0 |
| 76 | 275 | 595 | 542 | 0 | 0 | 0 | 256 | 0 | 0 | 0 | 16 | 131 | 0 | 2 | 0 |
| 77 | 685 | 555 | 269 | 0 | 0 | 0 | 145 | 0 | 0 | 0 | 22 | 0 | 13 | 0 | 0 |
| 78 | 504 | 582 | 415 | 0 | 0 | 0 | 219 | 0 | 0 | 0 | 16 | 4 | 0 | 0 | 0 |

FIG. 3 (con'd)

| Sample ID | Pathology | stage | Tumor | | | Volume | Site | Site Group | Final Assay Result |
|---|---|---|---|---|---|---|---|---|---|
| Units | | | 1st | 2nd | 3rd | cm³ | | | |
| 27 | Normal | N/A | N/A | N/A | N/A | N/A | N/A | N/A | Neg |
| 28 | Normal | N/A | N/A | N/A | N/A | N/A | N/A | N/A | Neg |
| 30 | Normal | N/A | N/A | N/A | N/A | N/A | N/A | N/A | Neg |
| 32 | Normal | N/A | N/A | N/A | N/A | N/A | N/A | N/A | Neg |
| 33 | Normal | N/A | N/A | N/A | N/A | N/A | N/A | N/A | Pos |
| 34 | Normal | N/A | N/A | N/A | N/A | N/A | N/A | N/A | Neg |
| 35 | Normal | N/A | N/A | N/A | N/A | N/A | N/A | N/A | Neg |
| 37 | Normal | N/A | N/A | N/A | N/A | N/A | N/A | N/A | Pos |
| 38 | Normal | N/A | N/A | N/A | N/A | N/A | N/A | N/A | Pos |
| 41 | Normal | N/A | N/A | N/A | N/A | N/A | N/A | N/A | Neg |
| 42 | Normal | N/A | N/A | N/A | N/A | N/A | N/A | N/A | Neg |
| 45 | Normal | N/A | N/A | N/A | N/A | N/A | N/A | N/A | Neg |
| 49 | Normal | N/A | N/A | N/A | N/A | N/A | N/A | N/A | Neg |
| 50 | Normal | N/A | N/A | N/A | N/A | N/A | N/A | N/A | Neg |
| 51 | Normal | N/A | N/A | N/A | N/A | N/A | N/A | N/A | Neg |
| 53 | Normal | N/A | N/A | N/A | N/A | N/A | N/A | N/A | Neg |
| 54 | Normal | N/A | N/A | N/A | N/A | N/A | N/A | N/A | Neg |
| 55 | Normal | N/A | N/A | N/A | N/A | N/A | N/A | N/A | Neg |
| 56 | Normal | N/A | N/A | N/A | N/A | N/A | N/A | N/A | Neg |
| 59 | Normal | N/A | N/A | N/A | N/A | N/A | N/A | N/A | Neg |
| 61 | Normal | N/A | N/A | N/A | N/A | N/A | N/A | N/A | Neg |
| 62 | Normal | N/A | N/A | N/A | N/A | N/A | N/A | N/A | Neg |
| 63 | Normal | N/A | N/A | N/A | N/A | N/A | N/A | N/A | Neg |
| 64 | Normal | N/A | N/A | N/A | N/A | N/A | N/A | N/A | Pos |
| 65 | Normal | N/A | N/A | N/A | N/A | N/A | N/A | N/A | Neg |
| 66 | Normal | N/A | N/A | N/A | N/A | N/A | N/A | N/A | Pos |
| 67 | Normal | N/A | N/A | N/A | N/A | N/A | N/A | N/A | Neg |
| 68 | Normal | N/A | N/A | N/A | N/A | N/A | N/A | N/A | Pos |
| 69 | Normal | N/A | N/A | N/A | N/A | N/A | N/A | N/A | Neg |
| 73 | Normal | N/A | N/A | N/A | N/A | N/A | N/A | N/A | Neg |
| 76 | Normal | N/A | N/A | N/A | N/A | N/A | N/A | N/A | Neg |
| 77 | Normal | N/A | N/A | N/A | N/A | N/A | N/A | N/A | Neg |
| 78 | Normal | N/A | N/A | N/A | N/A | N/A | N/A | N/A | Neg |

FIG. 3 (con'd)

| Sample ID | CEA | WTZF RASSF1 | ACTB | VAV3 | ZNF671 | CHST2 | FLI1 | JAM3 | SFMBT2 | PDGFD | DTX1 | TSPYL5 | ZNF568 | GRIN2D | QKI |
|---|---|---|---|---|---|---|---|---|---|---|---|---|---|---|---|
| Units | pg/mL | | | | | | | Strands/assay | | | | | | | |
| 80 | 1285 | 534 | 405 | 0 | 0 | 0 | 205 | 0 | 0 | 2 | 17 | 66 | 0 | 109 | 0 |
| 81 | 602 | 586 | 309 | 0 | 0 | 0 | 85 | 0 | 0 | 0 | 14 | 367 | 0 | 0 | 0 |
| 82 | 1316 | 768 | 922 | 0 | 4898 | 0 | 310 | 0 | 0 | 0 | 16 | 384 | 0 | 48 | 0 |
| 83 | 895 | 706 | 873 | 0 | 0 | 0 | 753 | 0 | 0 | 1 | 2 | 1779 | 32 | 12 | 0 |
| 84 | 424 | 805 | 960 | 0 | 0 | 7 | 540 | 0 | 0 | 19 | 25 | 707 | 0 | 1 | 0 |
| 85 | 499 | 548 | 721 | 0 | 0 | 0 | 254 | 8 | 0 | 6 | 8 | 159 | 0 | 5 | 0 |
| 86 | 820 | 563 | 541 | 0 | 0 | 0 | 290 | 0 | 0 | 11 | 4 | 181 | 0 | 24 | 0 |
| 89 | 1158 | 657 | 670 | 0 | 0 | 0 | 277 | 1 | 0 | 16 | 47 | 0 | 0 | 4 | 0 |
| 91 | 344 | 511 | 176 | 0 | 0 | 0 | 193 | 0 | 0 | 0 | 8 | 0 | 0 | 28 | 0 |
| 92 | 619 | 536 | 349 | 0 | 0 | 0 | 185 | 0 | 0 | 0 | 7 | 178 | 0 | 0 | 0 |
| 95 | 943 | 547 | 206 | 0 | 0 | 0 | 62 | 48 | 0 | 0 | 7 | 20 | 0 | 35 | 0 |
| 98 | 2002 | 651 | 322 | 0 | 0 | 0 | 139 | 0 | 0 | 0 | 2 | 22 | 26 | 0 | 0 |
| 99 | 1735 | 527 | 244 | 0 | 0 | 0 | 51 | 0 | 0 | 0 | 0 | 69 | 0 | 6 | 0 |
| 100 | 743 | 584 | 389 | 0 | 0 | 0 | 150 | 0 | 0 | 0 | 1 | 0 | 0 | 0 | 0 |
| 105 | 923 | 599 | 292 | 0 | 0 | 0 | 89 | 9 | 0 | 0 | 1 | 51 | 0 | 3 | 77 |
| 108 | 2804 | 525 | 119 | 0 | 0 | 0 | 77 | 0 | 0 | 0 | 1 | 0 | 0 | 28 | 0 |
| 109 | 427 | 605 | 581 | 0 | 0 | 0 | 292 | 0 | 0 | 0 | 0 | 86 | 0 | 0 | 0 |
| 112 | 2117 | 649 | 406 | 0 | 0 | 0 | 334 | 4 | 0 | 88 | 8 | 164 | 0 | 59 | 0 |
| 116 | 802 | 590 | 807 | 0 | 0 | 0 | 164 | 2 | 0 | 47 | 5 | 6 | 2 | 1 | 0 |
| 117 | 586 | 582 | 343 | 0 | 0 | 0 | 77 | 0 | 0 | 0 | 1 | 5 | 0 | 0 | 0 |
| 119 | 948 | 489 | 112 | 0 | 0 | 0 | 62 | 0 | 0 | 0 | 0 | 45 | 0 | 0 | 0 |
| 121 | 649 | 739 | 670 | 0 | 1 | 0 | 1049 | 0 | 0 | 0 | 58 | 429 | 3 | 54 | 0 |
| 123 | 1156 | 577 | 399 | 0 | 0 | 0 | 146 | 0 | 0 | 0 | 1 | 71 | 8 | 0 | 0 |
| 124 | 553 | 518 | 380 | 0 | 0 | 0 | 348 | 2 | 0 | 0 | 14 | 17 | 0 | 6 | 0 |
| 125 | 1239 | 472 | 204 | 0 | 0 | 0 | 205 | 0 | 0 | 0 | 0 | 21 | 3 | 11 | 0 |
| 130 | 219 | 813 | 352 | 0 | 0 | 0 | 225 | 0 | 0 | 0 | 57 | 348 | 8 | 41 | 0 |
| 137 | 632 | 887 | 592 | 0 | 0 | 0 | 483 | 0 | 0 | 0 | 57 | 191 | 43 | 9 | 0 |
| 141 | 1102 | 658 | 522 | 0 | 0 | 0 | 531 | 0 | 0 | 0 | 24 | 475 | 0 | 0 | 0 |
| 143 | 438 | 906 | 1127 | 0 | 0 | 0 | 1390 | 0 | 0 | 0 | 5 | 2854 | 50 | 251 | 124 |
| 146 | 656 | 719 | 669 | 0 | 0 | 0 | 325 | 0 | 0 | 0 | 23 | 76 | 0 | 1 | 0 |
| 147 | 702 | 577 | 513 | 0 | 0 | 0 | 137 | 0 | 0 | 24 | 8 | 14 | 0 | 0 | 0 |
| 149 | 944 | 692 | 1117 | 0 | 0 | 0 | 227 | 33 | 0 | 75 | 40 | 134 | 0 | 80 | 0 |
| 150 | 450 | 783 | 656 | 0 | 0 | 0 | 188 | 0 | 0 | 0 | 12 | 164 | 8 | 18 | 0 |

FIG. 3 (con'd)

| Sample ID | Pathology | stage | Tumor | | | Volume | Site | Site Group | Final Assay Result |
|---|---|---|---|---|---|---|---|---|---|
| | | | 1st | 2nd | 3rd | | | | |
| Units | | | | | | cm³ | | | |
| 80 | Normal | N/A | N/A | N/A | N/A | N/A | N/A | N/A | Neg |
| 81 | Normal | N/A | N/A | N/A | N/A | N/A | N/A | N/A | Neg |
| 82 | Normal | N/A | N/A | N/A | N/A | N/A | N/A | N/A | Pos |
| 83 | Normal | N/A | N/A | N/A | N/A | N/A | N/A | N/A | Neg |
| 84 | Normal | N/A | N/A | N/A | N/A | N/A | N/A | N/A | Neg |
| 85 | Normal | N/A | N/A | N/A | N/A | N/A | N/A | N/A | Neg |
| 86 | Normal | N/A | N/A | N/A | N/A | N/A | N/A | N/A | Neg |
| 89 | Normal | N/A | N/A | N/A | N/A | N/A | N/A | N/A | Neg |
| 91 | Normal | N/A | N/A | N/A | N/A | N/A | N/A | N/A | Neg |
| 92 | Normal | N/A | N/A | N/A | N/A | N/A | N/A | N/A | Neg |
| 95 | Normal | N/A | N/A | N/A | N/A | N/A | N/A | N/A | Neg |
| 98 | Normal | N/A | N/A | N/A | N/A | N/A | N/A | N/A | Neg |
| 99 | Normal | N/A | N/A | N/A | N/A | N/A | N/A | N/A | Neg |
| 100 | Normal | N/A | N/A | N/A | N/A | N/A | N/A | N/A | Neg |
| 105 | Normal | N/A | N/A | N/A | N/A | N/A | N/A | N/A | Neg |
| 108 | Normal | N/A | N/A | N/A | N/A | N/A | N/A | N/A | Neg |
| 109 | Normal | N/A | N/A | N/A | N/A | N/A | N/A | N/A | Neg |
| 112 | Normal | N/A | N/A | N/A | N/A | N/A | N/A | N/A | Neg |
| 116 | Normal | N/A | N/A | N/A | N/A | N/A | N/A | N/A | Neg |
| 117 | Normal | N/A | N/A | N/A | N/A | N/A | N/A | N/A | Neg |
| 119 | Normal | N/A | N/A | N/A | N/A | N/A | N/A | N/A | Neg |
| 121 | Normal | N/A | N/A | N/A | N/A | N/A | N/A | N/A | Neg |
| 123 | Normal | N/A | N/A | N/A | N/A | N/A | N/A | N/A | Neg |
| 124 | Normal | N/A | N/A | N/A | N/A | N/A | N/A | N/A | Neg |
| 125 | Normal | N/A | N/A | N/A | N/A | N/A | N/A | N/A | Neg |
| 130 | Normal | N/A | N/A | N/A | N/A | N/A | N/A | N/A | Neg |
| 137 | Normal | N/A | N/A | N/A | N/A | N/A | N/A | N/A | Neg |
| 141 | Normal | N/A | N/A | N/A | N/A | N/A | N/A | N/A | Neg |
| 143 | Normal | N/A | N/A | N/A | N/A | N/A | N/A | N/A | Neg |
| 146 | Normal | N/A | N/A | N/A | N/A | N/A | N/A | N/A | Neg |
| 147 | Normal | N/A | N/A | N/A | N/A | N/A | N/A | N/A | Neg |
| 149 | Normal | N/A | N/A | N/A | N/A | N/A | N/A | N/A | Neg |
| 150 | Normal | N/A | N/A | N/A | N/A | N/A | N/A | N/A | Neg |

FIG. 3 (con'd)

| Sample ID | CEA | WTZF RASSF1 | ACTB | VAV3 | ZNF671 | CHST2 | FLI1 | JAM3 | SFMBT2 | PDGFD | DTX1 | TSPYL5 | ZNF568 | GRIN2D | QKI |
|---|---|---|---|---|---|---|---|---|---|---|---|---|---|---|---|
| Units | pg/mL | | | | | | | Strands/assay | | | | | | | |
| 152 | 1851 | 975 | 1106 | 0 | 0 | 0 | 1799 | 24 | 0 | 1 | 943 | 1528 | 293 | 12 | 0 |
| 153 | 1600 | 730 | 643 | 0 | 0 | 0 | 295 | 0 | 0 | 15 | 127 | 986 | 16 | 222 | 0 |
| 154 | 1924 | 626 | 935 | 0 | 0 | 0 | 288 | 5 | 0 | 0 | 16 | 33 | 8 | 0 | 124 |
| 156 | 968 | 784 | 315 | 0 | 0 | 0 | 100 | 0 | 0 | 0 | 23 | 452 | 0 | 0 | 0 |
| 157 | 517 | 616 | 572 | 0 | 0 | 0 | 468 | 15 | 0 | 0 | 51 | 144 | 5 | 143 | 0 |
| 162 | 1401 | 686 | 929 | 0 | 0 | 0 | 297 | 0 | 0 | 0 | 7 | 432 | 0 | 0 | 0 |
| 163 | 641 | 578 | 554 | 0 | 0 | 0 | 153 | 0 | 0 | 0 | 1 | 329 | 0 | 67 | 0 |
| 164 | 1456 | 615 | 516 | 0 | 0 | 0 | 142 | 0 | 0 | 0 | 3 | 349 | 0 | 9 | 0 |
| 165 | 749 | 689 | 698 | 0 | 0 | 0 | 140 | 48 | 0 | 45 | 3 | 16 | 0 | 36 | 0 |
| 168 | 322 | 617 | 408 | 0 | 40 | 0 | 105 | 31 | 0 | 0 | 3 | 133 | 18 | 91 | 0 |
| 172 | 1159 | 547 | 362 | 0 | 0 | 0 | 141 | 0 | 0 | 15 | 2 | 0 | 0 | 32 | 0 |
| 175 | 360 | 544 | 328 | 0 | 0 | 0 | 277 | 0 | 0 | 0 | 8 | 0 | 0 | 20 | 0 |
| 176 | 639 | 586 | 551 | 0 | 0 | 0 | 233 | 0 | 0 | 0 | 8 | 82 | 0 | 0 | 0 |
| 180 | 2296 | 720 | 1247 | 0 | 0 | 0 | 289 | 118 | 0 | 0 | 3 | 70 | 0 | 42 | 0 |
| 182 | 883 | 665 | 371 | 0 | 0 | 0 | 127 | 0 | 0 | 0 | 1 | 15 | 0 | 22 | 0 |
| 185 | 758 | 663 | 911 | 0 | 0 | 0 | 93 | 121 | 0 | 0 | 5 | 75 | 0 | 17 | 0 |
| 186 | 422 | 647 | 387 | 0 | 0 | 0 | 90 | 5 | 0 | 0 | 1 | 97 | 12 | 0 | 0 |
| 187 | 740 | 785 | 559 | 0 | 0 | 0 | 182 | 0 | 0 | 2 | 6 | 454 | 0 | 80 | 0 |
| 188 | 634 | 814 | 1385 | 0 | 0 | 0 | 187 | 0 | 0 | 0 | 3 | 394 | 0 | 0 | 16 |

FIG. 3 (con'd)

| Sample ID | Pathology | stage | 1st | 2nd | 3rd | Volume | Site | Site Group | Final Assay Result |
|---|---|---|---|---|---|---|---|---|---|
| Units | | | Tumor | | | cm³ | | | |
| 152 | Normal | N/A | N/A | N/A | N/A | N/A | N/A | N/A | Pos |
| 153 | Normal | N/A | N/A | N/A | N/A | N/A | N/A | N/A | Neg |
| 154 | Normal | N/A | N/A | N/A | N/A | N/A | N/A | N/A | Neg |
| 156 | Normal | N/A | N/A | N/A | N/A | N/A | N/A | N/A | Neg |
| 157 | Normal | N/A | N/A | N/A | N/A | N/A | N/A | N/A | Neg |
| 162 | Normal | N/A | N/A | N/A | N/A | N/A | N/A | N/A | Neg |
| 163 | Normal | N/A | N/A | N/A | N/A | N/A | N/A | N/A | Neg |
| 164 | Normal | N/A | N/A | N/A | N/A | N/A | N/A | N/A | Neg |
| 165 | Normal | N/A | N/A | N/A | N/A | N/A | N/A | N/A | Neg |
| 168 | Normal | N/A | N/A | N/A | N/A | N/A | N/A | N/A | Neg |
| 172 | Normal | N/A | N/A | N/A | N/A | N/A | N/A | N/A | Neg |
| 175 | Normal | N/A | N/A | N/A | N/A | N/A | N/A | N/A | Neg |
| 176 | Normal | N/A | N/A | N/A | N/A | N/A | N/A | N/A | Neg |
| 180 | Normal | N/A | N/A | N/A | N/A | N/A | N/A | N/A | Neg |
| 182 | Normal | N/A | N/A | N/A | N/A | N/A | N/A | N/A | Neg |
| 185 | Normal | N/A | N/A | N/A | N/A | N/A | N/A | N/A | Neg |
| 186 | Normal | N/A | N/A | N/A | N/A | N/A | N/A | N/A | Neg |
| 187 | Normal | N/A | N/A | N/A | N/A | N/A | N/A | N/A | Neg |
| 188 | Normal | N/A | N/A | N/A | N/A | N/A | N/A | N/A | Neg |

FIG. 4

| Sample ID | Pathology | VAV3>8 | ZNF671>150 | CHST2>8 | FL11>1800 | JAM3>122 | SFMBT2>8 | PDGFD>111 | DTX1>128 | TSPYL5 2 2855 | ZNF568>91 | GRIN2D>252 | QKI>222 | CEA>2804 | Final Assay Result |
|---|---|---|---|---|---|---|---|---|---|---|---|---|---|---|---|
| Units | | | | | | | Individual marker assay result > 97.5% cutoff value | | | | | | | | |
| 4 | Cancer | Neg | Neg | Pos | Neg | Neg | Neg | Neg | Neg | Neg | Neg | Neg | Neg | Neg | Pos |
| 5 | Cancer | Neg | Neg | Neg | Neg | Neg | Neg | Neg | Neg | Neg | Neg | Neg | Neg | Neg | Neg |
| 29 | Cancer | Neg | Neg | Neg | Neg | Neg | Neg | Neg | Neg | Neg | Neg | Neg | Neg | Neg | Neg |
| 52 | Cancer | Neg | Neg | Neg | Neg | Neg | Neg | Neg | Neg | Neg | Neg | Neg | Neg | Neg | Neg |
| 58 | Cancer | Neg | Neg | Neg | Neg | Neg | Neg | Neg | Neg | Neg | Neg | Neg | Neg | Neg | Neg |
| 60 | Cancer | Neg | Neg | Neg | Neg | Neg | Neg | Neg | Neg | Neg | Neg | Neg | Neg | Neg | Neg |
| 70 | Cancer | Neg | Neg | Neg | Neg | Neg | Pos | Neg | Pos | Neg | Neg | Neg | Neg | Neg | Pos |
| 72 | Cancer | Neg | Neg | Neg | Neg | Pos | Neg | Neg | Neg | Neg | Neg | Neg | Neg | Neg | Pos |
| 75 | Cancer | Pos | Pos | Pos | Neg | Pos | Pos | Neg | Pos | Neg | Pos | Pos | Pos | Pos | Pos |
| 90 | Cancer | Neg | Neg | Neg | Neg | Neg | Neg | Neg | Neg | Neg | Neg | Neg | Neg | Neg | Neg |
| 94 | Cancer | Neg | Neg | Neg | Neg | Neg | Neg | Neg | Neg | Neg | Neg | Neg | Neg | Neg | Neg |
| 102 | Cancer | Neg | Neg | Neg | Neg | Neg | Neg | Neg | Neg | Neg | Neg | Neg | Neg | Neg | Neg |
| 120 | Cancer | Neg | Neg | Neg | Neg | Neg | Neg | Neg | Neg | Neg | Neg | Neg | Neg | Pos | Neg |
| 122 | Cancer | Neg | Neg | Neg | Neg | Neg | Neg | Pos | Neg | Neg | Neg | Neg | Neg | Neg | Pos |
| 128 | Neg | Pos | Neg | Neg | Neg | Neg | Neg | Neg | Neg | Neg | Neg | Neg | Neg | Neg | Neg |
| 133 | Cancer | Neg | Neg | Neg | Neg | Neg | Neg | Neg | Neg | Neg | Neg | Neg | Neg | Neg | Neg |
| 139 | Cancer | Neg | Neg | Neg | Neg | Neg | Pos | Neg | Pos | Neg | Neg | Neg | Neg | Neg | Pos |
| 142 | Cancer | Neg | Neg | Neg | Neg | Neg | Neg | Neg | Neg | Neg | Neg | Neg | Neg | Neg | Neg |
| 158 | Cancer | Neg | Neg | Neg | Neg | Neg | Neg | Neg | Neg | Neg | Neg | Neg | Neg | Neg | Neg |
| 177 | Cancer | Neg | Neg | Neg | Neg | Neg | Neg | Neg | Neg | Neg | Pos | Neg | Neg | Neg | Pos |
| 179 | Cancer | Neg | Neg | Pos | Neg | Pos | Pos | Pos | Neg | Neg | Neg | Neg | Neg | Neg | Pos |
| 3 | Cancer | Neg | Pos | Neg | Neg | Pos | Neg | Neg | Neg | Neg | Neg | Neg | Pos | Pos | Pos |
| 13 | Cancer | Neg | Neg | Pos | Neg | Neg | Neg | Pos | Neg | Neg | Neg | Neg | Neg | Neg | Pos |
| 16 | Cancer | Neg | Pos | Neg | Neg | Pos | Neg | Pos | Neg | Neg | Neg | Neg | Neg | Neg | Pos |
| 17 | Cancer | Neg | Pos | Neg | Neg | Neg | Neg | Neg | Neg | Neg | Pos | Neg | Neg | Neg | Pos |
| 24 | Cancer | Neg | Pos | Neg | Neg | Pos | Pos | Neg | Neg | Neg | Neg | Pos | Neg | Neg | Pos |
| 44 | Cancer | Pos | Neg | Neg | Neg | Neg | Neg | Pos | Neg | Neg | Neg | Neg | Neg | Neg | Pos |
| 48 | Cancer | Neg | Neg | Neg | Neg | Neg | Neg | Neg | Pos | Neg | Neg | Neg | Neg | Neg | Pos |
| 71 | Cancer | Neg | Neg | Pos | Neg | Neg | Neg | Neg | Neg | Neg | Neg | Neg | Neg | Pos | Pos |
| 74 | Cancer | Neg | Neg | Neg | Neg | Neg | Neg | Neg | Pos | Neg | Neg | Pos | Neg | Neg | Pos |
| 87 | Cancer | Neg | Neg | Neg | Neg | Neg | Neg | Neg | Neg | Neg | Neg | Neg | Neg | Neg | Neg |
| 96 | Cancer | Neg | Pos | Neg | Neg | Pos | Pos | Neg | Pos | Neg | Neg | Pos | Neg | Neg | Pos |
| 104 | Cancer | Neg | Neg | Neg | Neg | Neg | Neg | Neg | Neg | Neg | Pos | Neg | Neg | Neg | Pos |
| 106 | Cancer | Neg | Neg | Neg | Neg | Neg | Neg | Neg | Neg | Pos | Neg | Neg | Neg | Neg | Pos |
| 110 | Cancer | Pos | Pos | Neg | Neg | Pos | Pos | Pos | Neg | Neg | Pos | Neg | Neg | Neg | Pos |
| 126 | Cancer | Neg | Neg | Neg | Neg | Neg | Neg | Neg | Pos | Neg | Neg | Neg | Pos | Neg | Pos |
| 127 | Cancer | Neg | Pos | Neg | Neg | Neg | Pos | Neg | Pos | Neg | Pos | Pos | Neg | Neg | Pos |
| 129 | Cancer | Pos | Pos | Pos | Neg | Pos | Pos | Neg | Pos | Neg | Pos | Neg | Neg | Neg | Pos |
| 138 | Cancer | Neg | Neg | Neg | Pos | Neg | Neg | Neg | Neg | Pos | Pos | Pos | Neg | Neg | Pos |
| 140 | Cancer | Neg | Neg | Neg | Neg | Neg | Neg | Pos | Pos | Neg | Pos | Neg | Neg | Pos | Pos |
| 167 | Cancer | Neg | Neg | Neg | Neg | Neg | Neg | Neg | Neg | Neg | Neg | Neg | Pos | Neg | Pos |
| 170 | Cancer | Neg | Neg | Pos | Neg | Neg | Pos | Neg | Neg | Neg | Neg | Neg | Neg | Neg | Pos |
| 174 | Cancer | Neg | Neg | Neg | Neg | Neg | Neg | Neg | Neg | Neg | Neg | Pos | Neg | Pos | Pos |
| 178 | Cancer | Pos | Neg | Neg | Neg | Neg | Neg | Neg | Neg | Neg | Neg | Neg | Neg | Neg | Neg |
| 183 | Cancer | Neg | Neg | Neg | Neg | Neg | Neg | Neg | Neg | Neg | Neg | Neg | Neg | Neg | Neg |

FIG. 4 (cont'd)

| Sample ID | Pathology | VAV3>8 | ZNF671>150 | CHST2>8 | FLI1>1800 | JAM3>122 | SFMBT2>8 | PDGFD>111 | DTX1>128 | TSPYL5 2 2855 | ZNF568>91 | GRIN2D>252 | OKI>222 | CEA>2804 | Final Assay Result |
|---|---|---|---|---|---|---|---|---|---|---|---|---|---|---|---|
| Units | | | | | | | Individual marker assay result > 97.5% cutoff value | | | | | | | | |
| 184 | Cancer | Neg | Neg | Neg | Neg | Neg | Neg | Neg | Neg | Neg | Neg | Neg | Neg | Neg | Neg |
| 1 | Cancer | Neg | Pos | Neg | Neg | Neg | Neg | Neg | Pos | Neg | Neg | Pos | Neg | Neg | Pos |
| 2 | Cancer | Neg | Neg | Neg | Neg | Neg | Neg | Neg | Neg | Neg | Neg | Neg | Neg | Pos | Pos |
| 7 | Cancer | Neg | Neg | Neg | Neg | Neg | Neg | Pos | Neg | Neg | Neg | Pos | Neg | Neg | Pos |
| 18 | Cancer | Neg | Neg | Neg | Pos | Neg | Neg | Neg | Neg | Pos | Neg | Pos | Pos | Neg | Pos |
| 22 | Cancer | Neg | Neg | Neg | Neg | Neg | Pos | Neg | Neg | Neg | Neg | Neg | Neg | Neg | Neg |
| 36 | Cancer | Neg | Neg | Neg | Neg | Neg | Pos | Neg | Neg | Neg | Neg | Neg | Neg | Pos | Pos |
| 39 | Cancer | Pos | Pos | Pos | Pos | Pos | Pos | Pos | Pos | Pos | Pos | Pos | Pos | Pos | Pos |
| 40 | Cancer | Neg | Neg | Neg | Neg | Neg | Neg | Neg | Neg | Neg | Pos | Neg | Pos | Neg | Pos |
| 47 | Cancer | Pos | Pos | Pos | Neg | Pos | Neg | Pos | Neg | Neg | Pos | Pos | Pos | Neg | Pos |
| 93 | Cancer | Neg | Neg | Neg | Neg | Neg | Neg | Neg | Neg | Neg | Neg | Neg | Neg | Neg | Neg |
| 101 | Cancer | Neg | Neg | Pos | Neg | Neg | Pos | Pos | Neg | Neg | Neg | Neg | Neg | Neg | Pos |
| 107 | Cancer | Neg | Pos | Pos | Neg | Neg | Neg | Neg | Pos | Neg | Pos | Pos | Pos | Neg | Pos |
| 111 | Cancer | Pos | Pos | Pos | Neg | Pos | Neg | Neg | Pos | Neg | Pos | Neg | Pos | Pos | Pos |
| 114 | Cancer | Neg | Neg | Neg | Neg | Neg | Neg | Neg | Neg | Neg | Neg | Neg | Neg | Neg | Neg |
| 115 | Cancer | Neg | Neg | Neg | Neg | Neg | Neg | Neg | Neg | Neg | Neg | Neg | Neg | Neg | Neg |
| 131 | Cancer | Neg | Neg | Pos | Neg | Neg | Pos | Pos | Neg | Neg | Neg | Neg | Neg | Neg | Pos |
| 132 | Cancer | Pos | Pos | Pos | Neg | Neg | Neg | Neg | Neg | Neg | Pos | Neg | Neg | Pos | Pos |
| 135 | Cancer | Neg | Neg | Neg | Neg | Neg | Neg | Neg | Neg | Neg | Neg | Neg | Pos | Neg | Pos |
| 145 | Cancer | Neg | Neg | Neg | Neg | Neg | Neg | Neg | Neg | Neg | Neg | Neg | Neg | Neg | Neg |
| 148 | Cancer | Neg | Neg | Neg | Neg | Neg | Neg | Neg | Neg | Pos | Neg | Neg | Neg | Neg | Neg |
| 159 | Cancer | Neg | Neg | Neg | Neg | Neg | Neg | Neg | Neg | Neg | Neg | Pos | Neg | Neg | Pos |
| 160 | Cancer | Neg | Neg | Neg | Neg | Neg | Neg | Neg | Neg | Neg | Neg | Neg | Neg | Pos | Pos |
| 161 | Cancer | Neg | Neg | Neg | Neg | Neg | Neg | Neg | Neg | Neg | Neg | Neg | Neg | Neg | Neg |
| 169 | Cancer | Neg | Neg | Neg | Neg | Neg | Neg | Neg | Neg | Neg | Pos | Neg | Neg | Neg | Neg |
| 6 | Cancer | Pos | Neg | Neg | Neg | Pos | Pos | Pos | Neg | Pos | Neg | Neg | Neg | Neg | Pos |
| 10 | Cancer | Neg | Pos | Pos | Pos | Pos | Neg | Neg | Neg | Neg | Neg | Neg | Neg | Neg | Pos |
| 25 | Cancer | Pos | Pos | Pos | Pos | Pos | Neg | Pos | Pos | Neg | Neg | Pos | Pos | Pos | Pos |
| 31 | Cancer | Neg | Neg | Neg | Neg | Neg | Neg | Neg | Neg | Neg | Neg | Neg | Neg | Neg | Neg |
| 43 | Cancer | Pos | Pos | Pos | Pos | Neg | Neg | Neg | Neg | Pos | Neg | Pos | Pos | Pos | Pos |
| 46 | Cancer | Neg | Neg | Neg | Neg | Pos | Neg | Neg | Neg | Pos | Neg | Pos | Pos | Pos | Pos |
| 57 | Cancer | Pos | Neg | Pos | Pos | Pos | Pos | Neg | Neg | Neg | Neg | Neg | Neg | Neg | Pos |
| 79 | Cancer | Pos | Pos | Pos | Neg | Pos | Pos | Pos | Pos | Neg | Pos | Neg | Pos | Pos | Pos |
| 88 | Cancer | Pos | Pos | Pos | Pos | Pos | Pos | Neg | Pos | Pos | Pos | Pos | Pos | Neg | Pos |
| 103 | Cancer | Neg | Neg | Neg | Neg | Neg | Neg | Neg | Neg | Neg | Neg | Pos | Neg | Pos | Pos |
| 113 | Cancer | Pos | Pos | Pos | Pos | Pos | Neg | Pos | Neg | Pos | Pos | Neg | Neg | Pos | Pos |
| 118 | Cancer | Pos | Neg | Neg | Neg | Neg | Pos | Neg | Pos | Neg | Pos | Pos | Pos | Neg | Pos |
| 134 | Cancer | Neg | Pos | Neg | Neg | Neg | Neg | Neg | Neg | Neg | Pos | Neg | Neg | Neg | Neg |
| 136 | Cancer | Pos | Pos | Pos | Neg | Pos | Pos | Neg | Neg | Pos | Pos | Pos | Neg | Neg | Pos |
| 144 | Cancer | Pos | Pos | Pos | Neg | Pos | Pos | Pos | Pos | Neg | Pos | Pos | Pos | Pos | Pos |
| 151 | Cancer | Neg | Neg | Neg | Pos | Pos | Pos | Pos | Pos | Neg | Pos | Neg | Pos | Neg | Pos |
| 155 | Cancer | Pos | Pos | Pos | Pos | Pos | Pos | Neg | Pos | Pos | Pos | Pos | Pos | Neg | Pos |
| 166 | Cancer | Pos | Pos | Pos | Pos | Pos | Pos | Neg | Pos | Pos | Pos | Pos | Pos | Pos | Pos |

FIG. 4 (cont'd)

| Sample ID | Pathology | VAV3>8 | ZNF671>150 | CHST2>8 | FLI1>1800 | JAM3>122 | SFMBT2>8 | PDGFD>111 | DTX1>128 | TSPYL5 2 2855 | ZNF568>91 | GRIN2D>252 | QKI>222 | CEA>2804 | Final Assay Result |
|---|---|---|---|---|---|---|---|---|---|---|---|---|---|---|---|
| Units | | | | | | | Individual marker assay result > 97.5% cutoff value | | | | | | | | |
| 173 | Cancer | Pos | Pos | Pos | Pos | Pos | Neg | Pos | Pos | Pos | Pos | Pos | Pos | Pos | Pos |
| 8 | Normal | Neg | Neg | Neg | Neg | Neg | Neg | Neg | Neg | Neg | Neg | Neg | Neg | Neg | Neg |
| 9 | Normal | Neg | Neg | Neg | Neg | Neg | Neg | Neg | Neg | Neg | Neg | Neg | Neg | Neg | Neg |
| 11 | Normal | Neg | Neg | Neg | Neg | Neg | Neg | Neg | Neg | Neg | Neg | Neg | Neg | Neg | Neg |
| 12 | Normal | Neg | Neg | Neg | Neg | Neg | Neg | Neg | Neg | Neg | Neg | Neg | Neg | Neg | Neg |
| 14 | Normal | Neg | Neg | Neg | Neg | Neg | Neg | Neg | Neg | Neg | Neg | Neg | Neg | Neg | Neg |
| 15 | Normal | Neg | Neg | Neg | Neg | Neg | Neg | Neg | Neg | Neg | Neg | Neg | Neg | Neg | Neg |
| 19 | Normal | Neg | Neg | Neg | Neg | Neg | Neg | Neg | Neg | Neg | Neg | Neg | Neg | Neg | Neg |
| 20 | Normal | Neg | Neg | Neg | Neg | Neg | Neg | Neg | Neg | Neg | Neg | Neg | Neg | Neg | Neg |
| 21 | Normal | Neg | Neg | Neg | Neg | Neg | Neg | Neg | Neg | Neg | Neg | Neg | Neg | Neg | Neg |
| 23 | Normal | Neg | Neg | Neg | Neg | Neg | Neg | Neg | Neg | Neg | Neg | Neg | Neg | Neg | Neg |
| 26 | Normal | Neg | Neg | Neg | Neg | Neg | Neg | Neg | Neg | Neg | Neg | Neg | Neg | Neg | Neg |
| 27 | Normal | Neg | Neg | Neg | Neg | Neg | Neg | Neg | Neg | Neg | Neg | Neg | Neg | Neg | Neg |
| 28 | Normal | Neg | Neg | Neg | Neg | Neg | Neg | Neg | Neg | Neg | Neg | Neg | Neg | Neg | Neg |
| 30 | Normal | Neg | Neg | Neg | Neg | Neg | Neg | Neg | Neg | Neg | Neg | Neg | Neg | Neg | Neg |
| 32 | Normal | Neg | Neg | Neg | Neg | Neg | Neg | Neg | Neg | Neg | Neg | Neg | Neg | Neg | Neg |
| 33 | Normal | Neg | Neg | Neg | Neg | Neg | Neg | Neg | Neg | Neg | Neg | Neg | Neg | Pos | Pos |
| 34 | Normal | Neg | Neg | Neg | Neg | Neg | Neg | Neg | Neg | Neg | Neg | Neg | Neg | Neg | Neg |
| 35 | Normal | Neg | Neg | Neg | Neg | Neg | Neg | Neg | Neg | Neg | Neg | Neg | Neg | Neg | Neg |
| 37 | Normal | Neg | Neg | Neg | Pos | Neg | Neg | Pos | Pos | Pos | Neg | Pos | Neg | Neg | Pos |
| 38 | Normal | Neg | Pos | Neg | Neg | Neg | Neg | Neg | Neg | Neg | Neg | Neg | Neg | Neg | Pos |
| 41 | Normal | Neg | Neg | Neg | Neg | Neg | Neg | Neg | Neg | Neg | Neg | Neg | Neg | Neg | Neg |
| 42 | Normal | Neg | Neg | Neg | Neg | Neg | Neg | Neg | Neg | Neg | Neg | Neg | Neg | Neg | Neg |
| 45 | Normal | Neg | Neg | Neg | Neg | Neg | Neg | Neg | Neg | Neg | Neg | Neg | Neg | Neg | Neg |
| 49 | Normal | Neg | Neg | Neg | Neg | Neg | Neg | Pos | Neg | Neg | Neg | Neg | Neg | Neg | Pos |
| 50 | Normal | Neg | Neg | Neg | Neg | Neg | Neg | Neg | Neg | Neg | Neg | Neg | Neg | Neg | Neg |
| 51 | Normal | Neg | Neg | Neg | Neg | Neg | Neg | Neg | Neg | Neg | Neg | Neg | Neg | Neg | Neg |
| 53 | Normal | Neg | Neg | Neg | Neg | Neg | Neg | Neg | Neg | Neg | Neg | Neg | Neg | Neg | Neg |
| 54 | Normal | Neg | Neg | Neg | Neg | Neg | Neg | Neg | Neg | Neg | Neg | Neg | Neg | Neg | Neg |
| 55 | Normal | Neg | Neg | Neg | Neg | Neg | Neg | Neg | Neg | Neg | Neg | Neg | Neg | Neg | Neg |
| 56 | Normal | Neg | Neg | Neg | Neg | Neg | Neg | Neg | Neg | Neg | Neg | Neg | Neg | Neg | Neg |
| 59 | Normal | Neg | Neg | Neg | Neg | Neg | Neg | Neg | Neg | Neg | Neg | Neg | Neg | Neg | Neg |
| 61 | Normal | Neg | Neg | Neg | Neg | Neg | Neg | Neg | Neg | Neg | Neg | Neg | Neg | Neg | Neg |
| 62 | Normal | Neg | Neg | Neg | Neg | Neg | Neg | Neg | Neg | Neg | Neg | Neg | Neg | Neg | Neg |
| 63 | Normal | Neg | Neg | Neg | Neg | Neg | Neg | Neg | Neg | Neg | Neg | Neg | Neg | Pos | Pos |
| 64 | Normal | Neg | Neg | Neg | Neg | Neg | Neg | Neg | Neg | Neg | Neg | Neg | Neg | Neg | Neg |
| 65 | Normal | Neg | Neg | Neg | Neg | Neg | Neg | Neg | Neg | Neg | Neg | Neg | Pos | Neg | Pos |
| 66 | Normal | Neg | Neg | Neg | Neg | Neg | Neg | Neg | Neg | Neg | Neg | Neg | Neg | Neg | Neg |
| 67 | Normal | Neg | Pos | Neg | Neg | Neg | Neg | Pos | Neg | Neg | Neg | Neg | Neg | Neg | Pos |
| 68 | Normal | Neg | Neg | Neg | Neg | Neg | Neg | Neg | Neg | Neg | Neg | Neg | Neg | Neg | Neg |
| 69 | Normal | Neg | Neg | Neg | Neg | Neg | Neg | Neg | Neg | Neg | Neg | Neg | Neg | Neg | Neg |
| 73 | Normal | Neg | Neg | Neg | Neg | Neg | Neg | Neg | Neg | Neg | Neg | Neg | Neg | Neg | Neg |
| 76 | Normal | Neg | Neg | Neg | Neg | Neg | Neg | Neg | Neg | Neg | Neg | Neg | Neg | Neg | Neg |

FIG. 4 (cont'd)

| Sample ID | Pathology | VAV3>8 | ZNF671>150 | CHST2>8 | FL11>1800 | JAM3>122 | SFMBT2>8 | PDGFD>111 | DTX1>128 | TSPYL5_2_2855 | ZNF568>91 | GRIN2D>252 | OKI>222 | CEA>2804 | Final Assay Result |
|---|---|---|---|---|---|---|---|---|---|---|---|---|---|---|---|
| Units | | | | | | | Individual marker assay result > 97.5% cutoff value | | | | | | | | |
| 77 | Normal | Neg | Neg | Neg | Neg | Neg | Neg | Neg | Neg | Neg | Neg | Neg | Neg | Neg | Neg |
| 78 | Normal | Neg | Neg | Neg | Neg | Neg | Neg | Neg | Neg | Neg | Neg | Neg | Neg | Neg | Neg |
| 80 | Normal | Neg | Neg | Neg | Neg | Neg | Neg | Neg | Neg | Neg | Neg | Neg | Neg | Neg | Neg |
| 81 | Normal | Neg | Neg | Neg | Neg | Neg | Neg | Neg | Neg | Neg | Neg | Neg | Neg | Neg | Neg |
| 82 | Normal | Neg | Pos | Neg | Neg | Neg | Neg | Neg | Neg | Neg | Neg | Neg | Neg | Neg | Pos |
| 83 | Normal | Neg | Neg | Neg | Neg | Neg | Neg | Neg | Neg | Neg | Neg | Neg | Neg | Neg | Neg |
| 84 | Normal | Neg | Neg | Neg | Neg | Neg | Neg | Neg | Neg | Neg | Neg | Neg | Neg | Neg | Neg |
| 85 | Normal | Neg | Neg | Neg | Neg | Neg | Neg | Neg | Neg | Neg | Neg | Neg | Neg | Neg | Neg |
| 86 | Normal | Neg | Neg | Neg | Neg | Neg | Neg | Neg | Neg | Neg | Neg | Neg | Neg | Neg | Neg |
| 89 | Normal | Neg | Neg | Neg | Neg | Neg | Neg | Neg | Neg | Neg | Neg | Neg | Neg | Neg | Neg |
| 91 | Normal | Neg | Neg | Neg | Neg | Neg | Neg | Neg | Neg | Neg | Neg | Neg | Neg | Neg | Neg |
| 92 | Normal | Neg | Neg | Neg | Neg | Neg | Neg | Neg | Neg | Neg | Neg | Neg | Neg | Neg | Neg |
| 95 | Normal | Neg | Neg | Neg | Neg | Neg | Neg | Neg | Neg | Neg | Neg | Neg | Neg | Neg | Neg |
| 98 | Normal | Neg | Neg | Neg | Neg | Neg | Neg | Neg | Neg | Neg | Neg | Neg | Neg | Neg | Neg |
| 99 | Normal | Neg | Neg | Neg | Neg | Neg | Neg | Neg | Neg | Neg | Neg | Neg | Neg | Neg | Neg |
| 100 | Normal | Neg | Neg | Neg | Neg | Neg | Neg | Neg | Neg | Neg | Neg | Neg | Neg | Neg | Neg |
| 105 | Normal | Neg | Neg | Neg | Neg | Neg | Neg | Neg | Neg | Neg | Neg | Neg | Neg | Neg | Neg |
| 108 | Normal | Neg | Neg | Neg | Neg | Neg | Neg | Neg | Neg | Neg | Neg | Neg | Neg | Neg | Neg |
| 109 | Normal | Neg | Neg | Neg | Neg | Neg | Neg | Neg | Neg | Neg | Neg | Neg | Neg | Neg | Neg |
| 112 | Normal | Neg | Neg | Neg | Neg | Neg | Neg | Neg | Neg | Neg | Neg | Neg | Neg | Neg | Neg |
| 116 | Normal | Neg | Neg | Neg | Neg | Neg | Neg | Neg | Neg | Neg | Neg | Neg | Neg | Neg | Neg |
| 117 | Normal | Neg | Neg | Neg | Neg | Neg | Neg | Neg | Neg | Neg | Neg | Neg | Neg | Neg | Neg |
| 119 | Normal | Neg | Neg | Neg | Neg | Neg | Neg | Neg | Neg | Neg | Neg | Neg | Neg | Neg | Neg |
| 121 | Normal | Neg | Neg | Neg | Neg | Neg | Neg | Neg | Neg | Neg | Neg | Neg | Neg | Neg | Neg |
| 123 | Normal | Neg | Neg | Neg | Neg | Neg | Neg | Neg | Neg | Neg | Neg | Neg | Neg | Neg | Neg |
| 124 | Normal | Neg | Neg | Neg | Neg | Neg | Neg | Neg | Neg | Neg | Neg | Neg | Neg | Neg | Neg |
| 125 | Normal | Neg | Neg | Neg | Neg | Neg | Neg | Neg | Neg | Neg | Neg | Neg | Neg | Neg | Neg |
| 130 | Normal | Neg | Neg | Neg | Neg | Neg | Neg | Neg | Neg | Neg | Neg | Neg | Neg | Neg | Neg |
| 137 | Normal | Neg | Neg | Neg | Neg | Neg | Neg | Neg | Neg | Neg | Neg | Neg | Neg | Neg | Neg |
| 141 | Normal | Neg | Neg | Neg | Neg | Neg | Neg | Neg | Neg | Neg | Neg | Neg | Neg | Neg | Neg |
| 143 | Normal | Neg | Neg | Neg | Neg | Neg | Neg | Neg | Neg | Neg | Neg | Neg | Neg | Neg | Neg |
| 146 | Normal | Neg | Neg | Neg | Neg | Neg | Neg | Neg | Neg | Neg | Neg | Neg | Neg | Neg | Neg |
| 147 | Normal | Neg | Neg | Neg | Neg | Neg | Neg | Neg | Neg | Neg | Neg | Neg | Neg | Neg | Neg |
| 149 | Normal | Neg | Neg | Neg | Neg | Neg | Neg | Neg | Neg | Neg | Neg | Neg | Neg | Neg | Neg |
| 150 | Normal | Neg | Neg | Neg | Neg | Neg | Neg | Neg | Neg | Neg | Neg | Neg | Neg | Neg | Neg |
| 152 | Normal | Neg | Neg | Neg | Neg | Neg | Neg | Neg | Pos | Neg | Pos | Neg | Neg | Neg | Pos |
| 153 | Normal | Neg | Neg | Neg | Neg | Neg | Neg | Neg | Neg | Neg | Neg | Neg | Neg | Neg | Neg |
| 154 | Normal | Neg | Neg | Neg | Neg | Neg | Neg | Neg | Neg | Neg | Neg | Neg | Neg | Neg | Pos |
| 156 | Normal | Neg | Neg | Neg | Neg | Neg | Neg | Neg | Neg | Neg | Neg | Neg | Neg | Neg | Neg |
| 157 | Normal | Neg | Neg | Neg | Neg | Neg | Neg | Neg | Neg | Neg | Neg | Neg | Neg | Neg | Neg |
| 162 | Normal | Neg | Neg | Neg | Neg | Neg | Neg | Neg | Neg | Neg | Neg | Neg | Neg | Neg | Neg |
| 163 | Normal | Neg | Neg | Neg | Neg | Neg | Neg | Neg | Neg | Neg | Neg | Neg | Neg | Neg | Neg |
| 164 | Normal | Neg | Neg | Neg | Neg | Neg | Neg | Neg | Neg | Neg | Neg | Neg | Neg | Neg | Neg |

FIG. 4 (cont'd)

| Sample ID | Pathology | VAV3>8 | ZNF671>150 | CHST2>8 | FLI1>1800 | JAM3>122 | SFMBT2>8 | PDGFD>111 | DTX1>128 | TSPYL5 2 2855 | ZNF568>91 | GRIN2D>252 | QKI>222 | CEA>2804 | Final Assay Result |
|---|---|---|---|---|---|---|---|---|---|---|---|---|---|---|---|
| Units | | | | | | | Individual marker assay result > 97.5% cutoff value | | | | | | | | |
| 165 | Normal | Neg | Neg | Neg | Neg | Neg | Neg | Neg | Neg | Neg | Neg | Neg | Neg | Neg | Neg |
| 168 | Normal | Neg | Neg | Neg | Neg | Neg | Neg | Neg | Neg | Neg | Neg | Neg | Neg | Neg | Neg |
| 172 | Normal | Neg | Neg | Neg | Neg | Neg | Neg | Neg | Neg | Neg | Neg | Neg | Neg | Neg | Neg |
| 175 | Normal | Neg | Neg | Neg | Neg | Neg | Neg | Neg | Neg | Neg | Neg | Neg | Neg | Neg | Neg |
| 176 | Normal | Neg | Neg | Neg | Neg | Neg | Neg | Neg | Neg | Neg | Neg | Neg | Neg | Neg | Neg |
| 180 | Normal | Neg | Neg | Neg | Neg | Neg | Neg | Neg | Neg | Neg | Neg | Neg | Neg | Neg | Neg |
| 182 | Normal | Neg | Neg | Neg | Neg | Neg | Neg | Neg | Neg | Neg | Neg | Neg | Neg | Neg | Neg |
| 185 | Normal | Neg | Neg | Neg | Neg | Neg | Neg | Neg | Neg | Neg | Neg | Neg | Neg | Neg | Neg |
| 186 | Normal | Neg | Neg | Neg | Neg | Neg | Neg | Neg | Neg | Neg | Neg | Neg | Neg | Neg | Neg |
| 187 | Normal | Neg | Neg | Neg | Neg | Neg | Neg | Neg | Neg | Neg | Neg | Neg | Neg | Neg | Neg |
| 188 | Normal | Neg | Neg | Neg | Neg | Neg | Neg | Neg | Neg | Neg | Neg | Neg | Neg | Neg | Neg |

SEQUENCE LISTING

```
<160> NUMBER OF SEQ ID NOS: 182

<210> SEQ ID NO 1
<211> LENGTH: 109
<212> TYPE: DNA
<213> ORGANISM: Homo sapiens

<400> SEQUENCE: 1
ggagctacga cgagcagctg cggctggcga tggaactgtc ggcgcaggag caggaggaga      60
ggcggcggcg cgcgcgccag gaggaggagg agctggagcg catcctgag               109

<210> SEQ ID NO 2
<211> LENGTH: 109
<212> TYPE: DNA
<213> ORGANISM: Artificial sequence
<220> FEATURE:
<223> OTHER INFORMATION: Synthetic

<400> SEQUENCE: 2
ggagttacga cgagtagttg cggttggcga tggaattgtc ggcgtaggag taggaggaga      60
ggcggcggcg cgcgcgttag gaggaggagg agttggagcg tattttgag                109

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
agttacgacg agtagttgcg                                                  20

<210> SEQ ID NO 4
<211> LENGTH: 18
<212> TYPE: DNA
<213> ORGANISM: Artificial sequence
```

```
<220> FEATURE:
<223> OTHER INFORMATION: Synthetic

<400> SEQUENCE: 4
tcctcctact cctacgcc                                                 18

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
ccacggacgc gacaattcca t                                             21

<210> SEQ ID NO 6
<211> LENGTH: 139
<212> TYPE: DNA
<213> ORGANISM: Homo sapiens

<400> SEQUENCE: 6
ggccacacag gcccactctg gccctctgag ccccggcgg acccagggca ttcaaggagc    60
ggctctgggc tgccagcgca ggcctccgcg caaacacagc aggctggaag tggcgctcat  120
caccggcacg tcttcccag                                               139

<210> SEQ ID NO 7
<211> LENGTH: 139
<212> TYPE: DNA
<213> ORGANISM: Artificial sequence
<220> FEATURE:
<223> OTHER INFORMATION: Synthetic

<400> SEQUENCE: 7
ggttatatag gtttattttg gttttttgag ttttcggcgg atttagggta tttaaggagc   60
ggttttgggt tgttagcgta ggttttcgcg taaatatagt aggttggaag tggcgtttat  120
tatcggtacg tttttttag                                               139

<210> SEQ ID NO 8
<211> LENGTH: 28
<212> TYPE: DNA
<213> ORGANISM: Artificial sequence
<220> FEATURE:
<223> OTHER INFORMATION: Synthetic

<400> SEQUENCE: 8
ggtttatttt ggtttttga gttttcgg                                       28

<210> SEQ ID NO 9
<211> LENGTH: 24
<212> TYPE: DNA
<213> ORGANISM: Artificial sequence
<220> FEATURE:
<223> OTHER INFORMATION: Synthetic

<400> SEQUENCE: 9
tccaacctac tatatttacg cgaa                                          24

<210> SEQ ID NO 10
<211> LENGTH: 21
<212> TYPE: DNA
<213> ORGANISM: Artificial sequence
<220> FEATURE:
```

<223> OTHER INFORMATION: Synthetic

<400> SEQUENCE: 10
ccacggacgg cggatttagg g                                          21

<210> SEQ ID NO 11
<211> LENGTH: 154
<212> TYPE: DNA
<213> ORGANISM: Homo sapiens

<400> SEQUENCE: 11
cgctttcggc ctccgtgcgg cgaattttcc cacctctctg gcagcggtgg atggggcaca    60
gcgcgacccc gcagcggcgg cggcggctgc ttccatcacc gggaggatgc ccgggcggac   120
agcgcaggca accccccgccg ctccgcagcc tccg                             154

<210> SEQ ID NO 12
<211> LENGTH: 97
<212> TYPE: DNA
<213> ORGANISM: Artificial sequence
<220> FEATURE:
<223> OTHER INFORMATION: Synthetic

<400> SEQUENCE: 12
gcggtggatg gggtatagcg cgatttcgta gcggcggcgg cggttgtttt tattatcggg    60
aggatgttcg ggcggatagc gtaggtaatt ttcgtcg                            97

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
gtatagcgcg atttcgtagc g                                          21

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
aattacctac gctatccgcc c                                          21

<210> SEQ ID NO 15
<211> LENGTH: 21
<212> TYPE: DNA
<213> ORGANISM: Artificial sequence
<220> FEATURE:
<223> OTHER INFORMATION: Synthetic

<400> SEQUENCE: 15
ccacggacgc gaacatcctc c                                          21

<210> SEQ ID NO 16
<211> LENGTH: 110
<212> TYPE: DNA
<213> ORGANISM: Homo sapiens

<400> SEQUENCE: 16
ctgcacccag cgcagctgca cgtgatactg caggaagccg agcgagagct ggagggagga    60

```
ggagccggag ctgggaaccc agccgcaggc aggtcaccac gtgtacgccc            110

<210> SEQ ID NO 17
<211> LENGTH: 110
<212> TYPE: DNA
<213> ORGANISM: Artificial sequence
<220> FEATURE:
<223> OTHER INFORMATION: Synthetic

<400> SEQUENCE: 17
ttgtatttag cgtagttgta cgtgatattg taggaagtcg agcgagagtt ggagggagga   60
ggagtcggag ttgggaattt agtcgtaggt aggttattac gtgtacgttt            110

<210> SEQ ID NO 18
<211> LENGTH: 26
<212> TYPE: DNA
<213> ORGANISM: Artificial sequence
<220> FEATURE:
<223> OTHER INFORMATION: Synthetic

<400> SEQUENCE: 18
cgtagttgta cgtgatattg taggaa                                       26

<210> SEQ ID NO 19
<211> LENGTH: 22
<212> TYPE: DNA
<213> ORGANISM: Artificial sequence
<220> FEATURE:
<223> OTHER INFORMATION: Synthetic

<400> SEQUENCE: 19
gactaaattc ccaactccga ct                                           22

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
ccacggacga gtcgagcgag a                                            21

<210> SEQ ID NO 21
<211> LENGTH: 85
<212> TYPE: DNA
<213> ORGANISM: Homo sapiens

<400> SEQUENCE: 21 gccggcccg cagcatcctc ctgctcgcgg ctctcccgcc acctgtcccg ctccctgccg   60
cgccctgggg cccgcaccta cccac                                        85

<210> SEQ ID NO 22
<211> LENGTH: 85
<212> TYPE: DNA
<213> ORGANISM: Artificial sequence
<220> FEATURE:
<223> OTHER INFORMATION: Synthetic

<400> SEQUENCE: 22
gtcggtttcg tagtatttt ttgttcgcgg ttttttcgtt atttgtttcg tttttttgtcg  60 cgttttgggg ttcgtattta tttat                                        85
```

<210> SEQ ID NO 23
<211> LENGTH: 25
<212> TYPE: DNA
<213> ORGANISM: Artificial sequence
<220> FEATURE:
<223> OTHER INFORMATION: Synthetic

<400> SEQUENCE: 23
cggtttcgta gtattttttt gttcg                                           25

<210> SEQ ID NO 24
<211> LENGTH: 17
<212> TYPE: DNA
<213> ORGANISM: Artificial sequence
<220> FEATURE:
<223> OTHER INFORMATION: Synthetic

<400> SEQUENCE: 24
gaaccccaaa acgcgac                                                    17

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
cgccgagggc ggtttttcg                                                  20

<210> SEQ ID NO 26
<211> LENGTH: 134
<212> TYPE: DNA
<213> ORGANISM: Homo sapiens

<400> SEQUENCE: 26
cgcctcctgg gctcccccg gagtgggagg gagccgcggt cccgcctccg cgcccgttcc       60
ctcccaggcc cctcggccgc cgcgccgagc tttccgcgcg tggacagact gcccggccga    120
cggacggacg cagg                                                      134

<210> SEQ ID NO 27
<211> LENGTH: 134
<212> TYPE: DNA
<213> ORGANISM: Artificial sequence
<220> FEATURE:
<223> OTHER INFORMATION: Synthetic

<400> SEQUENCE: 27
cgttttttgg gttttttcg gagtgggagg gagtcgcggt ttcgttttcg cgttcgtttt      60
tttttaggtt tttcggtcgt cgcgtcgagt ttttcgcgcg tggatagatt gttcggtcga    120
cggacggacg tagg                                                      134

<210> SEQ ID NO 28
<211> LENGTH: 17
<212> TYPE: DNA
<213> ORGANISM: Artificial sequence
<220> FEATURE:
<223> OTHER INFORMATION: Synthetic

<400> SEQUENCE: 28
agggagtcgc ggtttcg                                                    17

```
<210> SEQ ID NO 29
<211> LENGTH: 18
<212> TYPE: DNA
<213> ORGANISM: Artificial sequence
<220> FEATURE:
<223> OTHER INFORMATION: Synthetic

<400> SEQUENCE: 29
gcgacgaccg aaaaacct                                                      18

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
cgccgagggt tttcgcgttc                                                    20

<210> SEQ ID NO 31
<211> LENGTH: 140
<212> TYPE: DNA
<213> ORGANISM: Homo sapiens

<400> SEQUENCE: 31
tagcagcagc cgcagccatg gcggggatga agacagcctc cggggactac atcgactcgt        60
catgggagct gcgggtgttt gtgggagagg aggacccaga ggccgagtcg gtcaccctgc       120
gggtcactgg ggagtcgcac                                                   140

<210> SEQ ID NO 32
<211> LENGTH: 140
<212> TYPE: DNA
<213> ORGANISM: Artificial sequence
<220> FEATURE:
<223> OTHER INFORMATION: Synthetic

<400> SEQUENCE: 32
tagtagtagt cgtagttatg gcggggatga agatagtttt cggggattat atcgattcgt        60
tatgggagtt gcgggtgttt gtgggagagg aggatttaga ggtcgagtcg gttattttgc       120
gggttattgg ggagtcgtat                                                   140

<210> SEQ ID NO 33
<211> LENGTH: 24
<212> TYPE: DNA
<213> ORGANISM: Artificial sequence
<220> FEATURE:
<223> OTHER INFORMATION: Synthetic

<400> SEQUENCE: 33
gttttcgggg attatatcga ttcg                                               24

<210> SEQ ID NO 34
<211> LENGTH: 22
<212> TYPE: DNA
<213> ORGANISM: Artificial sequence
<220> FEATURE:
<223> OTHER INFORMATION: Synthetic

<400> SEQUENCE: 34
cccaataacc cgcaaaataa cc                                                 22

<210> SEQ ID NO 35
```

```
<211> LENGTH: 20
<212> TYPE: DNA
<213> ORGANISM: Artificial sequence
<220> FEATURE:
<223> OTHER INFORMATION: Synthetic

<400> SEQUENCE: 35
cgccgaggcg actcgacctc                                              20

<210> SEQ ID NO 36
<211> LENGTH: 108
<212> TYPE: DNA
<213> ORGANISM: Homo sapiens

<400> SEQUENCE: 36
aggggctgcg aggtcaggct gtaaccgggt caatgtgtgg aatattgggg ggctcggctg   60
cagacttggc caaatggacg ggactattaa ggtaagcggc ggggcaac               108

<210> SEQ ID NO 37
<211> LENGTH: 108
<212> TYPE: DNA
<213> ORGANISM: Artificial sequence
<220> FEATURE:
<223> OTHER INFORMATION: Synthetic

<400> SEQUENCE: 37
aggggttgcg aggttaggtt gtaatcgggt taatgtgtgg aatattgggg ggttcggttg   60
tagatttggt taaatggacg ggattattaa ggtaagcggc ggggtaac               108

<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38
ggttgcgagg ttaggttgta a                                            21

<210> SEQ ID NO 39
<211> LENGTH: 25
<212> TYPE: DNA
<213> ORGANISM: Artificial sequence
<220> FEATURE:
<223> OTHER INFORMATION: Synthetic

<400> SEQUENCE: 39
tccatttaac caaatctaca accga                                        25

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
cgccgaggat cgggttaatg                                              20

<210> SEQ ID NO 41
<211> LENGTH: 141
<212> TYPE: DNA
<213> ORGANISM: Homo sapiens

<400> SEQUENCE: 41
```
cgccccctca cctccccgat catgccgttc cagacgccat cgatcttctt tccgtgcttg    60
ccattggtga ccaggtagag gtcgtagctg aagccgatgg tatgcgccag ccgcttcaga   120
atgtcgatgc agaaaccctt g                                             141

<210> SEQ ID NO 42
<211> LENGTH: 141
<212> TYPE: DNA
<213> ORGANISM: Artificial sequence
<220> FEATURE:
<223> OTHER INFORMATION: Synthetic

<400> SEQUENCE: 42
cgttttttta tttttttcgat tatgtcgttt tagacgttat cgattttttt ttcgtgtttg    60
ttattggtga ttaggtagag gtcgtagttg aagtcgatgg tatgcgttag tcgttttaga   120
atgtcgatgt agaaattttt g                                             141

<210> SEQ ID NO 43
<211> LENGTH: 27
<212> TYPE: DNA
<213> ORGANISM: Artificial sequence
<220> FEATURE:
<223> OTHER INFORMATION: Synthetic

<400> SEQUENCE: 43
tcgattatgt cgttttagac gttatcg                                        27

<210> SEQ ID NO 44
<211> LENGTH: 28
<212> TYPE: DNA
<213> ORGANISM: Artificial sequence
<220> FEATURE:
<223> OTHER INFORMATION: Synthetic

<400> SEQUENCE: 44
tctacatcga cattctaaaa cgactaac                                       28

<210> SEQ ID NO 45
<211> LENGTH: 21
<212> TYPE: DNA
<213> ORGANISM: Artificial sequence
<220> FEATURE:
<223> OTHER INFORMATION: Synthetic

<400> SEQUENCE: 45
ccacggacgc gcataccatc g                                              21

<210> SEQ ID NO 46
<211> LENGTH: 104
<212> TYPE: DNA
<213> ORGANISM: Homo sapiens

<400> SEQUENCE: 46
gagccggagt cgcggtggcc gcctcagcgc catgtcgagg gttgctgagg ggccagcggc    60
agcgcggcgc ggcttgtagt ccccgcgcgc atgcgcccag cctg                   104

<210> SEQ ID NO 47
<211> LENGTH: 104
<212> TYPE: DNA
<213> ORGANISM: Artificial sequence
<220> FEATURE:
<223> OTHER INFORMATION: Synthetic

<400> SEQUENCE: 47
gagtcggagt cgcggtggtc gttttagcgt tatgtcgagg gttgttgagg ggttagcggt    60
agcgcggcgc ggtttgtagt tttcgcgcgt atgcgtttag tttg                    104

<210> SEQ ID NO 48
<211> LENGTH: 22
<212> TYPE: DNA
<213> ORGANISM: Artificial sequence
<220> FEATURE:
<223> OTHER INFORMATION: Synthetic

<400> SEQUENCE: 48
tggtcgtttt agcgttatgt cg                                             22

<210> SEQ ID NO 49
<211> LENGTH: 19
<212> TYPE: DNA
<213> ORGANISM: Artificial sequence
<220> FEATURE:
<223> OTHER INFORMATION: Synthetic

<400> SEQUENCE: 49
cgaaaactac aaaccgcgc                                                 19

<210> SEQ ID NO 50
<211> LENGTH: 21
<212> TYPE: DNA
<213> ORGANISM: Artificial sequence
<220> FEATURE:
<223> OTHER INFORMATION: Synthetic

<400> SEQUENCE: 50
ccacggacgc cgcgctaccg c                                              21

<210> SEQ ID NO 51
<211> LENGTH: 97
<212> TYPE: DNA
<213> ORGANISM: Homo sapiens

<400> SEQUENCE: 51
ggcgcggcgc tggaaggcgc cggcgttaac cccgcgaggc aggcgacgga gggggagcgg    60
cgctaataca taagagcact gcatcacgct aatcttc                             97

<210> SEQ ID NO 52
<211> LENGTH: 97
<212> TYPE: DNA
<213> ORGANISM: Artificial sequence
<220> FEATURE:
<223> OTHER INFORMATION: Synthetic

<400> SEQUENCE: 52
ggcgcggcgt tggaaggcgt cggcgttaat ttcgcgaggt aggcgacgga gggggagcgg    60
cgttaatata taagagtatt gtattacgtt aattttt                             97

<210> SEQ ID NO 53
<211> LENGTH: 19
<212> TYPE: DNA
<213> ORGANISM: Artificial sequence
<220> FEATURE:
<223> OTHER INFORMATION: Synthetic

<400> SEQUENCE: 53
gcgttaattt cgcgaggta                                                 19

<210> SEQ ID NO 54
<211> LENGTH: 28
<212> TYPE: DNA
<213> ORGANISM: Artificial sequence
<220> FEATURE:
<223> OTHER INFORMATION: Synthetic

<400> SEQUENCE: 54
acaatactct tatatattaa cgccgctc                                          28

<210> SEQ ID NO 55
<211> LENGTH: 20
<212> TYPE: DNA
<213> ORGANISM: Artificial sequence
<220> FEATURE:
<223> OTHER INFORMATION: Synthetic

<400> SEQUENCE: 55
cgccgaggag gcgacggagg                                                   20

<210> SEQ ID NO 56
<211> LENGTH: 89
<212> TYPE: DNA
<213> ORGANISM: Homo sapiens

<400> SEQUENCE: 56
ctgtcagtgc tgaccgagcg ccgcgccttc cggccatacg ggctccacgg tgcgcggttc       60
cccagccctc gcggccctcc ccgcccccg                                         89

<210> SEQ ID NO 57
<211> LENGTH: 89
<212> TYPE: DNA
<213> ORGANISM: Artificial sequence
<220> FEATURE:
<223> OTHER INFORMATION: Synthetic

<400> SEQUENCE: 57
ttgttagtgt tgatcgagcg tcgcgttttt cggttatacg ggttttacgg tgcgcggttt       60
tttagttttc gcggtttttt tcgttttcg                                         89

<210> SEQ ID NO 58
<211> LENGTH: 22
<212> TYPE: DNA
<213> ORGANISM: Artificial sequence
<220> FEATURE:
<223> OTHER INFORMATION: Synthetic

<400> SEQUENCE: 58
cgtcgcgttt ttcggttata cg                                                22

<210> SEQ ID NO 59
<211> LENGTH: 21
<212> TYPE: DNA
<213> ORGANISM: Artificial sequence
<220> FEATURE:
<223> OTHER INFORMATION: Synthetic

<400> SEQUENCE: 59
cgcgaaaact aaaaaaccgc g                                                 21

<210> SEQ ID NO 60
<211> LENGTH: 21
<212> TYPE: DNA

```
<213> ORGANISM: Artificial sequence
<220> FEATURE:
<223> OTHER INFORMATION: Synthetic

<400> SEQUENCE: 60
ccacggacgg caccgtaaaa c                                              21

<210> SEQ ID NO 61
<211> LENGTH: 138
<212> TYPE: DNA
<213> ORGANISM: Homo sapiens

<400> SEQUENCE: 61
cggagggggc gaacaaacaa acgtcaacct gttgtttgtc ccgtcaccat ttatcagctc    60
agcaccacaa ggaagtgcgg cacccacacg cgctcggaaa gttcagcatg caggaagttt   120
ggggagagct cggcgatt                                                 138

<210> SEQ ID NO 62
<211> LENGTH: 111
<212> TYPE: DNA
<213> ORGANISM: Artificial sequence
<220> FEATURE:
<223> OTHER INFORMATION: Synthetic

<400> SEQUENCE: 62 aggggggcgaa taaataaacg ttaatttgtt gtttgtttcg ttattattta ttagtttagt   60
attataagga agtgcggtat ttatacgcgt tcggaaagtt tagtatgtag g             111

<210> SEQ ID NO 63
<211> LENGTH: 35
<212> TYPE: DNA
<213> ORGANISM: Artificial sequence
<220> FEATURE:
<223> OTHER INFORMATION: Synthetic

<400> SEQUENCE: 63
gcgaataaat aaacgttaat tgttgtttg tttcg                                35

<210> SEQ ID NO 64
<211> LENGTH: 24
<212> TYPE: DNA
<213> ORGANISM: Artificial sequence
<220> FEATURE:
<223> OTHER INFORMATION: Synthetic

<400> SEQUENCE: 64
actttccgaa cgcgtataaa tacc                                           24

<210> SEQ ID NO 65
<211> LENGTH: 21
<212> TYPE: DNA
<213> ORGANISM: Artificial sequence
<220> FEATURE:
<223> OTHER INFORMATION: Synthetic

<400> SEQUENCE: 65
ccacggacgc gcacttcctt a                                              21

<210> SEQ ID NO 66
<211> LENGTH: 85
<212> TYPE: DNA
<213> ORGANISM: Homo sapiens

<400> SEQUENCE: 66
```
ccggcgcgag ctgaccgagc actcggcggg cgcggcggga ctgcggcccg tggcggcgtg        60
cgcggggacc tgcgctgact aggtc                                             85

<210> SEQ ID NO 67
<211> LENGTH: 85
<212> TYPE: DNA
<213> ORGANISM: Artificial sequence
<220> FEATURE:
<223> OTHER INFORMATION: Synthetic

<400> SEQUENCE: 67
tcggcgcgag ttgatcgagt attcggcggg cgcggcggga ttgcggttcg tggcggcgtg        60
cgcggggatt tgcgttgatt aggtt                                             85

<210> SEQ ID NO 68
<211> LENGTH: 21
<212> TYPE: DNA
<213> ORGANISM: Artificial sequence
<220> FEATURE:
<223> OTHER INFORMATION: Synthetic

<400> SEQUENCE: 68
gcgagttgat cgagtattcg g                                                 21

<210> SEQ ID NO 69
<211> LENGTH: 21
<212> TYPE: DNA
<213> ORGANISM: Artificial sequence
<220> FEATURE:
<223> OTHER INFORMATION: Synthetic

<400> SEQUENCE: 69
ctaatcaacg caaatccccg c                                                 21

<210> SEQ ID NO 70
<211> LENGTH: 21
<212> TYPE: DNA
<213> ORGANISM: Artificial sequence
<220> FEATURE:
<223> OTHER INFORMATION: Synthetic

<400> SEQUENCE: 70
ccacggacgc gcacgccgcc a                                                 21

<210> SEQ ID NO 71
<211> LENGTH: 104
<212> TYPE: DNA
<213> ORGANISM: Homo sapiens

<400> SEQUENCE: 71
tgcgcgtggg gccaggctcg acctcactcc tgttgtcgct gcagacccgc gtgggctccc        60
gccgggccct cctgccgccc cccagcctcc ccgcccctgc cctt                       104

<210> SEQ ID NO 72
<211> LENGTH: 104
<212> TYPE: DNA
<213> ORGANISM: Artificial sequence
<220> FEATURE:
<223> OTHER INFORMATION: Synthetic

<400> SEQUENCE: 72
tgcgcgtggg gttaggttcg attttatttt tgttgtcgtt gtagattcgc gtgggttttc        60
gtcgggtttt tttgtcgttt tttagttttt tcgtttttgt tttt                              104

<210> SEQ ID NO 73
<211> LENGTH: 29
<212> TYPE: DNA
<213> ORGANISM: Artificial sequence
<220> FEATURE:
<223> OTHER INFORMATION: Synthetic

<400> SEQUENCE: 73
ttcgatttta tttttgttgt cgttgtaga                                               29

<210> SEQ ID NO 74
<211> LENGTH: 19
<212> TYPE: DNA
<213> ORGANISM: Artificial sequence
<220> FEATURE:
<223> OTHER INFORMATION: Synthetic

<400> SEQUENCE: 74
acgacaaaaa aacccgacg                                                          19

<210> SEQ ID NO 75
<211> LENGTH: 20
<212> TYPE: DNA
<213> ORGANISM: Artificial sequence
<220> FEATURE:
<223> OTHER INFORMATION: Synthetic

<400> SEQUENCE: 75
cgccgaggat tcgcgtgggt                                                         20

<210> SEQ ID NO 76
<211> LENGTH: 85
<212> TYPE: DNA
<213> ORGANISM: Homo sapiens

<400> SEQUENCE: 76
gccgagggcg cccggcgcag agtcccgcag aggcggacgc cgcggcacgc gcctcgaaaa             60
gcctcaaact cttatcctcg gctct                                                   85

<210> SEQ ID NO 77
<211> LENGTH: 85
<212> TYPE: DNA
<213> ORGANISM: Artificial sequence
<220> FEATURE:
<223> OTHER INFORMATION: Synthetic

<400> SEQUENCE: 77
gtcgagggcg ttcggcgtag agtttcgtag aggcggacgt cgcggtacgc gtttcgaaaa             60
gttttaaatt tttattttcg gtttt                                                   85

<210> SEQ ID NO 78
<211> LENGTH: 22
<212> TYPE: DNA
<213> ORGANISM: Artificial sequence
<220> FEATURE:
<223> OTHER INFORMATION: Synthetic

<400> SEQUENCE: 78
gttcggcgta gagtttcgta ga                                                      22

<210> SEQ ID NO 79
<211> LENGTH: 32

```
<212> TYPE: DNA
<213> ORGANISM: Artificial sequence
<220> FEATURE:
<223> OTHER INFORMATION: Synthetic

<400> SEQUENCE: 79
gaaaataaaa atttaaaact tttcgaaacg cg                                    32

<210> SEQ ID NO 80
<211> LENGTH: 20
<212> TYPE: DNA
<213> ORGANISM: Artificial sequence
<220> FEATURE:
<223> OTHER INFORMATION: Synthetic

<400> SEQUENCE: 80
cgccgagggt accgcgacgt                                                  20

<210> SEQ ID NO 81
<211> LENGTH: 113
<212> TYPE: DNA
<213> ORGANISM: Homo sapiens

<400> SEQUENCE: 81
tcggtgctcc cggcccacgg gctgcacaac ttggcggccc cgaaactggc gtggggagg       60 ggagggctgt ccacccgagc aggacgcggc tgtccactca gtcggaggtg agg            113

<210> SEQ ID NO 82
<211> LENGTH: 113
<212> TYPE: DNA
<213> ORGANISM: Artificial sequence
<220> FEATURE:
<223> OTHER INFORMATION: Synthetic

<400> SEQUENCE: 82
tcggtgtttt cggtttacgg gttgtataat ttggcggttt cgaaattggc gtggggagg       60 ggagggttgt ttattcgagt aggacgcggt tgtttattta gtcggaggtg agg            113

<210> SEQ ID NO 83
<211> LENGTH: 20
<212> TYPE: DNA
<213> ORGANISM: Artificial sequence
<220> FEATURE:
<223> OTHER INFORMATION: Synthetic

<400> SEQUENCE: 83
cgggttgtat aatttggcgg                                                  20

<210> SEQ ID NO 84
<211> LENGTH: 17
<212> TYPE: DNA
<213> ORGANISM: Artificial sequence
<220> FEATURE:
<223> OTHER INFORMATION: Synthetic

<400> SEQUENCE: 84
aaccgcgtcc tactcga                                                     17

<210> SEQ ID NO 85
<211> LENGTH: 20
<212> TYPE: DNA
<213> ORGANISM: Artificial sequence
<220> FEATURE:
<223> OTHER INFORMATION: Synthetic
```

```
<400> SEQUENCE: 85
cgccgagggt tcgaaattg                                          20

<210> SEQ ID NO 86
<211> LENGTH: 112
<212> TYPE: DNA
<213> ORGANISM: Homo sapiens

<400> SEQUENCE: 86
gtcgccgccc gggagggcac cggcctcgct cgcttgctcg ctcgcccgcc cttgcccgct    60
cgctccccgc ccgccgcctc cctcgcgcgc ccgctccggt cctccggctc cc           112

<210> SEQ ID NO 87
<211> LENGTH: 77
<212> TYPE: DNA
<213> ORGANISM: Artificial sequence
<220> FEATURE:
<223> OTHER INFORMATION: Synthetic

<400> SEQUENCE: 87
gtcgtcgttc gggagggtat cggtttcgtt cgtttgttcg ttcgttcgtt tttgttcgtt    60 cgttttcgt tcgtcgt                                                   77

<210> SEQ ID NO 88
<211> LENGTH: 19
<212> TYPE: DNA
<213> ORGANISM: Artificial sequence
<220> FEATURE:
<223> OTHER INFORMATION: Synthetic

<400> SEQUENCE: 88
gtcgtcgttc gagagggta                                          19

<210> SEQ ID NO 89
<211> LENGTH: 23
<212> TYPE: DNA
<213> ORGANISM: Artificial sequence
<220> FEATURE:
<223> OTHER INFORMATION: Synthetic

<400> SEQUENCE: 89
gaacaaaaac gaacgaacga aca                                     23

<210> SEQ ID NO 90
<211> LENGTH: 21
<212> TYPE: DNA
<213> ORGANISM: Artificial sequence
<220> FEATURE:
<223> OTHER INFORMATION: Synthetic

<400> SEQUENCE: 90
ccacggacga tcggtttcgt t                                       21

<210> SEQ ID NO 91
<211> LENGTH: 88
<212> TYPE: DNA
<213> ORGANISM: Homo sapiens

<400> SEQUENCE: 91
cggagctagg aggtggggc tcggagggcg caggaagagc ggctctgcga ggaaagggaa    60
aggagaggcc gcttctggga agggaccc                                     88
```

```
<210> SEQ ID NO 92
<211> LENGTH: 88
<212> TYPE: DNA
<213> ORGANISM: Artificial sequence
<220> FEATURE:
<223> OTHER INFORMATION: Synthetic

<400> SEQUENCE: 92
cggagttagg agggtggggt tcggagggcg taggaagagc ggttttgcga ggaaagggaa      60
aggagaggtc gttttfggga agggattt                                        88

<210> SEQ ID NO 93
<211> LENGTH: 18
<212> TYPE: DNA
<213> ORGANISM: Artificial sequence
<220> FEATURE:
<223> OTHER INFORMATION: Synthetic

<400> SEQUENCE: 93
ttaggagggt ggggttcg                                                   18

<210> SEQ ID NO 94
<211> LENGTH: 18
<212> TYPE: DNA
<213> ORGANISM: Artificial sequence
<220> FEATURE:
<223> OTHER INFORMATION: Synthetic

<400> SEQUENCE: 94
ctttcctcgc aaaaccgc                                                   18

<210> SEQ ID NO 95
<211> LENGTH: 21
<212> TYPE: DNA
<213> ORGANISM: Artificial sequence
<220> FEATURE:
<223> OTHER INFORMATION: Synthetic

<400> SEQUENCE: 95
ccacggacgg gagggcgtag g                                               21

<210> SEQ ID NO 96
<211> LENGTH: 108
<212> TYPE: DNA
<213> ORGANISM: Homo sapiens

<400> SEQUENCE: 96
ggaaggaaat tgcgggttcc cgtctgcctt gtctccagct tctctgctga agcccggtag     60
cagtgaatgc gcgctgactt tcagcgacga ctcctggaag caacgcca                 108

<210> SEQ ID NO 97
<211> LENGTH: 108
<212> TYPE: DNA
<213> ORGANISM: Artificial sequence
<220> FEATURE:
<223> OTHER INFORMATION: Synthetic

<400> SEQUENCE: 97
ggaaggaaat tgcgggtttt cgtttgtttt gttttagtt tttttgttga agttcggtag      60
tagtgaatgc gcgttgattt ttagcgacga tttttggaag taacgtta                 108

<210> SEQ ID NO 98
<211> LENGTH: 19
<212> TYPE: DNA
```

```
<213> ORGANISM: Artificial sequence
<220> FEATURE:
<223> OTHER INFORMATION: Synthetic

<400> SEQUENCE: 98
aggaaattgc gggttttcg                                                    19

<210> SEQ ID NO 99
<211> LENGTH: 25
<212> TYPE: DNA
<213> ORGANISM: Artificial sequence
<220> FEATURE:
<223> OTHER INFORMATION: Synthetic

<400> SEQUENCE: 99
ccaaaaatcg tcgctaaaaa tcaac                                             25

<210> SEQ ID NO 100
<211> LENGTH: 21
<212> TYPE: DNA
<213> ORGANISM: Artificial sequence
<220> FEATURE:
<223> OTHER INFORMATION: Synthetic

<400> SEQUENCE: 100
ccacggacgc gcgcattcac t                                                 21

<210> SEQ ID NO 101
<211> LENGTH: 119
<212> TYPE: DNA
<213> ORGANISM: Homo sapiens

<400> SEQUENCE: 101
gcctttgccc cggttttgg cgcgggagga ctttcgaccc cgacttcggc cgctcatggt        60
ggcggcggag gcagcttcaa agacacgctg tgaccctgcg gctcctgacg ccagctctc       119

<210> SEQ ID NO 102
<211> LENGTH: 119
<212> TYPE: DNA
<213> ORGANISM: Artificial sequence
<220> FEATURE:
<223> OTHER INFORMATION: Synthetic

<400> SEQUENCE: 102
gtttttgttt cggttttgg cgcgggagga ttttcgattt cgatttcggt cgtttatggt       60
ggcggcggag gtagttttaa agatacgttg tgattttgcg gttttgacg ttagttttt       119

<210> SEQ ID NO 103
<211> LENGTH: 19
<212> TYPE: DNA
<213> ORGANISM: Artificial sequence
<220> FEATURE:
<223> OTHER INFORMATION: Synthetic

<400> SEQUENCE: 103
tttgtttcgg tttttggcg                                                    19

<210> SEQ ID NO 104
<211> LENGTH: 21
<212> TYPE: DNA
<213> ORGANISM: Artificial sequence
<220> FEATURE:
<223> OTHER INFORMATION: Synthetic

<400> SEQUENCE: 104
```

```
accataaacg accgaaatcg a                                              21
```

<210> SEQ ID NO 105
<211> LENGTH: 21
<212> TYPE: DNA
<213> ORGANISM: Artificial sequence
<220> FEATURE:
<223> OTHER INFORMATION: Synthetic

<400> SEQUENCE: 105

```
ccacggacgg cgggaggatt t                                              21
```

<210> SEQ ID NO 106
<211> LENGTH: 72
<212> TYPE: DNA
<213> ORGANISM: Homo sapiens

<400> SEQUENCE: 106

```
gggaccggag ccgagcctag cgcggcgccc gcgacccgtc agccgcggct cctgctccct    60
cgatcccgcg cg                                                        72
```

<210> SEQ ID NO 107
<211> LENGTH: 72
<212> TYPE: DNA
<213> ORGANISM: Artificial sequence
<220> FEATURE:
<223> OTHER INFORMATION: Synthetic

<400> SEQUENCE: 107

```
gggatcggag tcgagtttag cgcggcgttc gcgattcgtt agtcgcggtt tttgtttttt    60
cgatttcgcg cg                                                        72
```

<210> SEQ ID NO 108
<211> LENGTH: 19
<212> TYPE: DNA
<213> ORGANISM: Artificial sequence
<220> FEATURE:
<223> OTHER INFORMATION: Synthetic

<400> SEQUENCE: 108

```
tcggagtcga gtttagcgc                                                 19
```

<210> SEQ ID NO 109
<211> LENGTH: 24
<212> TYPE: DNA
<213> ORGANISM: Artificial sequence
<220> FEATURE:
<223> OTHER INFORMATION: Synthetic

<400> SEQUENCE: 109

```
cgaaatcgaa aaacaaaaaa ccgc                                           24
```

<210> SEQ ID NO 110
<211> LENGTH: 20
<212> TYPE: DNA
<213> ORGANISM: Artificial sequence
<220> FEATURE:
<223> OTHER INFORMATION: Synthetic

<400> SEQUENCE: 110

```
cgccgaggcg gcgttcgcga                                                20
```

<210> SEQ ID NO 111

```
<211> LENGTH: 119
<212> TYPE: DNA
<213> ORGANISM: Homo sapiens

<400> SEQUENCE: 111
tgtcctcgtc ctcctaccgc aggatgttcg gcggcccggg caccgcgagc cggccgagct    60
ccagccggag ctacgtgact acgtccaccc gcacctacag cctgggcagc gcgctgcgc   119

<210> SEQ ID NO 112
<211> LENGTH: 119
<212> TYPE: DNA
<213> ORGANISM: Artificial sequence
<220> FEATURE:
<223> OTHER INFORMATION: Synthetic

<400> SEQUENCE: 112
tgttttcgtt ttttatcgt aggatgttcg gcggttcggg tatcgcgagt cggtcgagtt    60
ttagtcggag ttacgtgatt acgtttattc gtatttatag tttgggtagc gcgttgcgt   119

<210> SEQ ID NO 113
<211> LENGTH: 21
<212> TYPE: DNA
<213> ORGANISM: Artificial sequence
<220> FEATURE:
<223> OTHER INFORMATION: Synthetic

<400> SEQUENCE: 113
ttttatcgta ggatgttcgg c                                              21

<210> SEQ ID NO 114
<211> LENGTH: 20
<212> TYPE: DNA
<213> ORGANISM: Artificial sequence
<220> FEATURE:
<223> OTHER INFORMATION: Synthetic

<400> SEQUENCE: 114
tccgactaaa actcgaccga                                                20

<210> SEQ ID NO 115
<211> LENGTH: 21
<212> TYPE: DNA
<213> ORGANISM: Artificial sequence
<220> FEATURE:
<223> OTHER INFORMATION: Synthetic

<400> SEQUENCE: 115
ccacggacgc ggttcgggta t                                              21

<210> SEQ ID NO 116
<211> LENGTH: 70
<212> TYPE: DNA
<213> ORGANISM: Homo sapiens

<400> SEQUENCE: 116
ggggccgggg ccgacagccc acgctggcgc ggcaggcgcg tgcgcccgcc gttttcgtga    60
gcccgagcag                                                           70

<210> SEQ ID NO 117
<211> LENGTH: 70
<212> TYPE: DNA
<213> ORGANISM: Artificial sequence
<220> FEATURE:
<223> OTHER INFORMATION: Synthetic
```

-continued

<400> SEQUENCE: 117
ggggtcgggg tcgatagttt acgttggcgc ggtaggcgcg tgcgttcgtc gtttcgtga  60 gttcgagtag  70

<210> SEQ ID NO 118
<211> LENGTH: 20
<212> TYPE: DNA
<213> ORGANISM: Artificial sequence
<220> FEATURE:
<223> OTHER INFORMATION: Synthetic

<400> SEQUENCE: 118 gtcgggtcg atagtttacg  20

<210> SEQ ID NO 119
<211> LENGTH: 19
<212> TYPE: DNA
<213> ORGANISM: Artificial sequence
<220> FEATURE:
<223> OTHER INFORMATION: Synthetic

<400> SEQUENCE: 119
actcgaactc acgaaaacg  19

<210> SEQ ID NO 120
<211> LENGTH: 21
<212> TYPE: DNA
<213> ORGANISM: Artificial sequence
<220> FEATURE:
<223> OTHER INFORMATION: Synthetic

<400> SEQUENCE: 120
ccacggacgg acgaacgcac g  21

<210> SEQ ID NO 121
<211> LENGTH: 100
<212> TYPE: DNA
<213> ORGANISM: Homo sapiens

<400> SEQUENCE: 121
gctgctctgg gctgcagggg cgagacttct ggcgtcgccg tcgtgacgta ttttcctat  60 gcccggtccg tgcattctgg ttgtgaaggc tgagttctag  100

<210> SEQ ID NO 122
<211> LENGTH: 100
<212> TYPE: DNA
<213> ORGANISM: Artificial sequence
<220> FEATURE:
<223> OTHER INFORMATION: Synthetic

<400> SEQUENCE: 122
gttgttttgg gttgtagggg cgagattttt ggcgtcgtcg tcgtgacgta ttttttttat  60
gttcggttcg tgtattttgg ttgtgaaggt tgagttttag  100

<210> SEQ ID NO 123
<211> LENGTH: 19
<212> TYPE: DNA
<213> ORGANISM: Artificial sequence
<220> FEATURE:
<223> OTHER INFORMATION: Synthetic

<400> SEQUENCE: 123

-continued

```
gagattttg gcgtcgtcg                                              19
```

<210> SEQ ID NO 124
<211> LENGTH: 23
<212> TYPE: DNA
<213> ORGANISM: Artificial sequence
<220> FEATURE:
<223> OTHER INFORMATION: Synthetic

<400> SEQUENCE: 124

```
caaccaaaat acacgaaccg aac                                        23
```

<210> SEQ ID NO 125
<211> LENGTH: 21
<212> TYPE: DNA
<213> ORGANISM: Artificial sequence
<220> FEATURE:
<223> OTHER INFORMATION: Synthetic

<400> SEQUENCE: 125

```
ccacggacgg tcgtgacgta t                                          21
```

<210> SEQ ID NO 126
<211> LENGTH: 113
<212> TYPE: DNA
<213> ORGANISM: Homo sapiens

<400> SEQUENCE: 126

```
cgtcacctgc cggaaacacc cgaatgttca tcccgcgcgc agtttctgag atgctgggtg    60
aaggcgaccc gcagataggt ctgtgacaga cgcctaaagc gccgaaccat ccc          113
```

<210> SEQ ID NO 127
<211> LENGTH: 113
<212> TYPE: DNA
<213> ORGANISM: Artificial sequence
<220> FEATURE:
<223> OTHER INFORMATION: Synthetic

<400> SEQUENCE: 127

```
cgttatttgt cggaaatatt cgaatgttta tttcgcgcgt agtttttgag atgttgggtg    60
aaggcgattc gtagataggt ttgtgataga cgtttaaagc gtcgaattat ttt          113
```

<210> SEQ ID NO 128
<211> LENGTH: 27
<212> TYPE: DNA
<213> ORGANISM: Artificial sequence
<220> FEATURE:
<223> OTHER INFORMATION: Synthetic

<400> SEQUENCE: 128

```
cggaaatatt cgaatgttta tttcgcg                                    27
```

<210> SEQ ID NO 129
<211> LENGTH: 23
<212> TYPE: DNA
<213> ORGANISM: Artificial sequence
<220> FEATURE:
<223> OTHER INFORMATION: Synthetic

<400> SEQUENCE: 129

```
tcacaaacct atctacgaat cgc                                        23
```

<210> SEQ ID NO 130
<211> LENGTH: 20

```
<212> TYPE: DNA
<213> ORGANISM: Artificial sequence
<220> FEATURE:
<223> OTHER INFORMATION: Synthetic

<400> SEQUENCE: 130
cgccgagggc gtagtttttg                                                  20

<210> SEQ ID NO 131
<211> LENGTH: 117
<212> TYPE: DNA
<213> ORGANISM: Homo sapiens

<400> SEQUENCE: 131
ccgtgggcgc ggacagctgc cgggagcggc aggcgtctcg atcggggacg caggcacttc      60
cgtccctgca gagcatcaga cgcgtctcgg gacactgggg acaacatctc ctccgcg        117

<210> SEQ ID NO 132
<211> LENGTH: 117
<212> TYPE: DNA
<213> ORGANISM: Artificial sequence
<220> FEATURE:
<223> OTHER INFORMATION: Synthetic

<400> SEQUENCE: 132
tcgtgggcgc ggatagttgt cgggagcggt aggcgtttcg atcggggacg taggtatttt      60 cgttttgta gagtattaga cgcgtttcgg gatattgggg ataatatttt tttcgcg         117

<210> SEQ ID NO 133
<211> LENGTH: 18
<212> TYPE: DNA
<213> ORGANISM: Artificial sequence
<220> FEATURE:
<223> OTHER INFORMATION: Synthetic

<400> SEQUENCE: 133
gttgtcggga gcggtagg                                                    18

<210> SEQ ID NO 134
<211> LENGTH: 21
<212> TYPE: DNA
<213> ORGANISM: Artificial sequence
<220> FEATURE:
<223> OTHER INFORMATION: Synthetic

<400> SEQUENCE: 134
ccaatatccc gaaacgcgtc t                                                21

<210> SEQ ID NO 135
<211> LENGTH: 21
<212> TYPE: DNA
<213> ORGANISM: Artificial sequence
<220> FEATURE:
<223> OTHER INFORMATION: Synthetic

<400> SEQUENCE: 135
ccacggacgg cgtttcgatc g                                                21

<210> SEQ ID NO 136
<211> LENGTH: 154
<212> TYPE: DNA
<213> ORGANISM: Homo sapiens

<400> SEQUENCE: 136
```
tcaccaactc tttctgagag caaaaacatg gggccgagtc cggcagctgc acgcagaatc    60
caactctctg gcagctctcg gcaccgacga gctccagatc ccgcgttcgc atcccggcgc   120
tttgcgcgca gagctaagcc ttcggacccg tgga                               154

<210> SEQ ID NO 137
<211> LENGTH: 99
<212> TYPE: DNA
<213> ORGANISM: Artificial sequence
<220> FEATURE:
<223> OTHER INFORMATION: Synthetic

<400> SEQUENCE: 137
tatggggtcg agttcggtag ttgtacgtag aatttaattt tttggtagtt ttcggtatcg    60
acgagtttta gatttcgcgt tcgtatttcg gcgttttgc                           99

<210> SEQ ID NO 138
<211> LENGTH: 23
<212> TYPE: DNA
<213> ORGANISM: Artificial sequence
<220> FEATURE:
<223> OTHER INFORMATION: Synthetic

<400> SEQUENCE: 138
cgagttcggt agttgtacgt aga                                            23

<210> SEQ ID NO 139
<211> LENGTH: 27
<212> TYPE: DNA
<213> ORGANISM: Artificial sequence
<220> FEATURE:
<223> OTHER INFORMATION: Synthetic

<400> SEQUENCE: 139
cgaaatacga acgcgaaatc taaaact                                        27

<210> SEQ ID NO 140
<211> LENGTH: 21
<212> TYPE: DNA
<213> ORGANISM: Artificial sequence
<220> FEATURE:
<223> OTHER INFORMATION: Synthetic

<400> SEQUENCE: 140
ccacggacgt cgtcgatacc g                                              21

<210> SEQ ID NO 141
<211> LENGTH: 20
<212> TYPE: DNA
<213> ORGANISM: Artificial sequence
<220> FEATURE:
<223> OTHER INFORMATION: Synthetic

<400> SEQUENCE: 141
cgccgaggat cggtttcgtt                                                20

<210> SEQ ID NO 142
<211> LENGTH: 154
<212> TYPE: DNA
<213> ORGANISM: Homo sapiens

<400> SEQUENCE: 142
cgggcgcagc ctgtcccctc ccgccgccca ccttcctcgt ttctgcactc attttagcga    60
cgcagccgcc gctgctacct accccgcgct ccgcgtctc ctccgcgctg ggtctccccc   120

```
tttcttttgg tttgggtggg agaaaaagat ggtg                           154

<210> SEQ ID NO 143
<211> LENGTH: 77
<212> TYPE: DNA
<213> ORGANISM: Artificial sequence
<220> FEATURE:
<223> OTHER INFORMATION: Synthetic

<400> SEQUENCE: 143
gtatttattt tagcgacgta gtcgtcgttg ttatttattt cgcgttttcg cgtttttttc    60
gcgttggggt tttttt                                                    77

<210> SEQ ID NO 144
<211> LENGTH: 19
<212> TYPE: DNA
<213> ORGANISM: Artificial sequence
<220> FEATURE:
<223> OTHER INFORMATION: Synthetic

<400> SEQUENCE: 144
gcgacgtagt cgtcgttgt                                                 19

<210> SEQ ID NO 145
<211> LENGTH: 19
<212> TYPE: DNA
<213> ORGANISM: Artificial sequence
<220> FEATURE:
<223> OTHER INFORMATION: Synthetic

<400> SEQUENCE: 145
ccaacgcgaa aaaacgcg                                                  19

<210> SEQ ID NO 146
<211> LENGTH: 20
<212> TYPE: DNA
<213> ORGANISM: Artificial sequence
<220> FEATURE:
<223> OTHER INFORMATION: Synthetic

<400> SEQUENCE: 146
cgccgaggga aaacgcgaaa                                                20

<210> SEQ ID NO 147
<211> LENGTH: 21
<212> TYPE: DNA
<213> ORGANISM: Artificial sequence
<220> FEATURE:
<223> OTHER INFORMATION: Synthetic

<400> SEQUENCE: 147
ccacggacgc ggcgttcgcg a                                              21

<210> SEQ ID NO 148
<211> LENGTH: 165
<212> TYPE: DNA
<213> ORGANISM: Homo sapiens

<400> SEQUENCE: 148
ccggaggttg ttaagcagct ggcagagcag gactccatcg cggagggtct gcgcaaggtc    60
gaacacctga gccgagtccc aggtcacccg gtggttggtg ggcagcacct tgcaatggat   120
gagccactgc gcgcactgct tccacggctc catgcccgac ggctc                   165
```

<210> SEQ ID NO 149
<211> LENGTH: 165
<212> TYPE: DNA
<213> ORGANISM: Artificial sequence
<220> FEATURE:
<223> OTHER INFORMATION: Synthetic

<400> SEQUENCE: 149
tcggaggttg ttaagtagtt ggtagagtag gattttatcg cggagggttt gcgtaaggtc    60
gaatatttga gtcgagtttt aggttattcg gtggttggtg ggtagtattt tgtaatggat   120
gagttattgc gcgtattgtt tttacggttt tatgttcgac ggttt                   165

<210> SEQ ID NO 150
<211> LENGTH: 24
<212> TYPE: DNA
<213> ORGANISM: Artificial sequence
<220> FEATURE:
<223> OTHER INFORMATION: Synthetic

<400> SEQUENCE: 150
gagtcgagtt ttaggttatt cggt                                           24

<210> SEQ ID NO 151
<211> LENGTH: 26
<212> TYPE: DNA
<213> ORGANISM: Artificial sequence
<220> FEATURE:
<223> OTHER INFORMATION: Synthetic

<400> SEQUENCE: 151
cgtcgaacat aaaccgtaa aaacaa                                          26

<210> SEQ ID NO 152
<211> LENGTH: 21
<212> TYPE: DNA
<213> ORGANISM: Artificial sequence
<220> FEATURE:
<223> OTHER INFORMATION: Synthetic

<400> SEQUENCE: 152
ccacggacga tacgcgcaat a                                              21

<210> SEQ ID NO 153
<211> LENGTH: 118
<212> TYPE: DNA
<213> ORGANISM: Homo sapiens

<400> SEQUENCE: 153
cccgaatgga acgagcagct gagcttcgtg gagctcttcc cgccgctgac gcgcagcctc    60
cgcctgcagc tgcgggacga cgcgcccctg gtcgacgcgg cactcgctac gcacgtgc     118

<210> SEQ ID NO 154
<211> LENGTH: 118
<212> TYPE: DNA
<213> ORGANISM: Artificial sequence
<220> FEATURE:
<223> OTHER INFORMATION: Synthetic

<400> SEQUENCE: 154
ttcgaatgga acgagtagtt gagtttcgtg gagttttttt cgtcgttgac gcgtagtttt    60
cgtttgtagt tgcgggacga cgcgttttg gtcgacgcgg tattcgttac gtacgtgt     118

```
<210> SEQ ID NO 155
<211> LENGTH: 19
<212> TYPE: DNA
<213> ORGANISM: Artificial sequence
<220> FEATURE:
<223> OTHER INFORMATION: Synthetic

<400> SEQUENCE: 155
cgttgacgcg tagttttcg                                              19

<210> SEQ ID NO 156
<211> LENGTH: 18
<212> TYPE: DNA
<213> ORGANISM: Artificial sequence
<220> FEATURE:
<223> OTHER INFORMATION: Synthetic

<400> SEQUENCE: 156
gtcgaccaaa aacgcgtc                                               18

<210> SEQ ID NO 157
<211> LENGTH: 20
<212> TYPE: DNA
<213> ORGANISM: Artificial sequence
<220> FEATURE:
<223> OTHER INFORMATION: Synthetic

<400> SEQUENCE: 157
cgccgaggcg tcccgcaact                                             20

<210> SEQ ID NO 158
<211> LENGTH: 106
<212> TYPE: DNA
<213> ORGANISM: Danio rerio

<400> SEQUENCE: 158
tctggacagg tggagcagag ggaaggtggt gcgcatggtg ggcgagcgcg tgcgcctgga    60
ggaccccgat tggctgacgt gtaaaccagg acgaggacat gacttt                 106

<210> SEQ ID NO 159
<211> LENGTH: 126
<212> TYPE: DNA
<213> ORGANISM: Artificial sequence
<220> FEATURE:
<223> OTHER INFORMATION: Synthetic

<400> SEQUENCE: 159
gaattctttg dataggtgga gtagagggaa ggtggtgcgt atggtgggcg agcgcgtgcg    60
tttggaggat ttcgattggt tgacgtgtaa attaggacga ggatatgatt tttagttttg   120
gaattc                                                            126

<210> SEQ ID NO 160
<211> LENGTH: 17
<212> TYPE: DNA
<213> ORGANISM: Artificial sequence
<220> FEATURE:
<223> OTHER INFORMATION: Synthetic

<400> SEQUENCE: 160
tgcgtatggt gggcgag                                                17

<210> SEQ ID NO 161
<211> LENGTH: 26
<212> TYPE: DNA
```

<213> ORGANISM: Artificial sequence
<220> FEATURE:
<223> OTHER INFORMATION: Synthetic

<400> SEQUENCE: 161
cctaatttac acgtcaacca atcgaa        26

<210> SEQ ID NO 162
<211> LENGTH: 20
<212> TYPE: DNA
<213> ORGANISM: Artificial sequence
<220> FEATURE:
<223> OTHER INFORMATION: Synthetic

<400> SEQUENCE: 162
cgccgagggc gcgtgcgttt        20

<210> SEQ ID NO 163
<211> LENGTH: 224
<212> TYPE: DNA
<213> ORGANISM: Homo sapiens

<400> SEQUENCE: 163
ctctgacctg agtctccttt ggaactctgc aggttctatt tgcttttcc cagatgagct        60 cttttctgg tgtttgtctc tctgactagg tgtctaagac agtgttgtgg gtgtaggtac       120
taacactggc tcgtgtgaca aggccatgag gctggtgtaa agcggccttg gagtgtgtat      180
taagtaggtg cacagtaggt ctgaacagac tccccatccc aaga                     224

<210> SEQ ID NO 164
<211> LENGTH: 19
<212> TYPE: DNA
<213> ORGANISM: Artificial sequence
<220> FEATURE:
<223> OTHER INFORMATION: Synthetic

<400> SEQUENCE: 164
ccatgaggct ggtgtaaag        19

<210> SEQ ID NO 165
<211> LENGTH: 24
<212> TYPE: DNA
<213> ORGANISM: Artificial sequence
<220> FEATURE:
<223> OTHER INFORMATION: Synthetic

<400> SEQUENCE: 165
ctactgtgca cctacttaat acac        24

<210> SEQ ID NO 166
<211> LENGTH: 20
<212> TYPE: DNA
<213> ORGANISM: Artificial sequence
<220> FEATURE:
<223> OTHER INFORMATION: Synthetic

<400> SEQUENCE: 166
cgccgagggc ggccttggag        20

<210> SEQ ID NO 167
<211> LENGTH: 104
<212> TYPE: DNA
<213> ORGANISM: Homo sapiens

<400> SEQUENCE: 167

```
tggtgtttgt ttttttgatt aggtgtttaa gatagtgttg tgggtgtagg tattaatatt    60
ggtttgtgtg ataaggttat gaggttggtg taaagcggtt ttgg                    104
```

<210> SEQ ID NO 168
<211> LENGTH: 30
<212> TYPE: DNA
<213> ORGANISM: Artificial sequence
<220> FEATURE:
<223> OTHER INFORMATION: Synthetic

<400> SEQUENCE: 168

```
gtgtttgttt ttttgattag gtgtttaaga                                    30
```

<210> SEQ ID NO 169
<211> LENGTH: 26
<212> TYPE: DNA
<213> ORGANISM: Artificial sequence
<220> FEATURE:
<223> OTHER INFORMATION: Synthetic

<400> SEQUENCE: 169

```
ctttacacca acctcataac cttatc                                        26
```

<210> SEQ ID NO 170
<211> LENGTH: 21
<212> TYPE: DNA
<213> ORGANISM: Artificial sequence
<220> FEATURE:
<223> OTHER INFORMATION: Synthetic

<400> SEQUENCE: 170

```
gacgcggaga tagtgttgtg g                                             21
```

<210> SEQ ID NO 171
<211> LENGTH: 28
<212> TYPE: DNA
<213> ORGANISM: Artificial sequence
<220> FEATURE:
<223> OTHER INFORMATION: Synthetic

<400> SEQUENCE: 171

```
agccggtttt ccggctgaga cctcggcg                                      28
```

<210> SEQ ID NO 172
<211> LENGTH: 29
<212> TYPE: DNA
<213> ORGANISM: Artificial sequence
<220> FEATURE:
<223> OTHER INFORMATION: Synthetic

<400> SEQUENCE: 172

```
agccggtttt ccggctgaga cgtccgtgg                                     29
```

<210> SEQ ID NO 173
<211> LENGTH: 29
<212> TYPE: DNA
<213> ORGANISM: Artificial sequence
<220> FEATURE:
<223> OTHER INFORMATION: Synthetic

<400> SEQUENCE: 173

```
agccggtttt ccggctgaga ctccgcgtc                                     29
```

<210> SEQ ID NO 174

```
<211> LENGTH: 28
<212> TYPE: DNA
<213> ORGANISM: Artificial sequence
<220> FEATURE:
<223> OTHER INFORMATION: Synthetic

<400> SEQUENCE: 174
agccggtttt ccggctgaga cctcggcg                                              28

<210> SEQ ID NO 175
<211> LENGTH: 20
<212> TYPE: DNA
<213> ORGANISM: Artificial sequence
<220> FEATURE:
<223> OTHER INFORMATION: Synthetic

<400> SEQUENCE: 175
cgccgaggcg aacatcctcc                                                       20

<210> SEQ ID NO 176
<211> LENGTH: 20
<212> TYPE: DNA
<213> ORGANISM: Artificial sequence
<220> FEATURE:
<223> OTHER INFORMATION: Synthetic

<400> SEQUENCE: 176
cgccgaggtc gtcgataccg                                                       20

<210> SEQ ID NO 177
<211> LENGTH: 180
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (6)..(6)
<223> OTHER INFORMATION: N = 5-methyl cytosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (49)..(49)
<223> OTHER INFORMATION: N = 5-methyl cytosine
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: modified_base
<222> LOCATION: (60)..(60)
<223> OTHER INFORMATION: N = 5-methyl cytosine
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: modified_base
<222> LOCATION: (64)..(64)
<223> OTHER INFORMATION: N = 5-methyl cytosine
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: modified_base
<222> LOCATION: (66)..(66)
<223> OTHER INFORMATION: N = 5-methyl cytosine
<220> FEATURE:
<221> NAME/KEY: misc_feature
```

```
<222> LOCATION: (66)..(66)
<223> OTHER INFORMATION: n is a, c, g, or t
<220> FEATURE:
<221> NAME/KEY: modified_base
<222> LOCATION: (70)..(70)
<223> OTHER INFORMATION: N = 5-methyl cytosine
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: modified_base
<222> LOCATION: (84)..(84)
<223> OTHER INFORMATION: N = 5-methyl cytosine
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: modified_base
<222> LOCATION: (95)..(95)
<223> OTHER INFORMATION: N = 5-methyl cytosine
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: modified_base
<222> LOCATION: (109)..(109)
<223> OTHER INFORMATION: N = 5-methyl cytosine
<220> FEATURE:
<221> NAME/KEY: misc_feature
<222> LOCATION: (109)..(109)
<223> OTHER INFORMATION: n is a, c, g, or t

<400> SEQUENCE: 177
tccacngtgg tgcccactct ggacaggtgg agcagaggga aggtggtgng catggtgggn      60
gagngngtgn gcctggagga cccngattgg ctgangtgta aaccaggang aggacatgac    120
tttcagccct gcagccagac acagctgagc tggtgtgacc tgtgtggaga gttcatctgg    180

<210> SEQ ID NO 178
<211> LENGTH: 180
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (71)..(71)
<223> OTHER INFORMATION: N= 5-methyl cytosine
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: modified_base
<222> LOCATION: (85)..(85)
<223> OTHER INFORMATION: N= 5-methyl cytosine
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: modified_base
<222> LOCATION: (96)..(96)
<223> OTHER INFORMATION: N= 5-methyl cytosine
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: modified_base
<222> LOCATION: (110)..(110)
<223> OTHER INFORMATION: N= 5-methyl cytosine
<220> FEATURE:
```

```
<221> NAME/KEY: misc_feature
<222> LOCATION: (110)..(110)
<223> OTHER INFORMATION: n is a, c, g, or t
<220> FEATURE:
<221> NAME/KEY: modified_base
<222> LOCATION: (114)..(114)
<223> OTHER INFORMATION: N= 5-methyl cytosine
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: modified_base
<222> LOCATION: (116)..(116)
<223> OTHER INFORMATION: N= 5-methyl cytosine
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: modified_base
<222> LOCATION: (120)..(120)
<223> OTHER INFORMATION: N= 5-methyl cytosine
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: modified_base
<222> LOCATION: (131)..(131)
<223> OTHER INFORMATION: N= 5-methyl cytosine
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: modified_base
<222> LOCATION: (174)..(174)
<223> OTHER INFORMATION: N= 5-methyl cytosine
<220> FEATURE:
<221> NAME/KEY: misc_feature
<222> LOCATION: (174)..(174)
<223> OTHER INFORMATION: n is a, c, g, or t

<400> SEQUENCE: 178
ccagatgaac tctccacaca ggtcacacca gctcagctgt gtctggctgc agggctgaaa    60
gtcatgtcct ngtcctggtt tacangtcag ccaatngggg tcctccaggn gcangngctn   120
gcccaccatg ngcaccacct tccctctgct ccacctgtcc agagtgggca ccanggtgga   180

<210> SEQ ID NO 179
<211> LENGTH: 15
<212> TYPE: DNA
<213> ORGANISM: Artificial sequence
<220> FEATURE:
<223> OTHER INFORMATION: Synthetic

<400> SEQUENCE: 179
cgcatggtgg gcgag                                                     15

<210> SEQ ID NO 180
<211> LENGTH: 18
<212> TYPE: DNA
<213> ORGANISM: Artificial sequence
<220> FEATURE:
<223> OTHER INFORMATION: Synthetic

<400> SEQUENCE: 180
acacgtcagc caatcggg                                                  18

<210> SEQ ID NO 181
<211> LENGTH: 21
```

```
<212> TYPE: DNA
<213> ORGANISM: Artificial sequence
<220> FEATURE:
<223> OTHER INFORMATION: Synthetic

<400> SEQUENCE: 181
ccacggacgg cgcgtgcgtt t                                           21

<210> SEQ ID NO 182
<211> LENGTH: 29
<212> TYPE: DNA
<213> ORGANISM: Artificial sequence
<220> FEATURE:
<223> OTHER INFORMATION: Synthetic

<400> SEQUENCE: 182
agccggtttt ccggctgaga cgtccgtgg                                   29
```

DETECTION OF COLON NEOPLASIA BY ANALYSIS OF METHYLATED DNA

CROSS-REFERENCE TO RELATED APPLICATIONS

The present application is a continuation of U.S. patent application Ser. No. 15/881,409, filed Jan. 26, 2018, now issued as U.S. Pat. No. 11,118,228, which claims the priority benefit of U.S. Provisional Patent Application 62/451,327, filed Jan. 27, 2017 and U.S. Provisional Patent Application 62/622,107, filed Jan. 25, 2018, each of which is incorporated by reference in its entirety.

SEQUENCE LISTING

The text of the computer readable sequence listing filed herewith, titled "35006-304_SEQUENCE_LISTING_ST25", created Aug. 23, 2021, having a file size of 42,202 bytes, is hereby incorporated by reference in its entirety.

FIELD OF THE INVENTION

Provided herein is technology relating to detecting neoplasia and particularly, but not exclusively, to methods, compositions, and related uses for detecting neoplasms such as colon cancer.

BACKGROUND OF THE INVENTION

Colorectal cancer remains the $2^{nd}$ most common cancer in U.S. men and women combined (Siegel R, et al., CA Cancer J Clin 2013; 63:11-30). The underlying biology of progression from precursor lesion to cancer lends itself favorably to screening (Vogelstein B, et al., Science 2013; 339:1546-58). Evidence supports and guidelines endorse any of several tests and strategies (Levin B, et al., Gastroenterology 2008; 134:1570-95; Rex D K, et al., Am J Gastroenterol 2009; 104:739-50; Karl J, et al., Clin Gastroenterol Hepatol 2008; 6:1122-8). From a societal perspective, screening is considered cost-effective (Karl J, et al., Clin Gastroenterol Hepatol 2008; 6:1122-8; Heitman S J, et al., PLoS Med 2010; 7:e1000370; Parekh M, et al., Aliment Pharmacol Ther 2008; 27:697-712; Sharaf R N, et al., Am J Gastroenterol 2013; 108:120-32).

Colorectal cancer arises from accumulated genetic and epigenetic alterations, providing a basis for analysis of stool for tumor-specific changes (Berger B M, et al., Pathology 2012; 44:80-8). Previous large-scale studies of early generation stool-based DNA tests in the screening setting demonstrated only fair sensitivity for colorectal cancer and low sensitivity for advanced adenomas (Ahlquist D A, et al., Ann Intern Med 2008; 149:441-50, W81; Imperiale T F, et al., N Engl J Med 2004; 351:2704-14). Important advances have since been incorporated, including a stabilizing buffer (Boynton K A, et al., Clin Chem 2003; 49:1058-65; Zou H, et al., Cancer Epidemiol Biomarkers Prev 2006; 15:1115-9), more discriminant markers (Ahlquist D A, et al., Gastroenterology 2012; 142:248-56; Bardan E, et al., Israel journal of medical sciences 1997; 33:777-80), platforms with higher analytic sensitivity (Ahlquist D A, et al., Gastroenterology 2012; 142:248-56; Aronchick C A, et al., Gastrointestinal endoscopy 2000; 52:346-52), result determination using a logistic regression analysis rather than individual marker values, and automation.

Although screening reduces colorectal cancer mortality (Mandel J S, et al., N Engl J Med. 1993, 328:1365-71; Hardcastle J D, et al., Lancet. 1996, 348:1472-7; Kronborg O, et al., Scand J Gastroenterol. 2004, 39:846-51; Winawer S J, et al., J Natl Cancer Inst. 1993, 85:1311-8; Singh H, et al., JAMA. 2006, 295:2366-73), observed reductions have been modest (Singh H, et al., JAMA. 2006; 295, 2366-73; Heresbach D, et al., Eur J Gastroenterol Hepatol. 2006, 18:427-33) and more than one half of adults in the United States have not received screening (Meissner H I, Cancer Epidemiol Biomarkers Prev. 2006, 15:389-94).

An emerging approach to cancer screening involves the assay of tumor-specific DNA alterations in bodily samples from cancer patients, such as stool, serum, and urine (Osborn N K, Ahlquist D A. Gastroenterology 2005; 128:192-206; Ahlquist D A, et al., Gastroenterology 2000; 119:1219-27; Ahlquist D A, et al., Gastroenterology 2002; 122: Suppl A40; Chen W D, et al., J Natl Cancer Inst 2005; 97:1124-32; Zou H, et al., Cancer Epidemiol Biomarkers Prev 2006; 15:1115-9; Zou H Z, Clin Cancer Res 2002; 8:188-91; Hoque M O, J Clin Oncol 2005; 23:6569-75; Belinsky S A, et al., Cancer Res 2006; 66:3338-44; Itzkowitz S H, et al., Clin Gastroenterol Hepatol 2007; 5:111-7' Kann L, et al., Clin Chem 2006; 52:2299-302). It is important to select markers with high accuracy if efficiency and effectiveness are to be achieved in a cancer screening application. Due to the molecular heterogeneity of colorectal neoplasia, high detection rates often require a panel of markers.

Several methylated genes have been detected in the stool and serum/plasma samples from colorectal cancer patients (Ahlquist D A, Gastroenterology 2002; 122: Suppl A40; Chen W D, et al., J Natl Cancer Inst 2005; 97:1124-32; Zou H Z, et al., Clin Cancer Res 2002; 8:188-91; Itzkowitz S H, et al., Clin Gastroenterol Hepatol 2007; 5:111-7; Petko Z, et al., Clin Cancer Res 2005; 11:1203-9; Muller H M et al., Lancet 2004; 363:1283-5; Leung W K, et al., Clin Chem 2004; 50:2179-82; Ebert M P, et al., Gastroenterology 2006; 131:1418-30; Grady W M, et al., Cancer Res 2001; 61:900-2). Whereas some methylated genes have been found in a majority of colorectal cancers, the yield of bodily fluid-based assays remains suboptimal (Ahlquist D A, et al., Gastroenterology 2002; 122:Suppl A40; Chen W D, et al., J Natl Cancer Inst 2005; 97:1124-32; Zou H, et al., Cancer Epidemiol Biomarkers Prev 2006; 15:1115-9; Zou H Z, Clin Cancer Res 2002; 8:188-91; Belinsky S A, et al., Cancer Res 2006; 66: 3338-44; Itzkowitz S H, et al., Clin Gastroenterol Hepatol 2007; 5:111-7; Kann L, et al., Clin Chem 2006; 52:2299-302; Petko Z, et al., Clin Cancer Res 2005; 11:1203-9; Muller H M, et al., Lancet 2004; 363:1283-5; Leung W K, et al., Clin Chem 2004; 50: 2179-82; Ebert M P, et al., Gastroenterology 2006; 131:1418-30; Grady W M, et al., Cancer Res 2001; 61:900-2).

More accurate, user-friendly, and widely distributable tools to improve screening effectiveness, acceptability, and access are needed.

SUMMARY OF THE INVENTION

Provided herein is technology relating to detecting neoplasia and particularly, but not exclusively, to methods, compositions, and related uses for detecting premalignant and malignant colorectal cancer by analysis of blood and/or plasma samples from a subject, e.g., a patient. As the technology is described herein, the section headings used are for organizational purposes only and are not to be construed as limiting the subject matter in any way.

Provided herein is a panel of methylated DNA markers assayed on tissue that achieves extremely high discrimination for colorectal cancer while remaining negative in normal colorectal tissue. This panel can be applied, for example, to blood or bodily fluid-based testing, with applications in colorectal cancer screening.

Markers and/or panels of markers (e.g., a chromosomal region having an annotation selected from ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI) were identified in studies by comparing the methylation state of DNA markers from colorectal cancer samples to the corresponding markers in normal (non-cancerous) samples.

As described herein, the technology provides a number of methylated DNA markers and subsets thereof (e.g., sets of 2, 3, 4, 5, 6, 7, 8, 9, 10, 11, 12 or more markers) with high discrimination for colon cancer. Experiments applied a selection filter to candidate markers to identify markers that provide a high signal to noise ratio and a low background level to provide high specificity and selectivity for purposes of cancer screening or diagnosis. For example, as described herein below, a combination of 12 markers and carcinoembryonic antigen (CEA) protein resulted in 67.4% sensitivity (60/89 cancers) for all of the cancer plasma samples tested, with 92.6% specificity.

Accordingly, provided herein is technology related to a method of screening for colon cancer in a sample obtained from a subject, the method comprising assaying an amount of a methylated marker DNA, e.g., to assess a methylation state of a marker in a sample obtained from a subject; and identifying the subject as having colon cancer when the methylation state of the marker is different than a methylation state of the marker assayed in a subject that does not have a neoplasm. In some embodiments, the marker comprises a chromosomal region having an annotation selected from ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI. In some embodiments, the technology comprises assaying a plurality of markers, e.g., comprising assaying 2 to 20, preferably 2-14, more preferably 2-12 markers. For example in some embodiments, the method comprises analysis of the methylation status of two or more markers selected from VAV3; ZNF671; CHST2; FLI1; JAM3; SFMBT2; PDGFD; DTX1; TSPYL5; ZNF568; GRIN2D, and QKI. In preferred embodiments, the assay comprises detection of CEA protein.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker, i.e., relative to the methylation state of the marker in DNA from a subject who does not have a neoplasia. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

In some embodiments, the technology provides a method of generating a record reporting a colon neoplasm in a sample obtained from a subject comprising the steps of:

a) assaying a sample from a subject for an amount of at least one methylated marker gene selected from the group consisting of ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI in a sample obtained from a subject;

b) assaying said sample for an amount of reference marker in said sample;

c) comparing the amount of said at least one methylated marker gene to the amount of reference marker, preferably a methylated reference marker, in said sample to determine a methylation state for said at least one marker gene in said sample; and d) generating a record reporting the methylation state for said at least one marker gene in said sample.

The record reporting the methylation state of a marker is not limited to any particular form of report, and may comprise, for example, an update to an electronic medical record, a printed report, or an electronic message. In some embodiments, the laboratory data generated during the assaying is included in the report, while in some embodiments, only a summary of the data or a diagnostic result based on the determined methylation state for the at least one marker gene is included in the record.

In some embodiments, the sample is assayed for at least two of the markers, and preferably the at least one methylated marker gene is selected from the group consisting of VAV3; ZNF671; CHST2; FLI1; JAM3; SFMBT2; PDGFD; DTX1; TSPYL5; ZNF568; GRIN2D, and QKI. In still more preferred embodiments, the sample is assayed for a group of markers comprising of VAV3; ZNF671; CHST2; FLI1; JAM3; SFMBT2; PDGFD; DTX1; TSPYL5; ZNF568; GRIN2D, and QKI. In preferred embodiments, a sample from the subject is assayed for the presence of CEA protein.

In some embodiments the method used for assaying comprises obtaining a sample comprising DNA from a subject, and treating DNA obtained from the sample with a reagent that selectively modifies unmethylated cytosine residues in the obtained DNA to produce modified residues. In preferred embodiments the reagent comprises a bisulfate reagent.

The method is not limited to a particular size of a methylated marker region analyzed, or the number of nucleotides analyzed for methylation status. In some embodiments assaying the methylation state of the marker DNA in the sample comprises determining the methylation state of one base, while in other embodiments the assay comprises determining the extent of methylation at a plurality of bases. In some embodiments the methylation state of the marker comprises an increased or decreased methylation of the marker relative to a normal methylation state of the marker, while in some embodiments the methylation state of the marker comprises a different pattern of methylation, e.g., a different subset of methylated nucleotides in a methylated region of the marker relative to a normal methylation state of the marker.

The technology is not limited to particular sample types. For example, in some embodiments the sample is a tissue sample, a blood sample, a serum sample, or a sputum sample. In certain embodiments a tissue sample comprises colon tissue.

The technology is not limited to any particular method of assaying DNA samples. For example, in on some embodiments the assaying comprises using polymerase chain reaction, nucleic acid sequencing, mass spectrometry, methylation specific nuclease, mass-based separation, and/or target capture. In certain preferred embodiments the assaying comprises using a flap endonuclease assay. In particularly preferred embodiments the sample DNA and/or reference marker DNA are bisulfite-converted and the assay for determining the methylation level of the DNA is achieved by a technique comprising the use of methylation-specific PCR, quantitative methylation-specific PCR, methylation-sensitive DNA restriction enzyme analysis, quantitative bisulfite pyrosequencing, PCR-flap assay, flap endonuclease assay, and/or bisulfite genomic sequencing PCR.

In some embodiments, an oligonucleotide in said mixture comprises a reporter molecule, and in preferred embodiments, the reporter molecule comprises a fluorophore. In some embodiments the oligonucleotide comprises a flap sequence. In some embodiments the mixture further comprises one or more of a FRET cassette; a FEN-1 endonuclease and a thermostable DNA polymerase, preferably a bacterial DNA polymerase.

In some embodiments, the technology used comprises detecting multiple markers and/or multiple regions of a single marker using an assay that reports detection of the multiple markers and/or multiple regions of a single marker to a single signal output, e.g., a single fluorescent dye. For example, in some embodiments, an assay is configured to report the cleavage of flap endonuclease probes specific for multiple different target sites via a single FRET cassette.

In some embodiments, then, the assaying of a sample comprises preparing a reaction mixture comprising amplification reagents for amplifying at least two methylated marker DNAs, and flap cleavage reagents for performing a flap endonuclease assay on amplified marker DNAs, wherein said reagents comprise:
 i) a first primer pair for producing a first amplified region of a methylated marker DNA;
 ii) a first probe comprising a) a sequence complementary to at least a portion of said first amplified region a methylated marker DNA; and b) a flap portion having a first flap sequence that is not substantially complementary to said first amplified region of a methylated marker DNA;
 iii) a second primer pair for producing a second amplified region of a methylated marker DNA;
 iv) a second probe comprising a) a sequence complementary to at least a portion of said second region of a methylated marker DNA; and b) a flap portion having said first flap sequence, wherein said first flap sequence is not substantially complementary to said second amplified region of a methylated marker DNA;
 v) a DNA polymerase; and
 vi) a flap endonuclease.

In some embodiments, said first amplified region of a methylated marker DNA and said second amplified region of a methylated marker DNA are amplified from different regions of the same methylation marker gene, while in other embodiments, the first amplified region of a methylated marker DNA and the second amplified region of a methylated marker DNA are amplified from different methylation marker genes. In some preferred embodiments, amplifying the at least two methylated marker DNAs comprises amplifying at least two methylated marker DNAs selected from the group consisting of ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI.

In preferred embodiments, amplifying the at least two methylated marker DNAs comprises amplifying at least three methylated marker DNAs. In such embodiments, the reagents may preferably comprise a third primer pair for producing a third amplified region of a methylated marker DNA; and a third probe comprising a) a sequence complementary to at least a portion of the third amplified region of a methylated marker DNA; and b) a flap portion having the same first flap sequence, wherein the first flap sequence is not substantially complementary to the third amplified region of a methylated DNA.

In some embodiments, a reference nucleic acid is also assayed. In such embodiments, the reagents may further comprise a reference primer pair for producing an amplified region of the reference nucleic acid, and a reference probe comprising a) a sequence complementary to at least a portion of the amplified region of the reference nucleic acid; and b) a flap portion having a second flap sequence, wherein the second flap sequence is not substantially complementary to the amplified region of a reference nucleic acid or to the first FRET cassette; and a second FRET cassette comprising a sequence complementary to the second flap sequence.

The technology for detecting multiple nucleic acid sequences (e.g., multiple markers and/or multiple regions of a single marker) using an assay that reports detection of the multiple markers and/or multiple regions of a single marker to a single signal output, e.g., a single fluorescent dye, is not limited to analysis of methylation, or to detection or assaying of the sample types or markers discussed above. For example, in some embodiments the technology provides a method of characterizing any sample (e.g., from a subject) comprising detecting at least one target nucleic acid in a sample, wherein said detecting said at least one target nucleic acid in the sample comprises preparing a reaction mixture comprising amplification reagents for producing at least two different amplified DNAs, and flap cleavage reagents for performing a flap endonuclease assay on the at least two different amplified DNAs, wherein said reagents comprise:
 i) a first primer pair for producing a first amplified DNA;
 ii) a first probe comprising a) a sequence complementary to a region of said first amplified DNA; and b) a flap portion having a first flap sequence that is not substantially complementary to said first amplified DNA;
 iii) a second primer pair for producing a second amplified DNA;
 iv) a second probe comprising a) a sequence complementary to a region of said second amplified DNA; and b) a flap portion having said first flap sequence, wherein said first flap sequence is not substantially complementary to said second amplified DNA;
 v) a FRET cassette comprising a sequence complementary to said first flap sequence;
 vi) a DNA polymerase; and
 vii) a flap endonuclease.

In some embodiments, the at least two different target DNAs may comprise at least two different marker genes or marker regions in said sample, while in some embodiments, the at least two different target DNAs comprise at least two different regions of a single marker gene in the sample. The nucleic acids that can be analyzed using the methods disclosed herein are not limited to any particular type of nucleic acid, and may comprise any nucleic acid that can serve as a target for in vitro amplification, e.g., by PCR. In some embodiments, one or more of the at least one target nucleic acid in the sample is RNA. As discussed above, the method is not limited to analyzing two markers or regions, but may be applied to, for example, three, four, five, six, seven, etc. target sequences that report to the same FRET cassette. Further, assays may be combined so that multiple different target nucleic acids in an assay report to a first FRET cassette, multiple different targets in the same assay report to a second FRET cassette, multiple different targets in the same assay report to a third FRET cassette, etc.

The technology also provides kits. For example, in some embodiments a kit comprises a first primer pair for producing a first amplified DNA; a first probe comprising a) a sequence complementary to a region of said first amplified DNA; and b) a flap portion having a first flap sequence that is not substantially complementary to said first amplified DNA; a second primer pair for producing a second amplified DNA; a second probe comprising a) a sequence complementary to a region of said second amplified DNA; and b) a flap portion having said first flap sequence, wherein said first flap sequence is not substantially complementary to said second amplified DNA; a FRET cassette comprising a sequence complementary to said first flap sequence; a DNA polymerase; and a flap endonuclease.

In certain preferred embodiments the technology provides a kit, comprising a) at least one oligonucleotide, wherein at least a portion of the oligonucleotide specifically hybridizes to a marker selected from the group consisting of ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI, and b) at least one additional oligonucleotide, wherein at least a portion of the additional oligonucleotide specifically hybridizes to a reference nucleic acid. In preferred embodiments, the kit comprises an assay for detecting CEA protein. In some embodiments the kit comprises at least two additional oligonucleotides and, in some embodiments, the kit further comprises a bisulfate reagent.

In certain embodiments at least a portion of the oligonucleotide specifically hybridizes to a least one the marker selected from the group consisting of VAV3; ZNF671; CHST2; FLI1; JAM3; SFMBT2; PDGFD; DTX1; TSPYL5; ZNF568; GRIN2D, and QKI. In preferred embodiments, the kit comprises at least 12 oligonucleotides, wherein each of the markers in the group consisting of VAV3; ZNF671; CHST2; FLI1; JAM3; SFMBT2; PDGFD; DTX1; TSPYL5; ZNF568; GRIN2D, and QKI specifically hybridizes to at least one of the 12 oligonucleotides.

In preferred embodiments, oligonucleotide(s) provided in a kit are selected from one or more of a capture oligonucleotide, a pair of nucleic acid primers, a nucleic acid probe, and an invasive oligonucleotide.

In some embodiments any one of the kits describe above further comprises a solid support, such as a magnetic bead or particle. In preferred embodiments, a solid support comprises one or more capture reagents, e.g., oligonucleotides complementary said one or more markers genes.

The technology also provides compositions. For example, in some embodiments the technology provides a composition comprising a mixture, e.g., a reaction mixture, that comprises a first primer pair for producing a first amplified DNA; a first probe comprising a) a sequence complementary to a region of the first amplified DNA; and b) a flap portion having a first flap sequence that is not substantially complementary to the first amplified DNA; a second primer pair for producing a second amplified DNA; a second probe comprising a) a sequence complementary to a region of the second amplified DNA; and b) a flap portion having said first flap sequence, wherein the first flap sequence is not substantially complementary to the second amplified DNA; a FRET cassette comprising a sequence complementary to said first flap sequence; a DNA polymerase; and a flap endonuclease. In preferred embodiments, the composition further comprises the first amplified DNA and the second amplified DNA, wherein the first probe is not substantially complementary to the second amplified DNA, and wherein the second probe is not substantially complementary to the first amplified DNA. In some embodiments, the composition comprises a primer or a probe complexed to a DNA.

In some embodiments, the composition comprises a complex of a target nucleic acid selected from the group consisting of ANKRD13B; CHST2; GRIN2D; FLI1; JAM3; LRRC4; OPLAH; SEP9; SFMBT2; SLC12A8; TBX15; ZDHHC1; ZNF304; ZNF568; ZNF671; CNNM1; DOCK2; DTX1; FERMT3; PDGFD; PKIA; PPP2R5C; TSPYL5; VAV3; FER1L4; and QKI, and an oligonucleotide that specifically hybridizes to the target nucleic acid. In preferred embodiments, the mixture comprises a complex of a target nucleic acid selected from the group consisting of VAV3; ZNF671; CHST2; FLI1; JAM3; SFMBT2; PDGFD; DTX1; TSPYL5; ZNF568; GRIN2D, and QKI and an oligonucleotide that specifically hybridizes to the target nucleic acid. Oligonucleotides in the mixture include but are not limited to one or more of a capture oligonucleotide, a pair of nucleic acid primers, a hybridization probe, a hydrolysis probe, a flap assay probe, and an invasive oligonucleotide.

In some embodiments, the target nucleic acid in the mixture comprises a nucleic acid sequence selected from the group consisting of SEQ ID NOS: 1, 6, 11, 16, 21, 26, 31, 36, 41, 46, 51, 56, 61, 66, 71, 76, 81, 86, 91, 96, 101, 106, 111, 116, 121, 126, 131, and 136.

In some embodiments, the mixture comprises bisulfate-converted target nucleic acid that comprises a nucleic acid sequence selected from the group consisting of SEQ ID NOS:2, 7, 12, 17, 22, 27, 32, 37, 42, 47, 52, 57, 62, 67, 72, 77, 82, 87, 92, 97, 102, 107, 112, 117, 122, 127, 132, and 137.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g., Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J. Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. An exemplary reagent is a bisulfite reagent.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a nucleotide that is typically methylated and an unmethylated selected nucleotides refers specifically to a nucleotide that typically occurs in unmethylated form.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemi-methylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

The term "marker", as used herein, refers to a substance (e.g., a nucleic acid, or a region of a nucleic acid, or a protein) that may be used to distinguish non-normal cells (e.g., cancer cells) from normal cells, e.g., based on presence, absence, or status (e.g., methylation state) of the marker substance.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a colon cancer in a subject. The system can be provided, for example, as a commercial kit that can be used to screen for a risk of colon cancer or diagnose a colon cancer in a subject from whom a biological sample has been collected. An exemplary system provided in accordance with the present technology includes assessing the methylation state of a marker described herein.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties). 5'

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in, e.g., in U.S. Pat. Nos. 8,361,720; 8,715,937; 8,916,344; and 9,212,392, each of which is incorporated herein by reference for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

The term "probe oligonucleotide" or "flap oligonucleotide" when used in reference to flap assay, refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archival thermophiles organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect. In such embodiments, the cassette may be referred to as a "FRET cassette." See, for example, See also U.S. Patent Appl. Ser. Nos. 62/249,097, filed Oct. 30, 2015, Ser. No. 15/335,096, filed Oct. 26, 2016; and International Appl. Ser. No. PCT/US16/58875, filed Oct. 26, 2016, each of which is incorporated herein by reference in its entirety, for all purposes.

As used herein, the phrase "not substantially complementary" as used in reference to a probe flap or arm means that the flap portion is sufficiently non-complementary not to hybridize selectively to a nucleic acid sequence, e.g., a target nucleic acid or amplified DNA, under the designated annealing conditions or stringent conditions, encompassing the terms "substantially non-complementary" and "perfectly non-complementary."

The term "complementary" is used herein to mean that primers or probes are sufficiently complementary to hybridize selectively, e.g., to a target nucleic acid sequence under the designated annealing conditions or stringent conditions, encompassing the terms "substantially complementary" and "perfectly complementary."

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a "dark" quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired "flap" is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein in reference to data collected during real time PCR and PCR+ INVADER assays refer to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

As used herein, the term "control" when used in reference to nucleic acid detection or analysis refers to a nucleic acid having known features (e.g., known sequence, known copy-number per cell), for use in comparison to an experimental target (e.g., a nucleic acid of unknown concentration). A control may be an endogenous, preferably invariant gene against which a test or target nucleic acid in an assay can be normalized. Such normalizing controls for sample-to-sample variations that may occur in, for example, sample processing, assay efficiency, etc., and allows accurate sample-to-sample data comparison. Genes that find use for normalizing nucleic acid detection assays on human samples include, e.g., β-actin, ZDHHC1, and B3GALT6 (see, e.g., U.S. patent application Ser. Nos 14/966,617 and 62/364,082, each incorporated herein by reference.

Controls may also be external. For example, in quantitative assays such as qPCR, QuARTS, etc., a "calibrator" or "calibration control" is a nucleic acid of known sequence, e.g., having the same sequence as a portion of an experimental target nucleic acid, and a known concentration or series of concentrations (e.g., a serially diluted control target for generation of calibration curved in quantitative PCR). Typically, calibration controls are analyzed using the same reagents and reaction conditions as are used on an experimental DNA. In certain embodiments, the measurement of the calibrators is done at the same time, e.g., in the same thermal cycler, as the experimental assay. In preferred embodiments, multiple calibrators may be included in a single plasmid, such that the different calibrator sequences are easily provided in equimolar amounts. In particularly preferred embodiments, plasmid calibrators are digested, e.g., with one or more restriction enzymes, to release calibrator portion from the plasmid vector. See, e.g., WO 2015/066695, which is included herein by reference. In some embodiments, calibrator DNAs are synthetic, e.g. as described in U.S. patent application Ser. No. 15/105,178, incorporated herein by reference.

As used herein "ZDHHC1" refers to a gene encoding a protein characterized as a zinc finger, DHHC-type containing 1, located in human DNA on Chr 16 (16q22.1) and belonging to the DHHC palmitoyltransferase family.

As used herein, the term "process control" refers to an exogenous molecule, e.g., an exogenous nucleic acid added to a sample prior to extraction of target DNA that can be measured post-extraction to assess the efficiency of the process and be able to determine success or failure modes. The nature of the process control nucleic acid used is usually dependent on the assay type and the material that is being measured. For example, if the assay being used is for detection and/or quantification of double stranded DNA or mutations in it, then double stranded DNA process controls are typically spiked into the samples pre-extraction. Similarly, for assays that monitor mRNA or microRNAs, the process controls used are typically either RNA transcripts or synthetic RNA. See, e.g., U.S. Pat. Appl. Ser. No. 62/364,049, filed Jul. 19, 2016, which is incorporated herein by reference, and which describes use of zebrafish DNA as a process control for human samples.

As used herein, the term "zebrafish DNA" is distinct from bulk "fish DNA") e.g., purified salmon DNA) and refers to DNA isolated from *Danio rerio*, or created in vitro (e.g., enzymatically, synthetically) to have a sequence of nucleotides found in DNA from *Danio rerio*. In preferred embodiments, the zebrafish DNA is a methylated DNA added as a detectable control DNA, e.g., a process control for verifying DNA recovery through sample processing steps. In particular, zebrafish DNA comprising at least a portion of the RASSF1 gene finds use as a process control, e.g., for human samples, as described in U.S. Pat. Appl. Ser. No. 62/364,049.

As used herein the term "fish DNA" is distinct from zebrafish DNA and refers to bulk (e.g., genomic) DNA isolated from fish, e.g., as described in U.S. Pat. No. 9,212,392. Bulk purified fish DNA is commercially available, e.g., provided in the form of cod and/or herring sperm DNA (Roche Applied Science, Mannheim, Germany) or salmon DNA (USB/Affymetrix).

As used herein, the terms "particle" and "beads" are used interchangeably, and the terms "magnetic particles" and "magnetic beads" are used interchangeably and refer to particles or beads that respond to a magnetic field. Typically, magnetic particles comprise materials that have no magnetic field but that form a magnetic dipole when exposed to a magnetic field, e.g., materials capable of being magnetized in the presence of a magnetic field but that are not themselves magnetic in the absence of such a field. The term "magnetic" as used in this context includes materials that are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides.

The term "system" as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DESCRIPTION OF THE DRAWINGS

FIG. 1 shows schematic diagrams of marker target regions in unconverted form and bisulfite-converted form. Flap assay primers and probes for detection of bisulfite-converted target DNA are shown.

FIG. 2 provides a table of nucleic acid sequences and corresponding SEQ ID NOS.

FIG. 3 provides a table showing data and results from the assay of Example 2.

FIG. 4 provides a table showing data and results from the assay of Example 2.

DETAILED DESCRIPTION OF THE INVENTION

Figure 5:
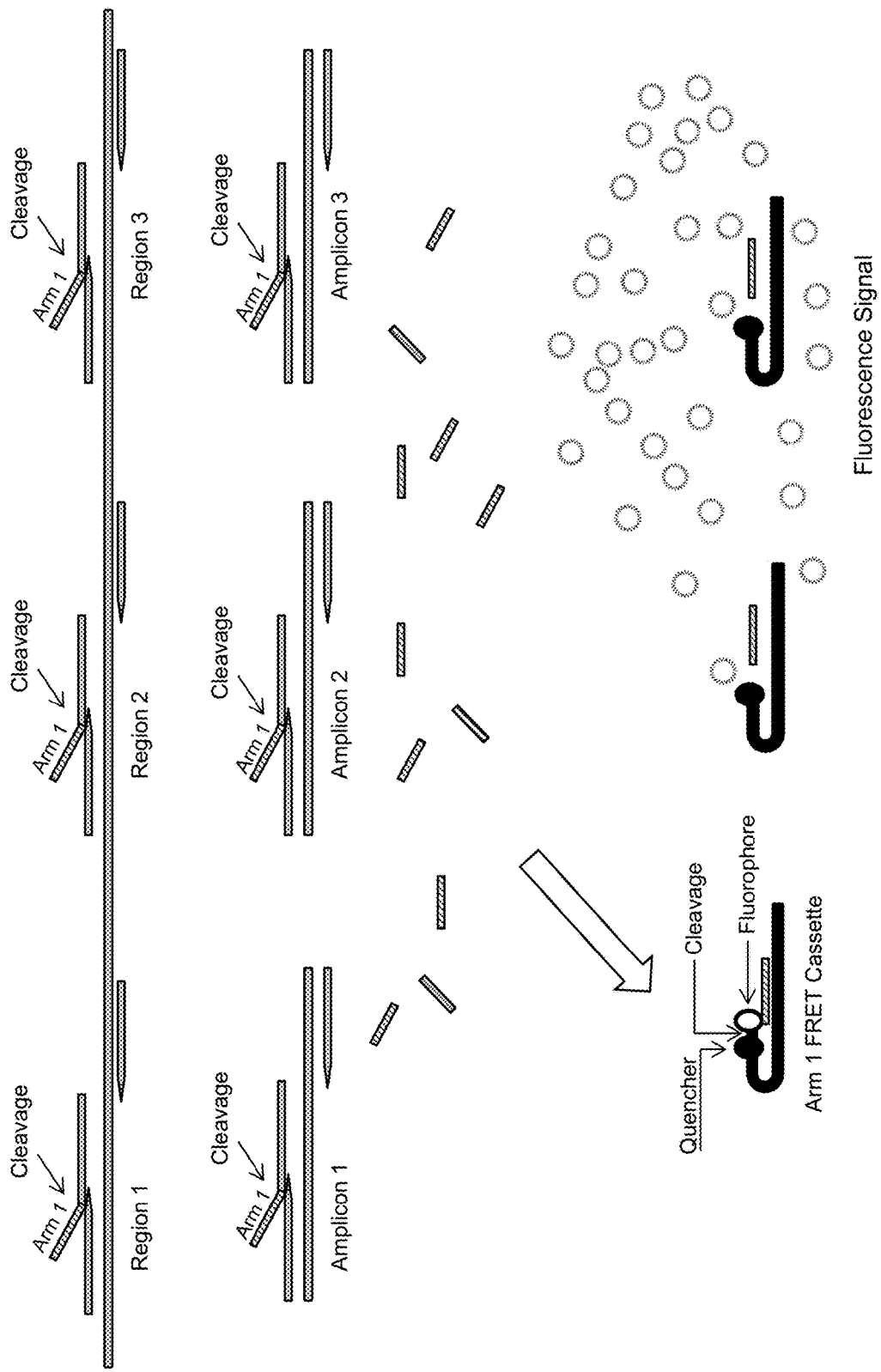
FIG. 5 provides a schematic drawing showing a combined PCR-invasive cleavage assay ("PCR-flap assay"), e.g., a QuARTS assay in which three different regions of a target nucleic acid, e.g., a methylation marker, are amplified by primer pairs specific for each of the different regions, and in the presence of different flap probes, each one specific for one of the different regions, but each having the same flap arm sequence. The flaps release during each of the PCR-flap assays all report to the same FRET cassette to produce fluorescence signal from the same fluorophore.

Provided herein is technology relating to selection and use of nucleic acid markers for use in assays for detection and quantification of DNA, e.g., methylated DNA. In particular, the technology relates to use of methylation assays to detect colon cancer.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

In some embodiments, analysis of target DNAs comprises analysis of multiple different DNAs in a single reaction. Typical instrumentation for real-time detection of amplification reactions allows for simultaneous detection and quantification of only 3-5 fluorescent dyes. This is mainly because spectral overlap between fluorophores makes it difficult to distinguish one dye from another when the many dyes with overlap excitation and/or emission spectra are used together. When detection of a specific disease from a biological specimen requires a panel comprising more than about 5 different markers, this presents a challenge, especially when the size of the sample is limited and the markers are present in low levels, a situation often requiring use of the entirety of a sample in a single amplification run.

In some embodiments, methods described herein allow for detection of multiple different markers in the same sample by having each sample produce a result from the same dye. In the embodiment described in detail herein, multiplexed flap cleavage assays (e.g., QuARTS flap endonuclease assays) for multiple different markers produce initial cleavage products that use the same FRET cassette to produce fluorescent signal.

In preferred embodiments, the combined assay comprises several different probe oligonucleotides that each have a portion that hybridizes to a different target nucleic acid, but that all have essentially the same 5' arm sequence. Cleavage of the probes in the presence of their respective target nucleic acids all release the same 5' arm, and all of the released arms then combine with FRET cassettes having the same flap-binding sequence and the same dye to produce fluorescence signal by endonuclease cleavage of the FRET cassette. In other embodiments, the probes for different targets may have different flap arms that report to different FRET cassettes, wherein the different FRET cassettes all use the same reporter fluorophore.

Combining assays in this manner has multiple advantages. For example, a sample can provide a result if any one of the target sequences associated with a condition (e.g., a disease state, such as colorectal cancer) is detected in the assay, without the need to divide the sample into multiple different assays, Further, if more than one of the target sequences provides such a result, aggregation of these signals into a single dye channel may provide a stronger signal over background, providing more certainty for the assay result. During development of the methods described herein, it was surprisingly found that combining a large number of primers and flap assay probes for detecting multiple different target sequences, along with a shared FRET cassette, in a single amplification plus flap cleavage assay reaction did not increase background signal in no-target controls or in negative samples.

In some embodiments, different target sequences reporting to a single FRET cassette and single dye channel may not be from different marker genes or regions, but may be from different regions within a single marker (e.g., a single methylation marker gene). As described in Example 4, configuring assays to detect multiple regions of a single marker gene in an assay where all the regions report to a single dye, e.g., via a single FRET cassette, boosts the level of detectable signal from the copies of the target gene present in the reaction.

In yet other embodiments, the different target sequences to be detected may be a mixture of multiple regions of one marker, along with one or more regions of a different marker or markers. The different target sequences may comprise any combination of methylation markers, mutation markers, deletions, insertions, or any other manner of nucleic acid variants detectable in an assay such as a QuARTS amplification/flap cleavage assay.

In some embodiments, a marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample, sputum, a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, chip or array hybridization, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a differentially methylated region (DMR). In some embodiments are provided an oligonucleotide comprising a sequence complementary to a chromosomal region having Kit embodiments are provided, e.g., a kit comprising a bisulfite reagent; and a control nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI and having a methylation state associated with a subject who does not have a cancer (e.g., colon cancer). In some embodiments, kits comprise a bisulfite reagent and an oligonucleotide as described herein. In some embodiments, kits comprise a bisulfite reagent; and a control nucleic acid comprising a sequence from such a chromosomal region and having a methylation state associated with a subject who has colon cancer.

The technology is related to embodiments of compositions (e.g., reaction mixtures). In some embodiments are provided a composition comprising a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI and a bisulfite reagent. Some embodiments provide a composition comprising a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI and an oligonucleotide as described herein. Some embodiments provide a composition comprising a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI and a methylation-sensitive restriction enzyme. Some embodiments provide a composition comprising a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI and a polymerase.

Additional related method embodiments are provided for screening for a neoplasm (e.g., colon carcinoma) in a sample obtained from a subject, e.g., a method comprising determining a methylation state of a marker in the sample comprising a base in a chromosomal region having an annotation selected from VAV3; ZNF671; CHST2; FLI1; JAM3; SFMBT2; PDGFD; DTX1; TSPYL5; ZNF568; GRIN2D, and QKI; comparing the methylation state of the marker from the subject sample to a methylation state of the marker from a normal control sample from a subject who does not have colon cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI with a bisulfate reagent to produce a bisulfate-reacted nucleic acid; sequencing the bisulfate-reacted nucleic acid to provide a nucleotide sequence of the bisulfite-reacted nucleic acid; comparing the nucleotide sequence of the bisulfate-reacted nucleic acid with a nucleotide sequence of a nucleic acid comprising the chromosomal region from a subject who does not have colon cancer to identify differences in the two sequences; and identifying the subject as having a neoplasm when a difference is present.

Systems for screening for colon cancer in a sample obtained from a subject are provided by the technology. Exemplary embodiments of systems include, e.g., a system for screening for colon cancer in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., a chromosomal region having an annotation selected from VAV3; ZNF671; CHST2; FLI1; JAM3; SFMBT2; PDGFD; DTX1; TSPYL5; ZNF568; GRIN2D, and QKI and calculating a value or result to report based on the multiple results. Some embodiments provide a database of weighted parameters associated with each chromosomal region having an annotation selected from VAV3; ZNF671; CHST2; FLI1; JAM3; SFMBT2; PDGFD; DTX1; TSPYL5; ZNF568; GRIN2D, and QKI provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a colon cancer risk in a subject.

In some embodiments of systems, a sample comprises a nucleic acid comprising a chromosomal region having an annotation selected from VAV3; ZNF671; CHST2; FLI1; JAM3; SFMBT2; PDGFD; DTX1; TSPYL5; ZNF568; GRIN2D, and QKI. In some embodiments the system further comprises a component for isolating a nucleic acid, a component for collecting a sample such as a component for collecting a stool sample. In some embodiments, the system comprises nucleic acid sequences comprising a chromosomal region having an annotation selected from VAV3; ZNF671; CHST2; FLI1; JAM3; SFMBT2; PDGFD; DTX1; TSPYL5; ZNF568; GRIN2D, and QKI. In some embodiments the database comprises nucleic acid sequences from subjects who do not have colon cancer. Also provided are nucleic acids, e.g., a set of nucleic acids, each nucleic acid having a sequence comprising a chromosomal region having an annotation selected from VAV3; ZNF671; CHST2; FLI1; JAM3; SFMBT2; PDGFD; DTX1; TSPYL5; ZNF568; GRIN2D, and QKI.

Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

In certain embodiments, methods for characterizing a sample obtained from a human subject are provided, comprising a) obtaining a sample from a human subject; b) assaying a methylation state of one or more markers in the sample, wherein the marker comprises a base in a chromosomal region having an annotation selected from the following groups of markers: VAV3; ZNF671; CHST2; FLI1; JAM3; SFMBT2; PDGFD; DTX1; TSPYL5; ZNF568; GRIN2D, and QKI; and c) comparing the methylation state of the assayed marker to the methylation state of the marker assayed in a subject that does not have a neoplasm.

In some embodiments, the technology is related to assessing the presence of and methylation state of one or more of the markers identified herein in a biological sample. These markers comprise one or more differentially methylated regions (DMR) as discussed herein. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) *Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) *Nucl. Acids Res.* 18: 687). In addition, other techniques have been reported that utilize bisulfite treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. Nos. 8,361,720; 8,715,937; 8,916,344; and 9,212,392).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primer pairs for amplifying a plurality of markers). Additional reagents for conducting a detection assay may also be provided (e.g., enzymes, buffers, positive and negative controls for conducting QuARTS, PCR, sequencing, bisulfate, or other assays). In some embodiments, the kits containing one or more reagents necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

Methods for isolating DNA suitable for these assay technologies are known in the art. In particular, some embodiments comprise isolation of nucleic acids as described in U.S. Pat. No. 9,000,146, which is incorporated herein by reference in its entirety.

Genomic DNA may be isolated by any means, including the use of commercially available kits. Briefly, wherein the DNA of interest is encapsulated by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 or 9,000,146, or by a related method.

The technology relates to the analysis of any sample associated with colon cancer. For example, in some embodiments the sample comprises a tissue and/or biological fluid obtained from a patient. In some embodiments, the sample comprises a secretion. In some embodiments, the sample comprises sputum, blood, serum, plasma, gastric secretions, colon tissue samples, colon cells or colon DNA recovered from stool. In some embodiments, the subject is human. Such samples can be obtained by any number of means known in the art, such as will be apparent to the skilled person.

I. Methylation Assays to Detect Colon Cancer

Candidate methylated DNA markers were identified by unbiased whole methylome sequencing of selected colon cancer case and colon control tissues. The top marker candidates were further evaluated in 89 cancer and 95 normal plasma samples. DNA extracted from patient tissue samples was bisulfite treated and then candidate markers and reference genes (e.g., β-actin or B3GALT6) as a normalizing genes were assayed by Quantitative Allele-Specific Real-time Target and Signal amplification (QuARTS amplification). QuARTS assay chemistry yields high discrimination for methylated marker selection and screening.

On receiver operator characteristics analyses of individual marker candidates, areas under the curve (AUCs) ranged from 0.63 to 0.75. At 92.6% specificity, a combined panel of 12 methylation markers (VAV3; ZNF671; CHST2; FLI1; JAMS; SFMBT2; PDGFD; DTX1; TSPYL5; ZNF568; GRIN2D, and QKI) plus an assay for the CEA protein yielded a sensitivity of 67.4% across all stages of colon cancer.

II. Methylation Detection Assays and Kits

The markers described herein find use in a variety of methylation detection assays. The most frequently used method for analyzing a nucleic acid for the presence of 5-methylcytosine is based upon the bisulfite method described by Frommer, et al. for the detection of 5-methyl-cytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; and in U.S. Pat. Nos. 8,361,720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199). In embodiments, described herein, the QuARTS assay can also be configured to detect multiple different targets in or different regions of the same target using a the same FRET cassette, producing an additive fluorescence signal from a single dye.

In some embodiments, the bisulfite-treated DNA is purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by reference in its entirety). In some embodiments, the bisulfite treated DNA is bound to a solid support, e.g., a magnetic bead, and desulfonation and washing occurs while the DNA is bound to the support. Examples of such embodiments are provided, e.g., in WO 2013/116375. In certain preferred embodiments, support-bound DNA is ready for a methylation assay immediately after desulfonation and washing on the support. In some embodiments, the desulfonated DNA is eluted from the support prior to assay.

In some embodiments, fragments of the treated DNA are amplified using sets of primer oligonucleotides according to the present invention (e.g., see FIG. 1) and an amplification enzyme. The amplification of several DNA segments can be carried out simultaneously in one and the same reaction vessel. Typically, the amplification is carried out using a polymerase chain reaction (PCR).

Methods for isolating DNA suitable for these assay technologies are known in the art. In particular, some embodiments comprise isolation of nucleic acids as described in U.S. patent application Ser. No. 13/470,251 ("Isolation of Nucleic Acids", published as US 2012/0288868), incorporated herein by reference in its entirety.

In some embodiments, the markers described herein find use in QuARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Applications

In some embodiments, diagnostic assays identify the presence of a disease or condition in an individual. In some embodiments, the disease is cancer (e.g., colon cancer). In some embodiments, markers whose aberrant methylation is associated with a colon cancer (e.g., one or more markers selected from the markers listed in Table 1, or preferably one or more of VAV3; ZNF671; CHST2; FLI1; JAM3; SFMBT2; PDGFD; DTX1; TSPYL5; ZNF568; GRIN2D, QKI, FER1L4) are used. In some embodiments, an assay further comprises detection of a reference gene (e.g., β-actin, ZDHHC1, B3GALT6).

In some embodiments, the technology finds application in treating a patient (e.g., a patient with colon cancer, with early stage colon cancer, or who may develop colon cancer), the method comprising determining the methylation state of one or more markers as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments, the technology finds application in methods for diagnosing colon cancer in a subject. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker, the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making a determination of a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers disclosed herein.

Further, in some embodiments of the technology, multiple determinations of the biomarkers over time can be made to facilitate diagnosis and/or prognosis. A temporal change in the biomarker can be used to predict a clinical outcome, monitor the progression of colon cancer, and/or monitor the efficacy of appropriate therapies directed against the cancer. In such an embodiment for example, one might expect to see a change in the methylation state of one or more biomarkers disclosed herein (and potentially one or more additional biomarker(s), if monitored) in a biological sample over time during the course of an effective therapy.

The technology further finds application in methods for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with risk for developing colon, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted above, in some embodiments multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome (e.g., suffering from colon cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with colon cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having colon cancer if, when compared to a control methylation state, there is a measurable difference in the methylation state of at least one biomarker in the sample. Conversely, when no change in methylation state is identified in the biological sample, the subject can be identified as not having colon cancer, not being at risk for the cancer, or as having a low risk of the cancer. In this regard, subjects having colon cancer or risk thereof can be differentiated from subjects having low to substantially no cancer or risk thereof. Those subjects having a risk of developing colon cancer can be placed on a more intensive and/or regular screening schedule. On the other hand, those subjects having low to substantially no risk may avoid being subjected to screening procedures, until such time as a future screening, for example, a screening conducted in accordance with the present technology, indicates that a risk of colon cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, colon cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Over recent years, it has become apparent that circulating epithelial cells, representing metastatic tumor cells, can be detected in the blood of many patients with cancer. Molecular profiling of rare cells is important in biological and clinical studies. Applications range from characterization of circulating epithelial cells (CEpCs) in the peripheral blood of cancer patients for disease prognosis and personalized treatment (See e.g., Cristofanilli M, et al. (2004) N Engl J Med 351:781-791; Hayes D F, et al. (2006) Clin Cancer Res 12:4218-4224; Budd G T, et al., (2006) Clin Cancer Res 12:6403-6409; Moreno J G, et al. (2005) Urology 65:713-718; Pantel et al., (2008) Nat Rev 8:329-340; and Cohen S J, et al. (2008) J Clin Oncol 26:3213-3221). Accordingly, embodiments of the present disclosure provide compositions and methods for detecting the presence of metastatic cancer in a subject by identifying the presence of methylated markers in plasma or whole blood.

EXPERIMENTAL EXAMPLES

Example 1

Sample Preparation Methods

Methods for DNA Isolation and QuARTS Assay

The following provides exemplary method for DNA isolation prior to analysis, and an exemplary QuARTS assay, such as may be used in accordance with embodiments of the technology. Application of QuARTS technology to DNA from blood and various tissue samples is described in this example, but the technology is readily applied to other nucleic acid samples, as shown in other examples.

DNA Isolation from Cells and Plasma

For cell lines, genomic DNA may be isolated from cell conditioned media using, for example, the "Maxwell® RSC ccfDNA Plasma Kit (Promega Corp., Madison, Wis.). Following the kit protocol, 1 mL of cell conditioned media (CCM) is used in place of plasma, and processed according to the kit procedure. The elution volume is 100 μL, of which 70 μL are generally used for bisulfite conversion. See also U.S. Patent Appl. Ser. Nos. 62/249,097, filed Oct. 30, 2015; Ser. Nos. 15/335,111 and 15/335,096, both filed Oct. 26, 2016; and International Appl. Ser. No. PCT/US16/58875, filed Oct. 26, 2016, each of which is incorporated herein by reference in its entirety, for all purposes.

An example of a complete process for isolating DNA from a blood sample for use, e.g., in a detection assay, is provided in this example. Optional bisulfite conversion and detection methods are also described.

I. Blood Processing

Whole blood is collected in anticoagulant EDTA or Streck Cell-Free DNA BCT tubes. An exemplary procedure is as follows:

1. Draw 10 mL whole blood into vacutainers tube (anticoagulant EDTA or Streck BCT), collecting the full volume to ensure correct blood to anticoagulant ratio.
2. After collection, gently mix the blood by inverting the tube 8 to 10 times to mix blood and anticoagulant and keep at room temperature until centrifugation, which should happen within 4 hours of the time of blood collection.
3. Centrifuge blood samples in a horizontal rotor (swing-out head) for 10 minutes at 1500 g (±100 g) at room temperature. Do not use brake to stop centrifuge.
4. Carefully aspirate the supernatant (plasma) at room temperature and pool in a centrifuge tube. Make sure not to disrupt the cell layer or transfer any cells.
5. Carefully transfer 4 mL aliquots of the supernatant into cryovial tubes.
6. Close the caps tightly and place on ice as soon as each aliquot is made. This process should be completed within 1 hour of centrifugation.
7. Ensure that the cryovials are adequately labeled with the relevant information, including details of additives present in the blood.
8. Specimens can be kept frozen at −20° C. for a maximum of 48 hours before transferring to a −80° C. freezer.

II. Preparation of a Synthetic Process Control DNA

Complementary strands of methylated zebrafish DNA are synthesized having the sequences as shown below using standard DNA synthesis methods such as phosphoramidite addition, incorporating 5-methyl C bases at the positions indicated. The synthetic strands are annealed to create a double-stranded DNA fragment for use as a process control.

| Oligo Name | SEQ ID NO: | Oligo Sequence |
|---|---|---|
| Zebrafish RASSF1 me synthetic Target Sense Strand | 177 | 5-TCCAC/iMe-dC/GTGGTGCCCACTCTGGAC AGGTGGAGCAGAGGGAAGGTGGTG/iMe-dC/G CATGGTGGG/iMe-dC/GAG/iMe-dC/G/iMe-dC/GTG/iMe-dC/GCCTGGAGGACCC/iMe-dC/GATTGGCTGA/iMe-dC/GTGTAAACCAGG A/iMe-dC/GAGGACATGACTTTCAGCCCTGCA GCCAGACACAGCTGAGCTGGTGTGACCTGTGTG GAGAGTTCATCTGG-3 |

-continued

| Oligo Name | SEQ ID NO: | Oligo Sequence |
|---|---|---|
| Zebrafish RASSF1 me synthetic Target Anti-Sense Strand | 178 | 5-CCAGATGAACTCTCCACACAGGTCACACCAGC TCAGCTGTGTCTGGCTGCAGGGCTGAAAGTCATG TCCT/iMe-dC/GTCCTGGTTTACA/iMe-dC/ GTCAGCCAAT/iMe-dC/GGGGTCCTCCAGG/ iMe-dC/GCA/iMe-dC/G/iMe-dC/GCT/ iMe-dC/GCCCACCATG/iMe-dC/GCACCACCT TCCCTCTGCTCCACCTGTCCAGAGTGGGCACCA/ iMe-dC/GGTGGA-3 |

A. Annealing and Preparation of Concentrated Zebrafish (ZF-RASS F1 180mer) Synthetic Process Control 1. Reconstitute the lyophilized, single stranded oligonucleotides in 10 mM Tris, pH 8.0, 0.1 mM EDTA, at a concentration of 1 µM.
2. Make 10× Annealing Buffer of 500 mM NaCl, 200 mM Tris-HCl pH 8.0, and 20 mM MgCl$_2$.
3. Anneal the synthetic strands:

In a total volume of 100 µL, combine equimolar amounts of each of the single-stranded oligonucleotides in 1× annealing buffer, e.g., as shown in the table below:

| Component | Stock Conc. | Final Conc. (copies/µl in 1 ml final volume) | Volume added (µL) |
|---|---|---|---|
| Zebrafish RASSF1 me synthetic Target Sense Strand | 1 µM | 1.0E+10 | 16.6 |
| Zebrafish RASSF1 me synthetic Target Anti-Sense Strand | 1 µM | 1.0E+10 | 16.6 |
| Annealing Buffer | 10X | NA | 10.0 |
| Water | NA | NA | 56.8 |
| | | total vol. | 100.0 µL |

4. Heat the annealing mixture to 98° C. for 11-15 minutes.
5. Remove the reaction tube from the heat and spin down briefly to collect condensation to bottom of tube.
6. Incubate the reaction tube at room temp for 10 to 25 minutes.
7. Add 0.9 mL fish DNA diluent (20 ng/mL bulk fish DNA in Te (10 mM Tris-HCl pH8.0, 0.1 mM EDTA)) to adjust to the concentration of zebrafish RASSF1 DNA fragment to $1.0 \times 10^{10}$ copies/µl of annealed, double-stranded synthetic zebrafish RASSF1 DNA in a carrier of genomic fish DNA.
8. Dilute the process control to a desired concentration with 10 mM Tris, pH 8.0, 0.1 mM EDTA, e.g., as described in the table below, and store at either −20° C. or −80° C.

| Initial Concentration | Target Addition | Te | Total Volume | Final Concentration |
|---|---|---|---|---|
| 1.00E+10 copies/µL | 10 µL | 990 µL | 1000 µL | 1.00E+08 copies/µL |
| 1.00E+08 copies/µL | 10 µL | 990 µL | 1000 µL | 1.00E+06 copies/µL |

B. Preparation of 100× Stock Process Control (12,000 Copies/4 Zebrafish RASSF1 DNA in 200 ng/µL Bulk Fish DNA)

1. Thaw reagents
2. Vortex and spin down thawed reagents
3. Add the following reagents into a 50 mL conical tube

| Reagent | Initial Concentration | Final Concentration | Volume to add (mL) |
|---|---|---|---|
| Stock carrier fish DNA | 10 µg/µL | 200 ng/µL | 0.40 |
| Zebrafish (ZF-RASS F1 180mer) | 1.00E+06 copies/µL | 1.20E+04 copies/µL | 0.24 |
| 10 mM Tris, pH 8.0, 0.1 mM EDTA | NA | NA | 19.36 |
| | | Total Volume | 20.00 |

4. Aliquot into labeled 0.5 mL tubes and store @ −20° C.

C. Preparation of 1× Stock of Process Control (120 Copies/ µL Zebrafish RASSF1 DNA in 2 ng/µL Fish DNA)

1. Thaw reagents
2. Vortex and spin down thawed reagents
3. Add the following reagents into a 50 mL conical tube:

| Reagent | 1 mL | 5 mL | 10 mL |
|---|---|---|---|
| 100× Zebrafish Process Control | 10 µL | 50 µL | 100 µL |
| 10 mM Tris, pH 8.0, 0.1 mM EDTA | 990 µL | 4950 µL | 9900 µL |

4. Aliquot 0.3 mL into labeled 0.5 mL tubes and store @ −20° C.

III. DNA Extraction from Plasma

1. Thaw plasma, prepare reagents, label tubes, and clean and setup biosafety cabinet for extraction
2. Add 300 µL Proteinase K (20 mg/mL) to one 50 mL conical tube for each sample.
3. Add 2-4 mL of plasma sample to each 50 mL conical tube (do not vortex).
4. Swirl or pipet to mix and let sit at room temp for 5 min.
5. Add 4-6 mL of lysis buffer 1 (LB1) solution to bring the volume up to approximately 8 mL.

LB1 formulation:
   0.1 mL of 120 copies/µL of zebrafish RASSF1 DNA process control, as described above;
   0.9-2.9 mL of 10 mM Tris, pH 8.0, 0.1 mM EDTA (e.g., use 2.9 mL for 2 mL plasma samples)
   3 mL of 4.3 M guanidine thiocyanate with 10% IGEPAL (from a stock of 5.3 g of IGEPAL CA-630 combined with 45 mL of 4.8 M guanidine thiocyanate)

6. Invert tubes 3 times.
7. Place tubes on bench top shaker (room temperature) at 500 rpm for 30 minutes at room temperature.
8. Add 200 µL of silica binding beads (16 µg of particles/ µL) and mix by swirling.
9. Add 7 mL of lysis buffer 2 (LB2) solution and mix by swirling.

LB2 formulation:
    4 mL 4.3 M guanidine thiocyanate mixed with 10% IGEPAL
    3 mL 100% Isopropanol
(Lysis buffer 2 may be added before, after, or concurrently with the silica binding beads)
  10. Invert tubes 3 times.
  11. Place tubes on bench top shaker at 500 rpm for 30 minutes at room temperature.
  12. Place tubes on capture aspirator and run program with magnetic collection of the beads for 10 minutes, then aspiration. This will collect the beads for 10 minutes then remove all liquid from the tubes.
  13. Add 0.9 mL of Wash Solution 1 (3 M guanidine hydrochloride or guanidine thiocyanate, 56.8% EtOH) to resuspend binding beads and mix by swirling.
  14. Place tubes on bench top shaker at 400 rpm for 2 minute at room temperature.
(All subsequent steps can be done on a STARlet automated platform.)
  15. Mix by repeated pipetting then transfer containing beads to 96 deep well plate.
  16. Place plate on magnetic rack for 10 min.
  17. Aspirate supernatant to waste.
  18. Add 1 mL of Wash Solution 2 (80% Ethanol, 10 mM Tris pH 8.0).
  19. Mix for 3 minutes.
  20. Place tubes on magnetic rack for 10 min.
  21. Aspirate supernatant to waste.
  22. Add 0.5 mL of Wash Solution 2.
  23. Mix for 3 minutes.
  24. Place tubes on magnetic rack for 5 min.
  25. Aspirate supernatant to waste.
  26. Add 0.25 mL of Wash Solution 2.
  27. Mix for 3 minutes.
  28. Place tubes on magnetic rack for 5 min.
  29. Aspirate supernatant to waste.
  30. Add 0.25 mL of Wash Solution 2.
  31. Mix for 3 minutes.
  32. Place tubes on magnetic rack for 5 min.
  33. Aspirate supernatant to waste.
  34. Place plate on heat block at 70° C., 15 minutes, with shaking.
  35. Add 125 µL of elution buffer (10 mM Tris-HCl, pH 8.0, 0.1 mM EDTA).
  36. Incubate 65° C. for 25 minutes with shaking.
  37. Place plate on magnet and let the beads collect and cool for 8 minutes.
  38. Transfer eluate to 96-well plate and store at −80° C. The recoverable/transferrable volume is about 100 µL.

IV. Pre-Bisulfate DNA Quantification

To measure DNA in samples using ACTB gene and to assess zebrafish process control recovery, the DNA may be measured prior to further treatment. Setup a QuARTS PCR-flap assay using 10 µL of the extracted DNA using the following protocol:
  1. Prepare 10× Oligo Mix containing forward and reverse primers each at 2 µM, the probe and FRET cassettes at 5 µM and deoxynucleoside triphosphates (dNTPs) at 250 µM each. (See below for primer, probe and FRET sequences)

| Oligo | Sequence (5'-3') | SEQ ID NO: | Concentration (µM) |
|---|---|---|---|
| ZF RASSF1 UT forward primer | CGCATGGTGGGCGAG | 179 | 2 |
| ZF RASSF1 UT reverse primer | ACACGTCAGCCAATCGGG | 180 | 2 |
| ZF RASSF1 UT Probe (Arm 3) | CCACGGACG GCGCGTGCGTT T/3C6/ | 181 | 5 |
| Arm 5 FAM FRET | /FAM/TCT/BHQ-1/AGCCGGTTTTCCGGCTGAG ACGTCCGTGG/3C6/ | 182 | 5 |
| ACTB forward primer 3 | CCATGAGGCTGGTGTAAAG | 164 | 2 |
| ACTB Reverse primer 3 | CTACTGTGCACCTACTTAATA CAC | 165 | 2 |
| ACTB probe with Arm 1 | CGCCGAGGGCGGCCTTGGAG/3C6/ | 166 | 5 |
| Arm 1 QUASAR670 FRET | /Q670/TCT/BHQ-2/AGCCGGTTTTCCGGCTGAG ACCTCGGCG/3C6/ | 174 | 5 |
| dNTP mix | | | 2500 |

2. Prepare a master mix as follows:

| Component | Volume per reaction (µL) |
|---|---|
| Water | 15.50 |
| 10X oligo Mix | 3.00 |
| 20X QuARTS Enzyme Mix* | 1.50 |
| total volume | 20.0 |

*20X enzyme mix contains 1 unit/µL GoTaq Hot start polymerase (Promega), 292 ng/µL Cleavase 2.0 flap endonuclease (Hologic).

3. Pipette 10 µL of each sample into a well of a 96 well plate.
  4. Add 20 µL of master mix to each well of the plate.
  5. Seal plate and centrifuge for 1 minutes at 3000 rpm.
  6. Run plates with following reaction conditions on an ABI7500 or Light Cycler 480 real time thermal cycler

| QuARTS Assay Reaction Cycle: | | | | |
|---|---|---|---|---|
| Stage | Temp/Time | Ramp Rate (° C. per second) | Number of Cycles | Signal Acquisition |
| Pre-incubation | 95° C./3 min | 4.4 | 1 | No |
| Amplification 1 | 95° C./2 sec | 4.4 | 5 | No |
| | 63° C./30 sec | 2.2 | | No |
| | 70° C./30 sec | 4.4 | | No |
| Amplification 2 | 95° C./20 sec | 4.4 | 40 | No |
| | 53° C./1 min | 2.2 | | Yes |
| | 70° C./30 sec | 4.4 | | No |
| Cooling | 40° C./30 sec | 2.2 | 1 | No |

V. Bisulfite Conversion and Purification of DNA
1. Thaw all extracted DNA samples from the DNA extraction from plasma step and spin down DNA.
2. Reagent Preparation:

| Component Abbreviation | Name | Formulation |
|---|---|---|
| BIS SLN | Bisulfite Conversion Solution | 56.6% Ammonium Bisulfite |
| DES SLN | Desulfonation Solution | 70% Isopropyl alcohol, 0.1N NaOH |
| BND BDS | Binding Beads | Maxwell RNA Beads (16 mg/mL), (Promega Corp.) |
| BND SLN | Binding Solution | 7M Guanidine HCl |
| CNV WSH | Conversion Wash | 10 mM Tris-HCl, 80% Ethanol |
| ELU BUF | Elution Buffer | 10 mM Tris, 0.1 mM EDTA, pH 8.0 |

3. Add 5 μL of 100 ng/μL BSA DNA Carrier Solution to each well in a deep well plate (DWP).
4. Add 80 μL of each sample into the DWP.
5. Add 5 μL of freshly prepared 1.6N NaOH to each well in the DWP(s).
6. Carefully mix by pipetting with pipette set to 30-40 μL to avoid bubbles.
7. Incubate at 42° C. for 20 minutes.
8. Add 120 μL of BIS SLN to each well.
9. Incubate at 66° C. for 75 minutes while mixing during the first 3 minutes.
10. Add 750 μL of BND SLN
11. Pre-mix of silica beads (BND BDS) and add of 50 μL of Silica beads (BND BDS) to the wells of DWP.
12. Mix at 30° C. on heater shaker at 1,200 rpm for 30 minutes.
13. Collect the beads on a plate magnet for 5 minutes followed by aspiration of solutions to waste.
14. Add 1 mL of wash buffer (CNV WSH) then move the plate to a heater shaker and mix at 1,200 rpm for 3 minutes.
15. Collect the beads on a plate magnet for 5 minutes followed by aspiration of solutions to waste.
16. Add 0.25 mL of wash buffer (CNV WSH) then move the plate to the heater shaker and mix at 1,200 rpm for 3 minutes.
17. Collect the beads on a plate magnet followed by aspiration of solutions to waste.
18. Add of 0.2 mL of desulfonation buffer (DES SLN) and mix at 1,200 rpm for 7 minutes at 30° C.
19. Collect the beads for 2 minutes on the magnet followed by aspiration of solutions to waste.
20. Add of 0.25 mL of wash buffer (CNV WSH) then move the plate to the heater shaker and mix at 1,200 rpm for 3 minutes.
21. Collect the beads for 2 minutes on the magnet followed by aspiration of solutions to waste.
22. Add of 0.25 mL of wash buffer (CNV WSH) then move the plate to the heater shaker and mix at 1,200 rpm for 3 minutes.
23. Collect the beads for 2 minutes on the magnet followed by aspiration of solutions to waste.
24. Allow the plate to dry by moving to heater shaker and incubating at 70° C. for 15 minutes while mixing at 1,200 rpm.
25. Add 80 μL of elution buffer (ELU BFR) across all samples in DWP.
26. Incubated at 65° C. for 25 minutes while mixing at 1,200 rpm.
27. Manually Transfer eluate to 96 well plate and store at −80° C.
28. The recoverable/transferrable volume is about 65 μt.

VI. QuARTS-X Multiplex Flap Assay for Methylated DNA Detection and Quantification
A. Multiplex PCR (mPCR) Setup:
1. Prepare a 10× primer mix containing forward and reverse primers for each methylated marker of interest to a final concentration of 750 nM each. Use 10 mM Tris-HCl, pH 8, 0.1 mM EDTA as diluent, as described in the examples above.
2. Prepare 10× multiplex PCR buffer containing 100 mM MOPS, pH 7.5, 75 mM MgCl2, 0.08% Tween 20, 0.08% IGEPAL CA-630, 2.5 mM dNTPs.
3. Prepare multiplex PCR master mix as follows:

| Component | Volume per reaction (μL) |
|---|---|
| Water | 9.62 |
| 10X Primer Mix (0.75 μM each) | 7.5 |
| mPCR Buffer | 7.5 |
| Hot Start GoTaq (5 units/μl) | 0.38 |
| total volume | 25.0 |

4. Thaw DNA and spin plate down.
5. Add 25 μL of master mix to a 96 well plate.
6. Transfer 50 μL of each sample to each well.
7. Seal plate with aluminum foil seal (do not use strip caps)
8. Place in heated-lid thermal cycler and proceed to cycle using the following profile, for about 5 to 20 cycles, preferably about 10 to 13 cycles:

| Stage | Temp/Time | Number of Cycles |
|---|---|---|
| Pre-incubation | 95° C./5 min | 1 |
| Amplification 1 | 95° C./30 sec | 12 |
|  | 64° C./60 sec |  |
| Cooling | 4° C./hold | 1 |

9. After completion of the thermal cycling, perform a 1:10 dilution of amplicon as follows:
a) Transfer 180 μL of 10 mM Tris-HCl, pH 8, 0.1 mM EDTA to each well of a deep well plate.
b) Add 20 μL of amplified sample to each pre-filled well.
c) Mix the diluted samples by repeated pipetting using fresh tips and a 200 μL pipettor (be careful not to generate aerosols).
d) Seal the diluted plate with a plastic seal.
e) Centrifuge the diluted plate at 1000 rpm for 1 min.
f) Seal any remaining multiplex PCR product that has not been diluted with a new aluminum foil seal. Place at −80° C.

B. QuARTS Assay on Multiplex-Amplified DNA:
1. Thaw fish DNA diluent (20 ng/μL) and use to dilute plasmid calibrators (see, e.g., U.S. patent application Ser. No. 15/033,803, which is incorporated herein by reference) needed in the assay. Use the following table as a dilution guide:

| Initial Plasmid Concentration, copies per μL | Final plasmid Concentration, copies per μL | μL of plasmid to add | μL of diluent to add | total volume, μL |
|---|---|---|---|---|
| 1.00E+05 | 1.00E+04 | 5 | 45 | 50 |
| 1.00E+04 | 1.00E+03 | 5 | 45 | 50 |
| 1.00E+03 | 1.00E+02 | 5 | 45 | 50 |
| 1.00E+02 | 1.00E+01 | 5 | 45 | 50 |

2. Prepare 10× triplex QuARTS oligo mix using the following table for markers A, B, and C (e.g., markers of interest, plus run control and internal controls such as β-actin or B3GALT6 (see, e.g., U.S. Pat. Appln. Ser. No. 62/364,082, incorporated herein by reference).

| Oligo | Sequence (5'-3') | SEQ ID NO: | Concentration (μM) |
|---|---|---|---|
| Marker A Forward primer | NA |  | 2 |
| Marker A Reverse primer | NA |  | 2 |
| Marker A probe-Arm 1 | NA |  | 5 |
| Marker B Forward primer | NA |  | 2 |
| Marker B Reverse primer | NA |  | 2 |
| Marker B probe-Arm 5 | NA |  | 5 |
| Marker C Forward primer | NA |  | 2 |
| Marker C Reverse primer | NA |  | 2 |
| Marker C probe-Arm 3 | NA |  | 5 |
| Arm 1 HEX FRET | /HEX/TCT/BHQ-1/AGCCGGTTTT CCGGCTGAGACCTCGGCG/3C6/ | 171 | 5 |
| Arm 5 FAM FRET | /FAM/TCT/BHQ-1/AGCCGGTTTT CCGGCTGAGACGTCCGTGG/3C6/ | 172 | 5 |
| Arm 3 QUASAR-670 FRET | /Q670/TCT/BHQ-2/AGCCGGTTTT CCGGCTGAGACTCCGCGTC/3C6/ | 173 | 5 |
| dNTP mix |  |  | 250 |

For example, the following might be used to detect bisulfite-treated β-actin, B3GALT6, and zebrafish RASSF1 markers:

| Oligo Description | Sequence (5'-3') | SEQ ID NO: | Concentration (μM) |
|---|---|---|---|
| ZF RASSF1 BT Forward primer | TGCGTATGGTGGGCGAG | 160 | 2 |
| ZF RASSF1 BT Reverse primer | CCTAATTTACACGTCAACCAATCGAA | 161 | 2 |
| ZF RASSF1 BT probe-Arm 5 | CCACGGACGGCGCGTGCGTTT/3C6/ | 162 | 5 |
| B3GALT6 Forward primer | GGTTTATTTTGGTTTTTTGAGTTTTCGG | 8 | 2 |
| B3GALT6 Reverse primer | TCCAACCTACTATATTTACGCGAA | 9 | 2 |
| B3GALT6 probe-Arm 1 | CGCCGAGGGCGGATTTAGGG/3C6/ | 10 | 5 |
| BTACT Forward primer | GTGTTTGTTTTTTTGATTAGGTGTTTAAGA | 168 | 2 |
| BTACT Reverse primer | CTTTACACCAACCTCATAACCTTATC | 169 | 2 |
| BTACT probe-Arm 3 | GACGCGGAGATAGTGTTGTGG/3C6/ | 170 | 5 |
| Arm 1 HEX FRET | /HEX/TCT/BHQ-1/AGCCGGTTTTC CGGCTGAGACCTCGGCG/3C6/ | 171 | 5 |
| Arm 5 FAM FRET | /FAM/TCT/BHQ-1/AGCCGGTTTTC CGGCTGAGACGTCCGTGG/3C6/ | 172 | 5 |
| Arm 3 QUASAR-670 FRET | /Q670/TCT/BHQ-2/AGCCGGTTTT CCGGCTGAGACTCCGCGTC/3C6/ | 173 | 5 |
| dNTP mix |  |  | 2500 |

3. Prepare a QuARTS flap assay master mix using the following table:

| Component | Volume per reaction (μL) |
|---|---|
| Water | 15.5 |
| 10X Triplex Oligo Mix | 3.0 |
| 20X QuARTS Enzyme mix | 1.5 |
| total volume | 20.0 |

*20X enzyme mix contains 1 unit/μL GoTaq Hot start polymerase (Promega), 292 ng/μL Cleavase 2.0 flap endonuclease (Hologic).

4. Using a 96 well ABI plates, pipette 20 μL of QuARTS master mix into each well.
5. Add 10 μL of appropriate calibrators or diluted mPCR samples.
6. Seal plate with ABI clear plastic seals.
7. Centrifuge the plate using 3000 rpm for 1 minute.

8. Place plate in ABI thermal cycler programmed to run the following thermal protocol then start the instrument QuARTS Reaction Cycle:

| Stage | Temp/Time | Ramp Rate (° C. per second) | Number of Cycles | Signal Acquisition |
|---|---|---|---|---|
| Pre-incubation | 95° C./3 min | 4.4 | 1 | none |
| Amplification 1 | 95° C./2 sec | 4.4 | 5 | none |
|  | 63° C./30 sec | 2.2 |  | none |
|  | 70° C./30 sec | 4.4 |  | none |
| Amplification 2 | 95° C./20 sec | 4.4 | 40 | none |
|  | 53° C./1 min | 2.2 |  | Yes |
|  | 70° C./30 sec | 4.4 |  | none |
| Cooling | 40° C./30 sec | 2.2 | 1 | none |

Aliquots of the diluted pre-amplified DNA (e.g., 10 μL) are used in a QuARTS PCR-flap assay, e.g., as described above. See also U.S. Patent Appl. Ser. No. 62/249,097, filed Oct. 30, 2015; Ser. No. 15/335,096, filed Oct. 26, 2016, and PCT/US16/58875, filed Oct. 26, 2016, each of which is incorporated herein by reference in its entirety, for all purposes.

Example 2

Selection and Testing of Methylation Markers for Colorectal Cancer Detection in Plasma Reduced Representation Bisulfite Sequencing (RRBS) data was obtained on tissues from 19 patients with colon cancer, 19 patients with polyps, 19 healthy patients, and 19 healthy patients buffy coat extracted DNA.

After alignment to an in silico bisulfate-converted version of the human genome sequence, average methylation at each CpG island was computed for each sample type (i.e., tissue or buffy coat) and marker regions were selected based on the following criteria:

Regions were selected to be 50 base pairs or longer.
For QuARTS flap assay designs, regions were selected to have a minimum of 1 methylated CpG under each of: a) the probe region, b) the forward primer binding region, and c) the reverse primer binding region. For the forward and reverse primers, it is preferred that the methylated CpGs are close to the 3'-ends of the primers, but not at the 3'terminal nucleotide. Exemplary flap endonuclease assay oligonucleotides are shown in FIG. 1.
Preferably, buffy coat methylation at any CpG in a region of interest is no more than >0.5%.
Preferably, cancer tissue methylation in a region of interest is >10%.
For assays designed for tissue analysis, normal tissue methylation in a region of interest is preferably <0.5%.

Based on the criteria above, the markers ANKRD13B; CHST2; CNNM1; GRIN2D; FLI1; JAM3; LRRC4; OPLAH; SEP9; SFMBT2; SLC12A8; TBX15; ZDHHC1; ZNF304; ZNF568; ZNF671; DOCK2; DTX1; FERMT3; PDGFD; PKIA; PPP2R5C; TSPYL5; VAV3; and QKI were selected and QuARTS flap assays were designed for them, as shown in FIG. 1.

The 27 markers selected from the tissue screening results were triplexed with the assay for bisulfite-converted β-actin and used for testing DNA isolated from plasma samples as described above. CEA protein in the plasma was measured using a Luminex Magplex assay, per manufacturer protocol (Luminex Corp.) DNA from 2 mL of plasma samples (89 cancer and 95 normal) was extracted and eluted in 125 μL. 10 μL aliquots of the extracted DNA were used in a QuARTS assay to detect β-actin and zebrafish synthetic targets. 80 μL aliquots of the DNA were bisulfite-converted as described in Example 1, and eluted in 70 μL.

A multiplex PCR reaction was performed on 50 μL aliquots of the bisulfate-converted DNA samples, using the forward and reverse primers for the targets shown in FIG. 1, and the markers were detected using QuARTS flap assays, as described in Example 1.

Based on individual marker sensitivities, the following 12 methylation markers were selected for further analysis: VAV3, ZNF671, CHST2, FLI1, JAM3, SFMBT2, PDGFD, DTX1, TSPYL5. ZNF568, GRIN2D, and QKI.

All 12 markers were pre-amplified together using primers as shown for these markers in FIG. 1. The pre-amplified material was analyzed in multiplexed QuARTS assays as described in Example 1, using the primers and probes shown in FIG. 1. The multiplexed assays were grouped as follows:

CHST2
FLI1
BTACT
VAV3
ZNF671
BTACT
TSPYL5
ZNF568
BTACT
JAM3
SFMBT2
BTACT
PDGFD
DTX1
BTACT
GRIN2D
QKI
BTACT
ZFRASSF1
B3GALT6
BTACT

In addition to the above, the CEA protein was measured for the same samples, as described above. The data and results are shown in FIGS. 3 and 4. The individual marker sensitivities at 90% specificity were as follows:

| Marker | Sensitivity @ 90% specificity |
|---|---|
| ZNF671 | 49% |
| TSPYL5 | 46% |
| QKI | 41% |
| JAM3 | 40% |
| DTX1 | 40% |
| GRIN2D | 38% |
| ZNF568 | 37% |
| CEA protein | 36% |
| FLI1 | 36% |
| SFMBT2 | 35% |
| PDGFD | 35% |
| CHST2 | 33% |
| VAV3 | 31% |

At 95% individual cutoff of the individual markers, the following final sensitivity was obtained for using the combined data set.

| Cancer Stage | Negative | Positive | Total # of samples | Sensitivity |
|---|---|---|---|---|
| I | 14 | 7 | 21 | 33% |
| II | 7 | 18 | 25 | 72% |
| III | 7 | 17 | 24 | 71% |
| IV | 1 | 18 | 19 | 95% |
| Overall | | 60 | 89 | 67% |

The combined specificity of the assay was (88/95=92.6%).

Thus, the combination of these 12 markers plus CEA protein resulted in 67% sensitivity (88 of 95 cancers) for all of the cancer tissues tested, with 92.6% specificity. This panel of methylated DNA markers assayed on tissue achieves extremely high discrimination for all types of colon cancer while remaining negative in normal colon tissue. Assays for this panel of markers can be also be applied to blood or bodily fluid-based testing, and finds applications in, e.g., colon cancer screening.

Multiple Target Sequences Reporting to One Dye

The following experiments related to amplification flap cleavage assays that are configured to have multiple target-specific primary cleavage reactions report to a single FRET cassette, thereby producing fluorescence signal in a single dye channel. Different targets to be detected may be, for example, different markers or genes, different mutations, or different regions of a single marker or gene. Example 3 relates to detecting methylation of multiple different markers associated with cancer, e.g., colorectal cancer, using a single FRET cassette and dye channel, and Example 4 relates to detecting multiple regions within a single marker using a single FRET cassette and dye channel.

Reagents Used in the Following Experiments:

| Reagents | Sequence (5'-3') |
|---|---|
| VAV3_877 Forward Primer | TCGGAGTCGAGTTTAGCGC (SEQ ID NO: 108) |
| VAV3_877 Reverse Primer v2 | CGAAATCGAAAAAACAAAAACCGC (SEQ ID NO: 109) |
| VAV3_877 Probe (arm 5) | CCACGGACGCGGCGTTCGCGA/3C6/ (SEQ ID NO: 146) |
| VAV3_11878 forward primer | GAGTCGAGTTTTAGGTTATTCGGT (SEQ ID NO: 150) |
| VAV3_11878 reverse primer | CGTCGAACATAAAACCGTAAAAACAA (SEQ ID NO: 151) |
| VAV3_11878 probe (arm 5) | CCACGGACGATACGCGCAATA/3C6/ (SEQ ID NO: 152) |
| SFMBT2_897 Forward Primer v5 | GTCGTCGTTCGAGAGGGTA (SEQ ID NO: 88) |
| SFMBT2_897 Forward Primer v4 | GAACAAAAACGAACGAACGAACA (SEQ ID NO: 89) |
| SFMBT2_897 Probe (arm 5) v5 | CCACGGACGATCGGTTTCGTT/3C6/ (SEQ ID NO: 90) |
| SFMBT2_897 probe (arm 1) | CGCCGAGGATCGGTTTCGTT/3C6/ (SEQ ID NO: 141) |
| SFMBT2_895 forward primer | GCGACGTAGTCGTCGTTGT (SEQ ID NO: 144) |
| SFMBT2_895 reverse primer | CCAACGCGAAAAAAACGCG (SEQ ID NO: 145) |
| SFMBT2_895 probe (arm 1) | CGCCGAGGGAAAACGCGAAA/3C6/ (SEQ ID NO: 146) |
| CHST2_7890 Forward Primer | GTATAGCGCGATTTCGTAGCG (SEQ ID NO: 13) |
| CHST2_7890 Reverse Primer | AATTACCTACGCTATCCGCCC (SEQ ID NO: 14) |
| CHST2_7890 Probe (arm 5) | CCACGGACGCGAACATCCTCC/3C6/ (SEQ ID NO: 15) |
| CHST2_7890 probe (arm 1) | CGCCGAGGCGAACATCCTCC/3C6/ (SEQ ID NO: 175) |
| CHST2_7889 forward primer | CGAGTTCGGTAGTTGTACGTAGA (SEQ ID NO: 138) |
| CHST2_7889 reverse primer | CGAAATACGAACGCGAAATCTAAAACT (SEQ ID NO: 139) |
| CHST2_7889 probe (arm 5) | CCACGGACGTCGTCGATACCG/3C6/ (SEQ ID NO: 140) |
| CHST2_7889 probe (arm 1) | CGCCGAGG-TCGTCGATACCG/3C6/ (SEQ ID NO: 176) |
| BTACT_FP65 Forward Primer | GTGTTTGTTTTTTTGATTAGGTGTTTAAGA SEQ ID NO: 139 |
| BTACT_RP65 Reverse Primer | CTTTACACCAACCTCATAACCTTATC SEQ ID NO: 140 |
| BTACT Probe A3 | GACGCGGAGATAGTGTTGTGG/3C6/ SEQ ID NO: 141 |
| Arm 1 FRET cassette HEX | SEQ ID NO: 170 |
| Arm 5 FRET cassette FAM | SEQ ID NO: 171 |
| Arm 1 FRET cassette QUASAR-670 | SEQ ID NO: 174 |
| Arm 3 FRET cassette QUASAR-670 | SEQ ID NO: 173 |

ECOR1 digested pUC57 plasmid (Genscript) containing SFMBT2_897 insert
ECOR1 digested pUC57 plasmid (Genscript) containing CHST2_7890 insert
ECOR1 digested pUC57 plasmid (Genscript) containing VAV3 insert
ECOR1 digested pUC57 plasmid (Genscript) containing BTACT insert
VAV3/BTACT Biplexed plasmids, serially diluted from 1e+04 copies/μL
SFMBT2_897/BTACT Biplexed plasmids, serially diluted from 1e+04 copies/μL
CHST2_7890/BTACT Biplexed plasmids, serially diluted from 1e+04 copies/μL
SFMBT2_897/VAV3/BTACT Biplexed plasmids, 1e+04 copies/μL
CHST2_7890/VAV3/BTACT Biplexed plasmids, 1e+04 copies/μL
CHST2_7890/SFMBT2_897/BTACT Biplexed plasmids, 1e+04 copies/μL
VAV3/CHST2_7890/SFMBT2_897/BTACT Triplexed plasmids, 1e+04 copies/μL
CHST2_7889 + 7890 Calibration curve dilution set (1e4-1e0 cp/ul)
SFMBT2_895 + 897 Calibration curve dilution set (1e4-1e0 cp/ul)
VAV3_877 + 11878 Calibration curve dilution set (1e4-1e0 cp/ul)

-continued

| Reagents | Sequence (5'-3') |
|---|---|
| VAV3/BTACT 10X Oligo Mix | |
| SFMBT2_897/BTACT 10X Oligo Mix | |
| CHST2_7890/BTACT 10X Oligo Mix | |
| VAV3/SFMBT2_897/CHST2_7890/BTACT 10X Oligo Mix | |
| VAV3/SFMBT2_897 (100 nM F. Primer)/CHST2_7890/ BTACT 10X Oligo Mix | |
| VAV3/SFMBT2_897 (50 nM F. Primer)/CHST2_7890/ BTACT 10X Oligo Mix | |
| VAV3/SFMBT2_897 (200 nM Probe)/CHST2_7890/BTACT 10X Oligo Mix | |
| VAV3/SFMBT2_897 (250 nM Probe)/CHST2_7890/BTACT 10X Oligo Mix | |
| VAV3/SFMBT2_897 (100 nM Probe)/CHST2_7890/BTACT 10X Oligo Mix | |
| VAV3 (400 nM Primers)/SFMBT2_897 (200 nM Probe)/ CHST2_7890/BTACT 10X Oligo Mix | |
| VAV3 (750 nM Probe)/SFMBT2_897 (200 nM Probe)/ CHST2_7890/BTACT 10X Oligo Mix | |
| 20X Enzyme mix, 1 U/µL Go Taq Hot Start polymerase (Promega), 292 ng/µL Cleavase 2.0 (Hologic) | |
| fDNA Diluent, 20 ng/µL fish DNA in 10 mM Tris, 0.1 mM EDTA | |
| fDNA Diluent, 20 ng/µL fish DNA in 10 mM Tris, 0.1 mM EDTA | |
| Mol. Biol. Grade water | |
| dNTPs, 25 mM (each dNTP) | |

Example 3

Multiple Markers Reporting to One Dye

As discussed above, in some embodiments it is desirable to have a larger number of markers in a single reaction, using a single FRET cassette and single dye channel. In developing a test for detecting multiple markers reporting to a single FRET cassette and single dye, markers having similar reaction efficiencies (i.e. that produce the same amount of detectable signal per target copy) were selected for combining in a multiplexed reaction reporting to a single dye channel. An advantage of combining detection assays that have the same or similar reaction efficiencies is that any individual calibrator for one of the assays may be used as a calibration standard for any and all of the efficiency-matched detection assays.

Three markers were selected for testing in a multiple marker/one dye system (SFMBT2, VAV3, and CHST2). These target DNAs were mixed in an oligonucleotide mix in which the assay oligonucleotides for all three markers were configured to report to the same FRET cassette and therefore to the same dye (FAM). The three disease-associated markers reporting to the FAM dye were combined in the same reaction with reagents to detect bisulfate-converted β-actin DNA (using a QUASAR 670 FRET cassette) as a control.

When testing on plasmid calibrators was performed, the data showed that using the multiple markers reporting to a single dye is an efficient approach that overcomes the need to run markers in separate wells.

Example 3.1

For QuARTS flap endonuclease assays for multiple different markers to be run in a multiplex reaction reporting to a single FRET cassette, the reaction efficiency for each individual marker was first analyzed so that the reactions could be balanced when combined in a multiplex configuration. Assays were run to determine the assay performance of three selected markers (VAV3, SFMBT2_897 and CHST2_7890) reporting to one dye (FAM), biplexed with bisulfite-converted β-actin (BTACT), which was configured to produce signal reporting to the Quasar 670 channel.

The assays were also configured to determine whether each marker would exhibit similar QuARTS assay performance (slopes/intercepts/Cps) when the three markers are reporting to the same channel (FAM).

An oligonucleotide mix comprising reagents to detect all three methylation markers reporting to a FAM FRET cassette was prepared. The oligonucleotide mix comprised reagents for detecting BTACT reporting to Quasar 670 as a control. This oligonucleotide mix was tested against plasmid targets containing individual plasmids comprising the marker target DNAs and BTACT DNA. Calculations were done to see whether a calibrator curve for one marker could be used to quantitate the other markers accurately. All reactions were done in replicates of 4.

Protocol:

Stock Plasmid dilutions comprising one marker plasmid and one BTACT control plasmid each (see Reagent Table, above) were prepared as follows, in a diluent of 20 ng/µL of fish DNA in 10 mM Tris, 0.1 mM EDTA:

| SFMBT2_897/ BTACT plasmid mix | Copies in stock solution,/µL | Copies final mixture/µL | µL to add |
|---|---|---|---|
| SFMBT2_897 Plasmid | 1.00E+05 | 1.00E+04 | 50 |
| BTACT Plasmid | 1.00E+05 | 1.00E+04 | 50 |
| Fish DNA Diluent | NA | NA | 400 |
| total volume | NA | NA | 500 |

| | Ci, cp/µL | Cf, cp/µL | µL to add |
|---|---|---|---|
| CHST2_7890/ BTACT plasmid mix | | | |
| CHST2_7890 Plasmid | 1.00E+05 | 1.00E+04 | 50 |
| BTACT Plasmid | 1.00E+05 | 1.00E+04 | 50 |
| fDNA Diluent | NA | NA | 400 |
| total volume | NA | NA | 500 |
| VAV3/BTACT plasmid mix | | | |
| VAV3 Plasmid | 1.00E+05 | 1.00E+04 | 50 |
| BTACT Plasmid | 1.00E+05 | 1.00E+04 | 50 |
| fDNA Diluent | NA | NA | 400 |
| total volume | NA | NA | 500 |

From the 3 plasmid mixtures prepared above, the following dilutions were prepared:

| Cf, cp/µL | Ci, cp/µL | df | µL Ci to add | µL diluent | total volume |
|---|---|---|---|---|---|
| 1.00E+05 | 1.00E+04 | 10 | 50 | 450 | 500 |
| 1.00E+04 | 1.00E+03 | 10 | 50 | 450 | 500 |
| 1.00E+03 | 1.00E+02 | 10 | 50 | 450 | 500 |
| 1.00E+02 | 1.00E+01 | 10 | 50 | 450 | 500 |
| 1.00E+01 | 1.00E+00 | 10 | 50 | 450 | 500 |

10× Oligonucleotide mixes comprising assay oligonucleotides (primers, probes, FRET cassettes) and dNTPs were made as follows:

| Marker | Reagent | Final Reaction Concentration (μM) | 10X oligo Mix Concentration (μM) |
|---|---|---|---|
| VAV3 | VAV3 Forward Primer | 0.2 | 2 |
| VAV3 | VAV3 Reverse Primer v2 | 0.2 | 2 |
| VAV3 | VAV3 Probe A5 | 0.5 | 5 |
| SFMBT2_897 | SFMBT2_897 Forward Primer v5 | 0.2 | 2 |
| SFMBT2_897 | SFMBT2_897 Forward Primer v4 | 0.2 | 2 |
| SFMBT2_897 | SFMBT2_897 Probe A5 v5 | 0.5 | 5 |
| CHST2_7890 | CHST2_7890 Forward Primer | 0.2 | 2 |
| CHST2_7890 | CHST2_7890 Reverse Primer | 0.2 | 2 |
| CHST2_7890 | CHST2_7890 Probe A5 | 0.5 | 5 |
|  | Arm 5 FAM FRET Cassette | 0.5 | 5 |
| BTACT | ACTB_BT_FP65 Forward Primer | 0.2 | 2 |
| BTACT | ACTB_BT_RP65 Reverse Primer | 0.2 | 2 |
| BTACT | ACTB BT Probe A3 | 0.5 | 5 |
|  | Arm 3 QUASAR FRET cassette | 0.5 | 5 |
|  | dNTPs (each dNTP) | 250 | 2500 |

QuARTS Flap Endonuclease Assay Reaction Set-Up:

Master mixes for the QuARTS amplification reactions are prepared as follows:

Master Mix Formulation: 96 Well Plate—

| Master Mix Formulation: 96 well plate - | | |
|---|---|---|
|  | μL vol of stock to add | |
| Reagent | per reaction | μL vol for 38 reactions |
| ddH2O | 15.50 | 589 |
| 10X oligo Mix | 3.00 | 114 |
| 20X Enzyme Mix | 1.50 | 57 |
| total volume master mix | 20.0 | 760 |
| use 20 ul master mix per well and add 10 ul sample | | |
| for 96 well plate = 30 ul final rxn vol | | |
| Sample* | 10 | 20.0 |

Reactions were set up as follows:
- Pipette 20 μl of master mix into a 96-well QuARTS plate, using a multichannel pipette
- Add 10 μl of a sample
- Seal plate and centrifuge for 1 min. at 3000 rpm.
- Run the plates using the following conditions on the LightCycler480, detecting on FAM, HEX and Quasar 670 channels: 465-510, 533-580, and 618-660 nm

| QuARTS Assay Reaction Cycle: | | | | |
|---|---|---|---|---|
| Stage | Temp/Time | Ramp Rate (° C. per second) | Number of Cycles | Signal Acquisition |
| Pre-incubation | 95° C./3 min | 4.4 | 1 | No |
| Amplification 1 | 95° C./20 sec | 4.4 | 5 | No |
|  | 63° C./30 sec | 2.2 |  | No |
|  | 70° C./30 sec | 4.4 |  | No |
| Amplification 2 | 95° C./20 sec | 4.4 | 40 | No |
|  | 53° C./1 min | 2.2 |  | Yes |
|  | 70° C./30 sec | 4.4 |  | No |
| Cooling | 40° C./30 sec | 2.2 | 1 | No |

Results:

Strand Counts Using VAV3/BTACT Plasmid Calibrator Standard Curve:

| VAV3/BTACT Plasmid Calibrator Standard Curve | |
|---|---|
| Slope | −3.147684 |
| Intercept | 32.08568 |
| Efficiency | 107.8% |

| Calibrator Strands/Rxn | Average Cp | Calculated Average Strands |
|---|---|---|
| VAV3/BTACT Plasmid Calibrator | | |
| 200000 | 15.36 | 205,254 |
| 20000 | 18.66 | 18,432 |
| 2000 | 21.58 | 2,178 |
| 200 | 24.88 | 194 |
| SFMBT2_897/BTACT Plasmid Calibrator | | |
| 200000 | 13.87 | 612,036 |
| 20000 | 17.17 | 54,780 |
| 2000 | 19.64 | 9,021 |
| 200 | 22.12 | 1,470 |
| CHST2_7890/BTACT Plasmid Calibrator | | |
| 200000 | 15.17 | 235,836 |
| 20000 | 18.05 | 28,813 |
| 2000 | 20.39 | 5,200 |
| 200 | 23.03 | 752 |

Strand Counts Using SFMBT2_897/BTACT Plasmid Calibrator Standard Curve:

| SFMBT2_897/BTACT Plasmid Calibrator Standard Curve | |
|---|---|
| Slope | −2.720157 |
| Intercept | 28.53753 |
| Efficiency | 133.1% |

| Calibrator Strands/Rxn | Average Cp | Calculated Average Strands |
|---|---|---|
| VAV3/BTACT Plasmid Calibrator | | |
| 200000 | 15.36 | 69,636 |
| 20000 | 18.66 | 4,282 |
| 2000 | 21.58 | 362 |
| 200 | 24.88 | 22 |
| SFMBT2_897/BTACT Plasmid Calibrator | | |
| 200000 | 13.87 | 246,543 |
| 20000 | 17.17 | 15,101 |
| 2000 | 19.64 | 1,873 |
| 200 | 22.12 | 229 |

-continued

| CHST2_7890/BTACT Plasmid Calibrator | | |
|---|---|---|
| 200000 | 15.17 | 81,777 |
| 20000 | 18.05 | 7,180 |
| 2000 | 20.39 | 990 |
| 200 | 23.03 | 106 |

Strand Counts Using CHST2_7890//BTACT Plasmid Calibrator Standard Curve:

| CHST2_7890/BTACT Plasmid Calibrator Standard Curve | |
|---|---|
| Slope | -2.59121 |
| Intercept | 29.01007 |
| Efficiency | 143.2% |

| Calibrator Strands/Rxn | Average Cp | Calculated Average Strands |
|---|---|---|
| VAV3/BTACT Plasmid Calibrator | | |
| 200000 | 15.36 | 184,582 |
| 20000 | 18.66 | 9,878 |
| 2000 | 21.58 | 738 |
| 200 | 24.88 | 39 |
| SFMBT2_897/BTACT Plasmid Calibrator | | |
| 200000 | 13.87 | 695,942 |
| 20000 | 17.17 | 37,096 |
| 2000 | 19.64 | 4,147 |
| 200 | 22.12 | 458 |
| CHST2_7890/BTACT Plasmid Calibrator | | |
| 200000 | 15.17 | 218,505 |
| 20000 | 18.05 | 16,997 |
| 2000 | 20.39 | 2,123 |
| 200 | 23.03 | 203 |

These data show:
 No cross reactivity or background signal was generated when markers and controls were amplified and detected together;
 Cp values were similar for CHST2_7890 and VAV3;
 Cp values for SFMBT2_897 come up at an earlier cycle than CHST2_7890 and VAV3, showing that this is a faster QuARTS assay reaction;
 SFMBT2_897 calibrator and oligonucleotide mix combination underestimates the count of strands present for VAV3 and CHST2_7890 because of the faster SFMBT2_897 reaction;
 The CHST2_7890 calibrator provides a VAV3 calculation indicating assay performance equal to the CHST2_7890 assay reaction, but overestimates the amount of SFMBT2_897;
 The VAV3 calibrator provides a CHST2_7890 calculation indicating assay performance equal to the VAV3 assay reaction, but produces an overestimate of the amount of SFMBT2_897; and
 To balance the reactions, the QuARTS assay performance in detecting SFMBT2_897 needs to be reduced to match that of SFMBT2_897 and CHST2_7890 targets.

Experiment 3.2

The data above showed that the SFMBT2_897 assay reaction produced higher signal, indicating that the reaction is faster. For the purposes of multiplexing these markers, the SFMBT2_897 assay should be refined to match the efficiency of the slower assays, (i.e., to match the signal output of the VAV3 and CHST2_7890 assays). The following experiment tested whether modifying the concentration of forward primer of the SFMBT2_897 would achieve this.

Protocol:

Assays were run as described in Experiment 3.1, above. 10× oligonucleotide mixes were assembled comprising the components listed above, but having the SFMBT2_897 forward primer in amounts reduced to produce final assay concentrations of 200 nM (as in Experiment 3.1), 100 nM, or 50 nM. The concentration of all other assay primers was 200 nM in the final reaction mixtures, and the Light Cycler protocol was as described in Exp. 3.1.

Results showed that reducing the SFMBT2_897 forward primer concentration seemed to have no effect on the slope or intercept of the signal curve reflecting of PCR efficiency (data not shown). In addition, the Cp value did not change, thus the number of strands calculated for SFMBT2_897 did not match the calculated number of strands of the other marker targets.

Experiment 3.3

The following experiment tested whether modifying the concentration of the SFMBT2_897 probe would reduce the efficiency of the SFMBT2_897 assay, to match the signal output of the CHST2_7890 and VAV3 amplification reactions.

Assays were run as described above in Experiment 3.1. 10× oligonucleotide mixes were assembled comprising the components listed above, but having the SFMBT2_897 probe oligonucleotide in amounts to produce final assay concentrations of 250 nM or 100 nM, with the CHST2_7890 and VAV3 probes present at 500 nM (as described in Experiment 3.1). The Light Cycler protocol was as described for Experiment 3.1.

Results:

Strand Counts Using VAV3/BTACT Plasmid Calibrator Standard Curve:

| VAV3/BTACT Plasmid Calibrator Standard Curve | |
|---|---|
| Slope | -3.12175 |
| Intercept | 31.55241 |
| Efficiency | 109.1% |

| Calibrator Strands/Rxn | Average Cp | Average Strands |
|---|---|---|
| VAV3/BTACT Plasmid Calibrator | | |
| 200000 | 14.95 | 207,537 |
| 20000 | 18.24 | 18,377 |
| 2000 | 21.17 | 2,120 |
| 200 | 24.38 | 198 |
| SFMBT2_897/BTACT Plasmid Calibrator | | |
| 200000 | 15.30 | 161,043 |
| 20000 | 18.50 | 15,172 |
| 2000 | 21.20 | 2,065 |
| 200 | 24.01 | 260 |
| CHST2_7890/BTACT Plasmid Calibrator | | |
| 200000 | 14.83 | 226,551 |
| 20000 | 18.08 | 20,670 |
| 2000 | 21.05 | 2,318 |
| 200 | 24.30 | 210 |

Strand Counts Using SFMBT2_897/BTACT Plasmid Calibrator Standard Curve:

| SFMBT2_897/BTACT Plasmid Calibrator Standard Curve | | |
|---|---|---|
| Slope | | −2.885069564 |
| Intercept | | 30.72006211 |
| Efficiency | | 122.1% |
| Calibrator Strands/Rxn | Average Cp | Average Strands |
| VAV3/BTACT Plasmid Calibrator | | |
| 200000 | 14.95 | 291,595 |
| 20000 | 18.24 | 21,164 |
| 2000 | 21.17 | 2,045 |
| 200 | 24.38 | 157 |
| SFMBT2_897/BTACT Plasmid Calibrator | | |
| 200000 | 15.30 | 221,611 |
| 20000 | 18.50 | 17,200 |
| 2000 | 21.20 | 1,988 |
| 200 | 24.01 | 211 |
| CHST2_7890/BTACT Plasmid Calibrator | | |
| 200000 | 14.83 | 320,609 |
| 20000 | 18.08 | 24,036 |
| 2000 | 21.05 | 2,252 |
| 200 | 24.30 | 168 |

Strand Counts Using CHST2_7890/BTACT Plasmid Calibrator Standard Curve:

| CHST2_7890/BTACT Plasmid Calibrator Standard Curve | | |
|---|---|---|
| Slope | | −3.136297934 |
| Intercept | | 31.48713495 |
| Efficiency | | 108.4% |
| Calibrator Strands/Rxn | Average Cp | Average Strands |
| VAV3/BTACT Plasmid Calibrator | | |
| 200000 | 14.95 | 186,901 |
| 20000 | 18.24 | 16,737 |
| 2000 | 21.17 | 1,950 |
| 200 | 24.38 | 184 |
| SFMBT2_897/BTACT Plasmid Calibrator | | |
| 200000 | 15.30 | 145,201 |
| 20000 | 18.50 | 13,830 |
| 2000 | 21.20 | 1,900 |
| 200 | 24.01 | 242 |
| CHST2_7890/BTACT Plasmid Calibrator | | |
| 200000 | 14.83 | 203,942 |
| 20000 | 18.08 | 18,815 |
| 2000 | 21.05 | 2,131 |
| 200 | 24.30 | 196 |

Results:

These data show that adjusting the probe concentrations lower caused the intercept to increase slightly and the PCR % efficiency to increase slightly. The Cp values also increased and therefore the calculation of strand counts gave values similar to the results calculated using the other markers as calibration standards.

The 250 nM SFMBT2_897 probe concentration made the three markers produce similar calculated strand counts, with the SFMBT2_897 strand count values being slightly higher than the other markers. The 50 nM concentration of the probe produced calculated results that slightly underestimated strand counts, but gave some improvement. Therefore, a SFMBT2_897 probe concentration of 200 nM probe was selected for further testing.

Experiment 3.4

This experiment tested the standard conditions described in Experiment 3.1 (all marker probes used at 500 nM) against the 10× oligonucleotide mix that provides 200 nM SFMBT2_897 probe, with the other probes at 500 nM. This experiment will also determine whether there is an additive effect of having multiple targets in single reaction that all report signal using the same FRET cassette and dye. Single, biplex and triplex combinations of the plasmid targets were used, with all target combinations including the BTACT target as a control.

Plasmid Dilutions for One Marker Plus Control:

For reactions with a single marker plasmid plus a BTACT control plasmid, mixtures were made containing 1.00E+04 copies/μL of each plasmid in a diluent of 20 ng/μL fish DNA in 10 mM Tris, 0.1 mM EDTA. The marker plasmids are described the Reagent Table in Experiment 3.1. The targets in the plasmid mixtures were as follows:

SFMBT2_897/BTACT
CHST2_7890/BTACT
VAV3/BTACT

Plasmid Dilutions for Two Markers Plus Control:

For reactions with two marker plasmids plus a BTACT control plasmid, mixtures were made containing 1.00E+04 copies/μL of each plasmid in a diluent of 20 ng/μL fish DNA in 10 mM Tris, 0.1 mM EDTA. The targets in the plasmid mixtures were as follows:

SFMBT2_897/VAV3/BTACT
CHST2_7890/VAV3/BTACT
CHST2_7890/SFMBT2_897/BTACT

Plasmid Dilutions for Three Markers Plus Control:

For reactions with three marker plasmids plus a BTACT control plasmid, a mixture was made containing 1.00E+04 copies/μL of each plasmid in a diluent of 20 ng/μL fish DNA in 10 mM Tris, 0.1 mM EDTA. The plasmid mixture was as follows:

VAV3/CHST2_7890/SFMBT2_897/BTACT

Each of the plasmid mixtures was used to prepare solutions having 1.00E+03 copies/μL and 1.00E+02 copies/μL of each of the plasmids, in fish DNA diluent.

A 10× oligonucleotide mix containing the primers and probes for all 3 markers and for the BTACT control plasmid, and having concentrations of probes to produce 500 nM probe in each QuARTS assay reaction except for the SFMBT2_897 probe, which was provided in an amount to produce a concentration of 200 nM SFMBT2_897 probe in each reaction. The QuARTS assay components were mixed and the assay was performed on a Light Cycler as described in Experiment 3.1.

Results:
Strand Counts Using VAV3/BTACT Plasmid Calibrator Standard Curve:

| VAV3/BTACT Plasmid Calibrator Standard Curve | |
|---|---|
| Slope | −3.164 |
| Intercept | 31.977 |
| % Efficiency | 107% |

Strand Counts for Single Markers, Plus Control Plasmids:

| Calibrator Strands/Rxn | Average Cp | Average Strands |
|---|---|---|
| VAV3/BTACT Plasmid Calibrator | | |
| 200000 | 15.23 | 195,918 |
| 20000 | 18.39 | 19,763 |
| 2000 | 21.42 | 2,179 |
| 200 | 24.77 | 190 |
| SFMBT2_897/BTACT Plasmid Calibrator | | |
| 200000 | 15.08 | 219,449 |
| 20000 | 18.00 | 26,151 |
| 2000 | 20.51 | 4,223 |
| 200 | 23.27 | 564 |
| CHST2_7890/BTACT Plasmid Calibrator | | |
| 200000 | 15.05 | 224,915 |
| 20000 | 17.89 | 28,288 |
| 2000 | 20.41 | 4,532 |
| 200 | 23.02 | 680 |

Strand Counts for Two Markers, Plus Control Plasmids:

| Calibrator Strands/Rxn | Average Cp | Average Strands |
|---|---|---|
| VAV3/CHST2_7890/BTACT Plasmid Calibrator | | |
| 200000 | 14.19 | 417,946 |
| 20000 | 17.33 | 42,756 |
| 2000 | 20.09 | 5,716 |
| 200 | 22.89 | 743 |
| Additive Expected Strands | | |
| VAV3/CHST2 Strands | | 420,833 |
| | | 48,051 |
| | | 6,711 |
| | | 870 |
| VAV3/SFMBT2_897/BTACT Plasmid Calibrator | | |
| 200000 | 14.16 | 429,911 |
| 20000 | 17.27 | 44,611 |
| 2000 | 20.08 | 5,744 |
| 200 | 22.75 | 823 |
| Additive Expected Strands | | |
| VAV3/SFMBT2 Strands | | 415,367 |
| | | 45,914 |
| | | 6,401 |
| | | 754 |
| CHST2_7890/SFMBT2_897/BTACT Plasmid Calibrator | | |
| 200000 | 13.99 | 485,917 |
| 20000 | 17.17 | 47,863 |
| 2000 | 19.80 | 7,068 |
| 200 | 22.34 | 1,113 |
| Additive Expected Strands | | |
| CHST2/SFMBT2 Strands | | 444,364 |
| | | 54,439 |
| | | 8,755 |
| | | 1,244 |

Strand Counts for Three Markers, Plus Control Plasmids:

| Calibrator Strands/Rxn | Average Cp | Average Strands |
|---|---|---|
| VAV3/CHST2_7890/SFMBT2_897/BTACT Plasmid Calibrator | | |
| 200000 | 13.44 | 722,434 |
| 20000 | 16.54 | 76,045 |
| 2000 | 19.21 | 10,847 |
| 200 | 21.85 | 1,589 |

-continued

| Calibrator Strands/Rxn | Average Cp | Average Strands |
|---|---|---|
| VAV3/CHST2_7890/SFMBT2_897/BTACT Plasmid Calibrator | | |
| Additive Expected Strands | | |
| VAV3/CHST2/SFMBT2 Strands | | 640,282 |
| | | 74,202 |
| | | 10,934 |
| | | 1,434 |

Strand Counts Using SFMBT2_897/BTACT Plasmid Calibrator Standard Curve:

| SFMBT2_897/BTACT Plasmid Calibrator Standard Curve | |
|---|---|
| Slope | −2.705 |
| Intercept | 29.369 |
| % Efficiency | 134% |

Strand Counts for Single Markers, Plus Control Plasmids:

| Calibrator Strands/Rxn | Average Cp | Average Strands |
|---|---|---|
| VAV3/BTACT Plasmid Calibrator | | |
| 200000 | 15.12 | 185,009 |
| 20000 | 18.26 | 12,793 |
| 2000 | 21.28 | 980 |
| 200 | 24.57 | 60 |
| SFMBT2_897/BTACT Plasmid Calibrator | | |
| 200000 | 14.98 | 209,356 |
| 20000 | 17.84 | 18,236 |
| 2000 | 20.38 | 2,097 |
| 200 | 23.15 | 200 |
| CHST2_7890/BTACT Plasmid Calibrator | | |
| 200000 | 14.89 | 225,658 |
| 20000 | 17.72 | 20,240 |
| 2000 | 20.29 | 2,275 |
| 200 | 22.86 | 256 |

Strand Counts for Two Markers, Plus Control Plasmids:

| Calibrator Strands/Rxn | Average Cp | Average Strands |
|---|---|---|
| VAV3/CHST2_7890/BTACT Plasmid Calibrator | | |
| 200000 | 14.09 | 446,402 |
| 20000 | 17.22 | 31,148 |
| 2000 | 19.99 | 2,926 |
| 200 | 22.72 | 288 |
| Additive Expected Strands | | |
| VAV3/CHST2 Strands | | 410,667 |
| | | 33,033 |
| | | 3,255 |
| | | 315 |
| VAV3/SFMBT2_897/BTACT Plasmid Calibrator | | |
| 200000 | 14.05 | 460,951 |
| 20000 | 17.17 | 32,470 |
| 2000 | 19.97 | 2,983 |
| 200 | 22.60 | 319 |
| Additive Expected Strands | | |
| VAV3/SFMBT2 Strands | | 394,365 |
| | | 31,029 |
| | | 3,077 |
| | | 260 |

-continued

| Calibrator Strands/Rxn | Average Cp | Average Strands |
|---|---|---|
| CHST2_7890/SFMBT2_897/BTACT Plasmid Calibrator | | |
| 200000 | 13.84 | 552,761 |
| 20000 | 17.08 | 34,990 |
| 2000 | 19.65 | 3,908 |
| 200 | 22.22 | 439 |
| Additive Expected Strands | | |
| CHST2/SFMBT2 Strands | | 435,015 |
| | | 38,476 |
| | | 4,372 |
| | | 455 |

Strand Counts for Three Markers, Plus Control Plasmids:

| Calibrator Strands/Rxn | Average Cp | Average Strands |
|---|---|---|
| VAV3/CHST2_7890/SFMBT2_897/BTACT Plasmid Calibrator | | |
| 200000 | 13.31 | 863,327 |
| 20000 | 16.40 | 62,334 |
| 2000 | 19.12 | 6,171 |
| 200 | 21.69 | 692 |
| Additive Expected Strands | | |
| VAV3/CHST2/SFMBT2 Strands | | 620,024 |
| | | 51,269 |
| | | 5,353 |
| | | 515 |

Strand Counts Using CHST2_7890/BTACT Plasmid Calibrator Standard Curve:

| CHST2_7890/BTACT Plasmid Calibrator Standard Curve | |
|---|---|
| Slope | −2.644 |
| Intercept | 29.02 |
| % Efficiency | 139% |

Strand Counts for Single Markers, Plus Control Plasmids:

| Calibrator Strands/Rxn | Average Cp | Average Strands |
|---|---|---|
| VAV3/BTACT Plasmid Calibrator | | |
| 200000 | 15.14 | 177,035 |
| 20000 | 18.28 | 11,490 |
| 2000 | 21.30 | 828 |
| 200 | 24.60 | 47 |
| SFMBT2_897/BTACT Plasmid Calibrator | | |
| 200000 | 15.01 | 199,391 |
| 20000 | 17.88 | 16,382 |
| 2000 | 20.41 | 1,808 |
| 200 | 23.17 | 162 |
| CHST2_7890/BTACT Plasmid Calibrator | | |
| 200000 | 14.93 | 213,922 |
| 20000 | 17.75 | 18,236 |
| 2000 | 20.31 | 1,966 |
| 200 | 22.89 | 209 |

Strand Counts for Two Markers, Plus Control Plasmids:

| Calibrator Strands/Rxn | Average Cp | Average Strands |
|---|---|---|
| VAV3/CHST2_7890/BTACT Plasmid Calibrator | | |
| 200000 | 14.11 | 436,308 |
| 20000 | 17.24 | 28,620 |
| 2000 | 20.02 | 2,542 |
| 200 | 22.75 | 235 |
| Additive Expected Strands | | |
| VAV3/CHST2 Strands | | 390,956 |
| | | 29,726 |
| | | 2,794 |
| | | 255 |
| VAV3/SFMBT2_897/BTACT Plasmid Calibrator | | |
| 200000 | 14.07 | 448,748 |
| 20000 | 17.18 | 29,908 |
| 2000 | 19.99 | 2,596 |
| 200 | 22.62 | 262 |
| Additive Expected Strands | | |
| VAV3/SFMBT2 Strands | | 376,425 |
| | | 27,872 |
| | | 2,637 |
| | | 209 |
| CHST2_7890/SFMBT2_897/BTACT Plasmid Calibrator | | |
| 200000 | 13.87 | 535,611 |
| 20000 | 17.10 | 32,329 |
| 2000 | 19.68 | 3,405 |
| 200 | 22.24 | 365 |
| Additive Expected Strands | | |
| CHST2/SFMBT2 Strands | | 413,312 |
| | | 34,618 |
| | | 3,774 |
| | | 371 |

Strand Counts for Three Markers, Plus Control Plasmids:

| Calibrator Strands/Rxn | Average Cp | Average Strands |
|---|---|---|
| VAV3/CHST2_7890/SFMBT2_897/BTACT Plasmid Calibrator | | |
| 200000 | 13.34 | 853,557 |
| 20000 | 16.42 | 57,973 |
| 2000 | 19.13 | 5,479 |
| 200 | 21.72 | 578 |
| Additive Expected Strands | | |
| VAV3/CHST2/SFMBT2 Strands | | 590,347 |
| | | 46,108 |
| | | 4,602 |
| | | 418 |

These data confirm the results shown in Experiment 3.2, showing that adjustment of the SFMBT2_897 probe concentration down to 200 nM aligns the efficiency of this assay reaction with the efficiencies of the reactions for detecting VAV3 and CHST2_7890. They also show that when multiple targets in a reaction report signal to the same FRET cassette and dye channel, the result shows an additive effect on the amount of fluorescence signal produced in the reaction. Surprisingly, no increase in background or cross reactivity is observed.

The data further show that, when the VAV3 dilution series is used as the calibration standard, the strand counts of SFMBT2_897 and CHST2_7890 DNAs calculated from the data at the low end of the curve are overestimates of the amounts actually added to these reactions. The VAV3 amplification curves are more variable at the lower end of the standard curve, causing overestimates of strand counts for the other markers.

Experiment 3.5

In this experiment, the probe and primer concentrations of the VAV3 marker were adjusted to reduce overestimation of low-level targets when the VAV3 calibrator curve is used for as the reference curve for calculating DNA concentrations.

For the VAV3 calibration curve, a dilution series having the VAV3 plasmid combined with the BTACT plasmid was as described in Experiment 3.4. Plasmid dilutions having all three markers plus the BTACT control were used.

10× oligonucleotide mixes containing the primers and probes for all 3 markers and for the BTACT control plasmid were made, having primers and probes provided to produce the concentrations shown below:
1. VAV3 (400 nM Primers)/SFMBT2_897 (200 nM Probe)/CHST2_7890/BTACT
2. VAV3 (750 nM Probe)/SFMBT2_897 (200 nM Probe)/CHST2_7890/BTACT
3. VAV3/SFMBT2_897 (200 nM Probe)/CHST2_7890/BTACT With the exception of the variations in primer and probe concentrations indicated above, the final reaction concentrations of all other primers was 200 nM each primer, and of all other probes was 500 nM for each probe. The QuARTS assay reactions were mixed and the assay was performed on a Light Cycler as described in Experiment 3.1. The VAV3 calibration reactions are shown in FIG. 5A-5D. FIG. 5E compares the fluorescence curves for reactions having 200 strands of target DNA, measured under each of the conditions.

Both condition modifications improve the slope of the low calibrator in the VAV3 assay, but these conditions do produce signal that is the same as the single marker oligonucleotide mix. The data show that the single marker mix does not have the issue of over-estimation of strand counts at the low end of the standard curve. Based on these data, 400 nM each VAV3 primer with 500 nM probe was selected for investigation of testing the assay on clinical samples.

Experiment 3.6

This experiment tests the multiple marker/1 dye sample configuration on human clinical plasma samples. Plasma samples were previously tested using the standard one marker:one dye method, as described in Example 2. The same samples were re-tested using an oligonucleotide mix that has VAV3, SFMBT2_897 and CHST2_7890 reporting to one fluorescent channel (FAM).

In Example 2, DNA was prepared from a series of plasma samples and the target DNAs were amplified QuARTs assays. Amplicon material produced in Example 2 from the samples 105-120 (see FIG. 3) was diluted 1:10, and tested using the 3-target/1control oligonucleotide mix described above in Experiment 3.5.

The single marker/BTACT plasmid calibrator dilutions were as described in Experiment 3.1. A 10× oligonucleotide mix comprising primers and probes for all three markers and for the BTACT control DNA, and configured to produce reactions having the 400 nM each VAV3 primer and 200 nM SFMBT2_897 probe, and having all other primers at 200 nM and all other probes at 500 nM, as described in Experiment 3.5, was used. The QuARTS assays were mixed and the assay was performed on a Light Cycler as described in Experiment 3.1. Each reaction was run in duplicate. The results are shown in FIG. 6.

The original data from clinical samples 105-120 tested with these markers (from FIG. 3) is summarized in FIG. 6A. The results using the triplexed assay in which all markers report to a single FRET cassette/single dye are summarized in FIG. 6B.

The counts of target strands for each of the samples were separately calculated using each of the three different marker calibration curves. The resulting strand count values were similar, regardless of which standard curve was used. In addition, the strand counts for each of the samples using the single-dye configuration were close to the combined strand counts for this set of markers measured in Example 2 using separate FRET cassettes and dye channels. Further, samples that had zero strands detected, i.e., that produced no signal in the Example 2 experiment, stayed at zero when using the multiple markers reporting to one dye configuration, showing that background signal is not increased when the multiplexed reactions report to a FRET cassette/single dye channel.

These results show that using multiple different target sites, e.g., multiple different marker genes, reporting to one FRET cassette and the same dye can increase the sensitivity of detection, and also show that multiplex combinations need not be limited by the number of available dye channels for signal detection. In addition, the use of this approach is not limited to having a single dye per reaction well. For example, an assay could be configured having three (or more) markers reporting to a first dye (e.g., FAM) and three (or more) markers reporting to a second dye (e.g., HEX), doubling the number of markers that may be tested in a single reaction, on a single preparation of nucleic acid sample. Additional dye channels may be used for additional sets of markers and/or for one or more internal control targets.

Example 4

Multiple Regions of a Marker Reporting to One Dye

For three methylation markers VAV3 (877), SFMBT2 (897), and CHST2 (7890), that showed low to zero strand counts in normal plasma using the methods described herein above, additional QuARTS assay oligonucleotide sets targeting other regions within each of the markers were designed and tested, to see whether detecting additional regions of the markers in the same reaction and reporting to the same dye channel would increase the signal-to-noise ratio for each marker, thus increasing the sensitivity of the assay, e.g., in detection of cancer.

For each of these markers, two different regions determined by RRBS to have differential methylation between cancer tissue and normal tissue were identified. Those regions are:
VAV3 region 877: chr1: 108507618-108507675
VAV3 region 11878: chr1: 108507406-108507499
SFMBT2 region 895: chr10: 7452337-7452406
SFMBT2 region 897: chr10: 7452865-7452922
CHST2 region 7890: chr3:142838847-142839000
CHST2 region 7889: chr3: 142838300-142838388

Experiment 4.1

The CHST2 regions (7889 and 7890) reporting to the HEX dye were tested both individually and in a combined reaction to evaluate any synergy between the two regions when combined. A calibrator plasmid containing CHST2 insert was diluted as described in Experiment 3.1 to produce a dilution series of 1E4 to 1E0 copies per μL. For individual detection of region 7889, assay reactions contained the forward and reverse primers and the arm 1 probe for CHST2_7889, the Arm 1 HEX FRET cassette, and the primers and the arm 3 probe for the BTACT control, along with the Arm 3 Quasar 670 FRET cassette. For individual detection of region 7890, assay reactions contained the forward and reverse primers and the arm 1 probe for CHST2_7890, the Arm 1 HEX FRET cassette, and the primers and arm 3 probe for the BTACT control, along with the Arm 3 Quasar 670 FRET cassette. The combined reaction contained the complete set of arm 1 probes and primers for both CHST2_7889 and 7890, along with the oligonucleotides for detection of BTACT and the same two FRET cassettes.

10× oligonucleotide mixes contained the primers and probes at concentrations to produce 500 nM of each probe and 200 nM of each primer in each QuARTS assay reaction. The QuARTS assay components were mixed and the assay was performed on a Light Cycler as described in Experiment 3.1.

It was found that in the combined reaction, having these two regions report to the same dye using a single FRET cassette did not result in any increase in signal. The CHST2_7889 amplification was substantially more efficient and appeared to dominate the resulting signal, suggesting that the different reactions should be modified to have more similar efficiencies, as discussed above in Example 3.

Experiment 4.2

Experiments were conducted to determine what probe concentration should be used for each pair of regions in each marker {CHST2 (7889 and 7890), SFMBT2 (895 and 897) and VAV3 (877 and 11878)} to balance the reaction kinetics between the different regions. 10× oligonucleotide mixes were made to provide the following mixtures of assay oligonucleotides at the indicated final concentrations:

| Marker | Oligo | Final 1X Conditions (μM) |
|---|---|---|
| CHST2_7890A (1 × Probe) | | |
| CHST2_7890 | CHST2_7890 FP | 0.2 |
| CHST2_7890 | CHST2_7890 RP | 0.2 |
| CHST2_7890 | Probe A5 CHST2_7890 | 0.5 |
| | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
| | A3 Quasar670 FRET | 0.5 |
| | dNTPs | 250 |
| | water | NA |
| CHST2_7889A (1 × Probe) | | |
| CHST2_7889 | F Primer CHST2_7889 | 0.2 |
| CHST2_7889 | R Primer CHST2_7889 | 0.2 |
| CHST2_7889 | Probe A5 CHST2_7889 | 0.5 |
| | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
| | A3 Quasar670 FRET | 0.5 |
| | dNTPs | 250 |
| | water | NA |
| CHST2_7890A (3 × Probe) | | |
| CHST2_7890 | CHST2_7890 FP | 0.2 |
| | CHST2_7890 RP | 0.2 |
| | Probe A5 CHST2_7890 | 1.5 |
| | A5 FAM FRET | 0.5 |
| ACTB | ACTB_BT_FP65 | 0.2 |
| | ACTB_BT_RP65 | 0.2 |
| | ACTB BT Pb A3 | 0.5 |
| | A3 Quasar670 FRET | 0.5 |
| | dNTPs | 250 |
| | water | NA |
| CHST2_7890A (2 × Probe) | | |
| CHST2_7890 | CHST2_7890 FP | 0.2 |
| | CHST2_7890 RP | 0.2 |
| | Probe A5 CHST2_7890 | 1 |
| | A5 FAM FRET | 0.5 |
| ACTB | ACTB_BT_FP65 | 0.2 |
| | ACTB_BT_RP65 | 0.2 |
| | ACTB BT Pb A3 | 0.5 |
| | A3 Quasar670 FRET | 0.5 |
| | dNTPs | 250 |
| | water | NA |
| CHST2_7889A (0.5 × Probe) | | |
| CHST2_7889 | F Primer CHST2_7889 | 0.2 |
| | R Primer CHST2_7889 | 0.2 |
| | Probe A5 CHST2_7889 | 0.25 |
| | A5 FAM FRET | 0.5 |
| ACTB | ACTB_BT_FP65 | 0.2 |
| | ACTB_BT_RP65 | 0.2 |
| | ACTB BT Pb A3 | 0.5 |
| | A3 Quasar670 FRET | 0.5 |
| | dNTPs | 250 |
| | water | NA |
| SFMBT2_895A (1 × Probe) | | |
| SFMBT2_895v2 | FP SFMBT2_895_v2 | 0.2 |
| | RP SFMBT2_895_v2 | 0.2 |
| | Prb A1 SFMBT2_895 v2 | 0.5 |
| | A1 HEX FRET | 0.5 |
| ACTB | ACTB_BT_FP65 | 0.2 |
| | ACTB_BT_RP65 | 0.2 |
| | ACTB BT Pb A3 | 0.5 |
| | A3 Quasar670 FRET | 0.5 |
| | dNTPs | 250 |
| | water | NA |

SFMBT2_897/BTACT

| Marker | Oligo | Final 1X Conditions (μM) |
|---|---|---|
| SFMBT2_897A (1 × Probe) | | |
| SFMBT2_897 | F Primer SFMBT2_897v5 | 0.2 |
| | R Primer SFMBT2_897v4 | 0.2 |
| | Probe A1 SFMBT2_897v5 | 0.5 |
| | A1 HEX FRET | 0.5 |
| ACTB | ACTB_BT_FP65 | 0.2 |
| | ACTB_BT_RP65 | 0.2 |
| | ACTB BT Pb A3 | 0.5 |
| | A3 Quasar670 FRET | 0.5 |
| | dNTPs | 250 |
| | water | NA |
| SFMBT2_897A (0.5 × Probe) | | |
| SFMBT2_897 | F Primer SFMBT2_897v5 | 0.2 |
| | R Primer SFMBT2_897v4 | 0.2 |
| | Probe A1 SFMBT2_897v5 | 0.25 |
| | A1 HEX FRET | 0.5 |

| Marker | Oligo | Final 1X Conditions (μM) |
|---|---|---|
| ACTB | ACTB_BT_FP65 | 0.2 |
|  | ACTB_BT_RP65 | 0.2 |
|  | ACTB BT Pb A3 | 0.5 |
|  | A3 Quasar670 FRET | 0.5 |
|  | dNTPs | 250 |
|  | water | NA |
| *SFMBT2_895A (2 × Probe)* | | |
| SFMBT2_895v2 | FP SFMBT2_895_v2 | 0.2 |
|  | RP SFMBT2_895_v2 | 0.2 |
|  | Prb A1 SFMBT2_895 v2 | 1 |
|  | A1 HEX FRET | 0.5 |
| ACTB | ACTB_BT_FP65 | 0.2 |
|  | ACTB_BT_RP65 | 0.2 |
|  | ACTB BT Pb A3 | 0.5 |
|  | A3 Quasar670 FRET | 0.5 |
|  | dNTPs | 250 |
|  | water | NA |
| *SFMBT2_897A (0.25 × Probe)* | | |
| SFMBT2_897 | F Primer SFMBT2_897v5 | 0.2 |
|  | R Primer SFMBT2_897v4 | 0.2 |
|  | Probe A1 SFMBT2_897v5 | 0.125 |
|  | A1 HEX FRET | 0.5 |
| ACTB | ACTB_BT_FP65 | 0.2 |
|  | ACTB_BT_RP65 | 0.2 |
|  | ACTB BT Pb A3 | 0.5 |
|  | A3 Quasar670 FRET | 0.5 |
|  | dNTPs | 250 |
|  | water | NA |
| *VAV3_877A (1 × Probe)* | | |
| VAV3_877 | F Primer VAV3 | 0.2 |
| VAV3_877 | R Primer VAV3 ver 2 | 0.2 |
| VAV3_877 | Probe A5 VAV3 | 0.5 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |
| *VAV3_878A (1 × Probe)* | | |
| VAV3_11878 | F Primer VAV3_11878 | 0.2 |
| VAV3_11878 | R Primer VAV3_11878 | 0.2 |
| VAV3_11878 | Probe A5 VAV3_11878 | 0.5 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |
| *VAV3_877A (1.5 × Probe)* | | |
| VAV3_877 | F Primer VAV3 | 0.2 |
| VAV3_877 | R Primer VAV3 ver 2 | 0.2 |
| VAV3_877 | Probe A5 VAV3 | 0.75 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |
| *VAV3_877A (2 × Probe)* | | |
| VAV3_877 | F Primer VAV3 | 0.2 |
| VAV3_877 | R Primer VAV3 ver 2 | 0.2 |
| VAV3_877 | Probe A5 VAV3 | 1 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |
| *VAV3_878 (0.75 × Probe)* | | |
| VAV3_11878 | F Primer VAV3_11878 | 0.2 |
| VAV3_11878 | R Primer VAV3_11878 | 0.2 |
| VAV3_11878 | Probe A5 VAV3_11878 | 0.375 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |
| *VAV3_878 (0.5 × Probe)* | | |
| VAV3_11878 | F Primer VAV3_11878 | 0.2 |
| VAV3_11878 | R Primer VAV3_11878 | 0.2 |
| VAV3_11878 | Probe A5 VAV3_11878 | 0.25 |
|  | A5 FAM FRET | 0.5 |
| BTACT | ACTB_BT_FP65 | 0.2 |
| BTACT | ACTB_BT_RP65 | 0.2 |
| BTACT | ACTB BT Pb A3 | 0.5 |
|  | A3 Quasar670 FRET | 0.5 |
|  | dNTPs | 250 |
|  | water | NA |

The QuARTS assay components were mixed and the assays were performed on a Light Cycler as described in Experiment 3.1 The average Cp values achieved under the different reaction conditions are as follows:

| | Average Cp Values | | | | |
|---|---|---|---|---|---|
| Plasmid Calibrator Concentration | CHST2_7890 1 × Probe Conc. | CHST2_7890 2 × Probe Conc. | CHST2_7890 3 × Probe Conc. | CHST2_7889 1 × Probe Conc. | CHST2_7889 0.5 × Probe Conc. |
| 200,000 | 15.4 | 14.8 | 14.2 | 13.9 | 14.7 |
| 20,000 | 18.6 | 18.0 | 17.4 | 17.1 | 18.1 |
| 2,000 | 22.1 | 21.4 | 21.0 | 20.6 | 21.2 |
| 200 | 25.2 | 24.9 | 24.2 | 24.0 | 24.7 |
| 20 | 28.7 | 27.8 | 27.0 | 27.2 | 28.1 |

-continued

| | Average Cp Values | | | | |
|---|---|---|---|---|---|
| Plasmid Calibrator Concentration | SFMBT2_895 1 × Probe Conc. | SFMBT2_895 2 × Probe Conc. | SFMBT2_897 1 × Probe Conc. | SFMBT2_897 0.25 × Probe Conc. | SFMBT2_897 0.5 × Probe Conc. |
| 200,000 | 16.5 | 15.2 | 14.5 | 16.7 | 16.0 |
| 20,000 | 20.1 | 19.1 | 18.0 | 20.1 | 19.3 |
| 2,000 | 23.4 | 22.6 | 21.3 | 23.3 | 22.5 |
| 200 | 27.1 | 26.1 | 24.4 | 26.5 | 25.8 |
| 20 | 30.2 | 29.4 | 27.4 | 30.6 | 29.3 |

| | Average CP Values | | | | |
|---|---|---|---|---|---|
| Plasmid Calibrator Concentration | VAV3_877 1 × Probe Conc. | VAV3_877 1.5 × Probe Conc. | VAV3_877 2 × Probe Conc. | VAV3_11878 1 × Probe Conc. | VAV3_11878 0.75 × Probe Conc. | VAV3_11878 0.5 × Probe Conc. |
| 200,000 | 15.0 | 14.5 | 14.2 | 13.4 | 13.8 | 14.3 |
| 20,000 | 18.2 | 17.9 | 17.6 | 16.9 | 17.0 | 17.8 |
| 2,000 | 21.6 | 21.3 | 21.0 | 20.3 | 20.3 | 21.1 |
| 200 | 25.2 | 24.4 | 24.2 | 23.4 | 23.8 | 24.2 |
| 20 | 27.9 | 28.1 | 27.3 | 26.7 | 27.5 | 27.5 |

| | Average Cp Values | | | | |
|---|---|---|---|---|---|
| Plasmid Calibrator Concentration | VAV3_877 1 × Probe Conc. | VAV3_877 1.5 × Probe Conc. | VAV3_877 2 × Probe Conc. | VAV3_11878 1 × Probe Conc. | VAV3_11878 0.75 × Probe Conc. | VAV3_11878 0.5 × Probe Conc. |
| 200,000 | 15.0 | 14.5 | 14.2 | 13.4 | 13.8 | 14.3 |
| 20,000 | 18.2 | 17.9 | 17.6 | 16.9 | 17.0 | 17.8 |
| 2,000 | 21.6 | 21.3 | 21.0 | 20.3 | 20.3 | 21.1 |
| 200 | 25.2 | 24.4 | 24.2 | 23.4 | 23.8 | 24.2 |
| 20 | 27.9 | 28.1 | 27.3 | 26.7 | 27.5 | 27.5 |

These data show that by varying the probe concentrations, it is possible to adjust the Cp values for the individual assays to the point where each of the five points of the calibration curve are within <1 Cp for each of the two regions for each marker. For the markers tested, use of the following probe concentrations in the QuARTS assay reactions produced balanced reaction efficiencies for the sets of target regions:

| Marker | [Probe]-A5-FAM | [Probe]-A1-HEX |
|---|---|---|
| SFMBT2_895 | — | 0.5 uM |
| SFMBT2_897 | — | 0.125 uM |
| CHST2_7889 | 0.25 uM | — |
| CHST2_7890 | 1 uM | — |
| VAV3_877 | 1 uM | — |
| VAV3_11878 | 0.25 uM | — |

Experiment 4.3

New triplex reactions (see Example 2 for original triplex reaction configurations) were designed to use the multiple region/one dye assay configurations in multiplexed reactions. "Pool 17" below lists a set of 6 markers co-amplified with a β-actin control, then analyzed in triplex QuARTS assays in the groupings shown below. Pool 17+MR-OD is adapted to include the multiple regions/one dye assay configurations for the SFMBT2, VAV3, and CHST2 markers. The JAM3, ZNF671, and ZNF568 assay designs were as shown in FIG. 1 and FIG. 2. The 3- or 4-letter abbreviations for each grouping in the pools are the first letter of each gene name, with A indicating the β-actin control.

| Pool 17 | | Pool 17 + MR-OD | |
|---|---|---|---|
| JSA | JAM3 | JSSA | JAM3 |
| | SFMBT2_897 | | SFMBT2_897 |
| | BTACT | | SFMBT2_895 |
| VZA | VAV3_877 | | BTACT |
| | ZNF671 | VVZA | VAV3_877 |
| | BTACT | | VAV3_11878 |
| CZA1 | CHST2_7890 | | ZNF671 |
| | ZNF568 | | BTACT |
| | BTACT | CCZA1 | CHST2_7890 |
| | | | CHST2_7889 |
| | | | ZNF568 |
| | | | BTACT |

The new triplex formulations were tested on a plasmid calibration dilution series comprising the Pool 17 multiplex, comprising all target regions in the groups listed above, in a series of dilutions providing 2e5 to 2e1 strands of each target per assay reaction. The final concentrations of the probes for the SFMBT2, VAV3, and CHST2 MR-OD were as described in the results of Experiment 4.2. The probes for JAM3, ZNF671, and ZNF568 markers and for the BTACT control were 1 μM. All FRET cassettes were at 500 nM in the final reactions mixtures. The QuARTS assay components were mixed and the assays were performed on a Light Cycler as described in Experiment 3.1

The triplex containing VAV3-877plus VAV-11878 performed as expected, giving approximately 2 to 3-fold increase in strand count over the count of target added to the reaction, while the targets having only one region targeted. However, the triplexes containing CHST2-7889_CHST-7890 and SFMBT2-895_SFMBT2-897 did not show the expected additive signal. Further experiments were conducted using different concentrations of the probes for CHST2-7889_CHST2-7890 and SFMBT2-895_SFMBT2-897, to test them in the multiplex QuARTS assays grouped as shown above. Within the triplex format, it was possible to modify the probe concentration of CHST2_7889 and CHST2_7890 to achieve the expected MR_OD results (i.e., results having the expected additive values of the individual reactions) based on a plasmid calibration curve. However, SFMBT2_895 and SFMBT2_897 assay, while improved using the modified probe concentrations, when used in the triplex format the assay still produced signal below the expected 200% level expected for detection of two regions. Nonetheless, the following modified probe concentrations were selected for testing the triplex assays on plasma samples.

| Revised Final Probe Concentrations for MR-OD Reactions | | |
|---|---|---|
| Marker_region | [Probe]-Arm5-FAM | [Probe]-Arm1-HEX |
| SFMBT2_895 | — | 1 uM |
| SFMBT2_897 | — | 0.25 uM |
| CHST2_7889 | 0.5 uM | — |
| CHST2_7890 | 1.5 uM | — |
| VAV3_877 | 1 uM | — |
| VAV3_11878 | 0.25 uM | — |

Experiment 4.4

This experiment examined the effect of combining multiplex pre-amplification and triplex QuARTS assay detection using the multiple regions-one dye assay designs to test human plasma samples from both normal and cancer patients. The experiment compared detection of 13 methylation markers (plus Process Control, ZF_RASSF1) of Pool 17 to detection using the Pool 17+MR_OD configuration on 63 normal plasma samples and 12 colon cancer plasma samples. The markers of Pool 17 were co-amplified together in a pre-amplification, then the pre-amplified DNA was detected in the list of grouped reactions listed below, and as described in detail in Example 1.

| Pool 17 | | Pool 17 + MR-OD | |
|---|---|---|---|
| JSA | JAM3 | JSSA | JAM3 |
| | SFMBT2 | | SFMBT2_897 |
| | BTACT | | SFMBT2_895 |
| PDA | PDGFD | | BTACT |
| | DTX1 | PDA | PDGFD |
| | BTACT | | DTX1 |
| GQA | GRIN2D | | BTACT |
| | QKI | GQA | GRIN2D |
| | BTACT | | QKI |
| VZA | VAV3 | | BTACT |
| | ZNF671 | VVZA | VAV3_877 |
| | BTACT | | VAV3_11878 |
| CZA1 | CHST2 | | ZNF671 |
| | ZNF568 | | BTACT |
| | BTACT | CCZA1 | CHST2_7890 |
| AFA | ANKRD13B | | CHST2_7889 |
| | FER1L4 | | ZNF568 |
| | BTACT | | BTACT |

| Pool 17 | | Pool 17 + MR-OD | |
|---|---|---|---|
| CZA2 | CNNM1 | AFA | ANKRD13B |
| | ZFRASSF1 | | FER1L4 |
| | BTACT | | BTACT |
| | | CZA2 | CNNM1 |
| | | | ZFRASSF1 |
| | | | BTACT |

The triplex names comprise the first letter of each included marker, plus 'A' for the β-actin control. Double letters in the triplex names (e.g., "JSSA") in the right-hand column indicate single markers tested at two different regions.

DNA was isolated from plasma samples as described in Example 1. Bisulfite conversion, multiplex pre-amplification, and QuARTS assay on multiplex-amplified DNA were conducted as described in Example 1. Prior to bisulfate conversion, aliquots of the isolated DNA were saved for testing KRAS 38A and 35C mutations on unconverted DNA. The amplification primers and detection probes used for each marker were as shown in FIGS. 1 and 2.

A logistic linear regression fit using strands-per-reaction for VAV3, SFMBT2, CHST2, and ZNF671 showed a considerable advantage when QuARTs is used in combination with MR_OD (multiple regions_one dye) as compared to the standard QuARTs assay configuration, as shown below. In these analysis, the marker ZNF671 was a major contributor to the detection results, and was included in the logistic fit for both QuARTs only and QuARTs+MR_OD. As noted above, KRAS 38A and 35C mutations the unconverted DNA were also tested.

The following sensitivity and specificity was obtained for using the multiplex pre-amplification with the standard triplex assays:

| Multiplex with standard QuARTs assay | | | | |
|---|---|---|---|---|
| | | Prediction | | |
| Stage | N Tested | Cancer | Normal | Sensitivity |
| I | 4 | 2 | 2 | 50% |
| II | 3 | 2 | 1 | 67% |
| III | 3 | 2 | 1 | 67% |
| IV | 2 | 2 | 0 | 100% |

| | | Prediction | | |
|---|---|---|---|---|
| Pathology | N Tested | Cancer | Normal | % Sensitivity/Specificity |
| Cancer | 12 | 8 | 4 | 67% |
| Normal | 62 | 0 | 62 | 100% |

When the multiple region/one dye configuration was used, the sensitivity and specificity were as follows:

| Multiplex with QuARTs assay using Multiple Regions_one Dye (MR_OD) | | | | |
|---|---|---|---|---|
| | | Prediction | | |
| Stage | N Tested | Cancer | Normal | Sensitivity |
| I | 4 | 4 | 0 | 100% |
| II | 3 | 3 | 0 | 100% |
| III | 3 | 2 | 1 | 67% |
| IV | 2 | 2 | 0 | 100% |
| | | Prediction | | |
| Pathology | N Tested | Cancer | Normal | % Sensitivity/Specificity |
| Cancer | 12 | 11 | 1 | 92% |
| Normal | 62 | 6 | 56 | 90% |

Although the sample size is small, the use of this multiple region-to-one dye (FRET cassette) configuration shows substantial improvement in sensitivity, but may result in some loss of specificity.

It should be noted that, while this example detected DNA isolated from plasma samples, this panel of markers and use of the multiplex QuARTS assay modified as described above can be applied to stool or other blood or bodily fluid-based testing, and find application in, e.g., colon cancer and other cancer screening.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

---

What is claimed is:

1. A method of characterizing a sample from a human subject, the method comprising assaying the sample for amounts of each of a plurality of different methylated marker DNAs and an amount of at least one control DNA, the method comprising:
   a) amplifying DNA from the sample with PCR amplification reagents in one or more reaction mixtures, wherein the PCR amplification reagents comprise:
      i) methylation marker primer pairs for amplifying target regions from two to thirteen different methylated marker DNAs selected from the group consisting of ankyrin repeat domain 13B (ANKRD13B); carbohydrate sulfotransferase 2 (CHST2); cyclin and CBS domain divalent metal cation transport mediator 1 (CNNM1); deltex E3 ubiquitin ligase 1 (DTX1); dysferlin (FER1L4); glutamate ionotropic receptor NMDA type subunit 2D (GRIN2D); junctional adhesion molecule 3 (JAM3); platelet derived growth factor D (PDGFD); QKI, KH domain containing RNA binding (QKI); Scm like with four mbt domains 2 (SFMBT2); vav guanine nucleotide exchange factor 3 (VAV3); zinc finger protein 568 (ZNF568); and zinc finger protein 671 (ZNF671); and
      ii) at least one control primer pair for amplifying a target region from at least one control DNA; and
   b) measuring amplified amounts of the target regions of the two to thirteen different methylated marker DNAs, and an amplified amount of the target region from the at least one control DNA, wherein the at least one control DNA comprises a region of a B3GALT6 gene.

2. The method of claim 1, wherein said amplifying DNA from the sample is in one reaction mixture.

3. The method of claim 1, wherein the sample comprises a blood sample, a plasma sample, a stool sample, or a tissue sample.

4. The method of claim 1, wherein the assaying comprises treating DNA obtained from the sample with a methylation-specific reagent.

5. The method of claim 4, wherein the methylation-specific reagent selectively modifies cytosine bases in the obtained DNA to produce modified bases.

6. The method of claim 5, wherein the methylation-specific reagent comprises a bisulfite reagent.

7. The method of claim 1, wherein the one or more reaction mixtures comprise methylation marker primer pairs for amplifying target regions from each methylated marker DNA in the group consisting of ANKRD13B, CHST2, CNNM1, DTX1, FER1L4, GRIN2D, JAM3, PDGFD, QKI, SFMBT2, VAV3, ZNF568, and ZNF671.

8. The method of claim 1, wherein the one or more reaction mixtures comprise bulk fish DNA.

9. The method of claim 1, wherein the one or more reaction mixtures comprise PCR-flap assay reagents, wherein the PCR-flap assay reagents comprise:
   i) flap oligonucleotides that specifically hybridize to target regions amplified from the two to thirteen methylated marker DNAs selected from the group consisting of ANKRD13B, CHST2, CNNM1, DTX1, FER1L4, GRIN2D, JAM3, PDGFD, QKI, SFMBT2, VAV3, ZNF568, and ZNF671; and
   ii) a flap oligonucleotide that specifically hybridizes to a target region from the at least one control DNA.

10. The method of claim 9, wherein the PCR-flap assay reagents further comprise at least one hairpin oligonucleotide comprising a region that is complementary to a 5' flap portion of at least one flap oligonucleotide.

11. The method of claim 10, wherein the at least one hairpin oligonucleotide is a FRET cassette.

12. The method of claim 9, wherein the PCR-flap assay reagents further comprise one or more of dNTPs, a buffer comprising $Mg^{++}$, a FRET cassette, and a FEN-1 endonuclease.

13. The method of 1, further comprising assaying the sample for carcinoembryonic antigen (CEA) protein.

* * * * *